US009783578B2

(12) United States Patent
Sasikumar et al.

(10) Patent No.: US 9,783,578 B2
(45) Date of Patent: Oct. 10, 2017

(54) IMMUNOSUPPRESSION MODULATING COMPOUNDS

(71) Applicants: Pottayil Govindan Nair Sasikumar, Bangalore (IN); Muralidhara Ramachandra, Bangalore (IN); Suresh Kumar Vadlamani, Bangalore (IN); Koteswara Rao Vemula, Bangalore (IN); Leena Khare Satyam, Bangalore (IN); Krishnaprasad Subbarao, Bangalore (IN); K. Rajeev Shrimali, Hyderabad (IN); Sreenivas Kandepu, Hyderabad (IN)

(72) Inventors: Pottayil Govindan Nair Sasikumar, Bangalore (IN); Muralidhara Ramachandra, Bangalore (IN); Suresh Kumar Vadlamani, Bangalore (IN); Koteswara Rao Vemula, Bangalore (IN); Leena Khare Satyam, Bangalore (IN); Krishnaprasad Subbarao, Bangalore (IN); K. Rajeev Shrimali, Hyderabad (IN); Sreenivas Kandepu, Hyderabad (IN)

(73) Assignee: AURIGENE DISCOVERY TECHNOLOGIES LIMITED, Bangalore (IN)

( * ) Notice: Subject to any disclaimer, the term of this patent is extended or adjusted under 35 U.S.C. 154(b) by 45 days.

(21) Appl. No.: 14/563,568

(22) Filed: Dec. 8, 2014

(65) Prior Publication Data
US 2015/0087581 A1 Mar. 26, 2015

Related U.S. Application Data

(63) Continuation-in-part of application No. 13/168,453, filed on Jun. 24, 2011, now Pat. No. 8,907,053.

(60) Provisional application No. 61/381,593, filed on Sep. 10, 2010.

(30) Foreign Application Priority Data

Jun. 25, 2010 (IN) .......................... 1805/CHE/2010

(51) Int. Cl.
C07K 14/00 (2006.01)
C07K 7/08 (2006.01)
C07K 9/00 (2006.01)
C07K 7/06 (2006.01)
C07K 14/705 (2006.01)
A61K 38/00 (2006.01)

(52) U.S. Cl.
CPC ............. *C07K 14/001* (2013.01); *C07K 7/06* (2013.01); *C07K 7/08* (2013.01); *C07K 9/00* (2013.01); *C07K 14/705* (2013.01); *A61K 38/00* (2013.01)

(58) Field of Classification Search
CPC ... C07K 2/00; C07K 4/00; C07K 7/00; C07K 9/00; A61K 38/10; A61K 38/08; A61K 38/16; A61K 38/00
See application file for complete search history.

(56) References Cited

U.S. PATENT DOCUMENTS

| 5,629,204 | A | 5/1997 | Honjo et al. | |
| 5,789,542 | A * | 8/1998 | McLaughlin | C12N 1/06 435/259 |
| 6,808,710 | B1 | 10/2004 | Wood et al. | |
| 6,936,704 | B1 | 8/2005 | Freeman et al. | |
| 7,038,013 | B2 | 5/2006 | Freeman et al. | |
| 7,105,328 | B2 | 9/2006 | Wood et al. | |
| 7,432,059 | B2 | 10/2008 | Freeman et al. | |
| 7,709,214 | B2 | 5/2010 | Freeman et al. | |
| 7,794,710 | B2 | 9/2010 | Chen et al. | |
| 7,943,743 | B2 | 5/2011 | Korman et al. | |
| 2009/0274666 | A1 | 11/2009 | Chen | |
| 2009/0305950 | A1 | 12/2009 | Minato et al. | |
| 2010/0055102 | A1 | 3/2010 | Langermann | |
| 2011/0081341 | A1 | 4/2011 | Honjo et al. | |

FOREIGN PATENT DOCUMENTS

| WO | 0200730 A2 | 1/2002 |
| WO | 03042402 A2 | 5/2003 |

(Continued)

OTHER PUBLICATIONS

Takashi Shinohara et ai, Structure and Chromosomal localization of human PD-1 Gene (PDCD-1); Genomics 1994, vol. 23, No. 3, p. 704-706.
Yasutoshi Agata et al., Expression of the PD-1 antigen on the surface of stimulated mouse T and B lymphocytes; International Immunoloov 1996,vol. 8, No. 5, p. 765.
Gordon J Freeman et ai, Engagement of the PD-1 Immunoinhibitory Receptor by a Novel 87 Family Member Leads to Negative Regulation of Lymphocyte Activation Journal of Experimental Medicine 2000 vol. 192, No. 7,paoe 1027-1034.
Yvette Latchman et al,PD-L2 is a second ligand for PD-1 and inhibits T cell activation Nature Immunoloov 2001, vol. 2, No. 3, paoe.261-267.
Yoshiko Iwai et al., PNAS USA 2002, vol. 99, No. 19, p. 12293-12297.

(Continued)

*Primary Examiner* — Lianko Garyu
(74) *Attorney, Agent, or Firm* — Benjamin Aaron Adler

(57) ABSTRACT

The present invention provides immunosuppression compounds to inhibit the programmed cell death 1 (PD1) signalling pathway. The present invention further provides peptide based compositions for treatment of cancer or treatment of infections via immunopotentiation caused by inhibition of immunosuppressive signaling induced by PD-1, PD-L1, or PD-L2 and therapies using them, immunopotentiative substrates included as the active ingredient. Further, the invention provides an application of the compositions containing the peptide moieties for preventive and/or therapeutic agents for cancer, cancer metastasis, immunodeficiency, an infectious disease or the like and an application of peptide moieties as a testing or diagnostic agent or a research agent for such a disease.

22 Claims, 7 Drawing Sheets

(56) References Cited

FOREIGN PATENT DOCUMENTS

Figure 1:
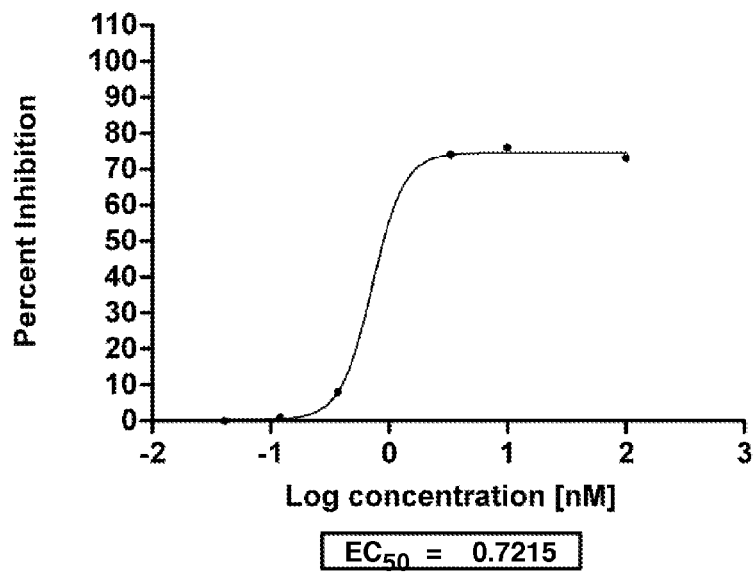

| WO | 2004056875 A1 | 7/2004 |
|---|---|---|
| WO | 2011066342 A2 | 6/2011 |

OTHER PUBLICATIONS

Christian Blank et al., PD-L IIB7H-1 Inhibits the Effector Phase of Tumor Rejection by T Cell Receptor (TCR) Transgenic CD8+ T Cells Cancer Research 2004, vol. 64, paoe 1140-1145.

Ludmila Prokunina et ai, A regulatory polymorphism in POCO 1 is associated with susceptibility to systemic lupus erythematosus in humans Nature Genetics 2002, vol. 32, No. 4, p. 666-669.

Hiroyuki Nishimura et ai, Immunological studies on PD-1 deficient mice: Implication of PD-1 as a negative regulator for B-cell responses InternationaiImmunoioov 1998, vol. 10, No. 10, p. 1563-1572.

Hiroyuki Nishimura et ai, Development of Lupus-like Autoimmune Diseases by Disruption of the PD-1 Gene Encoding an ITIM Motif-Carrying Immunoreceptor Immunity_1999, vol. 11, No. 2, p. 141-151.

Hiroyuki Nishimura et ai, Autoimmune Dilated Cardiomyopathy in PD-1Receptor-Deficient Mice Science 2001, vol. 291, No. 5502, p. 319-332.

Perumal Yogeeswari et al., An Update on GABA Analogs for CNS Drug Discovery Recent Patents on CNS Drug Discovery. 2006, vol. 1, No. 1, p. 113-118.

Lawrence R Finger et al., The human PD-1 gene: complete cDNA, genomic organization, and developmentally regulated expression in B cell progenitors Gene 1997, vol. 197, No. 1-2, p. 177-187.

Eszter Lazar-Molnar et ai, Crystal structure of the complex between programmed death-1 (PD-1) and its ligand PD-L2 PNAS 2008, vol. 105, No. 30, p. 10483-10488.

Satoe H. Nakagawa et.al., Perturbation of Insulin-Receptor Interactions by Intramolecular Hormone Cross-linking Journal of Biological Chemistry 1989, vol. 264. No. 1, p. 272-279.

Paul K Nakane, Recent progress in the peroxidase-labeled antibody method Ann. New York Acad. Sci., 1975, vol. 254, p. 203-211.

O'Shannessy 0 J, Hoffman W L Site-directed immobilization of glycoproteins on hydrazide-containing solid supports Biotechnology Applied Biochemistry 1987, vol. 9, No. 6, p. 488-496.

Brahmamdam, Pavan et. al., Delayed administration of anti-PD-1 antibody reverses immune dysfunction and improves survival during sepsis Journal of Leukocyte Biology. 2010, vol. 88, No. 2, p. 233-240.

Julie R. Brahmer et.al., Phase I Study of Single-Agent Anti-Programmed Death-1(MDX-1106) in Refractory Solid Tumors: Safety, Clinical Activity, Pharmacodynamics and Immunologic Correlates; Journal of Clinical Oncology; 2010; 3167-3175.

Taku Okazaki and Tasuku Honjo., PD-1 and PD-1 ligands: from discovery to clinical application International Immunology. 2007, vol. 19, No. 7, p. 813-824.

Brian T Fife et.al., Interactions between PD-1 and PD-L 1 promote tolerance by blocking the TCR-induce d stop signal Nature Immunology_2009, vol. 10, No. 11, p. 1185-1192.

Fumiya Hirano et.al., Blockade of B7-H1 and PD-1 by Monoclonal Antibodies Potentiates Cancer Therapeutic Immunity cancer Research 2005, vol. 65. No. 3, p. 1089-1096.

R. Houstonthompson et. ai, Implications of B7-H1 Expression in Clear Cell Carcinoma of the Kidney for Prognostication and Therapy clinical Cancer Research 2007, vol. 13, No. 2, p. 709S-715S.

Yoshiko Iwai et.al, PD-1 blockade inhibits hematogenous spread of poorly immunogenic tumor cells by enhanced recruitment of effector T cells International Immunology 2004, vol. 17, No. 2, p. 133-144.

David Yin-Wei Lin et.al., The PD-1/PD-L 1 complex resembles the antigen-binding Fv domains of antibodies and T cell receptors PNAS 2008, vol. 105, No. 8, p. 3011-3016.

Gordon J. Freeman, Structures of PD-1 with its ligands: Sideways and dancing cheek to cheek to cheek PNAS 2008. vol. 105, No. 30 p. 10275-10276.

Xin Huang et.al. PD-1 expression by macrophages plays a pathologiC role in altering microbial clearance and the innate inflammatory response to sepsis PNAS 2009, vol. 106, No. 15, p. 6303-6308.

Sand~Ijn M Van Schaik and Abdul K Abbas, Role of T cells in a murine model of *Escherichia coli* sepsis European Journal of Immunology 2001, vol. 37, No. 11, p. 3101-3110.

\* cited by examiner

IMMUNOSUPPRESSION MODULATING COMPOUNDS

CROSS-REFERENCE TO RELATED APPLICATIONS

This application is a continuation-in-part under 35 U.S.C §120 of pending nonprovisional application U.S. Ser. No. 13/168,453, filed Jun. 24, 2011, which claims benefit of priority under 35 U.S.C. §119(e) of provisional application U.S. Ser. No. 61/381,593, filed Sep. 10, 2010, and which claims benefit of priority under 35 U.S.C. §119(a) of Indian provisional Application No. 1805/CHE/2010, filed Jun. 25, 2010 all of which are hereby incorporated by reference.

BACKGROUND OF THE INVENTION

Field of the Invention

The present invention relates to novel peptide compound of formula-I

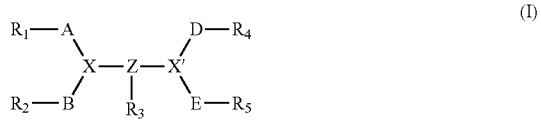

or pharmaceutically acceptable salt thereof; wherein; the compound comprises at least 5 amino acids useful as therapeutic agents capable of inhibiting the programmed cell death 1 (PD1) signalling pathway.

The invention also relates to modifications and derivatives of the therapeutic agents.

The invention further relates to pharmaceutical compositions comprising the said novel peptide compound of formula-I or pharmaceutically acceptable salt thereof as therapeutic agents.

The compounds of the present invention are useful in therapy relating to particular diseases or associated disorders where there is an advantage in immuno-potentiation comprising inhibition of an immunosuppressive signal induced due to PD-1, PD-L1, or PD-L2.

The present invention relates to novel peptides as therapeutic agents capable of inhibiting the programmed cell death 1 (PD1) signalling pathway.

The invention also relates to modifications and derivatives of the therapeutic agents.

The invention further relates to pharmaceutical compositions comprising the said novel peptides and their derivatives as therapeutic agents.

The invention also encompasses the use of the said therapeutic agents, modifications and derivatives for treatment of disorders via immuno-potentiation comprising inhibition of an immunosuppressive signal induced due to PD-1, PD-L1, or PD-L2.

Description of the Related Art

Programmed Cell Death 1 or PD-1 (also referred to as PDCD1) is a 50 to 55 kD type I membrane glycoprotein (Shinohara T et al, Genomics, 1994, Vol. 23, No. 3, pp. 704-706). PD-1 is a receptor of the CD28 superfamily that negatively regulates T cell antigen receptor signalling by interacting with the specific ligands and is suggested to play a role in the maintenance of self tolerance.

PD-1 peptide relates to almost every aspect of immune responses including autoimmunity, tumour immunity, infectious immunity, transplantation immunity, allergy and immunological privilege.

The PD-1 protein's structure comprises an extracellular IgV domain followed by a transmembrane region and an intracellular tail.

The intracellular tail contains two phosphorylation sites located in an immunoreceptor tyrosine-based inhibitory motif and an immunoreceptor tyrosine-based switch motif, which suggests that PD-1 negatively regulates TCR signals. Also, PD-1 is expressed on the surface of activated T cells, B cells, and macrophages, (Y. Agata et al., *Int Immunol* 8, 765, May 1996) suggesting that compared to CTLA-4 ((Cytotoxic T-Lymphocyte Antigen 4, also known as CD152 (Cluster of differentiation 152) is a protein that also plays an important regulatory role in the immune system), PD-1 more broadly negatively regulates immune responses.

PD-1 has two ligands, PD-L1 (Programmed Death Ligand 1 or PDCD1L1 or B7-H1) (Freeman G J et al, Journal of Experimental Medicine, 2000, Vol. 19, No. 7, pp. 1027-1034) and PD-L2 (Programmed Death Ligand 2 or PDCD1L2 or B7-DC) (Latchman Y et al, Nature Immunology, 2001, Vol. 2, No. 3, pp. 261-267), which are members of the B7 family. PD-L1 is known to be expressed not only in immune cells, but also in certain kinds of tumour cell lines (such as monocytic leukaemia-derived cell lines, mast cell tumour-derived cell lines, hematoma-derived cell lines, neuroblastoma-derived cell lines, and various mammary tumour-derived cell lines) and in cancer cells derived from diverse human cancer tissues (Latchman Y et al, Nature Immunology, 2001, Vol. 2, No. 3, pp. 261-267) and on almost all murine tumour cell lines, including PA1 myeloma, P815 mastocytoma, and B16 melanoma upon treatment with IFN-γ (Y. Iwai et al., *Proc Natl Acad Sci USA* 99, 12293, Sep. 17, 2002 and C. Blank et al., Cancer Res 64, 1140, February, 2004). Similarly PD-L2 expression is more restricted and is expressed mainly by dendritic cells and a few tumour cell lines. PD-L2 expression has been verified in Hodgkin's lymphoma cell lines and others. There is a hypothesis that some of the cancer or tumour cells take advantage from interaction between PD-1 and PD-L1 or PD-L2, for suppressing or intercepting T-cell immune responses to their own (Iwai Y et al, Proceedings of the National Academy of Science of the United States of America, 2002, Vol. 99, No. 19, pp. 12293-12297).

Tumour cells and virus (including HCV and HIV) infected cells are known to express the ligand for PD-1 (to create Immunosuppression) in order to escape immune surveillance by host T cells. It has been reported that the PD-1 gene is one of genes responsible for autoimmune diseases like systemic lupus erythematosis (Prokunina et al, Nature Genetics, 2002, Vol. 32, No. 4, 666-669). It has also been indicated that PD-1 serves as a regulatory factor for the onset of autoimmune diseases, particularly for peripheral self-tolerance, on the ground that PD-1-deficient mice develop lupus autoimmune diseases, such as glomerulonephritis and arthritis (Nishimura H et al, International Immunology, 1998, Vol. 10, No. 10, pp. 1563-1572; Nishimura H et al, Immunity, 1999, Vol. 11, No. 2, pp. 141-151), and dilated cardiomyopathy-like disease (Nishimura H et al, Science, 2001, Vol. 291, No. 5502, pp. 319-332).

Hence, in one approach, blocking the interaction of PD-1 with its ligand (PD-L1, PD-L2 or both) may provide an effective way for specific tumour and viral immunotherapy.

Wood et al in U.S. Pat. No. 6,808,710 discloses method for down modulating an immune response comprising contacting an immune cell expressing PD-1 with an antibody that binds to PD-1, in multivalent form, such that a negative signal is transduced via PD-1 to thereby down modulate the immune response. Such an antibody may be a cross-linked antibody to PD-1 or an immobilized antibody to PD-1.

Freeman et al in U.S. Pat. No. 6,936,704 and its divisional U.S. Pat. No. 7,038,013 discloses isolated nucleic acids molecules, designated B7-4 nucleic acid molecules, which encode novel B7-4 polypeptides, isolated B7-4 proteins, fusion proteins, antigenic peptides and anti-B7-4 antibodies, which co-stimulates T cell proliferation in vitro when the polypeptide is present on a first surface and an antigen or a polyclonal activator that transmits an activating signal via the T-cell receptor is present on a second, different surface.

There are some reports regarding substances inhibiting immunosuppressive activity of PD-1, or interaction between PD-1 and PD-L1 or PD-L2, as well as the uses thereof. A PD-1 inhibitory antibody or the concept of a PD-1 inhibitory peptide is reported in WO 01/14557, WO 2004/004771, and WO 2004/056875. On the other hand, a PD-L1 inhibitory antibody or a PD-L1 inhibitory peptide is reported in WO 02/079499, WO 03/042402, WO 2002/086083, and WO 2001/039722. A PD-L2 inhibitory antibody or a PD-L2 inhibitory peptide is reported in WO 03/042402 and WO 02/00730.

WO2007005874 describes isolated human monoclonal antibodies that specifically bind to PD-L1 with high affinity. The disclosure provides methods for treating various diseases including cancer using anti-PD-L1 antibodies.

US2009/0305950 describes multimers, particularly tetramers of an extracellular domain of PD-1 or PD-L1. The application describes therapeutic peptides.

Further, the specification mentions that peptides can be used therapeutically to treat disease, e.g., by altering co-stimulation in a patient. An isolated B7-4 or PD-1 protein, or a portion or fragment thereof (or a nucleic acid molecule encoding such a polypeptide), can be used as an immunogen to generate antibodies that bind B7-4 or PD-1 using standard techniques for polyclonal and monoclonal antibody preparation. A full-length B7-4 or PD-1 protein can be used, or alternatively, the invention provides antigenic peptide fragments of B7-4 or PD-1 for use as immunogens. The antigenic peptide of B7-4 or PD-1 comprises at least 8 amino acid residues and encompasses an epitope of B7-4 or PD-1 such that an antibody raised against the peptide forms a specific immune complex with B7-4 or PD-1. Preferably, the antigenic peptide comprises at least 10 amino acid residues, more preferably at least 15 amino acid residues, even more preferably at least amino acid residues, and most preferably at least 30 amino acid residues.

Freeman et al in US7432059 appears to disclose and claim methods of identifying compounds that up modulate T cell activation in the presence of a PD-1-mediated signal. Diagnostic and treatment methods utilizing compositions of the invention are also provided in the patent.

Further, Freeman et al in U.S. Pat. No. 7,709,214 appears to cover methods for up regulating an immune response with agents that inhibit the interactions between PD-L2 and PD-1.

Despite existence of many disclosures as discussed above, however, a significant unmet medical need still exists due to the lack of effective peptides or modified peptides as therapeutic agents as alternatives in the therapeutic area. It is known that synthetic peptides offer certain advantages over antibodies such as ease of production with newer technologies, better purity and lack of contamination by cellular materials, low immunogenicity, improved potency and specificity. Peptides may be more stable and offer better storage properties than antibodies. Moreover, often peptides possess better tissue penetration in comparison with antibodies, which could result in better efficacy. Peptides can also offer definite advantages over small molecule therapeutics counterparts such as lesser degree of toxicity and lower probability of drug-drug interaction.

The present invention therefore may provide the solution for this unmet medical need by offering novel synthetic peptide and its derivatives which are based on the PD1 ectodomain.

BRIEF DESCRIPTION OF ACCOMPANYING DRAWINGS

FIG. 1: Potency determination for compound 8 in assay for inhibition of binding of PD1 to PD-L2 using hPDL2 expressing HEK293 cells.

Figure 2:
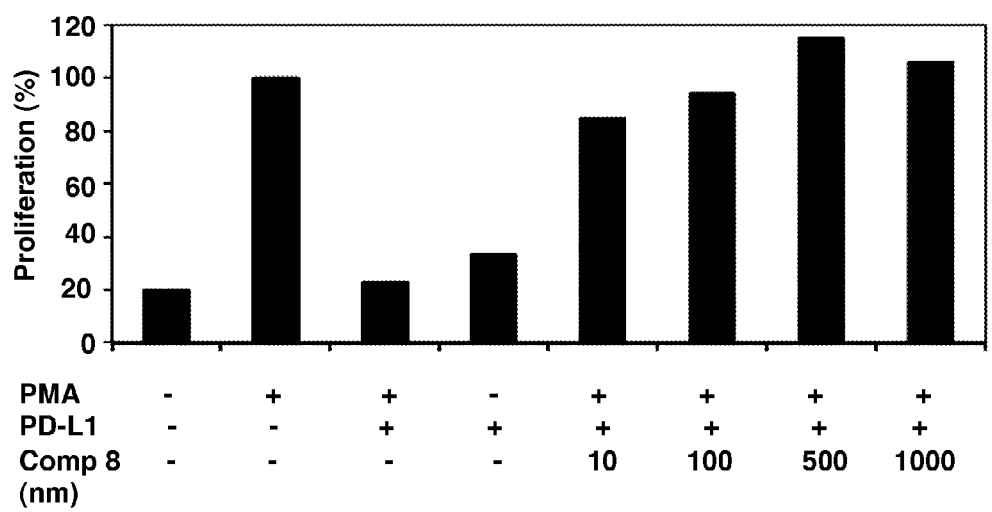

FIG. 2: Abrogation of PDL1 mediated inhibition of rat PBMC proliferation with compound 8

Figure 3:
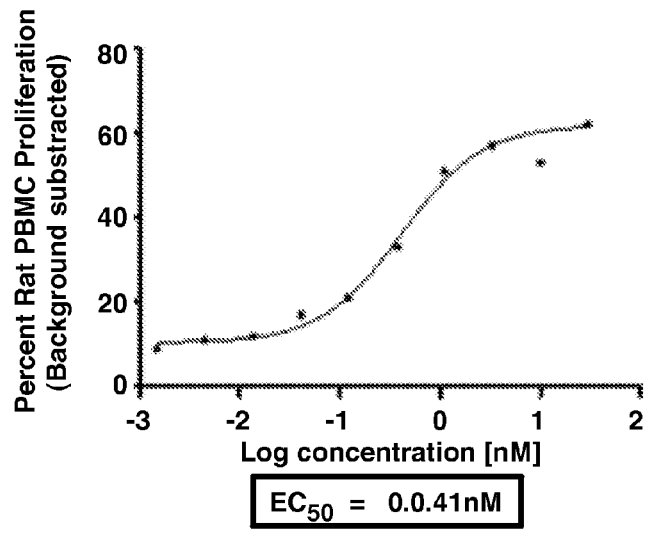

FIG. 3: $EC_{50}$ determination for compound 8 in rat PBMC proliferation assay in the context of PD-1/PD-L1 pathway.

Figure 4:
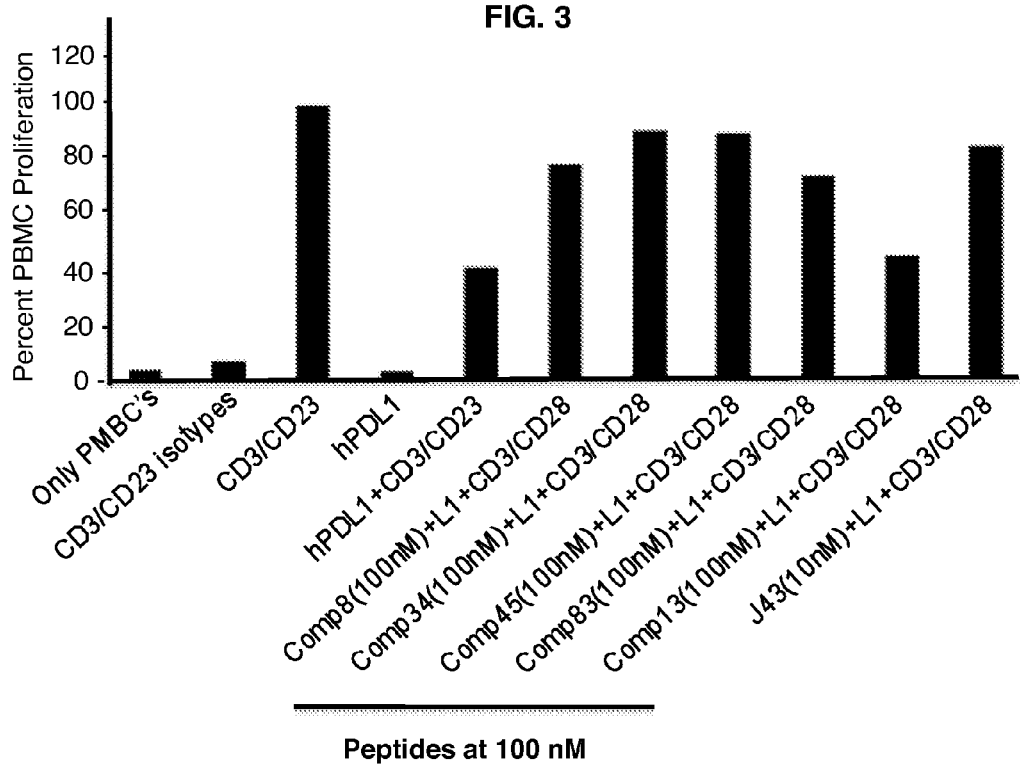

FIG. 4: Restoration of human PBMC proliferation in the context of human PDL1 with various compounds.

Figure 5:
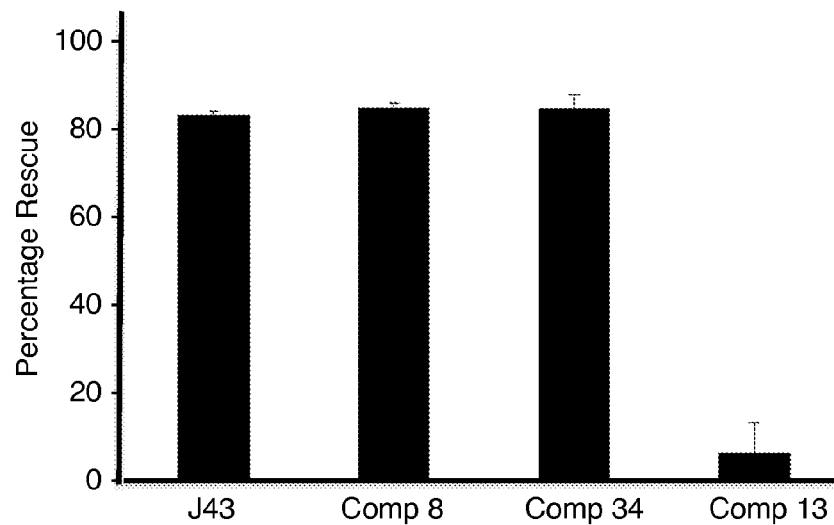

FIG. 5: Comparison of percentage mouse splenocyte proliferation rescue of compound 8, 13 and 34 with J43 antibody.

Figure 6:
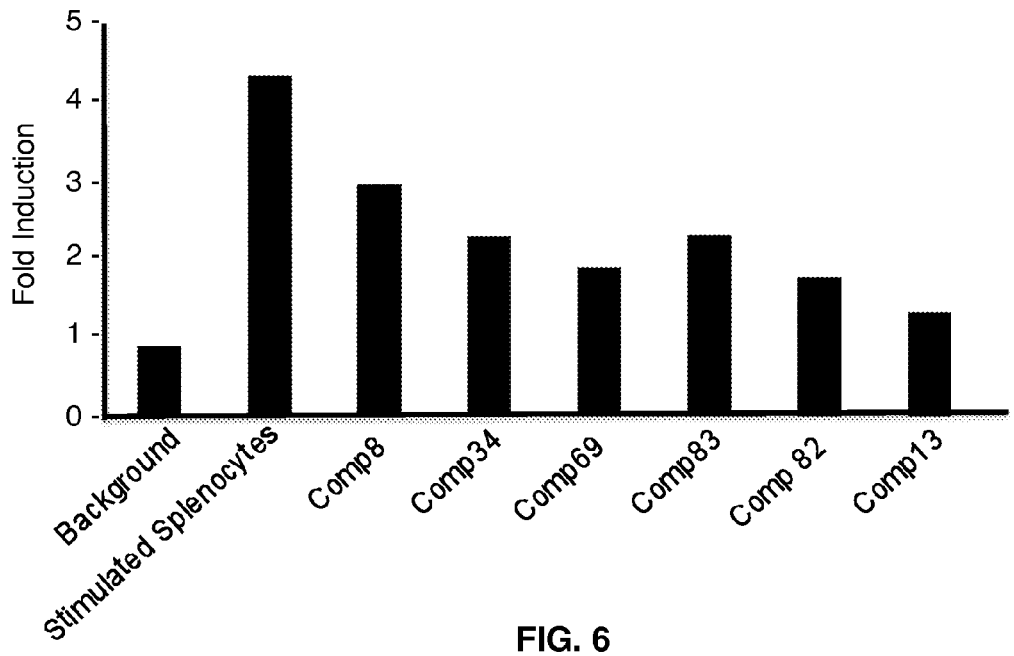

FIG. 6: Effect of various test compounds on IFN-γ production in Cytotoxic T Lymphocyte assay.

Figure 7:
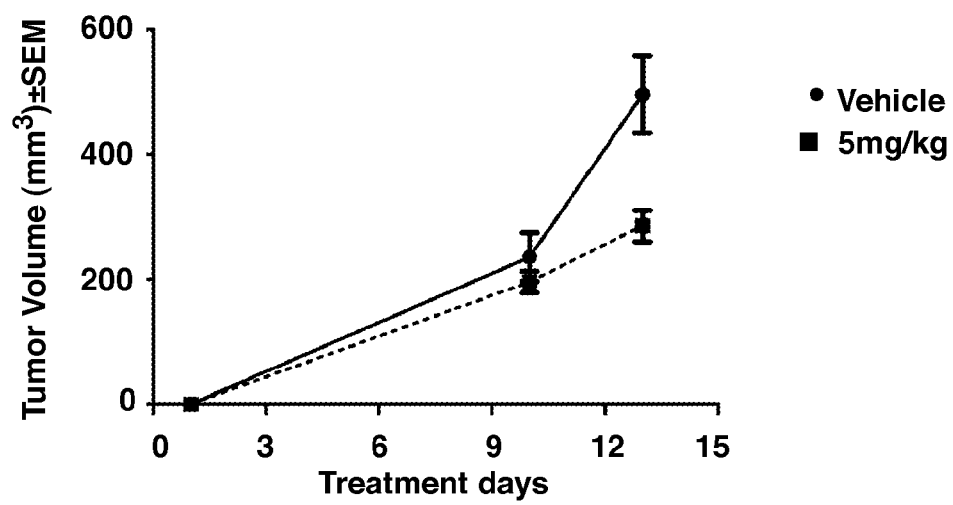

FIG. 7: Effect of compound 8 on tumour growth inhibition of B16F10 cells injected subcutaneously.

Figure 8:
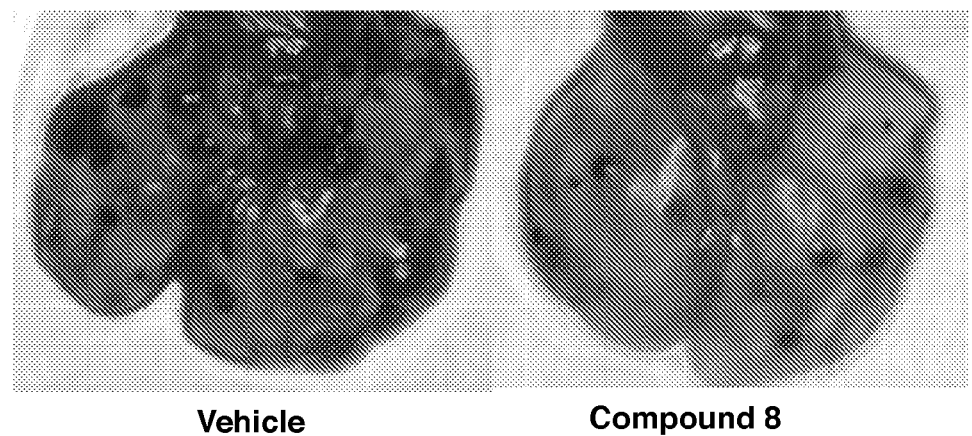

FIG. 8: Effect of compound 8 on lung metastasis of B16F10 cells injected i.v.

Figure 9:
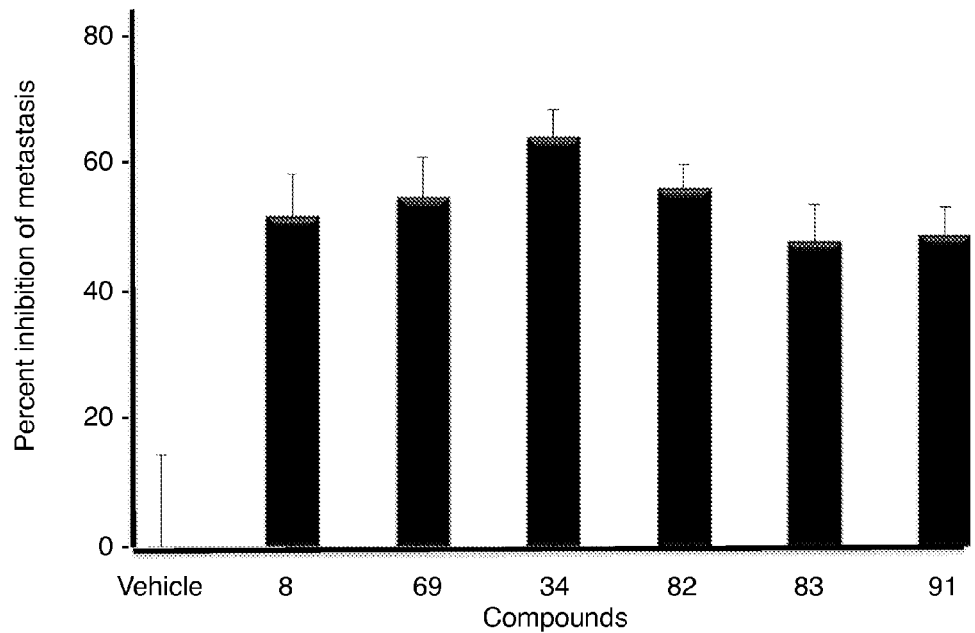

FIG. 9: Effect of various compounds on lung metastasis in B16F10 model.

Figure 10:
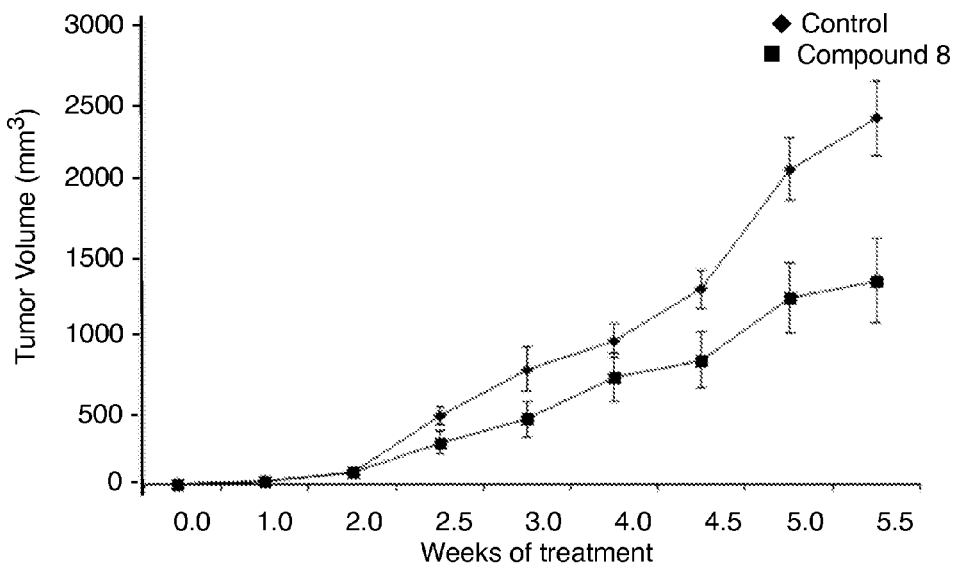

FIG. 10: Effect of compound 8 on tumour growth inhibition of 4T1 cells injected orthotopically to mammary fat pad.

Figure 11:
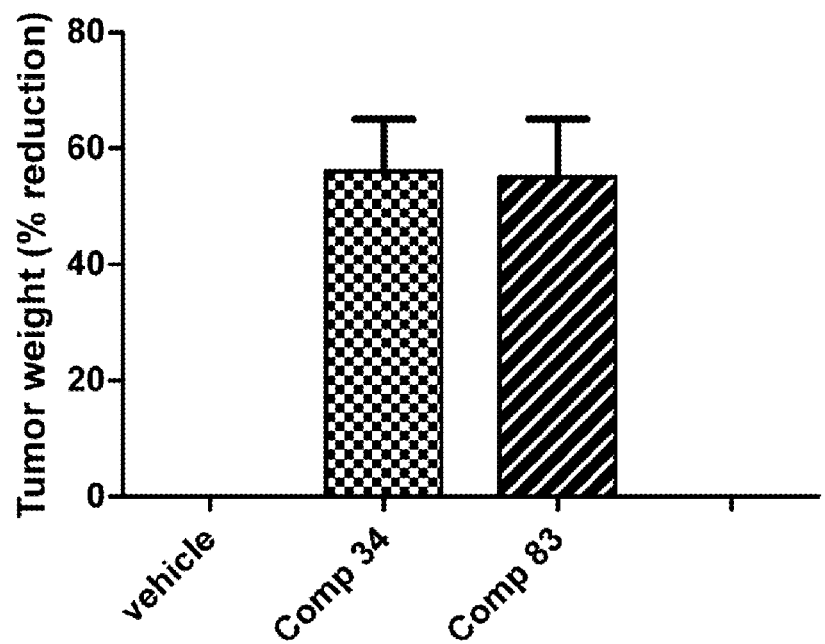

FIG. 11: Effect of peptides in reducing tumour burden in kidney injected orthotopically with RENCA cells.

Figure 12:
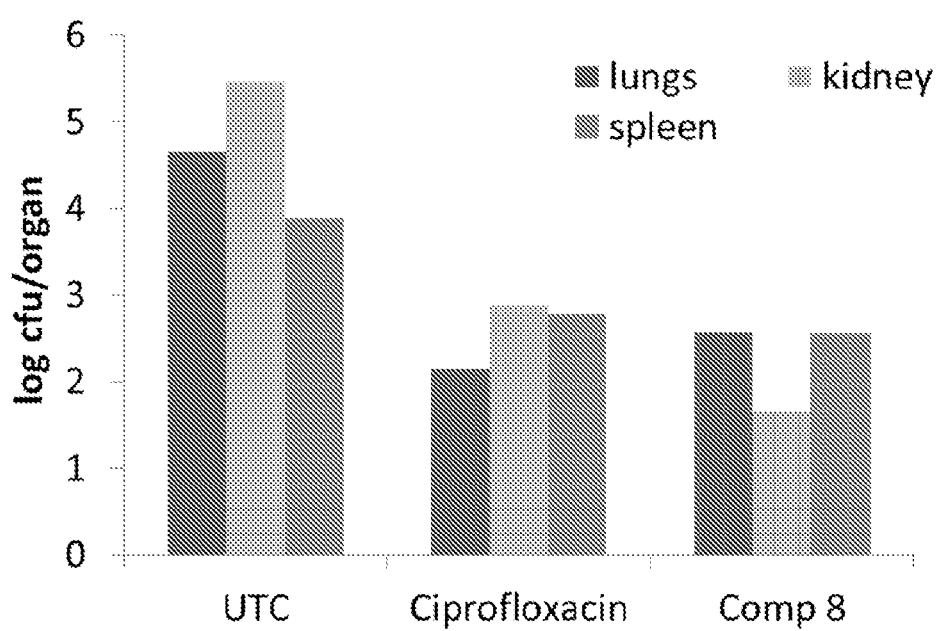

FIG. 12: In vivo efficacy of compound 8 against *E. coli* sepsis model.

Figure 13:
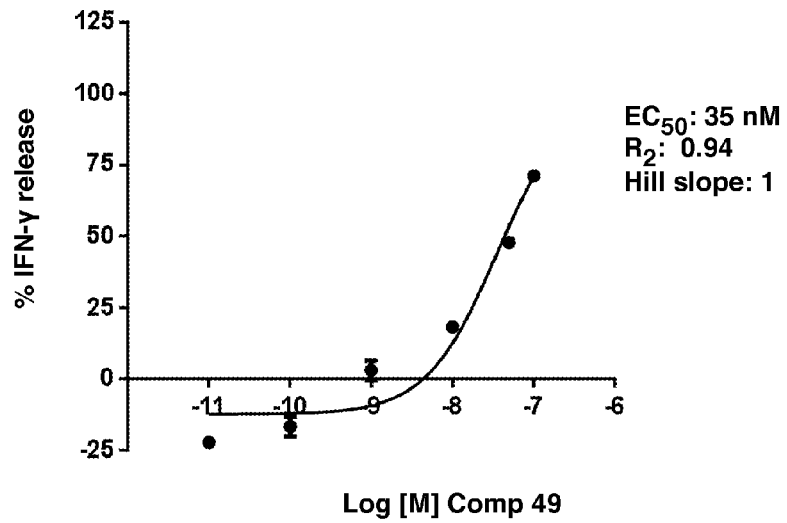

FIG. 13: Dose response effect of compound 49 in human PBMC IFN-γ assay against recombinant human PDL-1.

Figure 14:
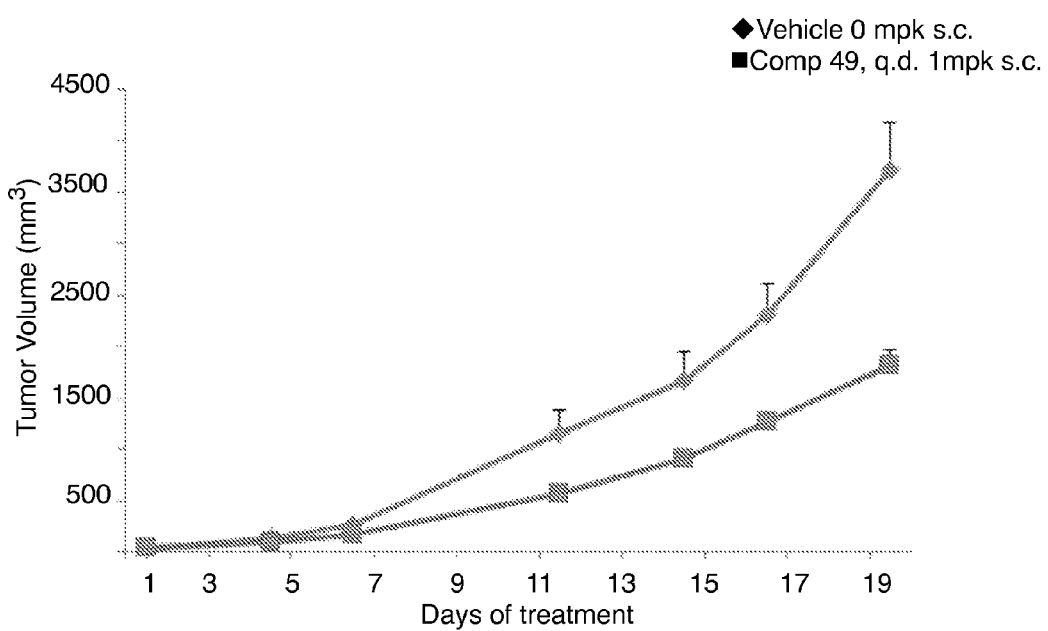

FIG. 14: Efficacy of compound 49 in CT-26 tumor model.

AMINO ACID SEQUENCE INFORMATION

SEQ ID NO: 1 shows amino acid sequence of human PD-1 ectodomain

SEQ ID NO: 2 shows amino acid sequence of A strand of human PD-1 ectodomain

SEQ ID NO: 3 shows amino acid sequence of B strand of human PD-1 ectodomain

SEQ ID NO: 4 shows amino acid sequence of BC loop of human PD-1 ectodomain

SEQ ID NO: 5 shows amino acid sequence of C strand of human PD-1 ectodomain

SEQ ID NO: 6 shows amino acid sequence of C-C' loop of human PD-1 ectodomain

SEQ ID NO: 7 shows amino acid sequence of C' strand of human PD-1 ectodomain

SEQ ID NO: 8 shows amino acid sequence of C'-C" loop of human PD-1 ectodomain

SEQ ID NO: 9 shows amino acid sequence of C" strand of human PD-1 ectodomain

SEQ ID NO: 10 shows amino acid sequence of C"-D loop of human PD-1 ectodomain

SEQ ID NO: 11 shows amino acid sequence of D strand of human PD-1 ectodomain

SEQ ID NO: 12 shows amino acid sequence of D-E loop of human PD-1 ectodomain

SEQ ID NO: 13 shows amino acid sequence of E strand of human PD-1 ectodomain

SEQ ID NO: 14 shows amino acid sequence of F strand of human PD-1 ectodomain

SEQ ID NO: 15 shows amino acid sequence of FG loop of human PD-1 ectodomain

SEQ ID NO: 16 shows amino acid sequence of G strand of human PD-1 ectodomain

SEQ ID NO: 17 shows amino acid sequence of mouse PD-1 ectodomain

SEQ ID NO: 18 shows amino acid sequence of rat PD-1 ectodomain

SEQ ID NO: 19 shows amino acid sequence of dog PD-1 ectodomain

SEQ ID NO: 20 shows amino acid sequence of horse PD-1 ectodomain

SEQ ID NO: 21 shows amino acid sequence of C' strand to C'C" loop of human PD-1 ectodomain SEQ ID NO: 22 shows amino acid sequence of C' strand to C" strand of human PD-1 ectodomain SEQ ID NO: 23 shows amino acid sequence of CC' loop to C' strand of human PD-1 ectodomain SEQ ID NO: 24 shows amino acid sequence of FG loop to G strand of human PD-1 ectodomain SEQ ID NO: 25 shows amino acid sequence of D strand to DE loop of human PD-1 ectodomain SEQ ID NO: 26 shows amino acid sequence of B strand of mouse PD-1 ectodomain SEQ ID NO: 27 shows amino acid sequence of BC loop of mouse PD-1 ectodomain SEQ ID NO: 28 shows amino acid sequence of C-Strand of mouse PD-1 ectodomain SEQ ID NO: 29 shows amino acid sequence of C-C' loop of mouse PD-1 ectodomain SEQ ID NO: 30 shows amino acid sequence of C'-strand of mouse PD-1 ectodomain SEQ ID NO: 31 shows amino acid sequence of C" strand of mouse PD-1 ectodomain SEQ ID NO: 32 shows amino acid sequence of C"-D-loop of mouse PD-1 ectodomain SEQ ID NO: 33 shows amino acid sequence of D-strand of mouse PD-1 ectodomain SEQ ID NO: 34 shows amino acid sequence of F-strand of mouse PD-1 ectodomain SEQ ID NO: 35 shows amino acid sequence of F-G loop of mouse PD-1 ectodomain SEQ ID NO: 36 shows amino acid sequence of G-strand of mouse PD-1 ectodomain SEQ ID NO: 37 shows amino acid sequence of C' strand to C'C" loop of mouse PD-1 ectodomain SEQ ID NO: 38 shows amino acid sequence of C' strand to C" strand of mouse PD-1 ectodomain SEQ ID NO: 39 shows amino acid sequence of CC' loop to C' strand of mouse PD-1 ectodomain SEQ ID NO: 40 shows amino acid sequence of FG loop to G strand of mouse PD-1 ectodomain SEQ ID NO: 41 shows amino acid sequence of D strand to DE loop of mouse PD-1 ectodomain

SUMMARY OF INVENTION

In accordance with the present invention, novel modified peptides are provided which are capable of suppressing and/or inhibiting the programmed cell death 1 (PD1) signalling pathway.

In one aspect of the present invention, it provides the structure of compounds as set forth in Formula I.

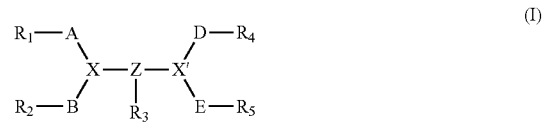

or pharmaceutically acceptable salt thereof; wherein; the compound comprises at least 5 amino acids, A is an amino acid sequence of from three amino acids to the full length of a peptide sequence of mammalian PD1 ectodomain fragments selected from FG loop, BC loop, C-C' loop, C strand, C' strand to C'-C" loop, C C' loop to C' strand, or is Glu-Asp, or is absent;

B is an amino acid sequence of from three amino acids to the full length of a peptide sequence of mammalian PD1 ectodomain fragments selected from BC loop, FG loop, C C' loop to C' strand, C strand, D strand, C' strand to C'-C" loop, or is Glu-Asp, or is absent;

Z is:
  (i). from one to four peptide sequences arranged in any order each being of from three amino acids up to the full length of a mammalian PD1 ectodomain fragment selected from BC loop, D strand, FG loop, G strand, C strand, F strand, C' strand, C" strand, C"-D loop, C' strand to C'-C" loop, C' strand to C" strand or D strand to DE loop;
  (ii). G-L-Z', where G is an amino acid sequence of from three amino acids to the full length of a peptide sequence of mammalian PD1 ectodomain fragments from D-strand or is absent; L is selected from —CO (CH$_2$)$_n$—NH—, or PEG 2-20 KD; 'n' is an integer selected from 2 to 10, both inclusive; and Z' is one to three peptide sequences arranged in any order each being of from three amino acids up to the full length of a mammalian PD1 ectodomain fragment selected from FG loop and G-strand; or
  (iii). from one to four peptide sequences arranged in any order each being of from three amino acids up to the full length of a mammalian PD1 ectodomain fragment selected from D-strand, FG loop and G strand, wherein two or more amino acids of the peptide sequence combine together to form a lactam bond between any of the two fragments or within the fragment;

D is up to two peptide sequences arranged in any order each being of from three amino acids up to the full length of a mammalian PD1 ectodomain fragment selected from BC loop, FG loop, C C' loop to C' strand or is absent;

E is up to four peptide sequences arranged in any order each being of from three amino acids up to the full length of a mammalian PD1 ectodomain fragment selected from BC loop, D strand, FG loop, C C' loop to C' strand, G strand, FG loop to G strand or is absent;

X and X' are independently selected from lysine, ornithine, diaminopropionic acid, diaminobutyric acid or olefinic amino acid of formula

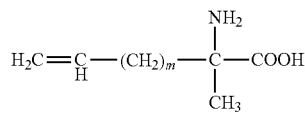

which is optionally linked with an additional lysine; or
X and X' combine together forming a ring with olefinic amino acid which is optionally linked with an additional lysine; or one of the X or X' is absent or both are absent;
'm' is an integer selected from 1 to 6, both inclusive;
$R_1$ is selected from group consisting of $C_2$-$C_{20}$ acyl, PEG 2-20 KD moiety; or absent.
$R_2$ and $R_3$ are independently selected from group consisting of $C_2$-$C_{20}$ acyl, PEG 2-20 KD, absent or $R_a$-L';
$R_a$ is selected from biotin or maleimido propionic acid;
L' is selected from linkers —CO(CH$_2$)$_n$—NH—, —CO(CH$_2$—CH$_2$—O—)$_n$NH or —COCH$_2$(—OCH$_2$—CH$_2$)$_n$NH—; and
'n' is an integer selected from 2 to 10, both inclusive;
$R_4$ and $R_5$ are independently NH$_2$, or one or both of $R_4$ or $R_5$ are absent,
with the proviso to the compound of Formula I, that in a compound of Formula I as above defined:
a) up to 5 but not more than 25% of the amino acids may be substituted with other natural or unnatural amino acids;
b) not more than 30% of the amino acids may be omitted;
c) in each said peptide sequence up to 2 amino acids may be added individually at any position;
d) up to 5 but not more than 25% of the peptide bonds may instead be replaced by reduced amide bond (—CH$_2$NH—);
e) up to 100% of the amino acids may be D-amino acids;
f) up to 100% of the amino acids may be in reverse order.

In another aspect of the present invention, it provides compound of Formula-I useful in the treatment or prevention of disease or disorder, where there is an advantage in inhibition of the programmed cell death 1 (PD1) signalling pathway and ability to reduce PD-L1 or PD-L2 binding to PD-1 and resulting immunosuppressive signalling by PD-1.

DETAILED DESCRIPTION OF THE INVENTION

The term 'peptide' is used herein to designate a sequence of natural or unnatural amino acids bonded in said sequence by peptide bonds or reduced peptide bond.

The term 'compound(s)' as used herein comprises peptides as disclosed in the present invention.

The following common abbreviations of the amino acids are used throughout this specification:

| | | |
|---|---|---|
| Gly (or G)—glycine | Ala (or A)—alanine | Val (or V)—valine |
| Leu (or L)—leucine | Ile (or I)—isoleucine | Orn—ornithine |
| Pro (or P)—proline | Phe (or F)—phenylalanine | Trp (or W)—tryptophan |
| Met (or M)—methionine | Ser (or S)—serine | Thr (or T)—threonine |
| Cys (or C)—cysteine | Tyr (or Y)—tyrosine | Asn (or N)—asparagine |
| Gln (or Q)—glutamine | Asp (or D)—aspartic acid | Glu (or E)—glutamic acid |
| Lys (or K)—lysine | Arg (or R)—arginine | His (or H)—histidine |
| DAP—2,3-Diaminopropionic Acid | DAB—2,4-Diaminobutyric Acid | |

The small letter codes are used to represent the D-amino acids throughout the specification.

Modifications of the peptides discussed hereinafter and wherever relevant include replacements of some or all of the L-amino acids by D-amino acids, bonding of amino acids at other than alpha amino groups, including at side chain amino or carboxylic groups, inclusion of non-peptide linkers between peptide sequences, cross-linking, lipidation, stapling, and PEGylation.

Modifications of the peptides discussed hereinafter and wherever relevant further comprise modified peptide bond between two amino acids, wherein the typical peptide bond (—CONH—) between two amino acids is replaced with reduced amide bond (—CH$_2$NH—). Using convention method of identification this is characterized as -Ψ[CH$_2$NH]— with the symbol "Ψ" designating a modified peptide bond.

As used herein, "unnatural amino acid" is an amino acid that is not naturally produced (e.g., encoded by the genetic code or resulting from a posttranslational modification) or naturally found in a mammal. Unnatural amino acids include amino acids that normally do not occur in proteins (e.g., an α-amino acid having the D-configuration, or a (D,L)-isomeric mixture thereof), homologues of naturally occurring amino acids (e.g., a β- or γ-amino acid analogue), an α,α-di-substituted analogue of a naturally occurring amino acid, or an α-amino acid wherein the amino acid side chain has been shortened by methylene groups which includes but are not limited to diaminopriopionic acid (DAP), diaminobutyric acid (DAB), ornithine (Orn) and the like; or lengthened to up to 10 carbon atoms; or lengthened up to 10 carbon atoms with olefinic groups which includes but are not limited to

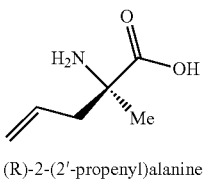

(R)-2-(2'-propenyl)alanine

Xaa

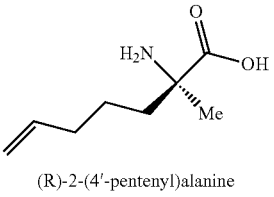

(R)-2-(4'-pentenyl)alanine

-continued

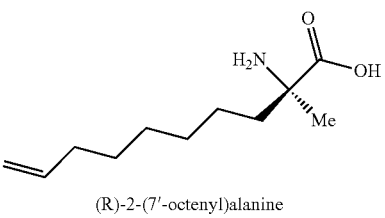

(R)-2-(7'-octenyl)alanine

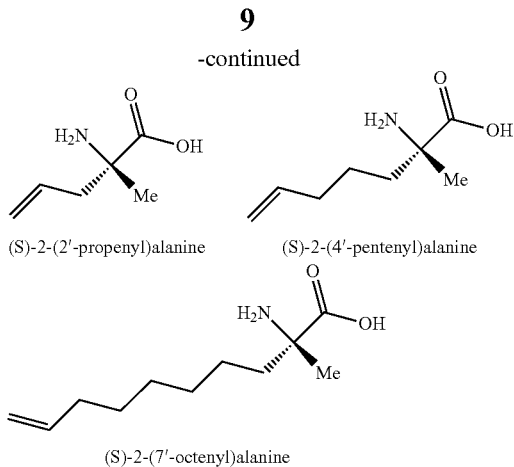

(S)-2-(2'-propenyl)alanine  (S)-2-(4'-pentenyl)alanine (S)-2-(7'-octenyl)alanine Other unnatural amino acids include γ-amino acids that are GABA analogues, such as (S)-3-(aminomethyl)-5-methylhexanoic acid (pregabalin), 2-[I-(aminomethyl)cyclohexyl]acetic acid (gabapentin), or those described in Yogeeswari et al., Recent Patents on CNS Drug Discovery 2006; 1:113-118, herein incorporated by reference.

The present invention provides immunosuppression modulating peptides capable of suppressing and/or inhibiting the programmed cell death 1 (PD1) signalling pathway.

The present invention further provides modifications, derivatives of the peptides and pharmaceutical compositions comprising the peptides for treatment of cancer or infection via immuno-potentiation caused by inhibition of immuno-suppressive signal induced by PD-1, PD-L1, or PD-L2 and therapies using them, immuno-potentiative substrates included as the active ingredients.

The complete amino acid sequence of human PD-1 is disclosed in U.S. Pat. No. 5,629,204 (Honjo et. al.) and Finger et al., (Gene, 1997, 197:177-187). Human and mouse PD-1 share around 60% amino acid identity, whereas the extracellular IgV domain shows only 21% and 16% sequence identity with CD28 and CTLA4, respectively.

PD-1 possesses an ectodomain having multiple loop structures and strands between the loops. The amino acid sequence of the human PD-1 ectodomain is set forth in SEQ ID NO: 1.

```
SEQ ID NO: 1 human PD-1:
PPTFSPALLVVTEGDNATFTCSFSNTSESFVLNWYRMSPSNQTDKLAA
FPEDRSQPGQDCRFRVTQLPNGRDFHMSVVRARRNDSGTYLCGAISLA
PKAQIKESLRAELRVTERRAEVPTAHPSPSPRSAGQFQTLV
```

The loop and strand sequences within the human PD-1 ectodomain sequence are:

| | |
|---|---|
| A strand: PPTFS | SEQ ID NO: 2 |
| B strand: ATFT CSF | SEQ ID NO: 3 |
| BC loop: SNTSESF | SEQ ID NO: 4 |
| C-Strand: VLNWYRM | SEQ ID NO: 5 |
| C-C' loop: SPS NQ | SEQ ID NO: 6 |
| C'-strand: TDKLAAFP | SEQ ID NO: 7 |
| C'-C" loop: ED | SEQ ID NO: 8 |
| C" strand: RSQP | SEQ ID NO: 9 |
| C"-D-loop: GQDCR | SEQ ID NO: 10 |
| D-strand: FRVTQ | SEQ ID NO: 11 |
| DE loop: LPNG R | SEQ ID NO: 12 |
| E strand: DFHMSV | SEQ ID NO: 13 |
| F-strand: GTYLC GATS | SEQ ID NO: 14 |
| F-G loop: LAPKA | SEQ ID NO: 15 |
| G-strand: QIKE | SEQ ID NO: 16 |
| C' strand to C'C" loop: FPED | SEQ ID NO: 21 |
| C' strand to C" strand: TDKLAAFP EDRSQP | SEQ ID NO: 22 |
| CC' loop to C' strand: SPSNQTDKL AAFP | SEQ ID NO: 23 |
| FG loop to G strand: LAPKAQIKE | SEQ ID NO: 24 |
| D strand to DE loop: FRVTQLPNGR | SEQ ID NO: 25 |

```
SEQ ID NO: 17 Mouse-PD-1
SLTFYPAWLTVSEGANATFTCSLSNWSEDLMLNWNRLSPSNQTEKQAA
FCNGLSQPVQDARFQIIQLPNRHDFHMNILDTRRNDSGIYLCGAISLH
PKAKIEESPGAELVVTERILETSTRYPSPSPKPEGRFQGMV
```

The loop and strand sequences within the mouse PD-1 ectodomain sequence are:

| | |
|---|---|
| B strand: ATFT CSL | SEQ ID NO: 26 |
| BC loop: SNWSEDL | SEQ ID NO: 27 |
| C-Strand: MLNWNRL | SEQ ID NO: 28 |
| C-C' loop: SPSNQ | SEQ ID NO: 29 |
| C'-strand: TEKQAAFC | SEQ ID NO: 30 |
| C" strand: LSQP | SEQ ID NO: 31 |
| C"-D-loop: VQDAR | SEQ ID NO: 32 |
| D-strand: FQIIQ | SEQ ID NO: 33 |
| F-strand: GIYLC GATS | SEQ ID NO: 34 |
| F-G loop: LHPKA | SEQ ID NO: 35 |
| G-strand: KIEE | SEQ ID NO: 36 |
| C' strand to C'C" loop: FCNG | SEQ ID NO: 37 |
| C' strand to C" strand: TEKQAAFCN GLSQP | SEQ ID NO: 38 |
| CC' loop to C' strand: SPSNQTEKQA AFC | SEQ ID NO: 39 |
| FG loop to G strand: LHPKAKIEE | SEQ ID NO: 40 |
| D strand to DE loop: FQIIQLPNRH | SEQ ID NO: 41 |

```
SEQ ID NO: 18 Rat-PD-1
QLSWQSGWLLVSEGANATFTCSFSNWSEDLKLNWYRLSPSNQTEKQA
AFCNGYSQPVRDARFQIVQLPNGHDFHMNILDARRNDSGIYLCGAIS
LPPKAQIKESPGAELVVTERILETPTRYPRPSPKPEGQFQGLV
```

```
SEQ ID NO: 19 Dog-PD-1
PLTFSPAQLTVQEGENATFTCSLADIPDSFVLNWYRLSPRNQTDKLA
AFQEDRIEPGRDRRFRVMRLPNGRDFHMSIVAARLNDSGIYLCGAIY
LPPNTQINESPRAELSVTERTLEPPTQSPSPPPRLSGQLQGLV

SEQ ID NO: 20 Horse-PD-1
PLTFSPARLMVPEGANATFTCSFSNTSEHFVLNWYRMSPSNQTDKLA
AFPEDSSQPGRSGRFRVTRLPNGRDFHMSVLAARRNDSGIYLCGAIS
LPPKTQINESPRAELTVTERIPEPPTEHPSPPPSPAGQLQGLV
```

These loop and strand assignments of amino acids are based on the 1.8-A-resolution structure of the murine PD-1/PD-L2 complex reported in Lazar-Molnar et al, (PNAS, 2008, 105, 30, 10483-10488) taking into account amino acid sequence variations between the human and murine proteins as reported there. Lazar-Molnar et al describes an alignment of the PD-1 ectodomain of mouse, human, rat, dog and horse PD-1 is shown with the β strands in mouse PD-1 denoted with arrow segments above the sequence.

The present invention further provides compounds comprising an ectodomain peptide fragment of murine, rat, dog or horse PD-1 (Lazar-Molnar et al, PNAS, 2008, 105, 30, 10483-10488).

Thus, in a compound comprising branched peptides, one or more branches may contain as a peptide moiety of the said ectodomain portion of human PD-1 (SEQ ID NO: 1) comprising of at least 5 amino acid residues.

In accordance with the present invention, in one of the embodiment there are provided compounds capable of inhibiting ability to inhibit the programmed cell death 1 (PD1) signalling pathway and being capable of reducing PD-L1 or PD-L2 binding to PD-1 and resulting immunosuppressive signalling by PD-1, wherein the compound comprises a peptide moiety comprising no more than 35, preferably no more than 30, amino acid residues.

The structure of compounds according to the invention is as set forth in Formula (I)

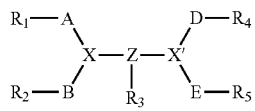

or pharmaceutically acceptable salt thereof; wherein; the compound comprises at least 5 amino acids, A is an amino acid sequence of from three amino acids to the full length of a peptide sequence of mammalian PD1 ectodomain fragments selected from FG loop, BC loop, C-C' loop, C strand, C' strand to C'-C" loop, C C' loop to C' strand, or is Glu-Asp, or is absent;

B is an amino acid sequence of from three amino acids to the full length of a peptide sequence of mammalian PD1 ectodomain fragments selected from BC loop, FG loop, C C' loop to C' strand, C strand, D strand, C' strand to C'-C" loop, or is Glu-Asp, or is absent;

Z is:
  (i) from one to four peptide sequences arranged in any order each being of from three amino acids up to the full length of a mammalian PD1 ectodomain fragment selected from BC loop, D strand, FG loop, G strand, C strand, F strand, C' strand, C" strand, C"-D loop, C' strand to C'-C" loop, C' strand to C" strand or D strand to DE loop;
  (ii) G-L-Z', where G is an amino acid sequence of from three amino acids to the full length of a peptide sequence of mammalian PD1 ectodomain fragments from D-strand or is absent; L is selected from —CO(CH$_2$)$_n$—NH—, or PEG 2-20 KD; 'n' is an integer selected from 2 to 10, both inclusive; and Z' is one to three peptide sequences arranged in any order each being of from three amino acids up to the full length of a mammalian PD1 ectodomain fragment selected from FG loop and G-strand; or
  (iii) from one to four peptide sequences arranged in any order each being of from three amino acids up to the full length of a mammalian PD1 ectodomain fragment selected from D-strand, FG loop and G strand, wherein two or more amino acids of the peptide sequence combine together to form a lactam bond between any of the two fragments or within the fragment;

D is up to two peptide sequences arranged in any order each being of from three amino acids up to the full length of a mammalian PD1 ectodomain fragment selected from BC loop, FG loop, C C' loop to C' strand or is absent;

E is up to four peptide sequences arranged in any order each being of from three amino acids up to the full length of a mammalian PD1 ectodomain fragment selected from BC loop, D strand, FG loop, C C' loop to C' strand, G strand, FG loop to G strand or is absent;

X and X' are independently selected from lysine, ornithine, diaminopropionic acid, diaminobutyric acid or olefinic amino acid of formula

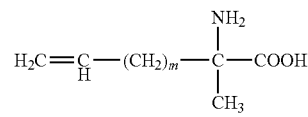

which is optionally linked with an additional lysine; or
X and X' combine together forming a ring with olefinic amino acid which is optionally linked with an additional lysine; or one of the X or X' is absent or both are absent;
  'm' is an integer selected from 1 to 6, both inclusive;
  R$_1$ is selected from group consisting of C$_2$-C$_{20}$ acyl, PEG 2-20 KD moiety; or absent.
  R$_2$ and R$_3$ are independently selected from group consisting of C$_2$-C$_{20}$ acyl, PEG 2-20 KD, absent or R$_a$-L'; R$_a$ is selected from biotin or maleimido propionic acid; L' is selected from linkers —CO(CH$_2$)$_n$—NH—, —CO(CH$_2$—CH$_2$—O—)$_n$NH or —COCH$_2$(—OCH$_2$—CH$_2$)$_n$NH—; and 'n' is an integer selected from 2 to 10, both inclusive;
  R$_4$ and R$_5$ are independently NH$_2$, or one or both of R$_4$ or R$_5$ are absent,
  with the proviso to the compound of Formula I, that in a compound of Formula I as above defined:
  a) up to 5 but not more than 25% of the amino acids may be substituted with other natural or unnatural amino acids;
  b) not more than 30% of the amino acids may be omitted;
  c) in each said peptide sequence up to 2 amino acids may be added individually at any position;
  d) up to 5 but not more than 25% of the peptide bonds may instead be replaced by reduced amide bond (—CH$_2$NH—);
  e) up to 100% of the amino acids may be D-amino acids;
  f) up to 100% of the amino acids may be in reverse order.

According to one embodiment, specifically provided are compounds of the formula (I) in which A is an amino acid sequence of from three amino acids to the full length of a peptide sequence of human or murine PD1 ectodomain fragments selected from FG loop, BC loop, C-C' loop, C strand, C' strand to C'-C" loop, C C' loop to C' strand as in table below, or is Glu-Asp, or is absent;

|  | hPD-1 | SEQ ID No | mPD-1 | SEQ ID No |
|---|---|---|---|---|
| BC Loop | SNTSESF | 4 | SNWSEDL | 27 |
| C Strand | VLNWYRM | 5 | MLNWNRL | 28 |
| C-C' loop | SPSNQ | 6 | SPSNQ | 29 |
| C' strand to C'-C" loop | FPED | 21 | FCNG | 37 |
| C C' loop to C' strand | SPSNQTDKLAAFP | 23 | SPSNQTEKQAAFC | 39 |
| FG loop | LAPKA | 15 | LHPKA | 35 |

B is an amino acid sequence of from three amino acids to the full length of a peptide sequence of human or murine PD1 ectodomain fragments selected from BC loop, FG loop, C C' loop to C' strand, C strand, D strand, C' strand to C'-C" loop as in table below, or is Glu-Asp, or is absent;

|  | hPD-1 | SEQ ID No | mPD-1 | SEQ ID No |
|---|---|---|---|---|
| BC Loop | SNTSESF | 4 | SNWSEDL | 27 |
| C Strand | VLNWYRM | 5 | MLNWNRL | 28 |
| C' strand to C'-C" loop | FPED | 21 | FCNG | 37 |
| C C' loop to C' strand | SPSNQTDKLAAFP | 23 | SPSNQTEKQAAFC | 39 |
| D Strand | FRVTQ | 11 | FQIIQ | 33 |
| FG loop | LAPKA | 15 | LHPKA | 35 |

Z is
(i) from one to four peptide sequences arranged in any order each being of from three amino acids up to the full length of a human or murine PD1 ectodomain fragment selected from BC loop, D strand, FG loop, G strand, C strand, F strand, C' strand, C" strand, C"-D loop, C' strand to C'-C" loop, C' strand to C" strand or D strand to DE loop;
(ii) G-L-Z' where G is an amino acid sequence of from three amino acids to the full length of a peptide sequence of human or murine PD1 ectodomain fragments from D-strand or is absent; L is selected from —CO(CH$_2$)$_n$—NH—, or PEG 2-20 KD; 'n' is an integer selected from 2 to 10, both inclusive; and Z' is one to three peptide sequences arranged in any order each being of from three amino acids up to the full length of a human or murine PD1 ectodomain fragment selected from FG loop and G-strand; or
(iii) from one to four peptide sequences arranged in any order each being of from three amino acids up to the full length of a human or murine PD1 ectodomain fragment selected from D-strand, FG loop and G strand, wherein two or more amino acids of the peptide sequence combine together to form a lactam bond between any of the two fragments or within the fragment;

wherein said fragments are as defined in table below;

|  | hPD-1 | SEQ ID No | mPD-1 | SEQ ID No |
|---|---|---|---|---|
| BC Loop | SNTSESF | 4 | SNWSEDL | 27 |
| C Strand | VLNWYRM | 5 | MLNWNRL | 28 |
| C' Strand | TDKLAAFP | 7 | TEKQAAFC | 30 |
| C' strand to C'-C" loop | FPED | 21 | FCNG | 37 |
| C' strand to C" strand | TDKLAAFPEDRSQP | 22 | TEKQAAFCNGLSQP | 38 |
| C" Strand | RSQP | 9 | LSQP | 31 |

-continued

|  | hPD-1 | SEQ ID No | mPD-1 | SEQ ID No |
|---|---|---|---|---|
| C"-D loop | GQDCR | 10 | VQDAR | 32 |
| D Strand | FRVTQ | 11 | FQIIQ | 33 |
| F strand | GTYLCGAIS | 14 | GIYLCGAIS | 34 |
| FG loop | LAPKA | 15 | LHPKA | 35 |
| G Strand | QIKE | 16 | KIEE | 36 |
| D strand to DE loop | FRVTQLPNGR | 25 | FQIIQLPNRH | 41 |

D is up to two peptide sequences arranged in any order each being of from three amino acids up to the full length of a human or murine PD1 ectodomain fragment selected from BC loop, FG loop, C C' loop to C' strand as in table below or is absent;

|  | hPD-1 | SEQ ID No | mPD-1 | SEQ ID No |
|---|---|---|---|---|
| BC Loop | SNTSESF | 4 | SNWSEDL | 27 |
| C C' loop to C' strand | SPSNQTDKLAAFP | 23 | SPSNQTEKQAAFC | 39 |
| FG loop | LAPKA | 15 | LHPKA | 35 |

E is up to four peptide sequences arranged in any order each being of from three amino acids up to the full length of a human or murine PD1 ectodomain fragment selected from BC loop, D strand, FG loop, C C' loop to C' strand, G strand, FG loop to G strand or is absent;

|  | hPD-1 | SEQ ID No | mPD-1 | SEQ ID No |
|---|---|---|---|---|
| BC Loop | SNTSESF | 4 | SNWSEDL | 27 |
| C C' loop to C' strand | SPSNQTDKLAAFP | 23 | SPSNQTEKQAAFC | 39 |
| D Strand | FRVTQ | 11 | FQIIQ | 33 |
| FG loop | LAPKA | 15 | LHPKA | 35 |
| G Strand | QIKE | 16 | KIEE | 36 |
| FG loop to G strand | LAPKAQIKE | 24 | LHPKAKIEE | 40 |

X and X' are independently selected from lysine, ornithine, diaminopropionic acid, diaminobutyric acid or olefinic amino acid of formula

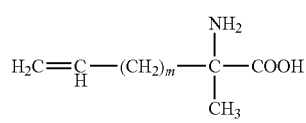

which is optionally linked with an additional lysine; or X and X' combine together forming a ring with olefinic amino acid which is optionally linked with an additional lysine; or one of the X or X' is absent or both are absent;

'm' is an integer selected from 1 to 6, both inclusive;
$R_1$ is selected from group consisting of $C_2$-$C_{20}$ acyl, PEG 2-20 KD moiety; or absent.
$R_2$ and $R_3$ are independently selected from group consisting of $C_2$-$C_{20}$ acyl, PEG 2-20 KD, absent or $R_a$-L'; $R_a$ is selected from biotin or maleimido propionic acid; L' is selected from linkers —CO(CH$_2$)$_n$—NH—, —CO(CH$_2$—CH$_2$—O—)$_n$NH or —COCH$_2$(—OCH$_2$—CH$_2$)$_n$NH—; and 'n' is an integer selected from 2 to 10, both inclusive;
$R_4$ and $R_5$ are independently NH$_2$, or one or both of $R_4$ or $R_5$ are absent,
with the proviso to the compound of Formula I, that in a compound of Formula I as above defined:
a) up to 5 but not more than 25% of the amino acids may be substituted with other natural or unnatural amino acids;
b) not more than 30% of the amino acids may be omitted;
c) in each said peptide sequence up to 2 amino acids may be added individually at any position;
d) up to 5 but not more than 25% of the peptide bonds may instead be replaced by reduced amide bond (—CH$_2$NH—);
e) up to 100% of the amino acids may be D-amino acids;
f) up to 100% of the amino acids may be in reverse order.

The embodiment below are illustrative of the present invention and are not intended to limit the claims to the specific embodiments exemplified.

According to one embodiment, specifically provided are compounds of the formula (I) in which Z consists of one said peptide sequence and at least one of A, B, D or E is not absent.

According to another embodiment, specifically provided are compounds of the formula (I) in which A, B, D and E are absent and Z comprises from 2 to 4 same or different peptide sequences.

According to yet another embodiment, specifically provided are compounds of the formula (I) in which Z is a combination of D strand, FG loop and G strand.

According to yet another embodiment, specifically provided are compounds of the formula (I) in which X is lysine and X' is absent.

According to yet another embodiment, specifically provided are compounds of the formula (I) in which both X and X' are lysine.

According to yet another embodiment, specifically provided are compounds of the formula (I) in which $R_2$ and $R_3$ are selected from $C_2$-$C_{20}$ acyl, or $R_a$-L'; wherein, $R_a$ is maleimido propionic acid; L' is —COCH$_2$(—OCH$_2$—CH$_2$)$_n$NH—; and 'n' is an integer selected from 2 to 10, both inclusive.

According to yet another embodiment the invention provides a compound of formula (Ia):

or pharmaceutically acceptable salt thereof; wherein;

A is an amino acid sequence of from three amino acids to the full length of a peptide sequence of human or murine PD1 ectodomain fragments selected from FG loop, BC loop, C' strand, C-C' loop, C strand, C' strand to C'-C" loop or is absent;

B is an amino acid sequence of from three amino acids to the full length of a peptide sequence of human or murine PD1 ectodomain fragments selected from BC loop, FG loop, C-C' loop to C' strand, C strand, D strand, C' strand to C'-C" loop or is absent;

Z is from one to three peptide sequences arranged in any order each being of from three amino acids up to the full length of a peptide sequence of human or murine PD1 ectodomain fragments selected from D strand, FG loop, G strand, C strand and F strand;

and X is lysine.

According to yet another embodiment, specifically provided are compounds of the formula (Ia) in which A and B are independently an amino acid sequence of from three amino acids to the full length of said BC loop.

According to yet another embodiment, specifically provided are compounds of the formula (Ia) in which A and B are independently the full length of said BC loop.

According to yet another embodiment specifically provided are compounds of the formula (Ia) in which A is BC loop wherein all the amino acids are in reverse order.

According to yet another embodiment, specifically provided are compounds of the formula (Ia) in which Z is D strand-FG loop-G strand.

According to yet another embodiment, specifically provided are compounds of the formula (Ia) in which $R_1$, $R_2$ and $R_3$ are absent.

According to yet another embodiment, specifically provided are compounds of the formula (Ia) in which $R_3$ is C16-acyl.

According to yet another embodiment, specifically provided are compounds of the formula (I) or (Ia) in which up to three amino acids are D-amino acids. Optionally up to 10%, alternatively up to 20%, alternatively up to 50%, alternatively up to 80% or up to 90% of the amino acids are D-amino acids, or in which at least 10%, or at least 20%, or at least 50%, or at least 80% or at least 90% are D-amino acids.

According to yet another embodiment, specifically provided are compounds of the formula (I) or (Ia) in which all amino acids are D-amino acids.

According to yet another embodiment, specifically provided are compounds of the formula (I) or (Ia) in which up to 5 but not more than 25% of the peptide bonds may instead be replaced by reduced amide bond (—CH$_2$NH—). Alternatively, one or up to 2 or 3 or not more than 20% or 10% of the peptide bonds may instead be replaced by reduced amide bond (—CH$_2$NH—).

According to yet another embodiment, specifically provided are compounds of the formula (I) or (Ia) in which all the amino acids are in reverse order or in which a sequence of two or more amino acids are in reverse order, optionally 5 or more or optionally 10 or more, or in which no more than 10, or no more than 5 are in reverse order.

According to yet another embodiment, specifically provided are compounds of the formula (I) or (Ia) in which up to 5 but not more than 25% of the amino acids may be substituted with other natural or unnatural amino acids.

According to yet another embodiment, specifically provided are compounds of the formula (I) or (Ia) in which not more than 30%, alternatively not more than 20%, or not more than 10% of the amino acids may be omitted.

According to yet another embodiment, specifically provided are compounds of the formula (I) or (Ia) in which in each said peptide sequence up to 3 amino acids may be added individually at any position, alternatively up to 2 amino acids, or alternatively up to only one amino acid.

The compounds of the invention may comprise linear or branched peptides, but compounds comprising branched peptide having more than one peptide moiety are preferred and more than one branch may be present.

One embodiment relates to the compounds of the present invention, said compounds are branched and wherein one or more branches contains a peptide moiety comprising a said ectodomain portion of human or murine PD-1 of at least 5 amino acid residues, wherein the said compound comprises a first N-terminal portion and a second N-terminal portion peptide moiety, both being joined at a branch point to a C-terminal portion peptide moiety.

Another embodiment relates to the compounds of the present invention, said compounds are branched and wherein one or more branches contains a peptide moiety comprising a said ectodomain portion of human or PD-1 of at least 5 amino acid residues. wherein the said compound comprises a first N-terminal portion and a second N-terminal portion peptide moiety, both being joined at a branch point to an intermediate peptide moiety portion which is in turn joined at a further branch point to each of a first C-terminal portion and a second C-terminal portion peptide moiety.

Yet another embodiments of the present invention relates to the compounds as disclosed in the present invention, wherein the compounds are lipidated and/or are glycosylated.

Further embodiment of the present invention relates to the compounds as disclosed in the present invention, wherein the compounds contain a PEG moiety.

Further embodiment of the present invention relates to the compounds as disclosed in the present invention, wherein one or more of the amino acids of the peptide moiety the compounds is substituted with a D-amino acid.

Yet another embodiment of the present invention relates to the compounds as disclosed in the present invention, wherein one or more of the amino acids of the peptide moiety the compounds is substituted with a D-amino acid, wherein D-amino acid is present within 5 amino acids of an N-terminus or the C-terminus of the peptide moiety.

Still yet another embodiment of the present invention relates to the compounds as disclosed in the present invention, wherein one or more of the amino acids of the peptide moiety the compounds is substituted with a D-amino acid, wherein the said D-amino acid is present at the N-terminus or the C-terminus of the peptide moiety.

In one of the embodiment of the present invention there is provided a compound having the ability to inhibit the programmed cell death 1 (PD1) signalling pathway and being capable of reducing PD-L1 or PD-L2 binding to PD-1 and resulting immunosuppressive signalling by PD-1, said compound comprising a peptide moiety of no more than 35 amino acid residues.

In another embodiment of the present invention there is provided a compound having the ability to inhibit the programmed cell death 1 (PD1) signalling pathway and being capable of reducing PD-L1 or PD-L2 binding to PD-1 and resulting immunosuppressive signalling by PD-1, said compound comprising a peptide moiety of no more than 35 amino acid residues, wherein said peptide moiety comprises an ectodomain domain portion of human PD-1 of at least 5 contiguous amino acid residues comprising one of the following three amino acid residue sequences:

```
from the A strand:
PPT
PTF
TFS
from the BC loop:
SNT
NTS
TSE
SES
ESF
from the C-C' loop
SPS
PSN
SNQ
from the C' strand:
TDK
DKL
KLA
LAA
AFP
from the C" strand:
RSQ
SQP
from the D strand:
FRV
RVT
VTQ
from the E strand:
DFH
FHM
HMS
MSV
from the F-G loop:
LAP
APK
PKA
from the F-G loop
and G strand
KAQ
AQI
C'strand to C"
strand
TDK
DKL
KLA
LAA
AAF
```

-continued

```
AFP
FPE
PED
EDR
DRS
RSQ
SQP
from the A'-B loop and
B strand:
NAT
ATF
TFT
FTC
TCS
CSF
from the C strand:
VLN
LNW
NWY
WYR
YRM
from the C-C' loop to C'
strand:
SNQ
NQT
QTD
TDK
from the C' strand to
C'-C" loop:
PED
EDR
from the C" strand to
C" D-loop
QPG
PGQ
GQD
QDC
from the D-E loop:
LPN
PNG
NGR
from the F strand:
GTY
TYL
YLC
LCG
CGA
GAI
AIS
from the G strand:
QIK
IKE
D strand to DE loop
FRV
RVT
VTQ
TQL
LPN
PNG
NGR
``` or containing a variant of such an ectodomain portion of human PD-1 of at least 5 contiguous amino acid residues, wherein not more than two of said residues are deleted, substituted or modified or not more than two additional amino acid residues are added.

Further embodiment of the present invention provides a compound as disclosed in the present invention, wherein the compound comprising at least one of the sequences:

| | SEQ ID NO | | SEQ ID NO |
|---|---|---|---|
| PPTFS | 2 | EDRSQ | 157 |
| NATFT | 149 | GQDCR | 10 |
| FTCSP | 150 | FRVTQ | 11 |
| SNTSESF | 4 | LPNGR | 12 |
| VLNWY | 151 | DFHMSV | 13 |
| NWYRM | 152 | GTYLC | 158 |
| SNQTDK | 153 | CGAIS | 159 |
| TDKLAA | 154 | LAPKA | 15 |
| KLAAFP | 155 | QIKE | 16 |
| PEDSQP | 156 | | |

Another embodiment relates to the compounds of the present invention, wherein no more than one of the amino acid residues included within a said three amino acid residue sequence is deleted, substituted or modified.

Yet another embodiment relates to the compounds of the present invention, wherein said compounds are branched and wherein one or more branches contains a peptide moiety comprising a said ectodomain portion of human PD-1 of at least 5 contiguous amino acid residues.

Yet another embodiment relates to the compounds of the present invention, said compounds are branched and wherein one or more branches contains a peptide moiety comprising a said ectodomain portion of human PD-1 of at least 5 contiguous amino acid residues, wherein the said compound comprises a first N-terminal portion and a second N-terminal portion peptide moiety, both being joined at a branch point to a C-terminal portion peptide moiety.

Yet another embodiment relates to the compounds of the present invention, where the compounds are branched and wherein one or more branches contains a peptide moiety comprising said ectodomain portion of human PD-1 of at least 5 contiguous amino acid residues, wherein the compound comprises a first N-terminal portion and a second N-terminal portion peptide moiety, both being joined at a branch point to an intermediate peptide moiety portion which is in turn joined at a further branch point to each of a first C-terminal portion and a second C-terminal portion peptide moiety.

Yet another embodiment of the present invention relates to the branched compounds of the present invention comprising the first N-terminal portion and the second N-terminal portion peptide moiety, wherein said first and/or said second N-terminal portion peptide moiety comprises an ectodomain portion of human PD-1 of at least 5 contiguous amino acid residues comprising one of the following three amino acid residue sequences:

```
from the BC loop:
SNT
NTS
TSE
SES
ESF from the C-C' loop to
C' strand:
SNQ
```

-continued

```
NQT
QTD
TDK from the D-E loop:
LPN
PNG
NGR
from the C-C' loop
SPS
PSN
SNQ from the C 'strand to
C'-C" loop:
PED
EDR from the F-G loop:
LAP
APK
PKA D strand to DE loop
FRV
RVT
VTQ
TQL
QLP
LPN
PNG
NGR
```

Yet another embodiment of the present invention relates to the branched compounds of the present invention comprising the first N-terminal portion and the second N-terminal portion peptide moiety, wherein said first and/or said second N-terminal portion peptide moiety comprises an ectodomain portion of human PD-1 of at least 5 contiguous amino acid residues comprising one of the following three amino acid residue sequences:

```
from the A strand:
PPT
PTF
TFS from the C strand:
VLN
LNW
NWY
WYR
YRM from the C" strand:
RSQ
SQP from the E strand:
DFH
FHM
HMS
MSV from the F-G loop to
G strand
KAQ
AQI from the G strand:
QIK
IKE from the A'-B loop
and B strand:
NAT
ATF
TFT
```

-continued

```
FTC
TCS
CSF from the C' strand:
TDK
DKL
KLA
LAA
AFP from the D strand:
FRV
RVT
VTQ from the F strand:
GTY
TYL
YLC
LCG
CGA
GAI
AIS
```

Yet another embodiment relates to the compounds of the present invention, said compounds are branched and wherein one or more branches contains a peptide moiety comprising a said ectodomain portion of human PD-1 of at least 5 contiguous amino acid residues, wherein the said compound comprises a first N-terminal portion and a second N-terminal portion peptide moiety, both being joined at a branch point to a C-terminal portion peptide moiety, wherein said C-terminal portion or the first and/or said second C-terminal portion comprises an ectodomain portion of human PD-1 of at least 5 contiguous amino acid residues comprising one of the following three amino acid residue sequences

```
from the A strand:
PPT
PTF
TFS from the C strand:
VLN
LNW
NWY
WYR
YRM from the C" strand:
RSQ
SQP from the E strand:
DFH
FHM
HMS
MSV from the F-G loop to
G strand
KAQ
AQI from the G strand:
QIK
IKE from the A'-B loop
and B strand:
NAT
ATF
TFT
FTC
```

-continued

```
TCS
CSF from the C' strand:
TDK
DKL
KLA
LAA
AFP from the D strand:
FRV
RVT
VTQ from the F strand:
GTY
TYL
YLC
LCG
CGA
GAI
AIS
```

Yet another embodiment relates to the compounds of the present invention, said compounds are branched and wherein one or more branches contains a peptide moiety comprising a said ectodomain portion of human PD-1 of at least 5 contiguous amino acid residues, wherein the said compound comprises a first N-terminal portion and a second N-terminal portion peptide moiety, both being joined at a branch point to an intermediate peptide moiety portion which is in turn joined at a further branch point to each of a first C-terminal portion and a second C-terminal portion peptide moiety, wherein one of said first and said second C-terminal portions comprises an ectodomain portion of human PD-1 of at least 5 contiguous amino acid residues comprising one of the following three amino acid residue sequences:

```
from the BC loop:
SNT
NTS
TSE
SES
ESF from the C-C' loop to
C' strand:
SNQ
NQT
QTD
TDK from the D-E loop:
LPN
PNG
NGR from the F-G loop to
G strand
KAQ
AQI C'strand to C" strand
TDK
DKL
KLA
LAA
AAF
AFP
FPE
PED
EDR
DRS
RSQ
```

-continued

SQP from the C-C' loop
SPS
PSN
SNQ from the C'-C" loop:
PED
EDR from the F-G loop:
LAP
APK
PKA D strand to DE loop
FRV
RVT -continued

VTQ
TQL
LPN
PNG
NGR

In one of the embodiment of the present invention there is provided a compound having the ability to inhibit the programmed cell death 1 (PD1) signalling pathway and being capable of reducing PD-L1 or PD-L2 binding to PD-1 and resulting immunosuppressive signalling by PD-1, said compound comprising a peptide moiety of no more than 35 amino acid residues.

Further embodiment of the present invention provides a compound as disclosed in the present invention, wherein the compound comprising at least one of the sequences selected from individual species as in table below:

| | hPD-1 | mPD-1 | rat PD-1 |
|---|---|---|---|
| A Strand | PPTFS (SEQ ID NO: 2) | SLTFY (SEQ ID NO: 160) | QLSWQ (SEQ ID NO: 163) |
| B strand | ATFTCSF (SEQ ID NO: 3) | ATFTCSL (SEQ ID NO: 26) | ATFTCSF (SEQ ID NO: 164) |
| BC Loop | SNTSESF (SEQ ID NO: 4) | SNWSEDL (SEQ ID NO: 27) | SNWSEDL (SEQ ID NO: 165) |
| C Strand | VLNWYRM (SEQ ID NO: 5) | MLNWNRL (SEQ ID NO: 28) | KLNWYRL (SEQ ID NO: 166) |
| C-C' loop | SPSNQ (SEQ ID NO: 6) | SPSNQ (SEQ ID NO: 29) | SPSNQ (SEQ ID NO: 167) |
| C' Strand | TDKLAAFP (SEQ ID NO: 7) | TEKQAAFC (SEQ ID NO: 30) | TEKQAAFC (SEQ ID NO: 168) |
| C'-C" loop | ED (SEQ ID NO: 8) | NG | NG |
| C" Strand | RSQP (SEQ ID NO: 9) | LSQP (SEQ ID NO: 31) | YSQP (SEQ ID NO: 169) |
| C"-D loop | GQDCR (SEQ ID NO: 10) | VQDAR (SEQ ID NO: 32) | VRDAR (SEQ ID NO: 170) |
| D Strand | FRVTQ (SEQ ID NO: 11) | FQIIQ (SEQ ID NO: 33) | FQIVQ (SEQ ID NO: 171) |
| D-E loop | LPNGR (SEQ ID NO: 12) | LPNRH (SEQ ID NO: 161) | LPNGH (SEQ ID NO: 172) |
| E strand | DFHMSV (SEQ ID NO: 13) | DFHMNI (SEQ ID NO: 162) | DFHMNI (SEQ ID NO: 173) |
| F strand | GTYLCGAIS (SEQ ID NO: 14) | GIYLCGAIS (SEQ ID NO: 34) | GIYLCGAIS (SEQ ID NO: 174) |
| FG loop | LAPKA (SEQ ID NO: 15) | LHPKA (SEQ ID NO: 35) | LPPKA (SEQ ID NO: 175) |
| G Strand | QIKE (SEQ ID NO: 16) | KIEE (SEQ ID NO: 36) | QIKE (SEQ ID NO: 176) |
| C' strand to C'-C" loop | FPED (SEQ ID NO: 21) | FCNG (SEQ ID NO: 37) | FCNG (SEQ ID NO: 177) |
| C C' loop to C' strand | SPSNQTDKLAAFP (SEQ ID NO: 23) | SPSNQTEKQAAFC (SEQ ID NO: 39) | SPSNQTEKQAAFC (SEQ ID NO: 178) |

| | | | |
|---|---|---|---|
| C' strand to C" strand | TDKLAAFPEDRSQP (SEQ ID NO: 22) | TEKQAAFCNGLSQP (SEQ ID NO: 38) | TEKQAAFCNGYSQP (SEQ ID NO: 179) |
| D strand to DE loop | FRVTQLPNGR (SEQ ID NO: 25) | FQIIQLPNRH (SEQ ID NO: 41) | FQIVQLPNGH (SEQ ID NO: 180) |
| FG loop to strand | △LAPKAQIKE (SEQ ID NO: 24) | LHPKAKIEE (SEQ ID NO: 40) | LPPKAQIKE (SEQ ID NO: 181) |

| | Dog PD-1 | Horse PD-1 |
|---|---|---|
| A Strand | PLTFS (SEQ ID NO: 182) | PLTFS (SEQ ID NO: 201) |
| B strand | ATFTCSL (SEQ ID NO: 183) | ATFTCSF (SEQ ID NO: 202) |
| BC Loop | ADIPDSF (SEQ ID NO: 184) | SNTSEHF (SEQ ID NO: 203) |
| C Strand | VLNWYRL (SEQ ID NO: 185) | VLNWYRM (SEQ ID NO: 204) |
| C-C' loop | SPRNQ (SEQ ID NO: 186) | SPSNQ (SEQ ID NO: 205) |
| C' Strand | TDKLAAFQ (SEQ ID NO: 187) | TDKLAAFP (SEQ ID NO: 206) |
| C'-C" loop | ED | ED |
| C" Strand | RIEP (SEQ ID NO: 188) | SSQP (SEQ ID NO: 207) |
| C"-D loop | GRDRR (SEQ ID NO: 189) | GRSGR (SEQ ID NO: 208) |
| D Strand | FRVMR (SEQ ID NO: 190) | FRVTR (SEQ ID NO: 209) |
| D-E loop | LPNGR (SEQ ID NO: 191) | LPNGR (SEQ ID NO: 210) |
| E strand | DFHMSI (SEQ ID NO: 192) | DFHMSV (SEQ ID NO: 211) |
| F strand | GIYLCGAIY (SEQ ID NO:) | GIYLCGAIS (SEQ ID NO: 212) |
| FG loop | LPPNT (SEQ ID NO: 194) | LPPKT (SEQ ID NO: 213) |
| G Strand | QINE (SEQ ID NO: 195) | QINE (SEQ ID NO: 214) |
| C' strand to C'-C" loop | FQED (SEQ ID NO: 196) | FPED (SEQ ID NO: 215) |
| C C' loop to C' strand | SPRNQTDKLAAFQ (SEQ ID NO: 197) | SNQTDKLAAFP (SEQ ID NO: 216) |
| C' strand to C" strand | TDKLAAFQEDRIEP (SEQ ID NO: 198) | TDKLAAFPEDSSQP (SEQ ID NO: 217) |
| D strand to DE loop | FRVMRLPNGR (SEQ ID NO: 199) | FRVTRLPNGR (SEQ ID NO: 218) |
| FG loop to strand | △LPPNTQINE (SEQ ID NO: 200) | LPPKTQINE (SEQ ID NO: 219) |

Below are the representative compounds, which are illustrative in nature only and are not intended to limit to the scope of the invention. The triangle represents lysine.

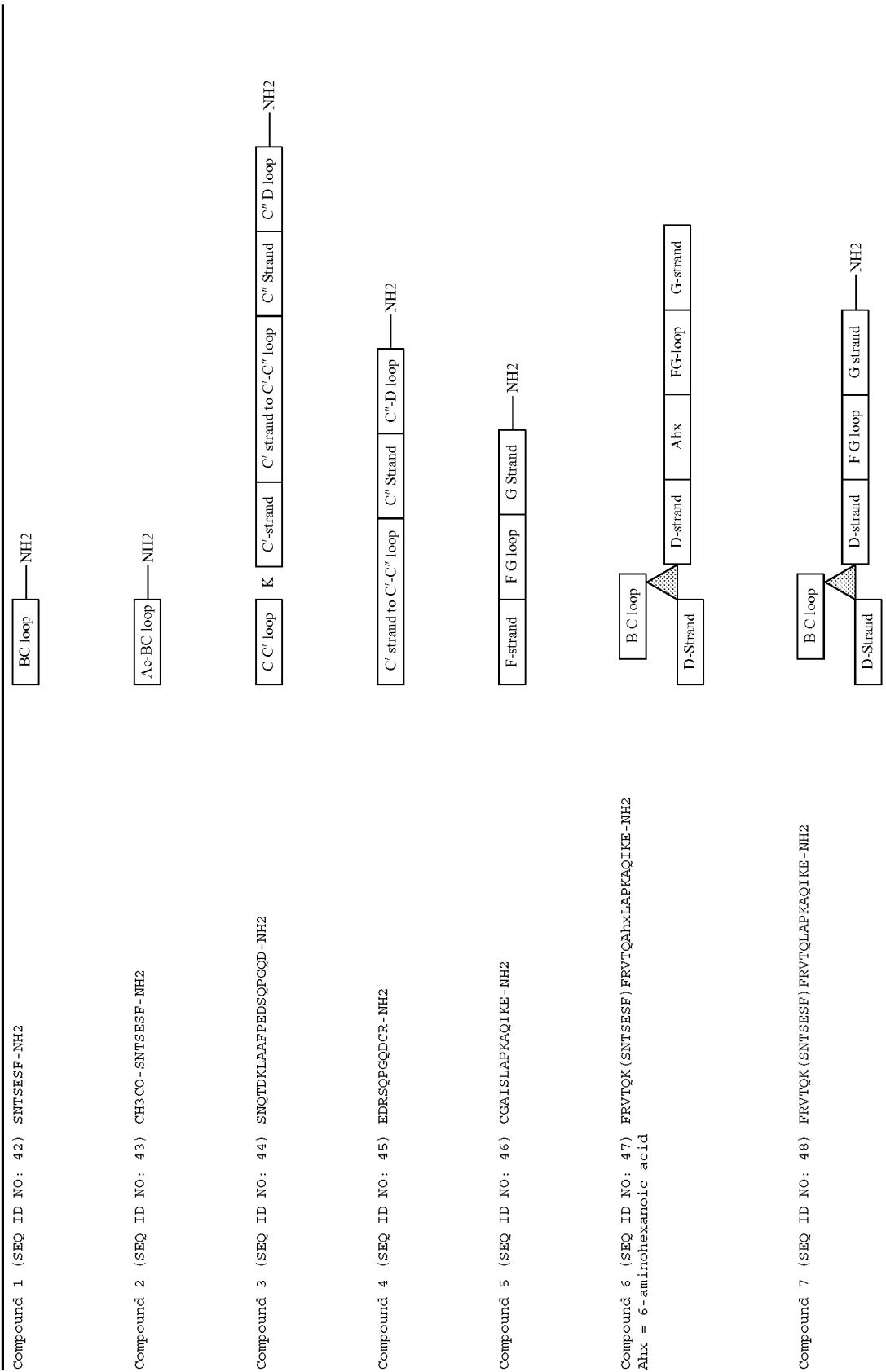

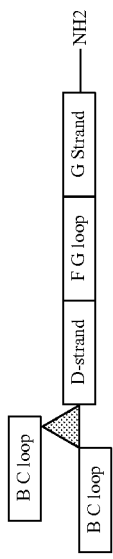
Compound 8 (SEQ ID NO: 49) SNTSESFK(SNTSESF)FRVTQLAPKAQIKE-NH2
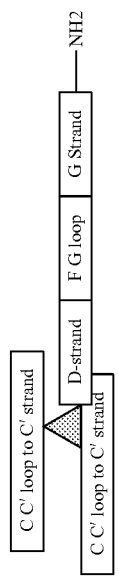
Compound 9 (SEQ ID NO: 50) SNQTDK(SNQTDK)FRVTQ LAPKAQIKE-NH2
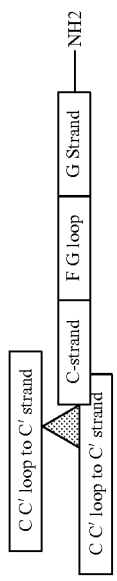
Compound 10 (SEQ ID NO: 51) SNQTDK(SNQTDK) VLNWYRM LAPKAQIKE-NH2
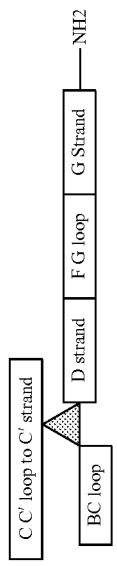
Compound 11 (SEQ ID NO: 52) SNTSESFK(SNQTDK)FRVTQLAPKAQIKE-NH2
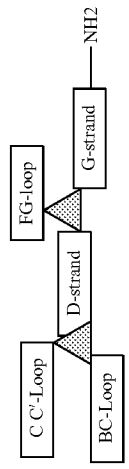
Compound 12 (SEQ ID NO: 53) SNTSESFK(SNQTDK)FRVTQK(LAP)AQIKE-NH2

-continued
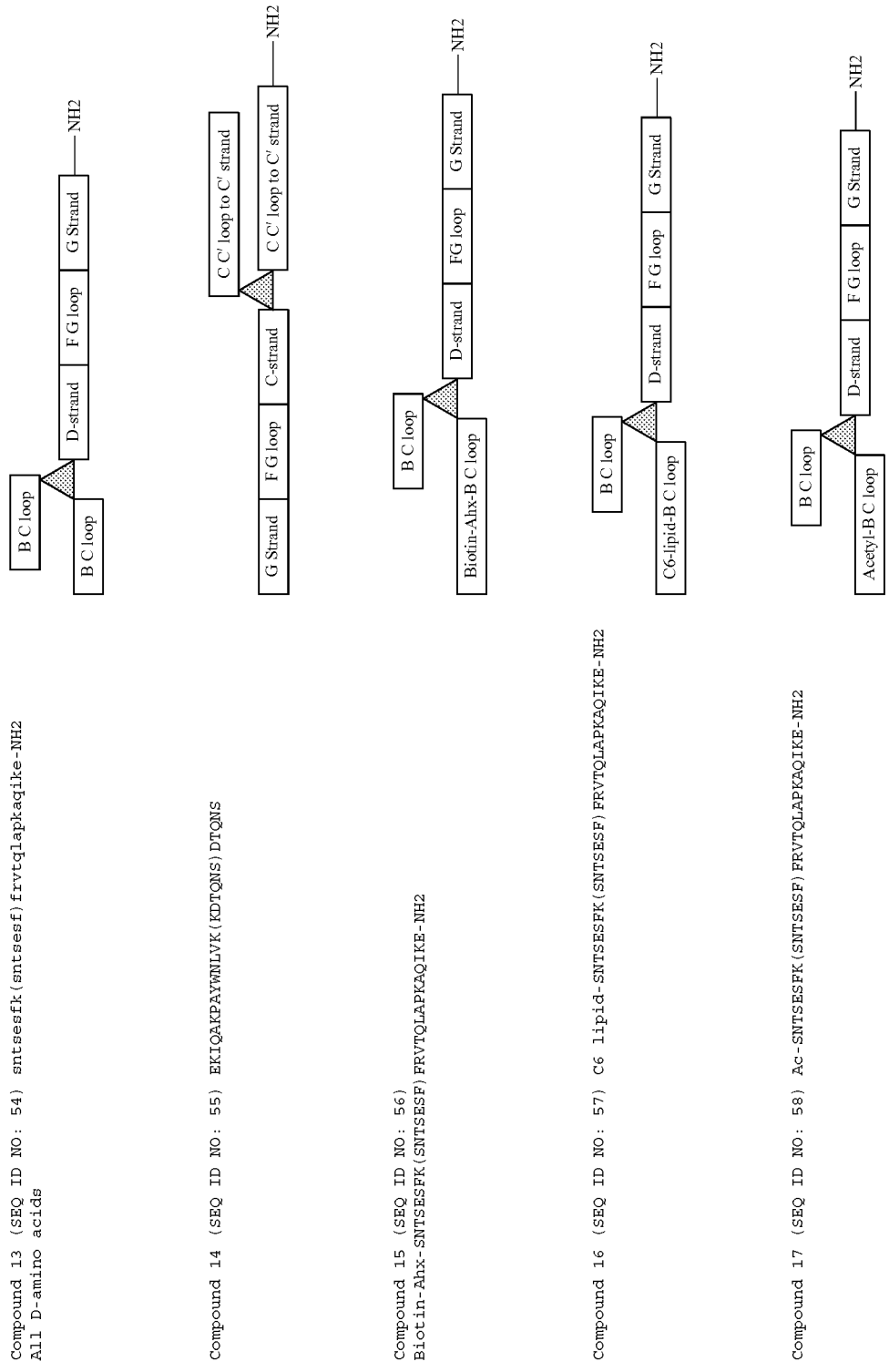
Compound 13 (SEQ ID NO: 54) sntsesfk(sntsesf)frvtqlapkaqike-NH2
All D-amino acids
Compound 14 (SEQ ID NO: 55) EKIQAKPAYWNLVK(KDTQNS)DTQNS
Compound 15 (SEQ ID NO: 56)
Biotin-Ahx-SNTSESFK(SNTSESF)FRVTQLAPKAQIKE-NH2
Compound 16 (SEQ ID NO: 57) C6 lipid-SNTSESFK(SNTSESF)FRVTQLAPKAQIKE-NH2
Compound 17 (SEQ ID NO: 58) Ac-SNTSESFK(SNTSESF)FRVTQLAPKAQIKE-NH2

-continued
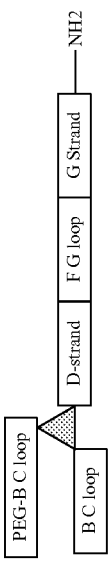
Compound 18 (SEQ ID NO: 59)
SNTSESFK(NH2-[PEG]11-CO-SNTSESF)FRVTQLAPKAQIKE-NH2
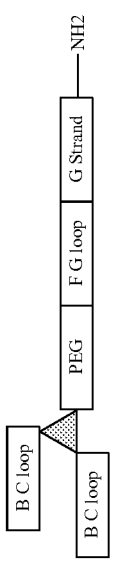
Compound 19 (SEQ ID NO: 60)
SNTSESFK(SNTSESF)-NH-[PEG]11-CO-)LAPKAQIKE-NH2
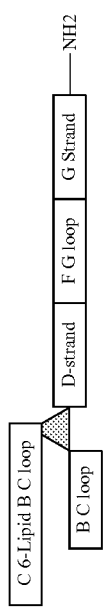
Compound 20 (SEQ ID NO: 61)
SNTSESFK(CH3(CH2)4CO-SNTSESF)FRVTQLAPKAQIKE-NH2
Lipid in branch
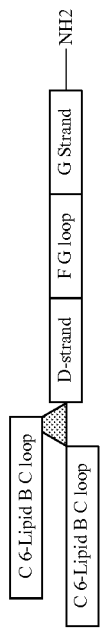
Compound 21 (SEQ ID NO: 62)
CH3(CH2)4CO-SNTSESFK(CH3(CH2)4CO-SNTSESF)FRVTQLAPKAQIKE-NH2
Lipid on both Branch & N-termini

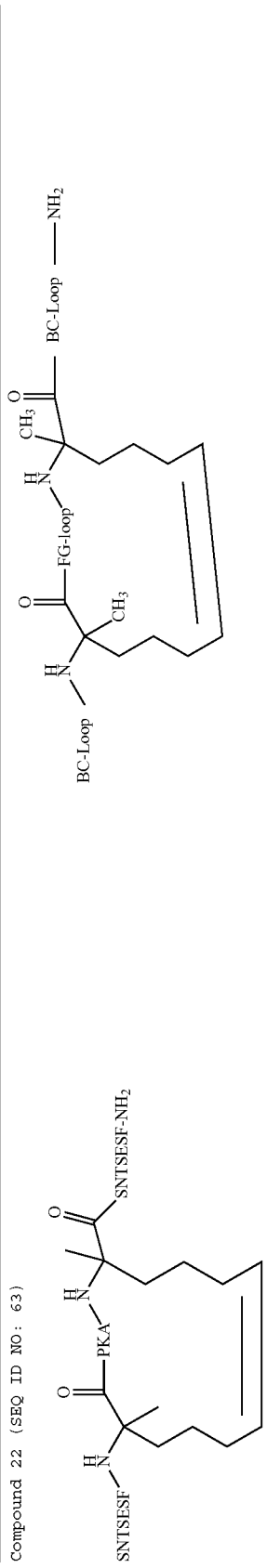
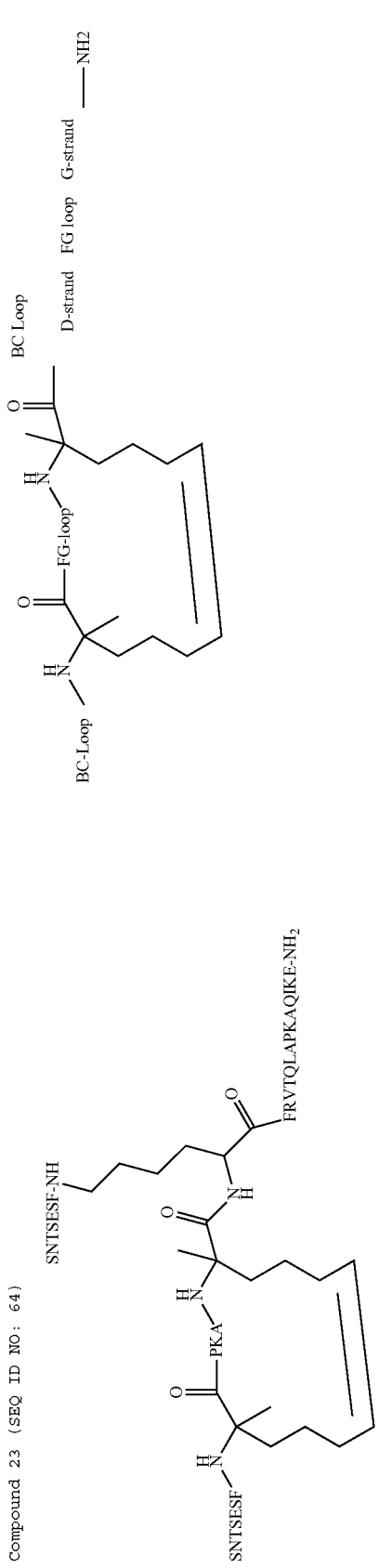

-continued
Compound 24 (SEQ ID NO: 65)
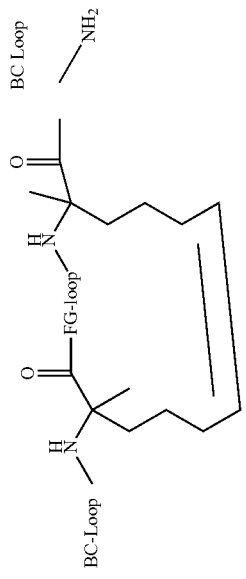
Compound 25 SNTSESFK(SNTSESF)FRVTQLAQIKE-NH2 (SEQ ID NO: 66)
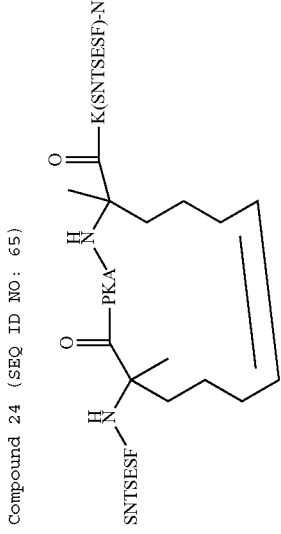
Compound 26 SNTSESFFRVTQLAPKAQIKE-NH2 (SEQ ID NO: 67)
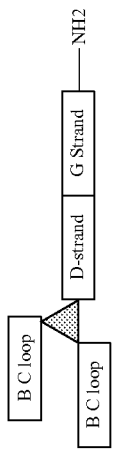
Compound 27 SNTSESFKFRVTQLAPKAQIKE-NH2 (SEQ ID NO: 68)
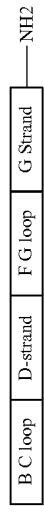
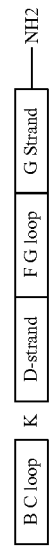
Compound 28 SNTSESFKSNTSESFFRVTQLAPKAQIKE-NH2 (SEQ ID NO: 69)
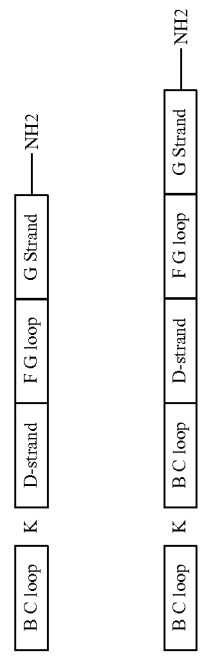

-continued
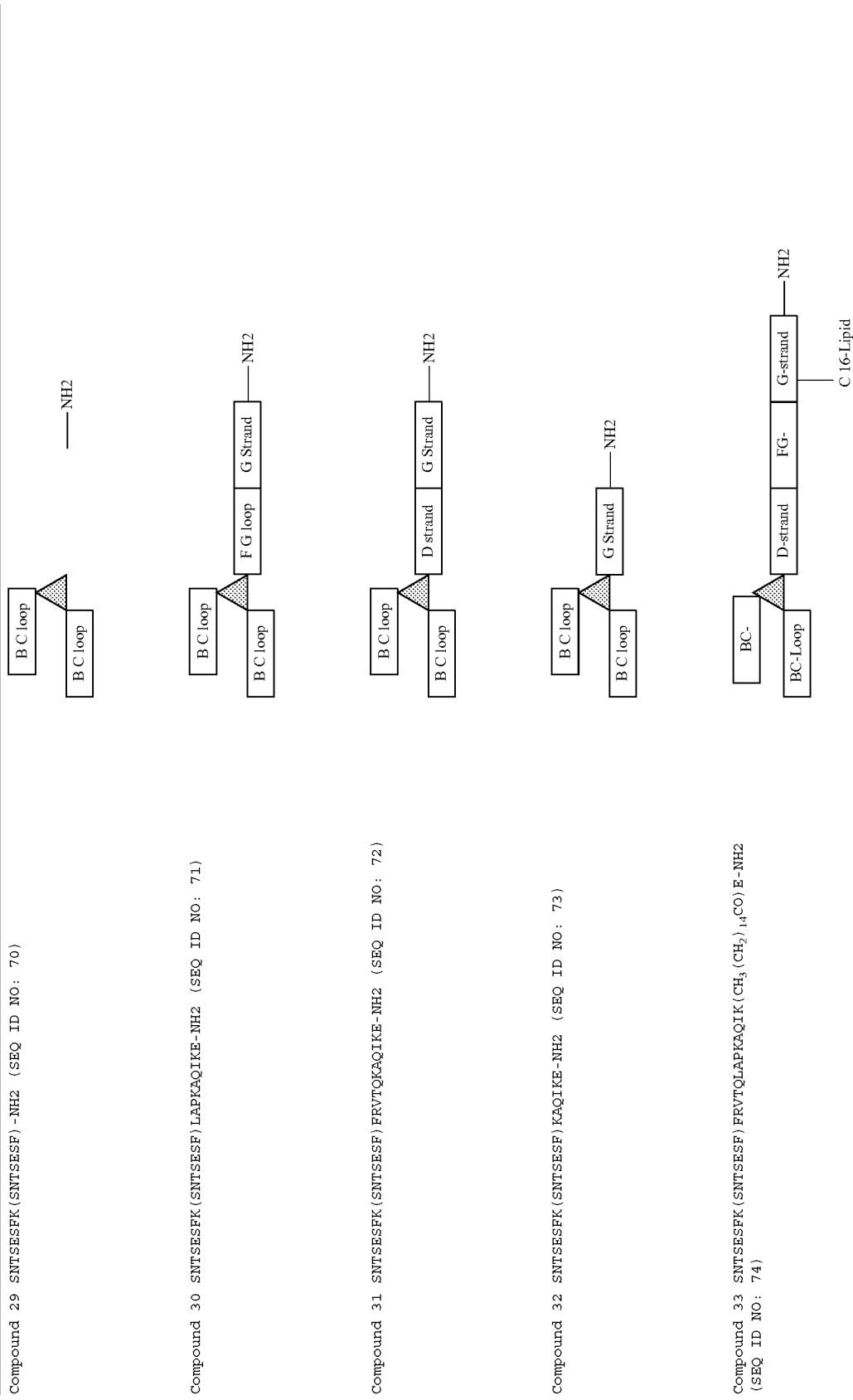
Compound 29 SNTSESFK(SNTSESF)-NH2 (SEQ ID NO: 70)
Compound 30 SNTSESFK(SNTSESF)LAPKAQIKE-NH2 (SEQ ID NO: 71)
Compound 31 SNTSESFK(SNTSESF)FRVTQKAQIKE-NH2 (SEQ ID NO: 72)
Compound 32 SNTSESFK(SNTSESF)KAQIKE-NH2 (SEQ ID NO: 73)
Compound 33 SNTSESFK(SNTSESF)FRVTQLAPKAQIK(CH$_3$(CH$_2$)$_{14}$CO)E-NH2 (SEQ ID NO: 74)

-continued
Compound 34 SNTSESFK(SNTSESF)FRVTQLAPK(CH$_3$(CH$_2$)$_{14}$CO)AQIKE-NH2
(SEQ ID NO: 75)
Compound 35 (SEQ ID NO: 76) SNTSESFK(SNTSESF)FRVTQK(LAP)KAQIKE-NH2
Compound 36 (SEQ ID NO: 77) SNTSESFK(SNTSESF)FRVTQLAK(PKA)QIKE-NH2
Compound 37 (SEQ ID NO: 78) SNTSESFK(LAP)FRVTQLAPKAQIKE-NH2
Compound 38 (SEQ ID NO: 79) LAPK(LAP)FRVTQLAPKAQIKE-NH2
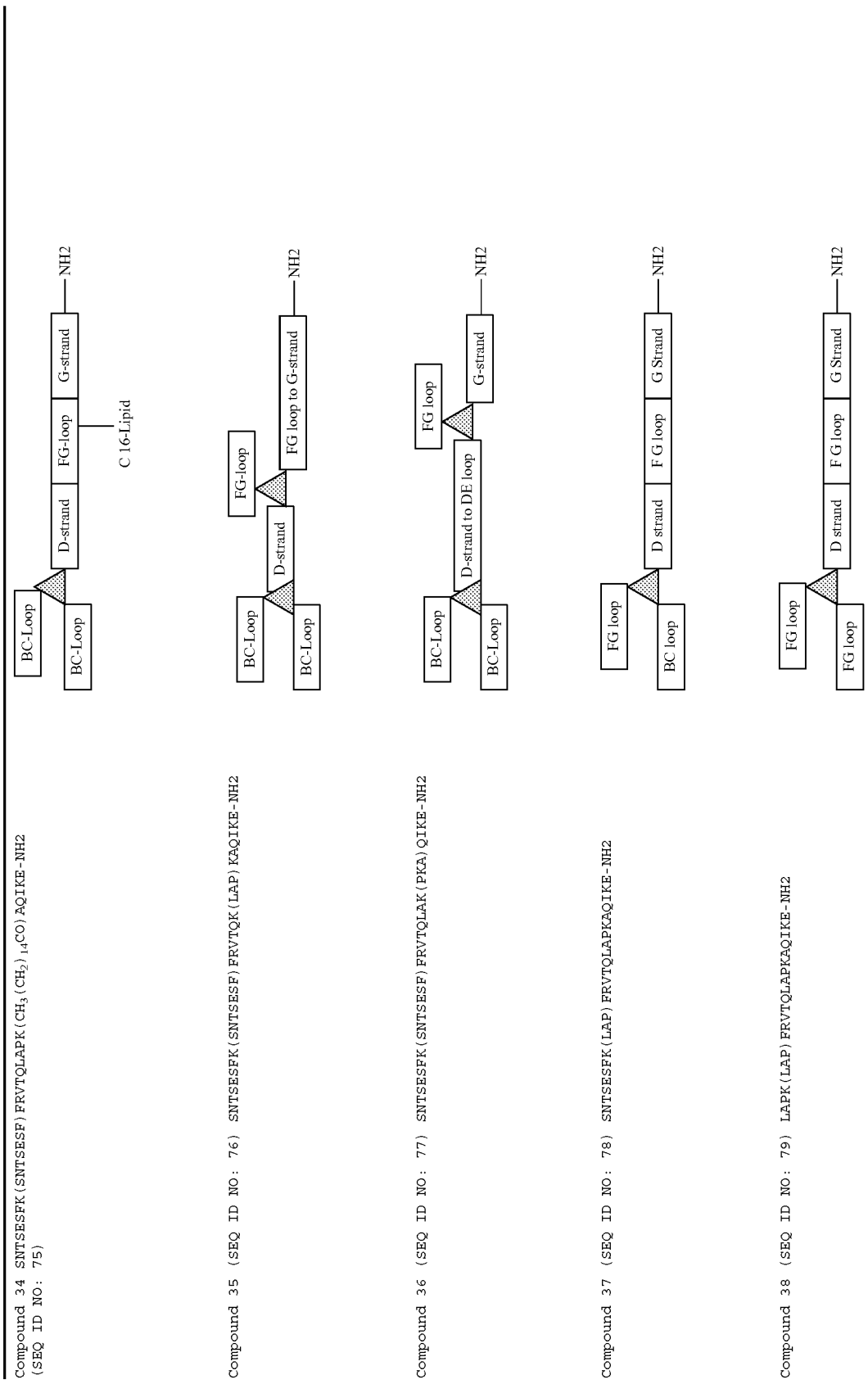

-continued
Compound 39 (SEQ ID NO: 80) LAPKAQIKE-NH2
Compound 40 (SEQ ID NO: 81)
SNTSESFK(SNTSESF)FK(CH3(CH2)14CO))VTQLAPKAQIKE-NH2
Arg in D strand replaced by Lys
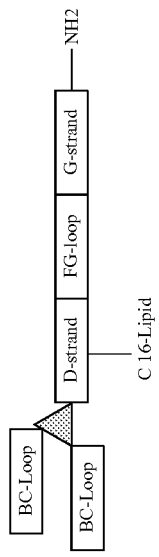
Compound 41 (SEQ ID NO: 82) SNTSESFK(SNTSESF)FRVTQLAP-NH2
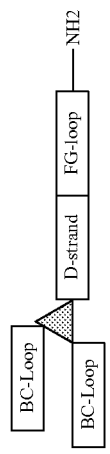
Compound 42 (SEQ ID NO: 83) SNTSESFFRVTQK(SNTSESF)LAPKAQIKE-NH2
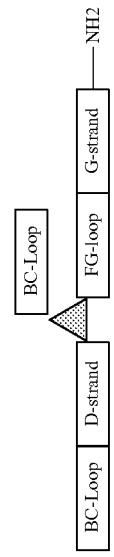
Compound 43 (SEQ ID NO: 84) FRVTQLAPKAQIKE-NH2
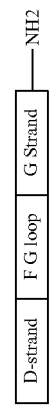

-continued

Compound 44 (SEQ ID NO: 85)
SNTSESFK(SNTSESF)FK(CH₃(CH₂)₆CO)VTQLAPKAQIKE-NH2
Arg in D strand replaced by Lys Compound 45 (SEQ ID NO: 86)
SNTSESFK(SNTSESF)FRVTQLAPK(CH₃(CH₂)₆CO)AQIKE-NH2

Compound 46 (SEQ ID NO: 87) SNTSESFK(SNTSESF)FRVTQLAPKAQIK(CH₃(CH₂)₆CO)E

Compound 47 (SEQ ID NO: 88) SNTSESFK(sntsesf)FRVTQLAPKAQIKE
D-amino acids in the branch Compound 48 (SEQ ID NO: 89) EKIQAKPALQTVRFK(FSESTNS)FSESTNS-NH2

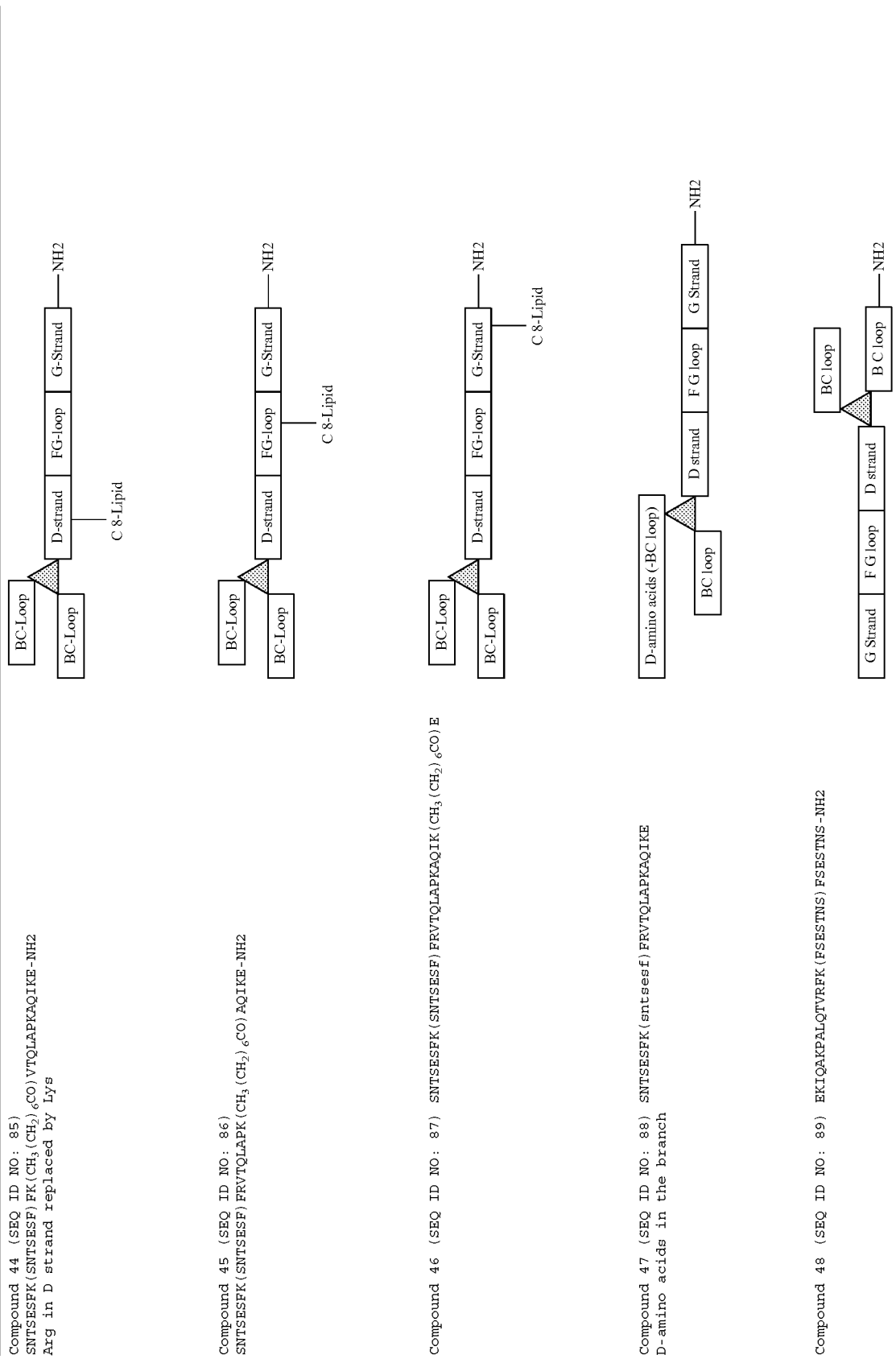

-continued
Compound 49 (SEQ ID NO: 90) ekiqakpalqtvrfk(fsestns)fsestns-NH₂
Retro inverso (All D-amino acid)
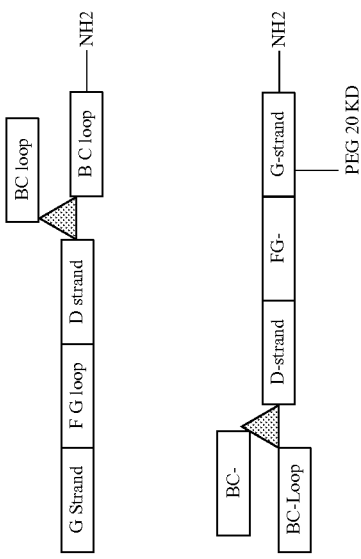
Compound 50 (SEQ ID NO: 91) SNTSESFK(SNTSESF)FRVTQLAPKAQIK(PEG-20KD)E-NH2
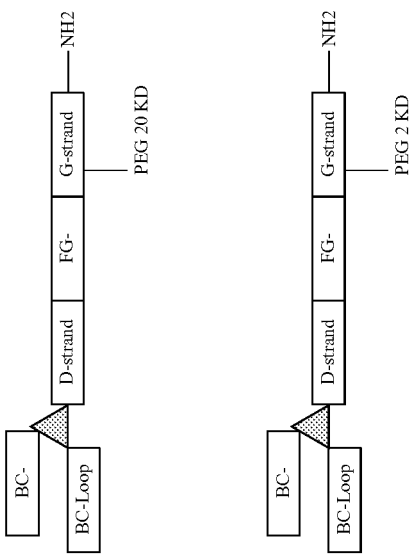
Compound 51 (SEQ ID NO: 92) SNTSESFK(SNTSESF)FRVTQLAPKAQIK(PEG-20KD)E-NH2
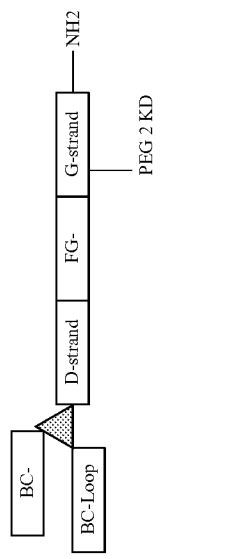
Compound 52 (SEQ ID NO: 93) SNTSESFK(SNTSESF)FRVTQLAPK(PEG 20KD)AQIKE-NH2
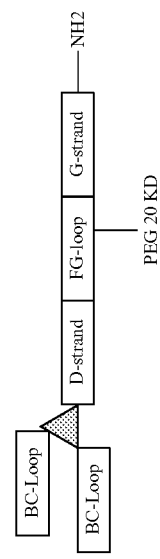

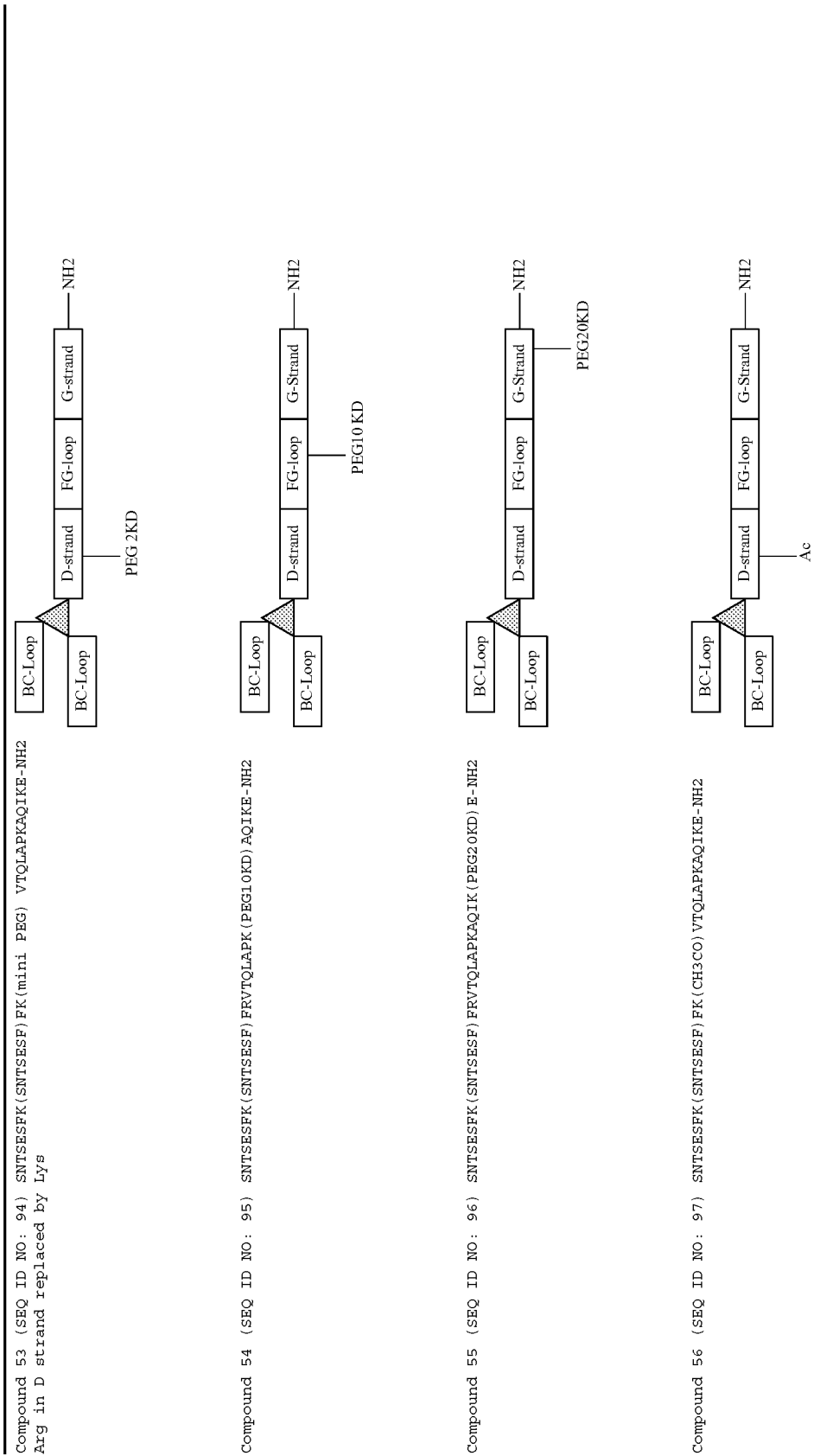

-continued
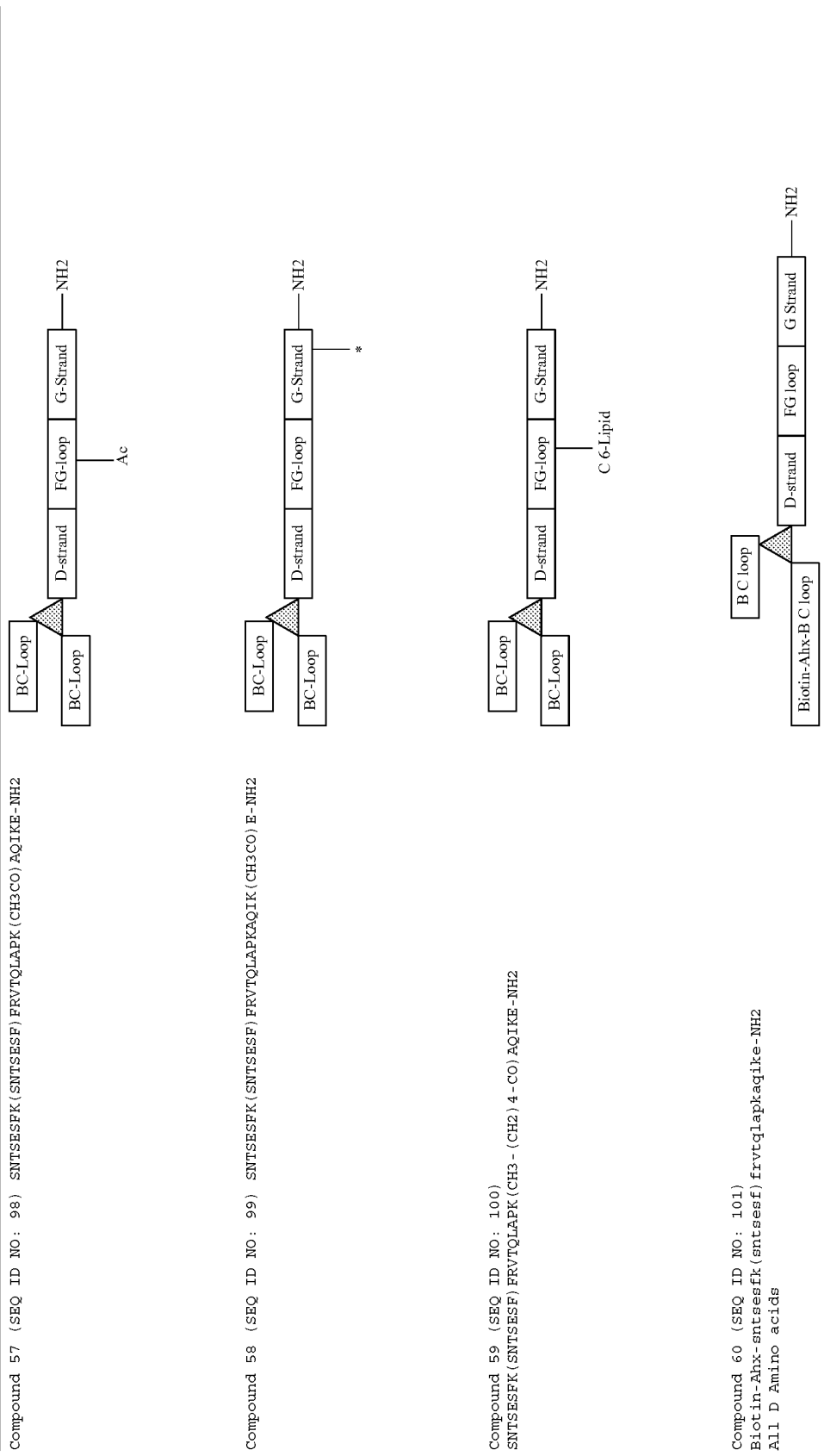
Compound 57 (SEQ ID NO: 98) SNTSESFK(SNTSESF)FRVTQLAPK(CH3CO)AQIKE-NH2
Compound 58 (SEQ ID NO: 99) SNTSESFK(SNTSESF)FRVTQLAPKAQIK(CH3CO)E-NH2
Compound 59 (SEQ ID NO: 100)
SNTSESFK(SNTSESF)FRVTQLAPK(CH3-(CH2)4-CO)AQIKE-NH2
Compound 60 (SEQ ID NO: 101)
Biotin-Ahx-sntsesfk(sntsesf)frvtqlapkaqike-NH2
All D Amino acids -continued

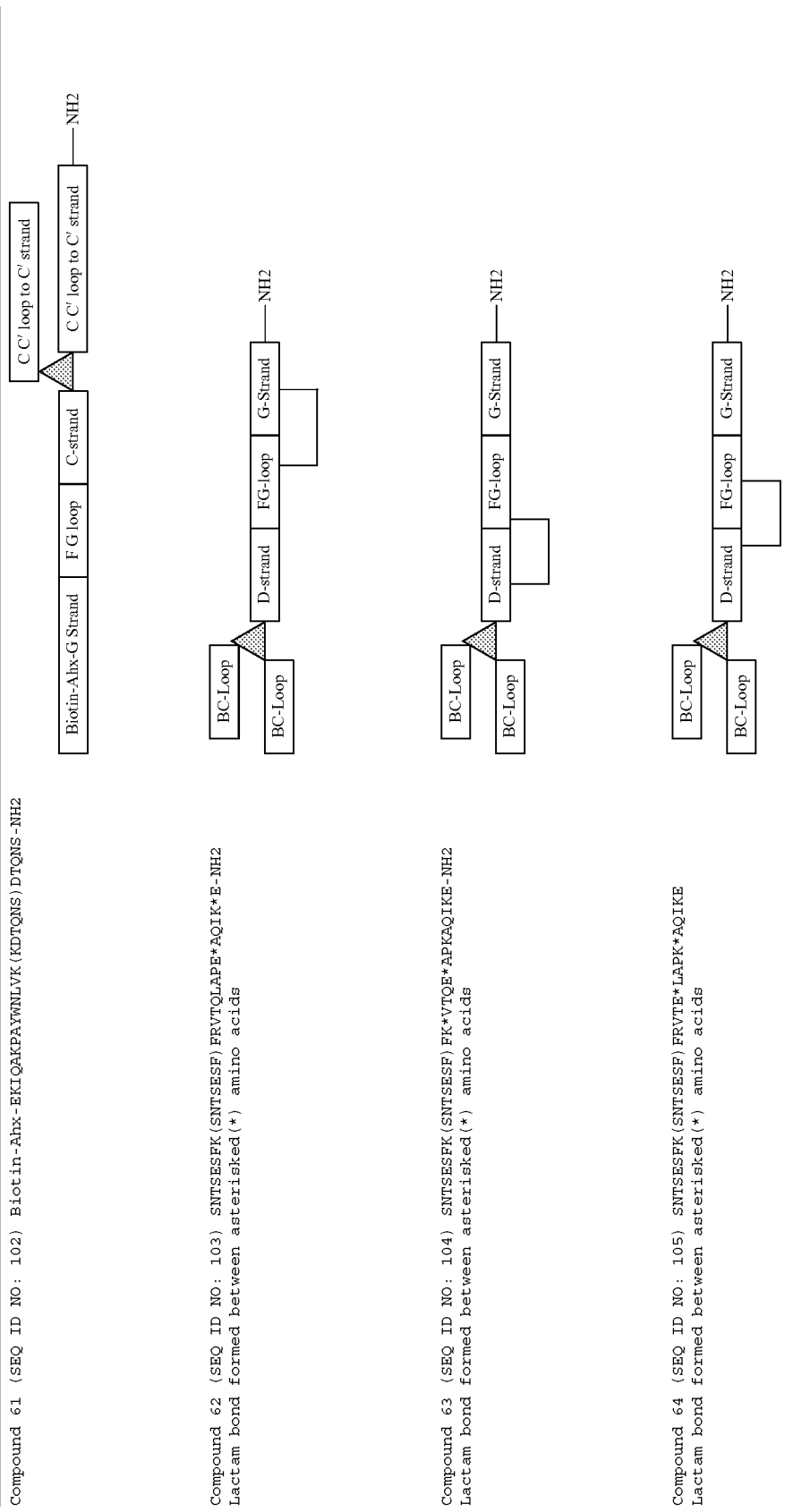

Compound 61 (SEQ ID NO: 102) Biotin-Ahx-EKIQAKPAYWNLVK(KDTQNS)DTQNS-NH2

Compound 62 (SEQ ID NO: 103) SNTSESFK(SNTSESF)FRVTQLAPE*AQIK*E-NH2
Lactam bond formed between asterisked(*) amino acids Compound 63 (SEQ ID NO: 104) SNTSESFK(SNTSESF)FK*VTQE*APKAQIKE-NH2
Lactam bond formed between asterisked(*) amino acids Compound 64 (SEQ ID NO: 105) SNTSESFK(SNTSESF)FRVTE*LAPK*AQIKE
Lactam bond formed between asterisked(*) amino acids -continued
Compound 65 (SEQ ID NO: 106)
CH3CO-SNTSESFK(CH3CO-SNTSESF)FRVTQLAPKAQIK(CH₃(CH₂)₆CO)E
Compound 66 (SEQ ID NO: 107)
CH3CO-SNTSESFK(CH3CO-SNTSESF)FRVTQLAPKAQIK(CH₃(CH₂)₁₄CO)E
Compound 67 (SEQ ID NO: 108)
8CH3CO-SNTSESFK(CH3CO-SNTSESF)FRVTQLAPKAQIK(CH₃(CH₂)₁₀CO)E at Lys
Compound 68 (SEQ ID NO: 109)
CH3CO-SNTSESFK(CH3CO-SNTSESF)FRVTQLAPKAQIK(CH₃(CH₂)₄CO)E
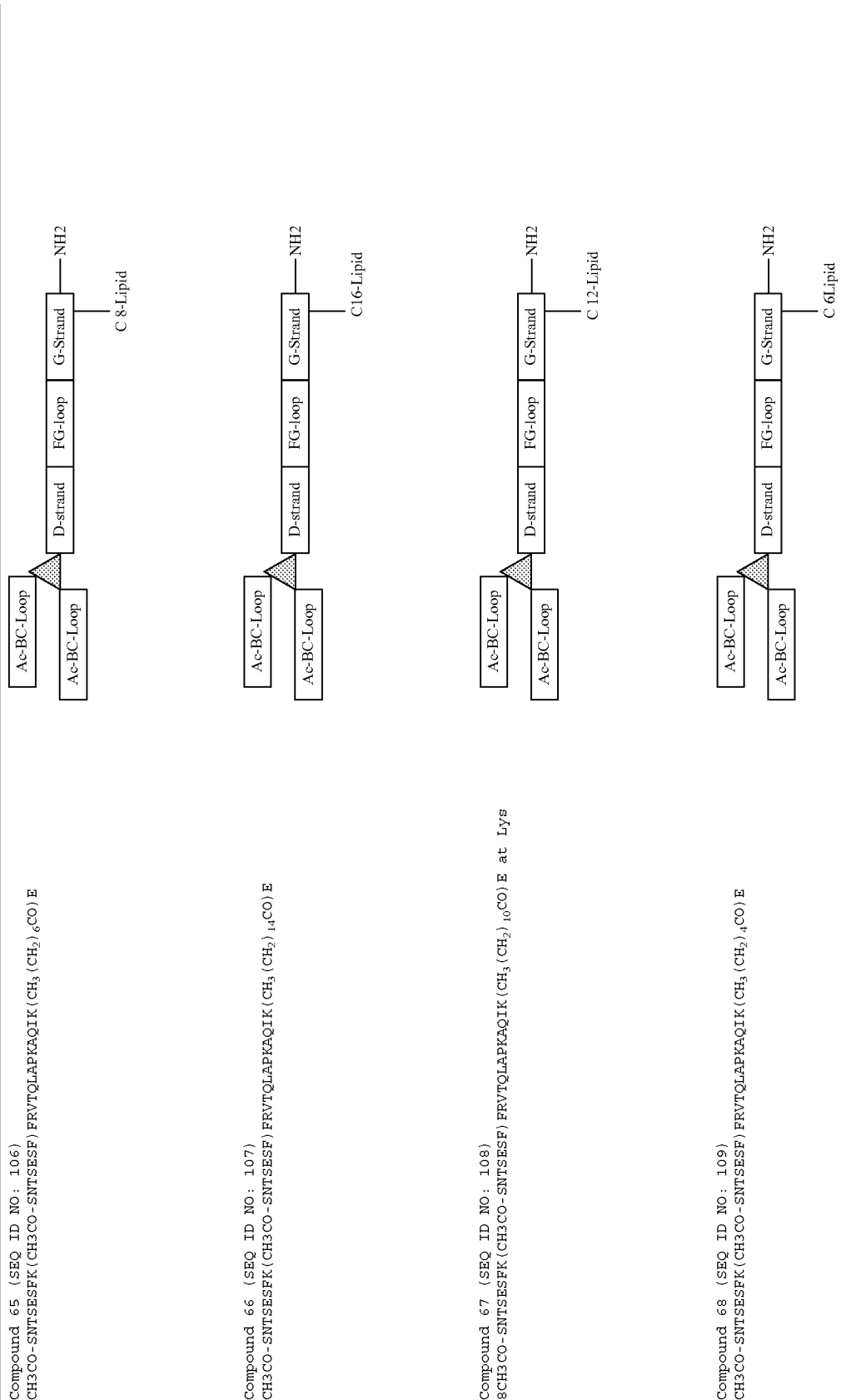

-continued
Compound 69 (SEQ ID NO: 110) SNWSEDLK(SNWSEDL)FQIIQLHPKAKIEE-NH2
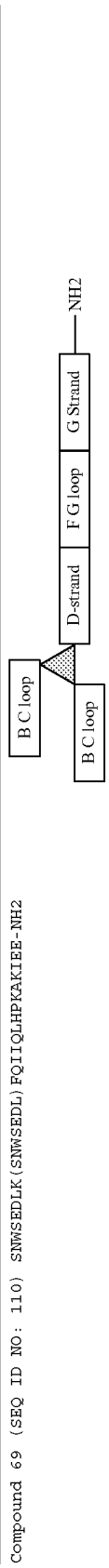
Compound 70 (SEQ ID NO: 111) EDK(ED)FRVTQLAPKAQIKE-NH2
Compound 71 (SEQ ID NO: 112) SNTSESFK(ED)FRVTQLAPKAQIKE-NH2
Compound 72 (SEQ ID NO: 113) LAPKAK(ED)FRVTQLAPKAQIKE-NH2
Compound 73 (SEQ ID NO: 114) SNQTDKK(ED)FRVTQLAPKAQIKE-NH2

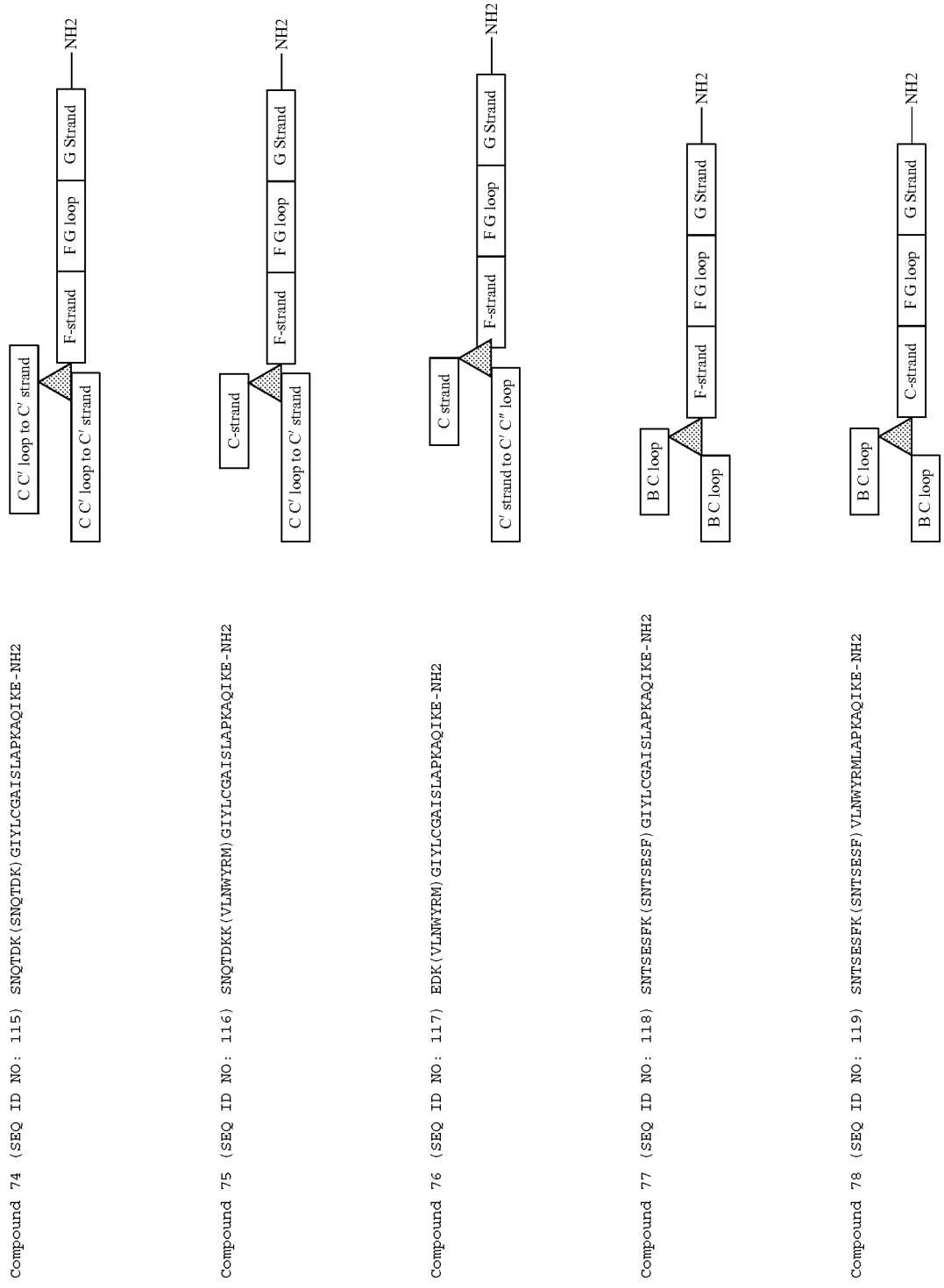
Compound 74 (SEQ ID NO: 115) SNQTDK(SNQTDK)GIYLCGAISLAPKAQIKE-NH2
Compound 75 (SEQ ID NO: 116) SNQTDKK(VLNWYRM)GIYLCGAISLAPKAQIKE-NH2
Compound 76 (SEQ ID NO: 117) EDK(VLNWYRM)GIYLCGAISLAPKAQIKE-NH2
Compound 77 (SEQ ID NO: 118) SNTSESFK(SNTSESF)GIYLCGAISLAPKAQIKE-NH2
Compound 78 (SEQ ID NO: 119) SNTSESFK(SNTSESF)VLNWYRMLAPKAQIKE-NH2

-continued
Compound 79 (SEQ ID NO: 120) VLNWYRMK(SNQTDK)GIYLCGAISLAPKAQIKE-NH2
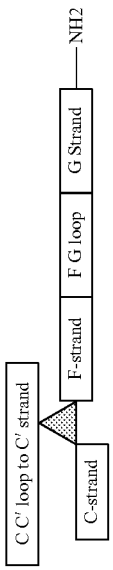
Compound 80 (SEQ ID NO: 121) GIYLCGAISLAPKAQIKE-NH2
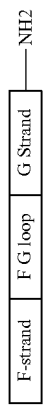
Compound 81 (SEQ ID NO: 122) SNQTDKK (SNQTDK) FRVTQ LAPKAQIKE-NH2
Compound 82 (SEQ ID NO: 123)
SNWSEDLK(SNWSEDL)FQIQLHPK(CH₃(CH₂)₁₄CO)AKIEE-NH2
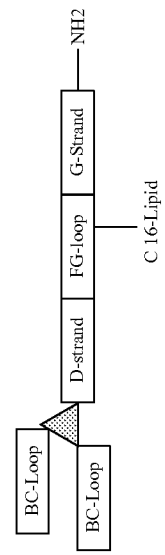

-continued
Compound 83 (SEQ ID NO: 124)
SNTSESFK(SNTSESF) FRVTQLAPK(MPA-NH-CH$_2$-CH$_2$-O-CH$_2$-CH$_2$-O-CO) AQIKE-NH2
Compound 84 (SEQ ID NO: 125) SNTSESFK(sNTSESF) FRVTQLAPKAQIKE-NH2
Compound 85 (SEQ ID NO: 126) sNTSESFK(SNTSESF) FRVTQLAPKAQIKE-NH2
Compound 86 (SEQ ID NO: 127) sNTSESFK(SNTSESF) FRVTQLAPKAQIKE-NH2
Compound 87 (SEQ ID NO: 128)
SNTSESFK(SNTSESF) FRVTQLAPKAQIK(MPA-NH-CH$_2$-CH$_2$-O-CH$_2$-CH$_2$-O-CO) E-NH2
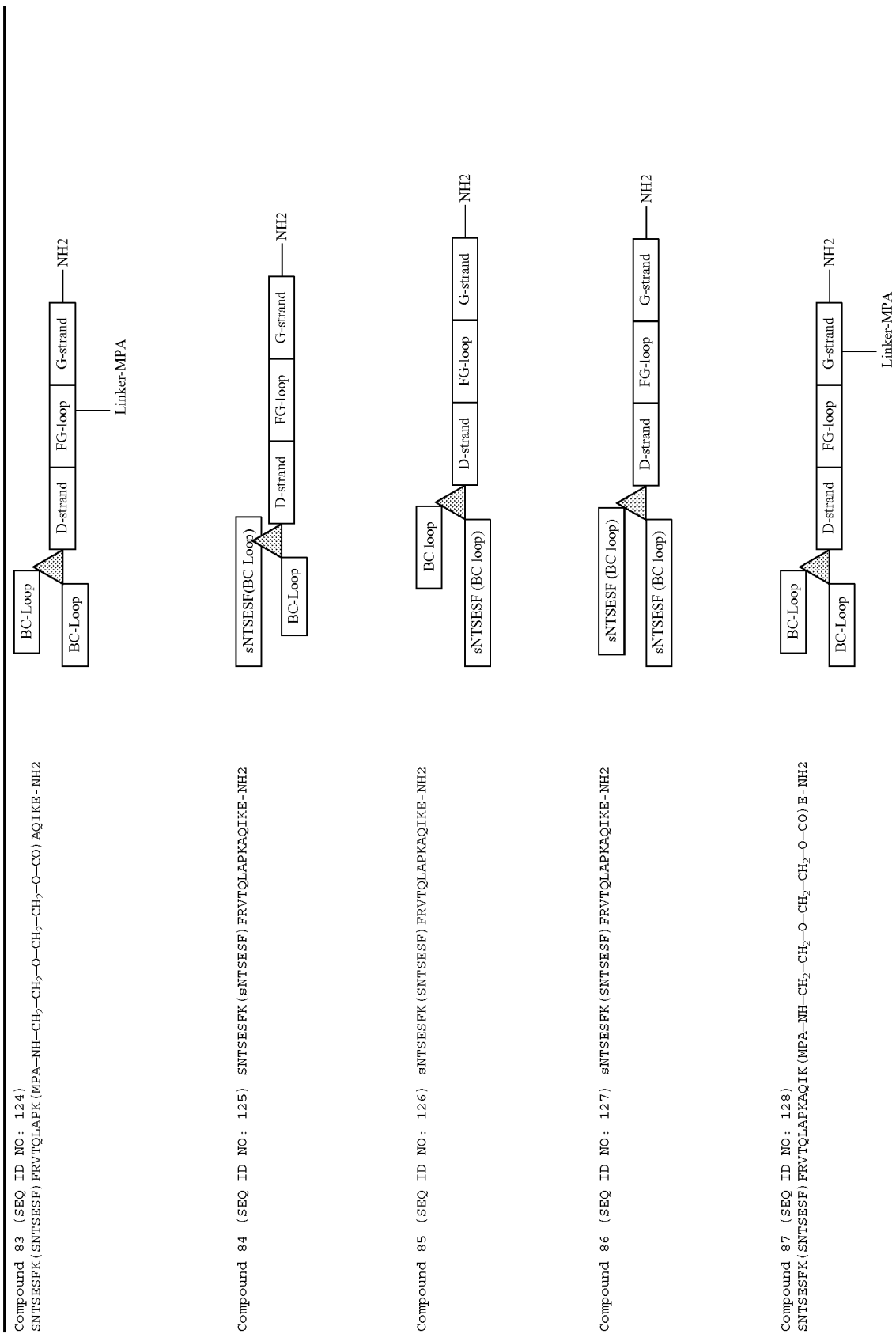

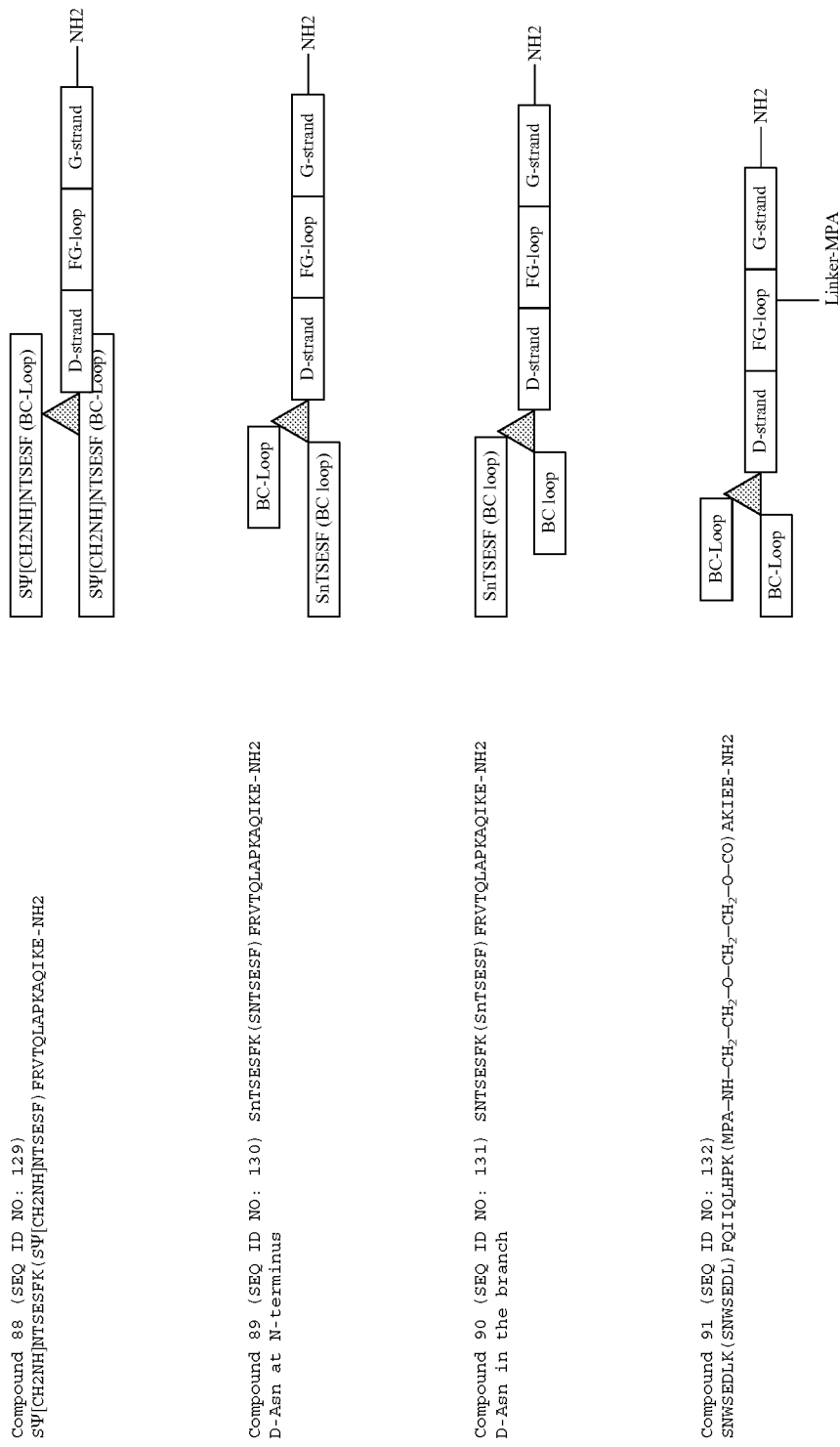
Compound 88 (SEQ ID NO: 129)
SΨ[CH2NH]NTSESFK(SΨ[CH2NH]NTSESF)FRVTQLAPKAQIKE-NH2
Compound 89 (SEQ ID NO: 130) SnTSESFK(SnTSESF)FRVTQLAPKAQIKE-NH2
D-Asn at N-terminus
Compound 90 (SEQ ID NO: 131) SNTSESFK(SnTSESF)FRVTQLAPKAQIKE-NH2
D-Asn in the branch
Compound 91 (SEQ ID NO: 132)
SNWSEDLK(SNWSEDL)FQIQLHPK(MPA-NH-CH$_2$-CH$_2$-O-CH$_2$-CH$_2$-O-CO)AKIEE-NH2

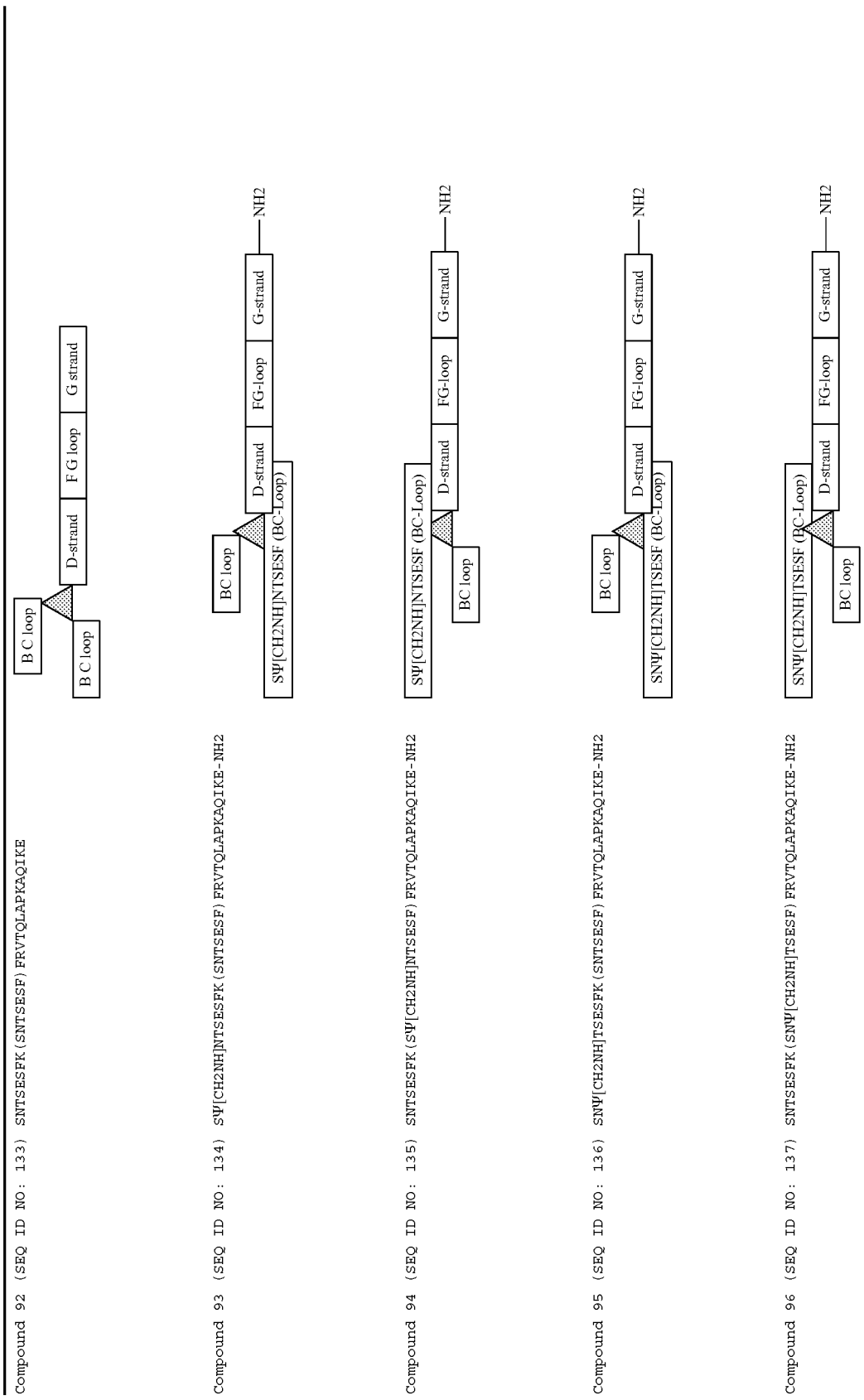

-continued
Compound 97 (SEQ ID NO: 138)
SN Ψ[CH2NH]TSESFK(SNΨ[CH2NH]TSESF) FRVTQLAPKAQIKE-NH2
Compound 98 (SEQ ID NO: 139) SNTSESFK(SNTSESF) FRVTQLAPK(CH$_3$(CH$_2$)$_{14}$CO)AQIKE
c-terminus acid
Compound 99 (SEQ ID NO: 140) SNTSESF-Orn-(SNTSESF) KAQIKE-NH2
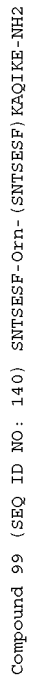
Compound 100 (SEQ ID NO: 141) SNTSESF-Dap-(SNTSESF) KAQIKE-NH2
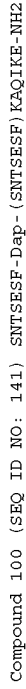

-continued

Compound 101 (SEQ ID NO: 142) SNTSESF-Dab-(SNTSESF)KAQIKE-NH2

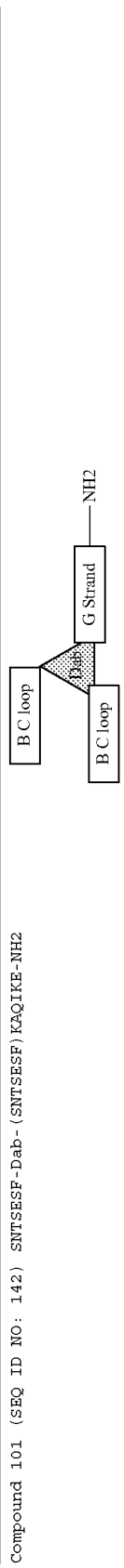

Compound 102 (SEQ ID NO: 143) SNTSESFK(SNTSESF)FRVTQLAPK*IAQE*KE-NH2
Lactam bond formed between asterisked(*) amino acids

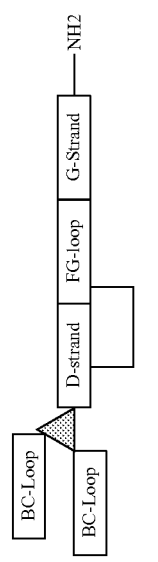

Compound 103 (SEQ ID NO: 144) SNTSESFK(SNTSESF)K*RVTE*LAPKAQIKE-NH2
Lactam bond formed between asterisked(*) amino acids

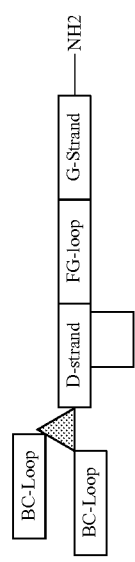

Compound 104 (SEQ ID NO: 145) SNTSESFK(SNTSESF)FRK*TQLE*PKAQIKE-NH2
Lactam bond formed between asterisked(*) amino acids

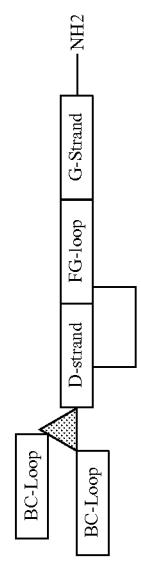

-continued
Compound 105 (SEQ ID NO: 146) SNTSESFK(SNTSESF)FRVE*QLAK*PAQIKE-NH2
Lactam bond formed between asterisked(*) amino acids
Compound 106 (SEQ ID NO: 147) LAPKA-NH2
Compound 107 (SEQ ID NO: 148) LAPKA(SNQTDK)FRVTQLAPKAQIKE-NH2
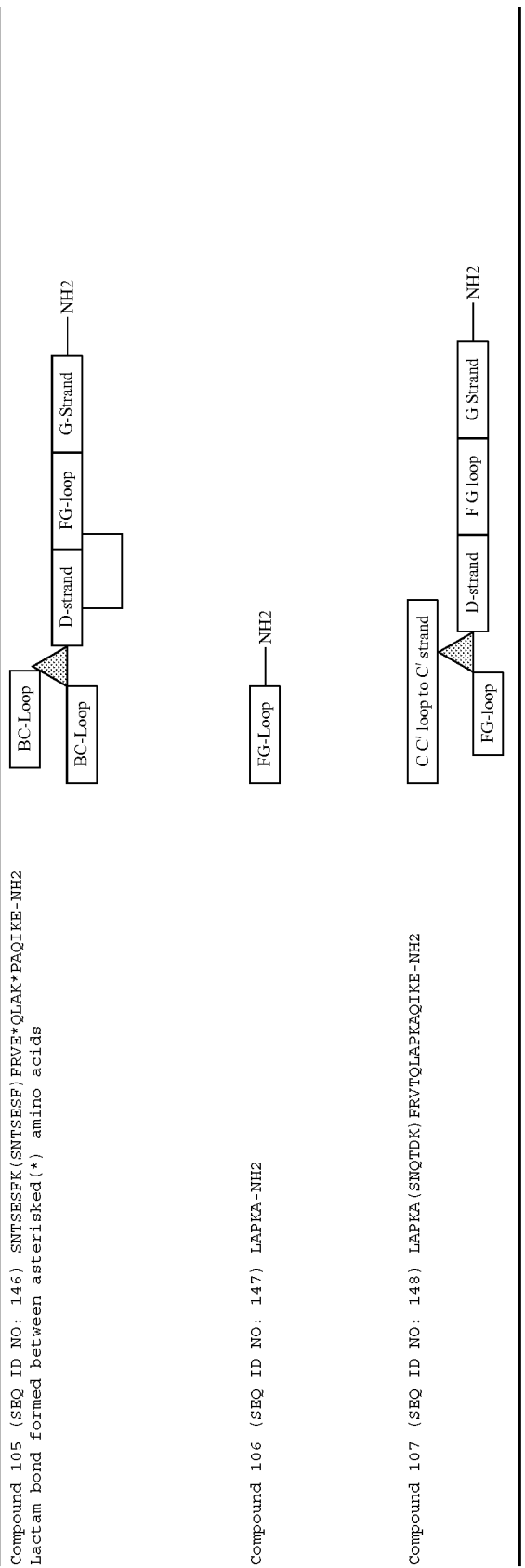

Compounds of the invention may comprise peptide moieties that are lipidated, PEGylated and/or are glycosylated. One or more of the amino acids of the peptide may be a D-amino acid with a view to increasing stability in vivo.

The invention includes compounds as described above, formulated for pharmaceutical administration, typically by combination with a pharmaceutically acceptable carrier or diluent.

The invention includes compounds as described above for use in a method of medical treatment, e.g. in the treatment of cancer, treatment of bacterial and viral infections The invention further includes a method of screening compounds for ability to block interaction between PD-1 and a PD-1 ligand, comprising contacting candidate compounds of the kind described above with PD-1 or a PD-1 ligand binding portion of PD-1 and with a PD-1 ligand or a PD-1 binding portion of a PD-1 ligand, and measuring the extent of PD-1/PD-1 ligand binding.

As indicated above, compounds of the invention may be peptides modified by PEGylation. Polymers have been used extensively to improve the pharmacokinetics and pharmacodynamics and hence, drug performance of drugs such as peptides, proteins, and small molecules. The most widely used polymer for pharmaceutical applications is polyethylene glycol ("PEG"). "PEGylation" is the process by which the drug is chemically modified to result in the covalent attachment ("coupling") of one or more PEG molecules to the drug (depending on how many sites are available on the drug to interact with, and be conjugated to PEG). The improved pharmacological and biological properties associated with PEGylation of drugs are well known in the pharmaceutical art. For example, PEGylation can increase therapeutic efficacy by means including, but not limited to, reducing degradation by proteolytic enzymes and thereby increasing drug concentration; increasing the size of the drug to which it is attached, thereby improving drug biodistribution; and shielding antigenic epitopes in reducing immunogenicity where desired. By increasing the therapeutic efficacy, the frequency of dosing and/or the amount of drug need to achieve a therapeutic effect may be reduced.

PEG, as a linear polyether, has the general structure: HO—(CH$_2$—CH$_2$O)n-CH$_2$CH$_2$—OH where n can typically range from about 10 to about 2000.

PEG may be modified which includes H2N—(CH$_2$—CH$_2$O)n-CH$_2$CH$_2$—COOH where n can typically range from about 10 to about 2000.

Many of the PEG modifications, in forming PEG derivatives (PEG and PEG derivatives are known in the art as "PEG"), are directed to the end groups ("functionalities") in adding or varying their chemically reactive functionalities to be used to covalently attach the PEG molecule to a drug. Various PEG derivatives are well known in the art. To couple PEG to a drug, typically a functionality of the PEG molecule needs to be activated so as to be chemically reactive. The type and specificity of functionality is based upon the choice of chemically reactive group on the drug to which the PEG molecule is to be coupled. Most commonly for proteins and peptides, the chemically reactive group is present on an amino acid which may be an internal amino acid having a side chain with a free chemically reactive group (e.g. including, but not limited to, lysine, cysteine, glutamic acid, serine, threonine, and the like), the N-terminal amino acid (having a N-terminal amine group, or a side chain amine group, as a free chemically reactive group), a C-terminal amino acid (having a C-terminal carboxylic acid, or side chain amine group as a free chemically reactive group) or a combination thereof. Of the sites of a peptide to be coupled to PEG, most frequently chosen is the N-terminal amine group ("alpha amine") of the peptide's N-terminal amino acid, and the epsilon amine group ("epsilon amine") of a lysine (a lysine found within the amino acid sequence which is not the N-terminal amino acid or the C-terminal amino acid of the peptide) or an epsilon amine group of lysine when the lysine is present in a peptide as a N-terminal amino acid or as a C-terminal amino acid.

Where there are multiple lysine groups in the peptide and multiple binding of PEG molecules is not desired, one can incorporate into its amino acid sequence at selected amino acid positions during synthesis, one or more amine groups (e.g. one or more of an alpha amine or an epsilon amine(s)) which is blocked with a chemical protecting agent from chemically reactive with amine-reactive functionality of PEG during PEGylation, thereby leaving available for PEGylation only the free amine group (s) in selected amino acid positions (through chemical modification) of the synthetic peptide to be covalently coupled to PEG.

Preferred polyols for use in PEGylation comprise a water-soluble poly(alkylen oxide) polymer, and can have a linear or branched chain. The term "polyol" preferably refers to a water-soluble, polyalcohol which may include, but is not limited to, polyethylene glycol ("PEG"), polypropylene glycol ("PPG"), diethylene glycol, triethylene glycol, ethylene glycol, dipropylene glycol, copolymers comprising PPG (e.g., ethylene glycol/PPG), copolymers comprising PEG (e.g., PEG/PPG), mPEG (monomethoxy-poly(ethylene)glycol), and the like. Suitable polyols encompass both homopolymers and copolymers, and further may have a structure comprising a branched structure or linear structure as known to those skilled in the art.

Preferably, the polymer is substantially non-toxic when used for in vivo applications in individuals. In a preferred embodiment, the polymer has a molecular weight in the range between about 200 daltons to about 40,000 daltons; and in a more preferred embodiment, the polymer has a molecular weight range between about 400 daltons to about 10,000 daltons. A preferred polymer for application in the present invention comprises a polyethylene glycol ("PEG"), and a more preferred polymer for application in the present invention comprises a polyethylene glycol having a molecular weight range, wherein the molecular weight range is no less than about 400 Daltons and is no more than about 20,000 daltons.

As described previously herein, there are various forms of PEG that typically differ in the end groups or chemically reactive functional groups to be used to covalently attach the PEG molecule to a drug. Various PEGs are well known in the art. A preferred PEG, for use in coupling to one or more unprotected amine groups of the synthetic peptide in accordance with the present invention, has a chemically reactive group (e.g. "functionality") which can be used covalently couple PEG to the to one or more unprotected amine groups. PEG may include but are not limited to, PEG-tresylate, heterobifunctional PEG, PEG dichlorotriazine, PEG succinimidyl carbonate, PEG benzotriazole carbonate, PEG p-nitrophenyl carbonate, PEG trichlorophenyl carbonate, PEG carbonylimidazole, PEG succinimidyl succinate, mPEG succinimidyl propionate, mPEG succinimidyl butanoate, PEG butyraldehyde, mPEG-propionaldehyde, PEG aldehyde, PEG-acetaldehyde, PEG acetaldehyde diethyl acetal, PEG carboxylic acid, mPEG phenyl ether succinimidyl carbonates, mPEG benzamide succinimidyl carbonates, PEG thioester, linear PEG, branched PEG, and linear forked PEG.

In addition, compounds of the invention may be combined with carrier molecules such as dendrimers, e.g. pAMAM dendrimers, liposomes, micro-particles and nanoparticles such as polycyanoacrylate nanoparticles, and these also may be PEGylated.

Compounds similar to those of the invention but where modifications are made that render the compound less active in blocking PD-1 signalling pathway may be useful, for instance as controls in screening protocols. Amongst such compounds are expected to be analogues of any of the compounds of the invention described herein where all or most of the amino acids are D-amino acids, analogues of any of the compounds of the invention described herein where all or most of the amino acids are reversed in sequence (retro-compounds) and analogues of such retro-compounds where all or most of the amino acids are D-amino acids, retroinverso-compounds.

Further embodiment of the present invention relates to the compounds as disclosed in the present invention, wherein one or more of the amino acids of the peptide moiety the compounds is substituted with a D-amino acid.

The compounds as disclosed in the present invention are formulated for pharmaceutical administration.

Another embodiment of the present invention provided a pharmaceutical composition comprising the compound as disclosed, and a pharmaceutically acceptable carrier or diluent.

Yet another embodiment of the present invention provides use of the compounds as disclosed in the present invention for the preparation of a medicament for the treatment of cancer.

Yet another embodiment of the present invention provides use of the compounds as disclosed in the present invention for the preparation of a medicament for the treatment of bacterial and viral infection.

Yet another embodiment of the present invention provides a method of treatment of cancer, wherein the method comprises administration of an effective amount of the compound and/or peptides of the present invention to the subject in need thereof. Yet another embodiment of the present invention provides a method for inhibiting growth of tumour cells and/or metastasis by administering an effective amount of the compound of the present invention to the subject in need thereof.

The said tumour cells include cancer such as but not limited to melanoma, renal cancer, prostate cancer, breast cancer, colon cancer and lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumours of childhood, lymphocytic lymphoma, cancer of the bladder, cancer of the kidney or ureter, carcinoma of the renal pelvis, neoplasm of the central nervous system (CNS), primary CNS lymphoma, tumour angiogenesis, spinal axis tumour, brain stem glioma, pituitary adenoma, Kaposi's sarcoma, epidermoid cancer, squamous cell cancer, T-cell lymphoma, environmentally induced cancers including those induced by asbestos, and combinations of said cancers.

Still yet another embodiment of the present invention provides a method of treatment of infectious disease via immunopotentiation caused by inhibition of immunosuppressive signal induced by PD-1, PD-L1, or PD-L2, wherein the method comprises administration of an effective amount of the compound and/or peptides of the present invention to the subject in need thereof.

The infectious disease includes but not limited to HIV, Influenza, Herpes, *Giardia, Malaria, Leishmania*, the pathogenic infection by the virus Hepatitis (A, B, & C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria chlamydia, rickettsial bacteria, mycobacteria, staphylococci, streptococci, pneumonococci, meningococci and conococci, *klebsiella, proteus, serratia*, pseudomonas, *E. coli, legionella*, diphtheria, *salmonella*, bacilli, cholera, tetanus, botulism, anthrax, plague, leptospirosis, and Lyme's disease bacteria, pathogenic infection by the fungi *Candida* (*albicans, krusei, glabrata, tropicalis*, etc.), *Cryptococcus neoformans, Aspergillus* (*fumigatus, niger*, etc.), Genus Mucorales (*mucor, absidia, rhizophus*), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis.*

The compounds of the present invention are for use in a method of medical treatment.

The compounds of the present invention may be used as single drugs or as a pharmaceutical composition in which the compound is mixed with various pharmacologically acceptable materials.

The pharmaceutical composition is usually administered by a parenteral administration route, but can be administered by oral or inhalation routes. Examples of the parenteral administration include administration by injection, and percutaneous, transmucosal, transnasal and transpulmonary administrations.

The injectable materials include a solution, a suspension, and a solid injection that is dissolved or suspended in a solvent before use.

The injection is used after one or more active ingredients are dissolved, suspended or emulsified in a solvent. Examples of the solvent include water-soluble solvents (e.g., distilled water, physiological saline and Ringer's solution), oil solvents (e.g., vegetable oils such as olive oil, sesame oil, cotton oil and corn oil, and alcohols such as propylene glycol, polyethylene glycol and ethanol), and combinations thereof.

Further, the injection may contain a stabilizer (e.g., human serum albumin), solubilizing agent (e.g., polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate), suspending agent (e.g., surfactants such as stearyl triethanolamine, sodium lauryl sulfate, lauryl amino-propionic acid, lecithin, benzalkonium chloride, benzethonium chloride and glyceryl monostearate; hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose; polysorbates; and polyoxyethylene hardened castor oil), emulsifier, soothing agent (e.g., benzyl alcohol), tonicity agent (e.g., sodium chloride, glycerin, D-mannitol, D-sorbitol and glucose), buffer, preservative (e.g., methylparaben, propylparaben, benzyl alcohol, chlorobutanol and phenol), antiseptic (e.g., paraoxybenzoic esters, chlorobutanol, benzyl alcohol, phenethyl alcohol, dehydroacetic acid and sorbic acid), antioxidant (e.g., sulfite and ascorbate) and dispersant (e.g., Polysorbate 80, Polyoxyethylene hardened castor oil 60, ethylene glycol, carboxymethyl cellulose and sodium alginate).

These injections may be prepared by known methods in the formulation technology field, such as by a method described in various Pharmacopoeia. They are prepared, for example, through a sterilization process at the final stage, or by aseptic manipulation. It is also possible to use an aseptic solid formulation, such as a freeze dried product, wherein the aseptic solid formulation is prepared and dissolved in aseptic or sterilized distilled water for injection or other solvents before use.

These parenteral solutions may be supplied in a vessel with a standard capacity, such as a plastic or glass vial, ampoule, syringe and injector, or in a vessel with a large capacity, such as a bottle.

The dosage of the compounds of the present invention varies depending on age, weight, symptom, therapeutic efficacy, dosing regimen and/or treatment time. Generally, they may be administered by a parenteral route (preferably intravenous administration) in an amount of 1 ng to 100 mg per time, from once a couple of days, once 3 days, once 2 days, once a day to a couple of times a day, in the case of an adult, or continuously administered by intravenous administration from 1 to 24 hours a day. Since the dosage is affected by various conditions, an amount less than the above dosage may sometimes work well enough, or higher dosage may be required in some cases.

Parenteral administration by injection includes all forms of injections, and also includes intravenous fluids. For example, it includes intramuscular injections, subcutaneous injections, intradermal injections, intraarterial injections, intravenous injections, intraperitoneal injections, injections to spinal cavity, and intravenous drops.

The compounds of the present invention may be administered in combination with other drugs for (1) complementation and/or enhancement of prevention and/or therapeutic efficacy of the preventive and/or therapeutic drug of the present invention, (2) dynamics, absorption improvement, dosage reduction of the preventive and/or therapeutic drug of the present invention, and/or (3) reduction of the side effects of the preventive and/or therapeutic drug of the present invention.

A concomitant medicine comprising the peptide of the present invention and other drug may be administered as a combination preparation in which both components are contained in a single formulation, or administered as separate formulations. The administration by separate formulations includes simultaneous administration and administration with some time intervals. In the case of the administration with some time intervals, the compound of the present invention can be administered first, followed by another drug or another drug can be administered first, followed by the compound of the present invention. The administration method of the respective drugs may be the same or different.

The dosage of the other drug can be properly selected, based on a dosage that has been clinically used. The compounding ratio of the compound of the present invention and the other drug can be properly selected according to age and weight of a subject to be administered, administration method, administration time, disorder to be treated, symptom and combination thereof. For example, the other drug may be used in an amount of 0.01 to 100 parts by mass, based on 1 part by mass of the compound of the present invention. The other drug may be a combination of two or more kind of arbitrary drugs in a proper proportion. The other drug that complements and/or enhances the preventive and/or therapeutic efficacy of the compound of the present invention includes not only those that have already been discovered, but those that will be discovered in future, based on the above mechanism.

Diseases on which this concomitant use exerts a preventive and/or therapeutic effect are not particularly limited. The concomitant medicine can be used for any diseases, as long as it complements and/or enhances the preventive and/or therapeutic efficacy of the compound of the present invention.

Particularly, since the compound of the present invention exhibits an effect of stimulating or proliferating lymphoid cells, the concomitant use is able to reduce a dosage of chemotherapeutics commonly used or an irradiation dosage in radio therapy. This results in suppression of side effects that accompany with chemotherapy and radio therapy.

The compound of the present invention can be used with an existing chemotherapeutic concomitantly or in a mixture form. Examples of the chemotherapeutic include an alkylation agent, nitrosourea agent, antimetabolite, anticancer antibiotics, vegetable-origin alkaloid, topoisomerase inhibitor, hormone drug, hormone antagonist, aromatase inhibitor, P-glycoprotein inhibitor, platinum complex derivative, other immunotherapeutic drugs and other anticancer drugs. Further, it can be used with a cancer treatment adjunct, such as a leucopenia (neutrophenia) treatment drug, thrombocytopenia treatment drug, antiemetic and cancer pain intervention drug, concomitantly or in a mixture form.

The compound of the present invention can be used with other immunomodulators concomitantly or in a mixture form. Examples of the immunomodulator include various cytokines. Examples of the cytokines that stimulates immune responses include GM-CSF, M-CSF, G-CSF, interferon-$\alpha$, $\beta$, or $\gamma$, IL-1, IL-2, IL-3 and IL-12.

The concomitant use of the compound of the present invention and a cancer antigen is able to give an additive or synergetic enhancement effect. Examples of the cancer antigen include HLA-A1 and HLA-A2 derived peptides derived from MAGE-1 or MAGE-3 of malignant melanoma, MART-1 and gp100, HER2/neu peptide of breast cancer and ovarian cancer, MUC-1 peptide of adenocarcinoma and NY-ESO-1 of metastatic cancer.

Since a compound of the present invention binds to its ligand molecule strongly and specifically, the labelling agent thereof is able to be used as a test or diagnostic drug or a research reagent for diseases in which the cell surface functional molecule or the ligand molecule is involved.

Examples of the labelling agent that can label the compounds of the present invention include radioisotopes, enzymes, fluorescent materials, luminous materials, ultraviolet absorption materials.

When a compound of the present invention is used in an enzyme-linked immunosorbent assay (EIA) method, it can be used by labelling it with enzymes, such as alkali phosphatase, β-galactosidase, peroxidase, microperoxidase, glucose oxidase, glucose-6-phosphate dehydrogenase, acetylcholinesterase, malate dehydrogenase and luciferase.

When a compound of the present invention is used in a radioimmunoassay (RIA) method, it can be used by labelling it with a radioisotope, such as $^{131}I$, $^{125}I$, $^{99m}Tc$, $^{35}S$, $^{32}P$, $^{14}C$ and $^{3}H$.

When a compound of the present invention is used in a fluorescence immunoassay (FIA) method, it can be used by labelling it with a fluorescent material, such as fluorescein, dansyl, fluorescamine, coumarin, naphthylamine, fluorescein isothiocyanate, rhodamine, rhodamine X isothiocyanate, sulforhodamine 101, Lucifer yellow, acridine, acridine isothiocyanate, riboflavin and the derivatives, and europium (Eu).

When the compound of the present invention is used in a chemiluminescent immunoassay (CLIA) method, it can be used by labelling it with a luminous material, such as luminol derivatives, e.g., luciferin, isoluminol, luminol, aminoethyl isoluminol, aminoethylethyl isoluminol, aminopropyl isoluminol, aminobutyl isoluminol and aminohexylethyl isoluminol; luciferin; lucigenin; and bis(2,4,6-trifluorophenyl) oxalate.

When a compound of the present invention is used in an ultraviolet absorption method, it can be used by labelling it with a substance that has absorption in a wavelength of ultraviolet rays, such as phenol, naphthol, anthracene and derivatives thereof.

When a compound of the present invention is used in an electron spin resonance (ESR) method, it can be used by labeling it with a spin labelling agent represented by a compound having an oxyl group, such as 4-amino-2,2,6,6-tetramethylpiperidine-1-oxyl, 3-amino-2,2,5,5-tetramethylpyrrolidine-1-oxyl, 2,6-di-t-butyl-α-(3,5-di-t-butyl-4-oxo-2,5-cyclohexadien-1-ylidene)-p-tolyl oxyl.

Further, the compound of the present invention can be labelled with any labelling agents that are commonly used in the field.

In order to bind the above labelling agent to the peptide moiety of the compound of the present invention, known labelling methods, which are commonly performed in EIA, RIA, FIA and the like, are applied, such as those described in "Medical Chemistry Experimental Course, 1st Ed., Vol. 8, Edited by U. Yamamura, published by Nakayama Bookstore, 1971; Illustrated Fluorescent Antibody, 1st Ed., written by A. Kawao, published by Softscience, 1983; and Enzyme-linked immunoassay, 2nd Ed., compiled by E. Ishikawa, T. Kawai and K. Muroi, published by Igakushoin, 1982".

Of such labelling methods, a preferred method includes that exploits a reaction between avidin (or sreptavidin) and biotin. In the case of exploiting the reaction between avidin (or streptavidin) and biotin, a method for binding biotin with the peptide moiety of the compound of the present invention includes a method for reacting a commercially available biotinylating agent (e.g., an agent prepared by binding biotin to which a succineimide group (e.g., NHS-biotin) is introduced or N-hydroxysuccinic acid imide (NHS) with biotin through a spacer) with an amino group in protein (Journal of Biological Chemistry, 1989, Vol. 264, pp. 272-279); a method for reacting a commercially available biotin-HPDP (N-[6-(biotinamide)hexyl]-3'-(2'-pyridylthio)propione amide) or N-iodoacetyl-N-biotinylhexylenediamine with a thiol group in protein (Ann. New York Acad. Sci., 1975, Vol. 254, No. 203); or a method for reacting biotin, to which a hydrazine group is introduced, with an aldehyde group in aldehyded protein (Biotech. Apple. Biochem., 1987, Vol. 9, pp. 488-496).

The invention will be further described and illustrated in the Examples below. Automated peptide synthesis was carried out in Symphony parallel synthesizer from Protein Technologies Inc.

Protocol Using Symphony Parallel Synthesizer

TABLE I

Program for swelling, first residue attachment and capping

| # | Step | Time |
|---|------|------|
| 1 | DCM (7.5 mL) | 30 min × 2 |
| 2 | DMF (7.5 mL) | 30 min × 2 |
| 3 | Deprotection: 20% Piperdine/DMF (5 mL) | 7.30 min × 2 |
| 4 | Washing: DMF, DCM, DMF (10 mL) | 30 sec × 3 each |
| 5 | Coupling: 0.25M Fmoc AA (2.5 mL)/0.25M HBTU/1M NMM/DMF (2.5 mL) | 2 h × 1 |
| 6 | DMF, DCM, DMF (10 mL) | 30 sec × 3 each |
| 7 | Acylation (Acetic anhydride:Pyridine:DCM; 1:8:8) (5 mL) | 7.30 min × 2 |
| 8 | DCM, DMF (10 mL) | 30 sec × 3 each |

TABLE II

Program for coupling of amino acids

| # | Step | Time |
|---|------|------|
| 1 | Deprotection: 20% Piperidine/DMF (5 mL) | 7.30 min × 2 |
| 2 | Washing: DMF, DCM, DMF (10 mL) | 30 sec × 3 each |
| 3 | Coupling: 0.25M Fmoc AA (2.5 mL)/0.25M HBTU/1M NMM/DMF (2.5 mL) | 2 h × 1 |
| 4 | DMF, DCM, DMF (10 mL) | 30 sec × 3 each |

TABLE III

Program for coupling of N-terminal amino acid

| # | Step | Time |
|---|------|------|
| 1 | Deprotection: 20% Piperidine/DMF (5 mL) | 7.30 min × 2 |
| 2 | Washing: DMF, DCM, DMF (10 mL) | 30 sec × 3 each |
| 3 | Coupling: 0.25M Fmoc AA (2.5 mL)/0.25M HBTU/1M NMM/DMF (2.5 mL) | 2 h × 1 |
| 4 | DMF, DCM, DMF (10 mL) | 30 sec × 3 each |
| 5 | Deprotection: 20% Piperidine/DMF (5 mL) | 7.30 min × 2 |
| 6 | Washing: DMF, DCM, DMF (10 mL) | 30 sec × 3 each |

Procedure for Cleavage of Peptidyl Resin and Global Deprotection

The peptidyl Resin was washed with MeOH (6×15 ml) and solvent ether (3×15 ml) and dried under vacuum. The cleavage of the peptides from the solid support is achieved by treating the peptide-resin with cleavage cocktail as specified for each peptide at room temperature for 2.5 h. Cleavage mixture was collected by filtration and the resin was washed with TFA and DCM. The excess TFA and DCM was concentrated to small volume under nitrogen and DCM was added to the residue and evaporated under nitrogen. The process was repeated 3-4 times to remove most of the volatile impurities. The residue was cooled to 0° C. and anhydrous ether was added to precipitate the peptide. The precipitated peptide was centrifuged and the supernatant ether was removed and fresh ether was added to the peptide and re-centrifuged. The residue was dissolved in Millipore water and lyophilized to obtain the crude peptide.

Cleavage cocktail A=82.5% TFA/5% phenol/5% thioanisole/2.5% 1,2 ethanedithiol/5% water;

Cleavage cocktail B=80% TFA/5% phenol/5% thioanisole/2.5% 1,2 ethanedithiol/5% DCM/2.5% DMS; and Cleavage Cocktail C=90% TFA/5% TIPS/5% water.

Purification and Characterization of Peptide

The Reverse phase analytical HPLC was performed using on Zorbax Eclipse XDB-C18 silica column (4.6 mm×250 mm, 5 μm).

The elution conditions used are:

Method-1: Buffer A: 0.1% TFA/Water, Buffer B: 0.1% TFA in 9:1 acetonitrile/water.

Equilibration of the column with 2% buffer B and elution by a gradient of 2% to 70% buffer B during 15 min.

Method-2: Buffer A: 0.1% TFA/Water, Buffer B: 0.1% TFA in 9:1 acetonitrile/water.

Equilibration of the column with 2% buffer B and elution by a gradient of 2% to 25% buffer B in 5 min and from 25% to 40% buffer B in total run time of 20 min Method-3: Buffer A: 0.1% TFA/Water, Buffer B: 0.1% TFA in 9:1 acetonitrile/water.

Equilibration of the column with 2% buffer B and elution by a gradient of 0-15 min=2-70% buffer B, 15-20 min=70-95% buffer B LCMS was performed on AP1 2000 LC/MS/MS triple quad (Applied biosystems) with Agilent 1100 series HPLC with G1315 B DAD diode array detector, using Mercury MS column.

Example 1

Synthesis of Sequence Shown in SEQ ID NO: 47

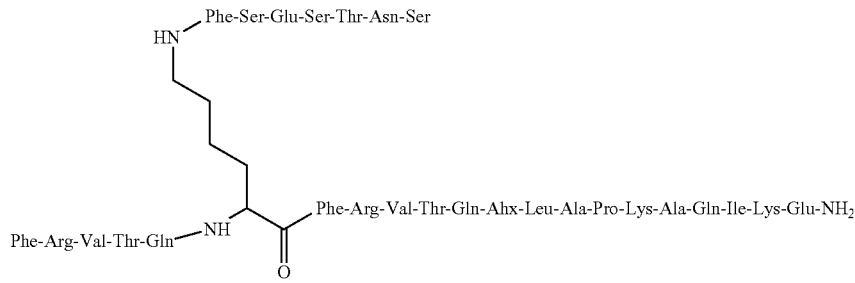

Synthesis of Linear Fragment: FRVTQKFRVTQ[Ahx]LAPKAQIKE-NH2

Desiccated CLEAR-Amide resin ((100-200 mesh) 0.4 mmol/g, 0.5 g) was distributed in 2 polyethylene vessels equipped with a polypropylene filter. The linear peptide synthesis on solid phase were carried out automatically, using Symphony parallel synthesizer (PTI) using the synthesis programs mentioned in the table below. Swelling, C-terminal amino acid [Fmoc-Glu(OtBu)-OH] attachment and capping of the peptidyl resin was carried out as per the protocol in Table I. Subsequent amino acid coupling was carried out as mentioned in Table II. The amino acids used in the synthesis were Fmoc Phe-OH, Fmoc-Arg(Pbf)-OH, Fmoc-Val-OH, Fmoc-Thr(OtBu)-OH, Fmoc-Gln(Trt)-OH, Fmoc-Lys(Boc)-OH, Fmoc-Ahx-OH (Fmoc-6-aminohexanoic acid), Fmoc-Leu-OH, Fmoc-Ala-OH, Fmoc-Pro-OH, Fmoc-Ile-OH. After the completion of linear synthesis fragment in automated peptide synthesiser, the resin was taken out, pooled together and synthesis was carried out manually.

The N-terminal amino acid phenylalanine in the linear chain of the peptide was coupled as N-Boc amino acid in the same procedure as employed for N-Fmoc amino acid. The ε-amino group of sixth lysine (from N terminus) used as branching point was protected with Dde group. After completion of the linear peptide chain Dde protection of ε-amino group of the lysine was orthogonally deprotected by treating the resin with 2.5% (v/v) Hydrazine hydrate solution in DMF for 5 and 15 minutes. The resin is then filtered and washed with DMF (6×10 mL), DCM (6×10 mL) and DMF (6×10 mL). Deprotection is confirmed by positive ninhydrin test.

Fmoc-Phe-OH (0.39 g; 5 equiv 1 mmol) in dry DMF was added to the deprotected resin and coupling was initiated with DIC (0.16 mL; 5 equiv) and HOBT (0.14 g; 5 equiv) in DMF. The concentration of each reactant in the reaction mixture was approximately 0.4 M. The mixture was rotated on a rotor at room temperature for 2 h. Resin was filtered and washed with DMF (6×10 mL), DCM (6×10 mL) and DMF (6×10 mL). Kaiser test on peptide resin aliquot upon completion of coupling was negative. The Fmoc group of the peptidyl resin was deprotected by treating it twice with 20% (v/v) piperidine/DMF solution for 5 and 15 min (10 mL). The resin was washed with DMF (6×10 mL), DCM (6×10 mL) and DMF (6×10 mL). Kaiser test on peptide resin aliquot upon completion of Fmoc-deprotection was positive.

Next amino acid in the peptide sequence Fmoc-Ser (OtBu)-OH (0.39 g; 5 equiv 1 m mol) in dry DMF was added to the deprotected resin and coupling was initiated with DIC (0.16 m L; 5 equiv) and HOBT (0.14 g; 5 equiv) in DMF. The concentration of each reactant in the reaction mixture was approximately 0.4 M. The mixture was rotated on a rotor at room temperature for 2 h. Resin was filtered and washed with DMF (6×10 mL), DCM (6×10 mL) and DMF (6×10 mL). Kaiser test on peptide resin aliquot upon completion of coupling was negative. On completion of Serine coupling Fmoc group on the Serine was deprotected by treating it twice with 20% (v/v) piperidine/DMF solution for 5 and 15 min (10 mL). The resin was washed with DMF (6×10 mL), DCM (6×10 mL) and DMF (6×10 mL). Kaiser test on peptide resin aliquot upon completion of Fmoc-deprotection was positive.

Next amino acid Fmoc-Glu (OtBu)-OH (0.43 g; 5 equiv 1 mmol) in dry DMF was added to the deprotected resin and coupling was initiated with DIC (0.16 mL; 5 equiv) and HOBT (0.14 g; 5 equiv) in DMF. The concentration of each reactant in the reaction mixture was approximately 0.4 M. The mixture was rotated on a rotor at room temperature for 2 h. Resin was filtered and washed with DMF (6×10 mL), DCM (6×10 mL) and DMF (6×10 mL). Kaiser test on peptide resin aliquot upon completion of coupling was negative. The Fmoc group on the peptidyl resin was deprotected by treating it twice with 20% (v/v) piperidine/DMF solution for 5 and 15 min (10 mL). The resin was washed with DMF (6×10 mL), DCM (6×10 mL) and DMF (6×10 mL). Kaiser test on peptide resin aliquot upon completion of Fmoc-deprotection was positive. Next amino acid Fmoc-Ser (OtBu)-OH (0.39 g; 5 equiv 1 mmol) in dry DMF was added to the deprotected resin and coupling was initiated with DIC (0.16 mL; 5 equiv) and HOBT (0.14 g; 5 equiv) in DMF. The concentration of each reactant in the reaction mixture was approximately 0.4 M. The mixture was rotated on a rotor at room temperature for 2 h. Resin was filtered and washed with DMF (6×10 mL), DCM (6×10 mL) and DMF (6×10 mL). Kaiser test on peptide resin aliquot upon completion of coupling was negative. The Fmoc group on the peptidyl resin was deprotected by treating it twice with 20% (v/v) piperidine/DMF solution for 5 and 15 min (10 mL). The resin was washed with DMF (6×10 mL), DCM (6×10 mL) and DMF (6×10 mL). Kaiser test on peptide resin aliquot upon completion of Fmoc-deprotection was positive.

Next amino acid Fmoc-Thr (OtBu)-OH (0.4 g; 5 equiv 1 mmol) in dry DMF was added to the deprotected resin and coupling was initiated with DIC (0.16 mL; 5 equiv) and HOBT (0.14 g; 5 equiv) in DMF. The concentration of each reactant in the reaction mixture was approximately 0.4 M. The mixture was rotated on a rotor at room temperature for 2 h. Resin was filtered and washed with DMF (6×10 mL), DCM (6×10 mL) and DMF (6×10 mL). Kaiser test on peptide resin aliquot upon completion of coupling was negative. The Fmoc group on the peptidyl resin was deprotected by treating it twice with 20% (v/v) piperidine/DMF solution for 5 and 15 min (10 mL). The resin was washed with DMF (6×10 mL), DCM (6×10 mL) and DMF (6×10 mL). Kaiser test on peptide resin aliquot upon completion of Fmoc-deprotection was positive. Next amino acid Fmoc-Asn (Trt)-OH (0.6 g; 5 equiv 1 mmol) in dry DMF was added to the deprotected resin and coupling was initiated with DIC (0.16 mL; 5 equiv) and HOBT (0.14 g; 5 equiv) in DMF. The concentration of each reactant in the reaction mixture was approximately 0.4 M. The mixture was rotated on a rotor at room temperature for 2 h. Resin was filtered and washed with DMF (6×10 mL), DCM (6×10 mL) and DMF (6×10 mL). Kaiser test on peptide resin aliquot upon completion of coupling was negative. The Fmoc group on the peptidyl resin was deprotected by treating it twice with 20% (v/v) piperidine/DMF solution for 5 and 15 min (10 mL). The resin was washed with DMF (6×10 mL), DCM (6×10 mL) and DMF (6×10 mL). Kaiser test on peptide resin aliquot upon completion of Fmoc-deprotection was positive.

Next amino acid Fmoc-Ser (OtBu)-OH (0.39 g; 5 equiv 1 mmol) in dry DMF was added to the deprotected resin and coupling was initiated with DIC (0.16 mL; 5 equiv) and HOBT (0.14 g; 5 equiv) in DMF. The concentration of each reactant in the reaction mixture was approximately 0.4 M. The mixture was rotated on a rotor at room temperature for 2 h. Resin was filtered and washed with DMF (6×10 mL), DCM (6×10 mL) and DMF (6×10 mL). Kaiser test on peptide resin aliquot upon completion of coupling was negative. The Fmoc group on the peptidyl resin was deprotected by treating it twice with 20% (v/v) piperidine/DMF solution for 5 and 15 min (10 mL). The resin was washed with DMF (6×10 mL), DCM (6×10 mL) and DMF (6×10 mL). Kaiser test on peptide resin aliquot upon completion of Fmoc-deprotection was positive. The peptidyl resin was cleaved as mentioned in procedure for cleavage using cleavage cocktail A to yield (450 mg), 69% yield. The crude material was purified by preparative HPLC on Zorbax Eclipse XDB-C18 column (9.4 mm×250 mm, 5 μm) with buffer A: 0.1% TFA/Water, buffer B: 0.1% TFA in 9:1 acetonitrile/water. The peptide was eluted by gradient elution 0-5 min=5-20% buffer B, 5-40 min=20-35% buffer B with a flow rate of 5 mL/min. HPLC: (method 2): RT—14.6 min (94.4%); LCMS Calculated Mass: 3237.83, Observed Mass: 1619.9 [M/2+H]$^+$;1080.2 [M/3+H]$^+$ Example 2

Synthesis of Sequence Shown in SEQ ID NO: 49

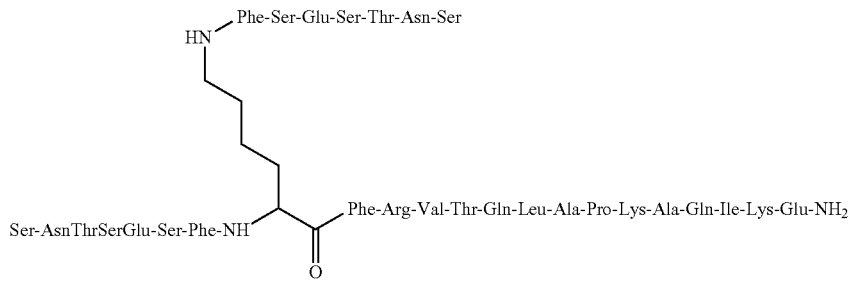

Synthesis of Linear Fragment—Fmoc-FRVTQLAPKAQ-IKE

Desiccated CLEAR-Amide resin ((100-200 mesh) 0.4 mmol/g, 0.5 g) was distributed in 2 polyethylene vessels equipped with a polypropylene filter. The linear peptide synthesis on solid phase were carried out automatically, using Symphony parallel synthesizer (PTI) using the synthesis programs mentioned in the table below. Swelling, C-terminal amino acid [Fmoc-Glu(OtBu)-OH] attachment and capping of the peptidyl resin was carried out as per the protocol in Table I. Subsequent amino acid coupling was carried out as mentioned in Table II. The amino acids used in the synthesis were Fmoc Phe-OH, Fmoc-Arg(Pbf)-OH, Fmoc-Val-OH, Fmoc-Thr(OtBu)-OH, Fmoc-Gln(Trt)-OH, Fmoc-Lys(Boc)-OH, Fmoc-Leu-OH, Fmoc-Ala-OH, Fmoc-Pro-OH, Fmoc-Ile-OH. After the completion of Fmoc-Phe-OH coupling the resin was taken out form peptide synthesiser and manual coupling was carried out as follows.

Fmoc-Phe-OH peptidyl resin from automated synthesiser was pooled in to a glass vessel with frit. The Fmoc group of the peptidyl resin was deprotected by treating it twice with 20% (v/v) piperidine/DMF solution for 5 and 15 min (10 mL). The resin was washed with DMF (6×15 mL), DCM (6×15 mL) and DMF (6×15 mL). Kaiser test on peptide resin aliquot upon completion of Fmoc-deprotection was positive.

Fmoc-Lys (Fmoc)-OH (0.48 g; 4 equiv. 0.8 mmol) in dry DMF was added to the deprotected resin and coupling was initiated with DIC (0.15 mL; 5 equiv, 1 mmol) and HOBT (0.08 g; 5 equiv, 0.6 mmol) in DMF. The concentration of each reactant in the reaction mixture was approximately 0.4 M. The mixture was rotated on a rotor at room temperature for 3 h. Resin was filtered and washed with DMF (6×15 mL), DCM (6×15 mL) and DMF (6×15 mL). Kaiser test on peptide resin aliquot upon completion of coupling was negative. The Fmoc group on the peptidyl resin is deprotected by treating it twice with 20% (v/v) piperidine/DMF solution for 5 and 15 min (15 mL). The resin was washed with DMF (6×15 mL), DCM (6×15 mL) and DMF (6×15 mL). Kaiser test on peptide resin aliquot upon completion of Fmoc-deprotection was positive.

After the deprotection of Fmoc group on Fmoc-Lys (Fmoc)-attached peptidyl resin the peptide chain growth was carried out from both the free amino terminus suing 8 equivalent excess of amino acid (1.6 mmol, 8 equivalent excess of HOBt (0.22 g, 1.6 mmol) and 10 equivalent excess of DIC (0.32 mL, 2 mmol) relative to resin loading. The coupling was carried out at room temperature for 3 h. The amino acids coupled to the peptidyl resin were; Fmoc-Phe-OH (0.62 g; 8 equiv, 1.6 mmol), Fmoc-Ser (OtBu)-OH (0.62 g; 8 equiv, 1.6 mmol), Fmoc-Glu (OtBu)-OH (0.68 g; 8 equiv, 1.6 mmol), Fmoc-Ser (OtBu)-OH (0.62 g; 8 equiv, 1.6 mmol), Fmoc-Thr (OtBu)-OH (0.64 g; 8 equiv, 1.6 mmol), Fmoc-Asn (Trt)-OH (0.95 g; 8 equiv, 1.6 m mol) and N-terminus amino acids as Boc-Ser (OtBu)-OH (0.41 g; 8 equiv, 1.6 mmol) The peptidyl resin was cleaved as mentioned in procedure for cleavage using cleavage cocktail A to yield (565 mg), 70% yield. The crude material was purified by preparative HPLC on Zorbax Eclipse XDB-C18 column (9.4 mm×250 mm, 5 µm) with buffer A: 0.1% TFA/Water, buffer B: Acetonitrile. The peptide was eluted by gradient elution 0-5 min=5-10% buffer B, 10-20 min=29% buffer B with a flow rate of 7 mL/min. HPLC: (method 1): RT—12 min (96%); LCMS Calculated Mass: 3261.62, Observed Mass: 1631.6 [M/2+H]⁺; 1088 [M/3+H]⁺;); 816.2[M/4+H]⁺.

Example 3

Synthesis of the Sequence in SEQ ID NO: 102 using Symphony parallel synthesizer (PTI) using the synthesis programs mentioned in the table below. Swelling, C-terminal amino acid [Fmoc-Ser(OtBu)-OH] attachment and capping of the peptidyl resin was carried out as per the protocol in Table I. Subsequent Fmoc-Amino acids are coupled as mentioned in Table II. The amino acids used in the synthesis were Fmoc-Glu(OtBu)-OH, Fmoc-Tyr(OtBu)-OH, Fmoc-Trp(Boc)-OH, Fmoc-Asp(OtBu)-OH, Fmoc-Val-OH, Fmoc-Thr(OtBu)-OH, Fmoc-Gln(Trt)-OH, Fmoc-Lys (Boc)-OH, Fmoc-Leu-OH, Fmoc-Asn(Trt)-OH Fmoc-Ala-OH, Fmoc-Pro-OH, Fmoc-Ile-OH, Fmoc-Ahx-OH. In the case of Biotin coupling the Biotin (0.15 g in 2.5 mL DMF) was dissolved in DMF/DMSO (1:1) and added manually to the reaction vessel in automated peptide synthesiser and coupling reaction was continued as in steps 3 and 4 Table II (Amino acid is replaced with biotin).

Orthogonal Deprotection of Dde Croup

The ε-amino group of sixteenth residue lysine (from N-terminus) used as branching point was protected with Dde group. After completion of the linear peptide chain Dde protection of E-amino group of the lysine was orthogonally deprotected by treating the resin with 2.5% (v/v) Hydrazine hydrate solution in DMF (2×7.30 min) was carried out in automated synthesizer via manual addition of hydrazine hydrate solution. The resin was further washed on a manual program in parallel synthesizer as in step 4, Table II. The coupling of amino acid in the branch was carried out by the incorporation of subsequent amino acids using program for amino acid coupling as mentioned in Table II starting with Fmoc-Ser (OtBu)-OH. The N-terminus acid in the branch peptidyl resin; Fmoc-Lys(Boc)-OH was coupled using the program as mentioned in Table III. The peptidyl resin was cleaved as mentioned in procedure for cleavage using cleavage cocktail B to yield (516 mg), 65% yield. The crude material was purified by preparative HPLC on Zorbax Eclipse XDB-C18 column (9.4 mm×250 mm, 5 µm) with buffer A: 0.1% TFA/Water, buffer B: acetonitrile. The peptide was eluted by gradient elution 0-4 min=10% buffer B,

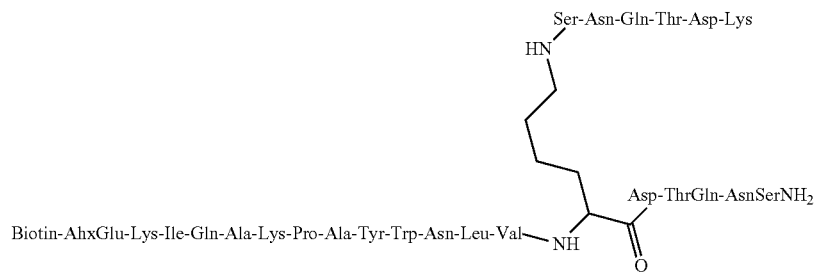

Desiccated CLEAR-Amide resin ((100-200 mesh) 0.49 mmol/g, 0.5 g) was distributed in 2 polyethylene vessels equipped with a polypropylene filter. The linear peptide synthesis on solid phase were carried out automatically, 4-25 min=10-28% buffer B with a flow rate of 7 mL/min. HPLC: (method 1): RT—11.94 min (96%); LCMS Calculated Mass: 3245.69, Observed Mass: 1623 [M/2+H]⁺; 1082.3 [M/3+H]⁺; 811.8 [M/4+H]⁺.

Example 4

Synthesis of Sequence Shown in SEQ ID NO: 61

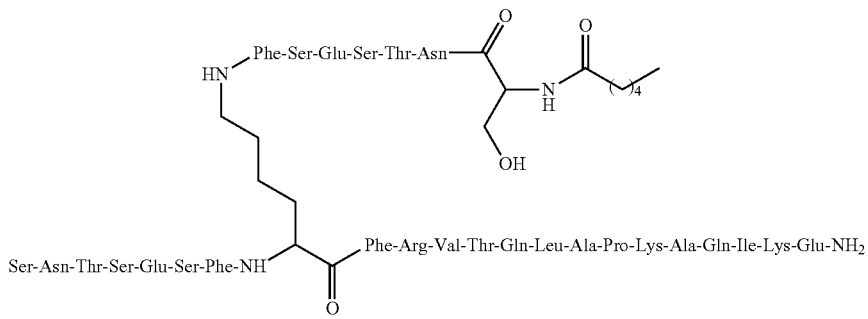

Desiccated CLEAR-Amide resin ((100-200 mesh) 0.4 mmol/g, 0.3 g) was taken in polyethylene vessel equipped with a polypropylene filter. The linear peptide synthesis on solid phase were carried out automatically, using Symphony parallel synthesizer (PTI) using the synthesis programs mentioned in the table below. Swelling, C-terminal amino acid [Fmoc-Glu(OtBu)-OH] attachment and capping of the peptidyl resin was carried out as per the protocol in Table I. Subsequent Fmoc-Amino acids are coupled as mentioned in Table II. The amino acids used in the synthesis were Fmoc Phe-OH, Fmoc-Arg(Pbf)-OH, Fmoc-Val-OH, Fmoc-Thr (OtBu)-OH, Fmoc-Gln(Trt)-OH, Fmoc-Lys(Boc)-OH, Fmoc-Leu-OH, Fmoc-Ala-OH, Fmoc-Pro-OH, Fmoc-Asn (Trt)-OH, Fmoc-Ile-OH, Fmoc-Ser(OtBu)-OH, Fmoc-Glu (OtBu)-OH.

Orthogonal Deprotection of Dde Croup

The N-terminal amino acid Ser(OtBu)-OH in the linear chain of the peptide was coupled as N-Boc amino acid in the same procedure as employed for N-Fmoc amino acid. The ε-amino group of fifteenth residue lysine (from C-terminus) used as branching point was protected with Dde group. After completion of the linear peptide chain Dde protection of ε-amino group of the lysine was orthogonally deprotected by treating the resin with 2.5% (v/v) Hydrazine hydrate solution in DMF (2×7.30 min) was carried out in automated synthesizer via manual addition of hydrazine hydrate solution. The resin was further washed on a manual program in parallel synthesizer as in step 4, Table II. The coupling of amino acid in the branch was carried out by the incorporation of subsequent amino acids using program for amino acid coupling as mentioned in table II starting with Fmoc-Phe-OH. The amino acids used in the synthesis were Fmoc-Thr(OtBu)-OH, Fmoc-Asn(Trt)-OH, Fmoc-Ser(OtBu)-OH, Fmoc-Glu(OtBu)-OH. The N-terminus amino acid coupling was carried out using hexanoic acid (0.22 g in 2.5 mL DMF) was added manually to the reaction vessel in automated peptide synthesiser and coupling reaction was continued as in step 3 and 4 table 2 (Amino acid is replaced with hexanoic acid). The peptidyl resin was cleaved as mentioned in procedure for cleavage using cleavage cocktail A to yield (320 mg), 74% yield. The crude material was purified by preparative HPLC on Zorbax Eclipse XDB-C18 column (9.4 mm×250 mm, 5 μm) with buffer A: 0.1% TFA/Water, buffer B: 0.1% TFA in 9:1 acetonitrile/water. The peptide was eluted by gradient elution 0-25 min=5-50% buffer B with a flow rate of 7 mL/min. HPLC: (Method 1): RT—12.8 min (94.4%); LCMS Calculated Mass: 3359.62, Observed Mass: 1680.3 [M/2+H]$^+$; 1120.4 [M/3+H]$^+$; 840.5 [M/4+H]$^+$.

Example 5

Synthesis of Sequence Shown in SEQ ID NO: 64

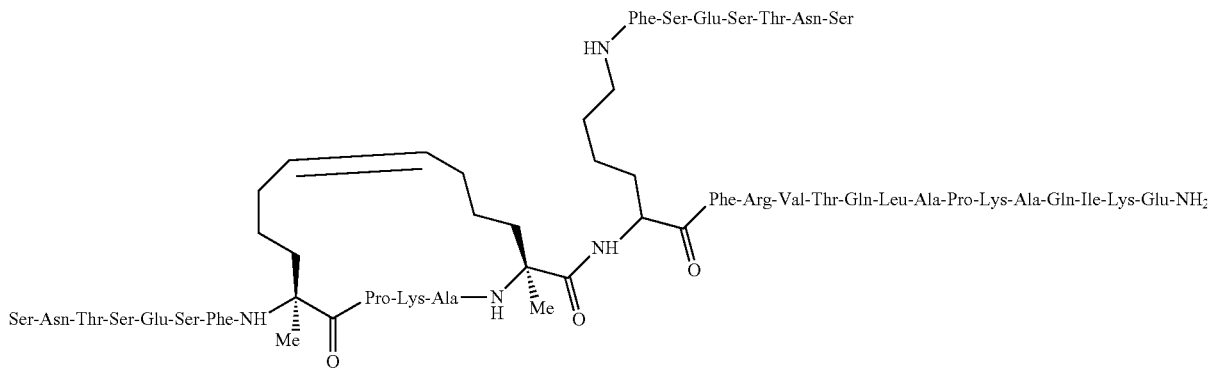

The synthesis of Example 5 was performed on Clear amide resin (0.46 mmol/g; 500 mg) from peptide international using Symphony parallel synthesizer in two reaction vessels. First amino acid attachment and capping of the peptidyl resin was carried out as per the protocol in Table I. Subsequent amino acid coupling was carried out as mentioned in Table II. During the automated synthesis for the coupling of position 8 and 12, the sequence was paused after wash step (step 2) in Table II followed by manual addition of Fmoc-(R)-2-(4'-pentenyl) Alanine and subsequent manual program addition of reagent as mentioned in step 3, 4 in Table 2 and the sequence is resumed for subsequent amino acid coupling. The N-terminus amino acids are attached as Boc amino acid using similar procedures used for Fmoc-amino acid.

Orthogonal Deprotection of Dde Group

The ε-amino group of fifteenth residue lysine from C-terminus was used as branching point and was protected with Dde group. After completion of the linear peptide chain Dde protection of ε-amino group of the lysine was orthogonally deprotected by treating the resin with 2.5% (v/v) Hydrazine hydrate solution in DMF (2×7.30 min) was carried out in automated synthesizer via manual addition of hydrazine hydrate solution. The resin was further washed as manual program as in step 4, Table II. The coupling of amino acid in the branch was carried out by the incorporation of subsequent amino acids using program for amino acid coupling as mentioned in table II starting with Fmoc-Phe-OH. The amino acids used in the synthesis were Fmoc-Thr (OtBu)-OH, Fmoc-Asn(Trt)-OH, Fmoc-Ser(OtBu)-OH, Fmoc-Glu(OtBu)-OH. The N-terminus amino acids are attached as Boc amino acid using similar procedures used for Fmoc-amino acid.

Stitching of Olefinic Amino Acids

Stitching of the two olefinic amino acids was carried out in customized solid phase peptide vessel of 20 mL capacity with a sintered disc. After the completion of the linear peptide sequence, ring closure metathesis of resin bound N-terminal capped peptides was performed using 20 mol % Grubbs catalyst (1.7 g in 15 ml) in degassed 1, 2 dichloroethane (DCE) for 2 hours at room temperature. After 2 h the resin was washed with DCE, DCM, methanol and then dried in Vacuum over night. The peptidyl resin was cleaved as mentioned in procedure for cleavage using cleavage cocktail C to yield (530 mg), 63% yield. The crude material was purified by preparative HPLC on Zorbax Eclipse XDB-C18 column (9.4 mm×250 mm, 5 μm) with buffer A: 0.1% TFA/Water, buffer B: acetonitrile. The peptide was eluted by gradient elution 0-30 min=10-80% buffer B, with a flow rate of 7 mL/min. HPLC: (method 1): RT—12.9 min (95.4%); LCMS Calculated Mass: 3697, Observed Mass: 1232.5 [M/3+H]⁺; 924.9 [M/4+H]⁺; 740.2[M/5+H]⁺.

Example 6

Synthesis of Sequence Shown in SEQ ID NO: 69

```
Ser-Asn-Thr-Ser-Glu-Ser-Phe-Lys-Ser-Asn-Thr-Ser-
Glu-Ser-Phe-Phe-Arg-Val-Thr-Gln-Leu-Ala-Pro-Lys-
Ala-Gln-Ile-Lys-Glu-NH2
```

Desiccated CLEAR-Amide resin ((100-200 mesh) 0.46 mmol/g, 0.25 g) was taken in polyethylene vessel equipped with a polypropylene filter. The linear peptide synthesis on solid phase were carried out automatically, using Symphony parallel synthesizer (PTI) using the synthesis programs mentioned in the table below. Swelling, C-terminal amino acid [Fmoc-Glu(OtBu)-OH] attachment and capping of the peptidyl resin was carried out as per the protocol in Table I. Subsequent Fmoc-Amino acids are coupled as mentioned in Table II. The amino acids used in the synthesis were Fmoc Phe-OH, Fmoc-Arg(Pbf)-OH, Fmoc-Val-OH, Fmoc-Thr (OtBu)-OH, Fmoc-Asn(Trt)-OH, Fmoc-Gln(Trt)-OH, Fmoc-Lys(Boc)-OH, Fmoc-Leu-OH, Fmoc-Ala-OH, Fmoc-Pro-OH, Fmoc-Ile-OH, Fmoc-Ser(OtBu)-OH. The N-terminus amino acid Fmoc-Ser(OtBu) was coupled as per the program in table III. The peptidyl resin was cleaved as mentioned in procedure for cleavage using cleavage cocktail A to yield (265 mg), 70% yield. The crude material was purified by preparative HPLC on Zorbax Eclipse XDB-C18 column (9.4 mm×250 mm, 5 μm) with buffer A: 0.1% TFA/Water, buffer B: acetonitrile. The peptide was eluted by gradient elution 0-30 min=10-80% buffer B, with a flow rate of 7 mL/min. HPLC: (method 1): RT—12.04 min (95.2%); LCMS Calculated Mass: 3261.8, Observed Mass: 1630.7 [M/2+H]⁺; 1087.5 [M/3+H]⁺.

Example 7

Synthesis of Sequence Shown in SEQ ID NO: 83

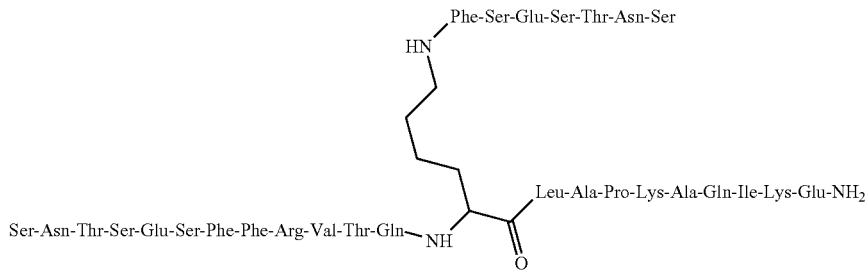

Desiccated CLEAR-Amide resin ((100-200 mesh) 0.4 mmol/g, 0.3 g) was taken in polyethylene vessels equipped with a polypropylene filter. The linear peptide synthesis on solid phase were carried out automatically, using Symphony parallel synthesizer (PTI) using the synthesis programs mentioned in the table below. Swelling, C-terminal amino acid [Fmoc-Glu(OtBu)-OH] attachment and capping of the peptidyl resin was carried out as per the protocol in Table I. Subsequent amino acid coupling was carried out as mentioned in Table II. The amino acids used in the synthesis were Fmoc Phe-OH, Fmoc-Arg(Pbf)-OH, Fmoc-Val-OH, Fmoc-Thr(OtBu)-OH, Fmoc-Gln(Trt)-OH, Fmoc-Asn(Trt)-

OH, Fmoc-Lys(Boc)-OH, Fmoc-Leu-OH, Fmoc-Ala-OH, Fmoc-Pro-OH, Fmoc-Ile-OH.

Orthogonal Deprotection of Dde Group

The N-terminal amino acid Ser(OtBu)-OH in the linear chain of the peptide was coupled as N-Boc amino acid in the same procedure as employed for N-Fmoc amino acid. The ε-amino group of thirteenth residue lysine from N-terminus used as branching point was protected with Dde group. After completion of the linear peptide chain Dde protection of ε-amino group of the lysine was orthogonally deprotected by treating the resin with 2.5% (v/v) Hydrazine hydrate solution in DMF (2×7.30 min) was carried out in automated synthesizer via manual addition of hydrazine hydrate solution. The resin was further washed as in step 4, table II. The coupling of amino acid in the branch was carried out by the incorporation of subsequent amino acids using program for amino acid coupling as mentioned in table II starting with Fmoc-Phe-OH. The amino acids used in the synthesis were Fmoc-Thr(OtBu)-OH, Fmoc-Asn(Trt)-OH, Fmoc-Ser(OtBu)-OH, Fmoc-Glu(OtBu)-OH. The N-terminus amino acid Fmoc-Ser(OtBu) was coupled as per the program in table III. The peptidyl resin was cleaved as mentioned in procedure for cleavage using cleavage cocktail A to yield (320 mg), 74% yield. The crude material was purified by preparative HPLC on Zorbax Eclipse XDB-C18 Prep-HT column (21.2 mm×150 mm, 5 μm) with buffer A: 0.1% TFA/Water, buffer B: 0.1% TFA in acetonitrile. The peptide was eluted by gradient elution 0-5 min=5-20% buffer B, 5-22 min=20-30% buffer B with a flow rate of 18 mL/min. HPLC: (method 1): RT—12.5 min (97.6%); LCMS Calculated Mass: 3261.62, Observed Mass: 1631.6 [M/2+H]$^+$; 1088 [M/3+H]$^+$; 816.2 [M/4+H]$^+$.

Example 8

Synthesis of Sequence Shown in SEQ ID NO: 88 acid [Fmoc-Glu(OtBu)-OH] attachment and capping of the peptidyl resin was carried out as per the protocol in Table I. Subsequent amino acid coupling was carried out as mentioned in Table II. 5 equivalent excess of amino acid and coupling reagent relative to resin loading was used for coupling. The amino acids used in the synthesis were Fmoc-Phe-OH, Fmoc-Arg(Pbf)-OH, Fmoc-Val-OH, Fmoc-Thr(OtBu)-OH, Fmoc-Gln(Trt)-OH, Fmoc-Asn(Trt)-OH, Fmoc-Lys(Boc)-OH, Fmoc-Leu-OH, Fmoc-Ala-OH, Fmoc-Pro-OH, Fmoc-Ile-OH.

Orthogonal Deprotection of Dde Group

The N-terminal amino acid Ser(OtBu)-OH in the linear chain of the peptide was coupled as N-Boc amino acid in the same procedure as employed for N-Fmoc amino acid. The ε-amino group of eighth residue lysine used as branching point was protected with Dde group. After completion of the linear peptide chain Dde protection of ε-amino group of the lysine was orthogonally deprotected by treating the resin with 2.5% (v/v) Hydrazine hydrate solution in DMF (2×7.30 min) was carried out in automated synthesizer via manual addition of hydrazine hydrate solution. The resin was further washed as in step 4, Table II. The coupling of amino acid in the branch was carried out by the incorporation of subsequent D-amino acids using program for amino acid coupling as mentioned in table II starting with Fmoc-D-Phe-OH. The amino acids used in the synthesis were Fmoc-D-Thr(OtBu)-OH, Fmoc-D-Asn(Trt)-OH, Fmoc-D-Ser(OtBu)-OH, Fmoc-D-Glu(OtBu)-OH. The N-terminus amino acid Fmoc-D-Ser(OtBu) was coupled as per the program in Table III. The peptidyl resin was cleaved as mentioned in procedure for cleavage using cleavage cocktail A to yield (350 mg), 89% yield. The crude material was purified by preparative HPLC on Zorbax Eclipse XDB-C18 Prep-HT column (21.2 mm×150 mm, 5 μm) with buffer A: 0.1% TFA/Water, buffer

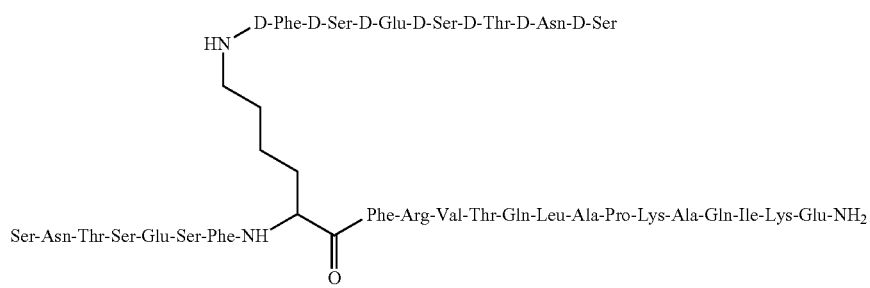

Desiccated CLEAR-Amide resin ((100-200 mesh) 0.4 mmol/g, 0.3 g) was taken in polyethylene vessels equipped with a polypropylene filter. The linear peptide synthesis on solid phase were carried out automatically, using Symphony parallel synthesizer (PTI) using the synthesis programs mentioned in the table below. Swelling, C-terminal amino B: 0.1% TFA in acetonitrile. The peptide was eluted by gradient elution 0-5 min=5-20% buffer B, 5-18 min=20-27% buffer B with a flow rate of 18 mL/min. HPLC: (method 1): RT—12.06 min (96.6%); LCMS Calculated Mass: 3261.6, Observed Mass: 1631.6 [M/2+H]$^+$; 1088 [M/3+H]$^+$; 816.2 [M/4+H]$^+$.

Example 9
Synthesis of Sequence Shown in SEQ ID NO: 134
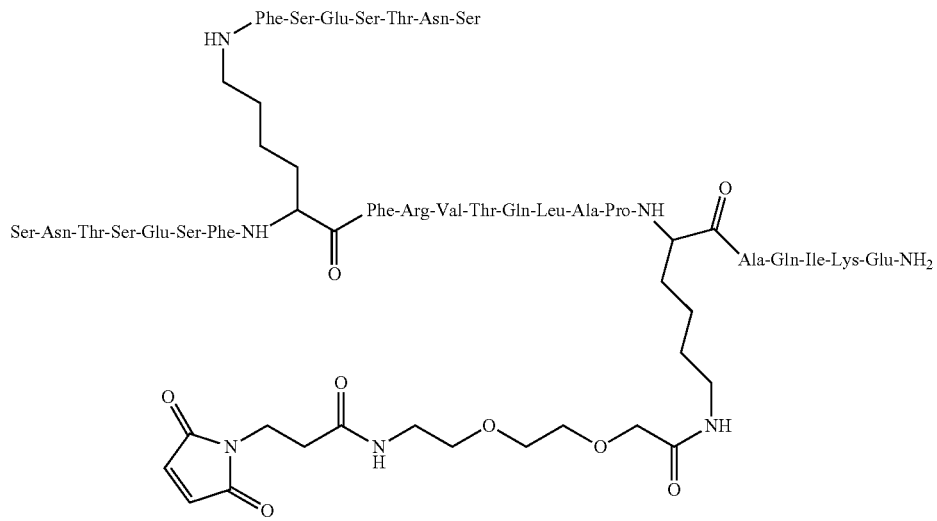

Desiccated Rink-Amide MBHA resin (100-200 mesh) 0.66 mmol/g, 1 g) was distributed in 4 polyethylene vessels equipped with a polypropylene filter. The linear peptide synthesis on solid phase were carried out automatically, using Symphony parallel synthesizer (PTI) using the synthesis programs mentioned in the table below. Swelling, C-terminal amino acid [Fmoc-Glu(OtBu)-OH] attachment and capping of the peptidyl resin was carried out as per the protocol in Table I. Subsequent amino acid coupling was carried out as mentioned in Table II. The amino acids used in the synthesis were Fmoc Phe-OH, Fmoc-Arg(Pbf)-OH, Fmoc-Val-OH, Fmoc-Thr(OtBu)-OH, Fmoc-Gln(Trt)-OH, Fmoc-Asn(Trt)-OH, Fmoc-Lys(Boc)-OH, Fmoc-Leu-OH, Fmoc-Ala-OH, Fmoc-Pro-OH, Fmoc-Ile-OH. In the linear sequence $8^{th}$ amino acid from the N-terminus, Lys, was coupled as Fmoc-Lys(Fmoc)-OH. From the next residue onwards (Fmoc-Phe-OH) the coupling of subsequent amino acids was carried out as in Table II with 10 equivalents excess of amino acid (5 mL each of 0.25 M amino acid, 0.25 M HBTU in 1 M NMM/DMF) coupling reagent relative to resin loading was used for coupling. The N-terminal amino acid Ser(OtBu)-OH at the both N-terminus of the peptide was coupled as N-Boc amino acid in the same procedure as employed for N-Fmoc amino acid.

Orthogonal Deprotection of Dde Group

The ϵ-amino group of seventeenth residue lysine from N-terminus used as branching point was protected with Dde group. After completion of the linear peptide chain Dde protection of ϵ-amino group of the lysine was orthogonally deprotected by treating the resin with 2.5% (v/v) Hydrazine hydrate solution in DMF (2×7.30 min) was carried out in automated synthesizer via manual addition of hydrazine hydrate solution. The resin was further washed using manual program in synthesizer as in step 4, Table II. The coupling of amino acid in the branch was carried out by the incorporation of subsequent amino acids using program for amino acid coupling as mentioned in table II starting with Fmoc-8-amino 3,6-dioxaoctanoic acid (0.24 g in 2.5 mL DMF) and for maleimdo propanoic acid (0.1 g in 2.5 mL DMF). The peptidyl resin was cleaved as mentioned in procedure for cleavage using cleavage cocktail C to yield (1.6 g), 70% yield. The crude material was purified by preparative HPLC on Phenomenex-C18 silica column (10 mm×250 mm, 5 μm) with buffer A: 0.1% TFA/Water, buffer B: acetonitrile. The peptide was eluted by gradient elution 0-9 min=10-15% buffer B with a flow rate of 6 mL/min. HPLC: (method 1): RT—11.7 min (95%); LCMS Calculated Mass: 3557.09, Observed Mass: 1779.8[M/2+H]$^+$1187.1[M/3+H]$^+$.

Example 10

Synthesis of Sequence Shown in SEQ ID NO: 77

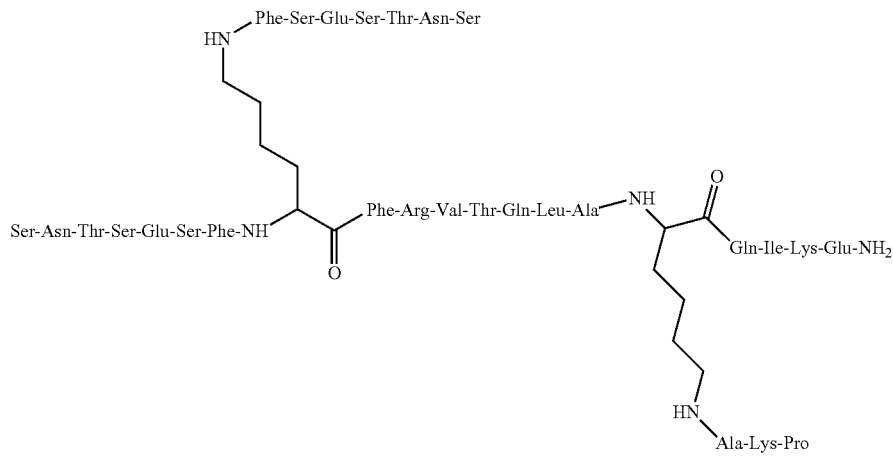

Desiccated CLEAR amide (100-200 mesh) 0.4 mmol/g, 0.3 g) was taken in polyethylene vessels equipped with a polypropylene filter. The linear peptide synthesis on solid phase were carried out automatically, using Symphony parallel synthesizer (PTI) using the synthesis programs mentioned in the table below. Swelling, C-terminal amino acid [Fmoc-Glu(OtBu)-OH] attachment and capping of the peptidyl resin was carried out as per the protocol in Table I. Subsequent amino acid coupling was carried out as mentioned in Table II. In the linear sequence 8$^{th}$ amino acid from the N-terminus, Lys, was coupled as Fmoc-Lys (Dde)-OH. The Sixteenth Lysine residue in the linear chain was coupled as Fmoc-Lys (Alloc)-OH. The N-terminal amino acid Ser (OtBu)-OH in the linear chain of the peptide was coupled as N-Boc amino acid in the same procedure as employed for N-Fmoc amino acid.

Orthogonal Deprotection of Dde Group

The ϵ-amino group of eighth residue lysine from N-terminus used as branching point was protected with Dde group. After completion of the linear peptide chain Dde protection of ϵ-amino group of the lysine was orthogonally deprotected by treating the resin with 2.5% (v/v) Hydrazine hydrate solution in DMF (2×7.30 min) was carried out in automated synthesizer via manual addition of hydrazine hydrate solution. The resin was further washed as in step 4, table II. The coupling of amino acid in the branch was carried out by the incorporation of subsequent amino acids using program for amino acid coupling as mentioned in table II. The amino acids used were Fmoc-Phe-OH, Fmoc-Thr (OtBu)-OH, Fmoc-Asn(Trt)-OH, Fmoc-Ser(OtBu)-OH, Fmoc-Glu(OtBu)-OH. OH. The N-terminal amino acid in the branch, Ser(OtBu)-OH in the linear chain of the peptide was coupled as N-Boc amino acid in the same procedure as employed for N-Fmoc amino acid.

Deprotection of Alloc Protecting Group

The ϵ-amino group sixteenth residue Lysine from N-terminus was coupled as Lys(Alloc) to initiate an additional branching point in the linear sequence. Alloc protecting group fromLys (Alloc) was removed from the peptidyl resin by treating with tetrakistriphenylphosphine palladium (0) (5 Equiv; 2.8 g) and Phenylsilane (10 eqv 0.65 mL) in a solution of chloroform/N-methylpyrrolidine (95/5 v/v) for 6 h under argon. The resin was washed with a solution of 10% NMP in chloroform (6×10 mL), 1% DIEPA in DMF (6×10 mL), DCM (6×10 mL), DMF (6×10 mL). After the completion of Alloc deprotection the resin was loaded back to automated peptide synthesiser. The free amino group was used as second branch point in the sequence. The coupling of amino acid in the branch was carried out by the incorporation of subsequent amino acids using program for amino acid coupling as mentioned in table II. The amino acids used were Fmoc-Lys(Boc)-OH, Fmoc-Ala-OH, Boc-Pro-OH. The N-terminal amino acid in the branch, Proline was coupled as N-Boc amino acid in the same procedure as employed for N-Fmoc amino acid. The peptidyl resin was cleaved as mentioned in procedure for cleavage using cleavage cocktail A to yield (200 mg), 50% yield. The crude material was purified by preparative HPLC on Zorbax Eclipse XDB-C18 column (9.4 mm×250 mm, 5 μm) with buffer A: 0.1% TFA/Water, buffer B: 0.1% TFA in acetonitrile. The peptide was eluted by gradient elution 0-2 min=10-20% buffer B, 2-8 min=20-25% buffer B, 8-19 min=25-29% buffer B with a flow rate of 7 mL/min. HPLC: (method 1): RT—12.3 min (94%); LCMS Calculated Mass: 3389.8, Observed Mass: 1695.2 [M/2+H]$^+$;1130.5 [M/3+H]$^+$848.3 [M/4+H]$^+$.

Example 11

Synthesis of the Sequence Shown in SEQ ID NO: 129

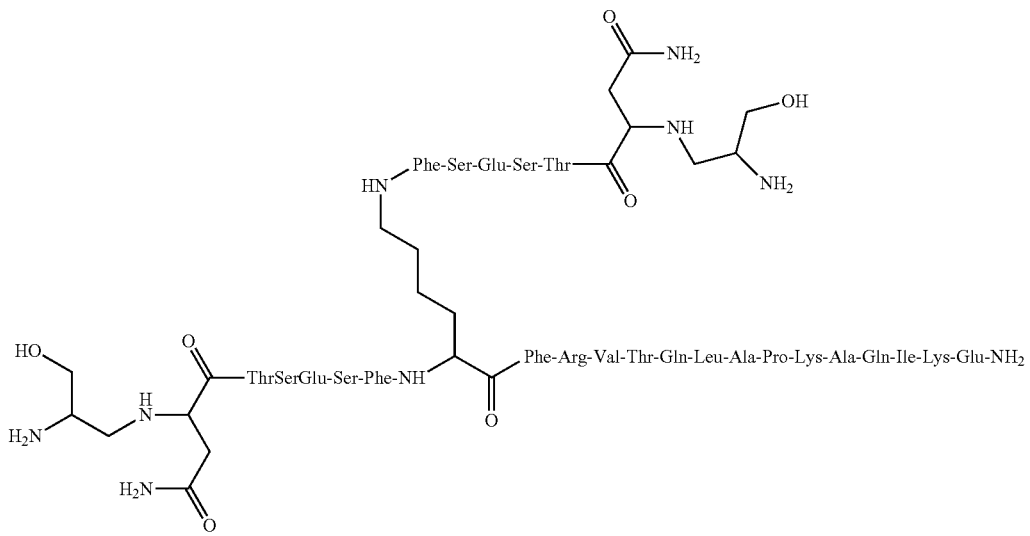

Synthesis of Building Block

To a solution of N-Boc amino acid (10.0 g, 38.28 mmol) in THF (100 mL) at −20° C., was added N-methyl morpholine (NMM, 4.25 g, 42.11 mmol) and ethylchloroformate (4.57 g, 42.11 mmol) and the resultant mixture was stirred at same temperature for 20 min. The inorganic salts were filtered off and the filtrate was treated with moist $NaBH_4$ (2.9 g, 76.56 mmol) for 10-15 min. The reaction mixture was then partitioned between water and EtOAc. Organic layer was washed with water, 10% $NaHCO_3$ solution (100 mL×2) and brine, dried over $Na_2SO_4$ and evaporated under reduced pressure to yield N-Boc aminol, which was further purified by silica gel column chromatography (eluent: 0-50% EtOAc in Hexane) to yield 8.2 g of product [yield: 85.4%, Mass: Cal. 247.3, Obs: 248.2 (M+1), 270.2 (M+Na)].

To the solution of N-Boc-aminol (3.0 g, 12.13 mmol) in distilled DCM (30.0 mL) was added Dess-Martin periodinane (10.3 g, 24.27 mmol) in a portion wise manner at 0° C. and stirred at rt under $N_2$ atmosphere for 30 min until the reactants were consumed as determined by TLC analysis. The reaction mixture was quenched by adding 1.0M $Na_2S_2O_3$ solution, and the product was extracted with DCM. The organic extract was washed with (5%, 1:1) $Na_2S_2O_3$/$NaHCO_3$ solution (20 mL×2), brine (20 mL) and dried over $Na_2SO_4$. The solvent was removed under reduced pressure to give the crude product, which was further purified by silica gel column chromatography (eluent: 0-20% EtOAc in Hexane) to yield 2.4 g pure product 1 (yield—82%, Mass-Cal. 245.32, Obs—247.9 (M+1), 265.1 (M+Na)).

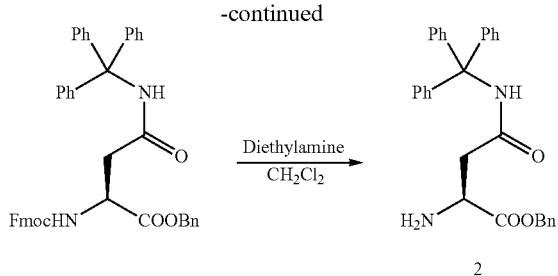

To a solution of Fmoc-Asn(trt)-OH (4.0 g, 6.7 mmol) in 30.0 mL of DMF was added Cs$_2$CO$_3$ (2.62 g, 8.0 mmol). The mixture was then cooled to 0° C. and benzyl bromide (1.37 g, 8.0 mmol) was added and the resultant solution was stirred for 30 min at 0° C. and then at rt for 12 h. The reaction mixture was concentrated under reduced pressure and diluted with EtOAc (50 mL), the organic layer was washed with NaHCO$_3$ (2×50 mL) and brine (1×50 mL), dried over Na$_2$SO$_4$, filtered and concentrated in vacuuo and purified by silica gel column chromatography (eluent: 0-30% EtOAc in Hexane) to furnish Fmoc-Asn(trt)-OBn as white solid [yield: 4.5 g, 98.0%; Mass: Cal. 686.28, Obs—687.3 (M+1), 709.1 (M+Na].

To a solution of Fmoc-Asn(Trt)-OBn (3.5 g, 5.1 mmol) in DCM (14.0 mL), diethylamine (14.0 mL) was added and stirred for 1 h at rt. The resulting solution was concentrated in vacuuo and the thick-residue was purified by neutral alumina column chromatography (eluent: 0-50% EtOAc in Hexane then 0-5% MeOH in CHCl$_3$) to yield H-Asn(trt)-Obn 2 (yield: 1.75 g, 73.0%; Mass: Cal. 464.21, Obs—465.3 (M+1), 487.2 (M+Na]).

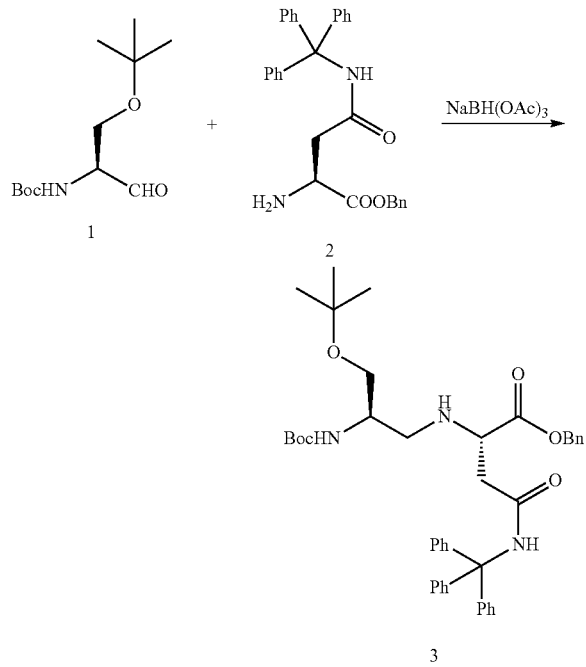

H-Asn(Trt)-OBn (4.5 g, 9.7 mmol), DIPEA (2.5 g, 19.4 mmol) and Boc-Ser(OtBu)-CHO (2.4 g, 9.7 mmol) were mixed in DCM (45 mL) at 0° C. and then allowed to stir at room temperature for 1 h. Again the reaction mixture was cooled to 0° C. and treated with sodium triacetoxyborohydride (4.1 g, 19.4 mmol) and then mixture was allowed to stir at room temperature under N$_2$ atmosphere for 6 h until the reactants were consumed as determined by TLC analysis. The reaction mixture was quenched by adding water, and the product was extracted with DCM. The organic extract was washed with 5% NaHCO$_3$ solution (50 mL×2), 5% citric acid solution (50 mL×2), brine (50 mL) and dried over Na$_2$SO$_4$. The solvent was evaporated to give the crude product which was further purified by silica gel column chromatography (eluent: 5-40% EtOAc in Hexane) to furnish the desired product 3 (yield: 4.2 g, 62.0%; Mass: Cal. 693.27, Obs—694.4 (M+1), 716.0 (M+Na)).

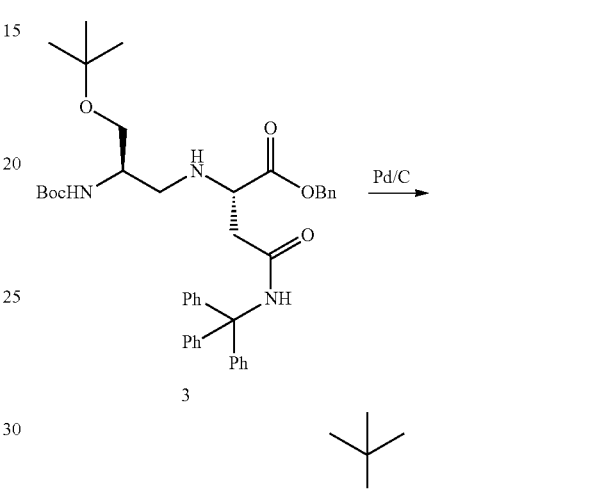

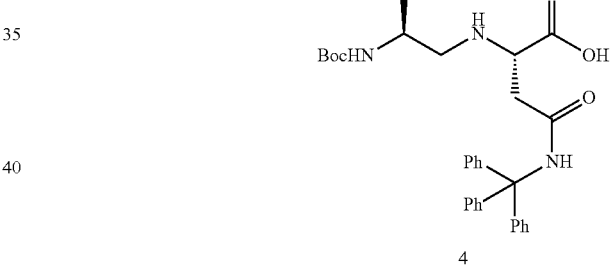

To a solution of compound 3 (4.0 g) in methanol (70.0 mL) under inert atmosphere, was added 10% Pd—C (1.0 g) and the mixture was stirred for 4 h under H$_2$ atmosphere. The completion of the reaction was confirmed by TLC analysis. The catalyst was then removed by filtration through a celite pad, which was then washed with 50 mL of methanol. The combined organic filtrate, on evaporation under reduced pressure resulted in the isolation of the product 4, (Yield: 3.3 g, 96.0%; Mass: Cal. 603.25, Obs—604.4 (M+1), 626.4 (M+Na).

Peptide Synthesis

Desiccated Rink-Amide MBHA resin (100-200 mesh) 0.66 mmol/g, 0.1 g) was taken in polyethylene vessel equipped with a polypropylene filter. The linear peptide synthesis on solid phase were carried out automatically, using Symphony parallel synthesizer (PTI) using the synthesis programs mentioned in the table below. Swelling, C-terminal amino acid [Fmoc-Glu(OtBu)-OH] attachment and capping of the peptidyl resin was carried out as per the protocol in Table I. Subsequent amino acid coupling was carried out as mentioned in Table II. 5 equivalent excess of amino acid and coupling reagent relative to resin loading was used for coupling. The amino acids used in the synthesis were Fmoc Phe-OH, Fmoc-Arg(Pbf)-OH, Fmoc-Val-OH, Fmoc-Thr(OtBu)-OH, Fmoc-Gln(Trt)-OH, Fmoc-Asn(Trt)-OH, Fmoc-Lys(Boc)-OH, Fmoc-Leu-OH, Fmoc-Ala-OH, Fmoc-Pro-OH, Fmoc-Ile-OH. In the linear sequence $8^{th}$ amino acid from the N-terminus, Lys, was coupled as Fmoc-Lys(Fmoc)-OH.

From the next residue onwards (Fmoc-Phe-OH) the coupling of subsequent amino acids was carried out as in Table II with 10 equivalents excess of amino acid (5 mL each of 0.25 M amino acid, 0.25 M HBTU in 1 M NMM/DMF) coupling reagent relative to resin loading was used for coupling. The amino acids used in the synthesis were Fmoc-Thr(OtBu)-OH, Fmoc-Ser(OtBu)-OH, Fmoc-Glu (OtBu)-OH The N-terminal amino acid Boc-SerΨ[CH2NH] Asn(Trt)-OH (0.4 g in 5 mL) at the both N-terminus was coupled as N-Boc amino acid in the same procedure as employed for N-Fmoc amino acid. The peptidyl resin was cleaved as mentioned in procedure for cleavage using cleavage cocktail C to yield (150 mg), 70% yield. The crude sample was preparative HPLC purified and Lyophilised. The crude material was purified by preparative HPLC on Zorbax Eclipse XDB-C18 column (9.4 mm×250 mm, 5 µm) with buffer A: 0.1% TFA/Water, buffer B: acetonitrile. The peptide was eluted by gradient elution 0-25 min=2-30% buffer B, with a flow rate of 7 mL/min. HPLC: (method 1): RT—12 min (93%); LCMS Calculated Mass: 3232.8, Observed Mass: 1617.4[M/2+H]$^+$809.6[M/4+H]$^+$.

Example 12

Synthesis of the Sequence Shown in SEQ ID NO: 75 equiv. 49.5 mmol) dissolved in dry DMF was distributed in equal volume to all the five glass reactor. The coupling was initiated by addition of DIC (7.6 m L; 5 equiv, 49.5 mmol) and HOBT (6.7 g; 49.5 mmol) dissolved DMF distributed equally to the 5 glass reactor vessel. The concentration of each reactant in the reaction mixture was approximately 0.4 M. The mixture was rotated on a rotor at room temperature for 2 h. Resin was filtered and washed with DMF (6×30 mL), DCM (6×30 mL) and DMF (6×30 mL). Kaiser test on peptide resin aliquot upon completion of coupling was negative After the first amino acid attachment, the unreacted amino group, if any, in the resin is capped used acetic anhydride/pyridine/DCM (1:8:8) for 20 minutes to avoid any deletion of the sequence. After capping, resin in individual reactor was washed with DCM (6×30 mL), DMF (6×30 mL), DCM (6×30 mL) and DMF (6×30 mL). The Fmoc group on the C-terminal amino acid attached peptidyl resin was deprotected by treating it twice with 20% (v/v) piperidine/DMF solution for 5 and 15 min (30 mL). The resin was washed with DMF (6×30 mL), DCM (6×30 mL) and DMF (6×30 mL). Kaiser test on peptide resin aliquot upon completion of Fmoc-deprotection was positive.

The subsequent amino acids Fmoc-Lys(Boc)-OH, Fmoc-Ile-OH, Fmoc-Gln(Trt)-OH and Fmoc-Ala-OH was coupled using 5 equivalent excess each of amino acid, DIC and HOBt relative to resin loading. The Sixth residue from the C-terminus Lys was coupled as Fmoc-Lys(Dde)-OH. Fmoc-Lys(Dde)-OH (16 g; 3 equiv. 29.7 mmol) dissolved in dry DMF was distributed in equal volume to all the five glass reactor. The coupling was initiated by addition of DIC (4.5 mL; 3 equiv, 29.7 mmol) and HOBT (4 g; 3 equiv, 29.7

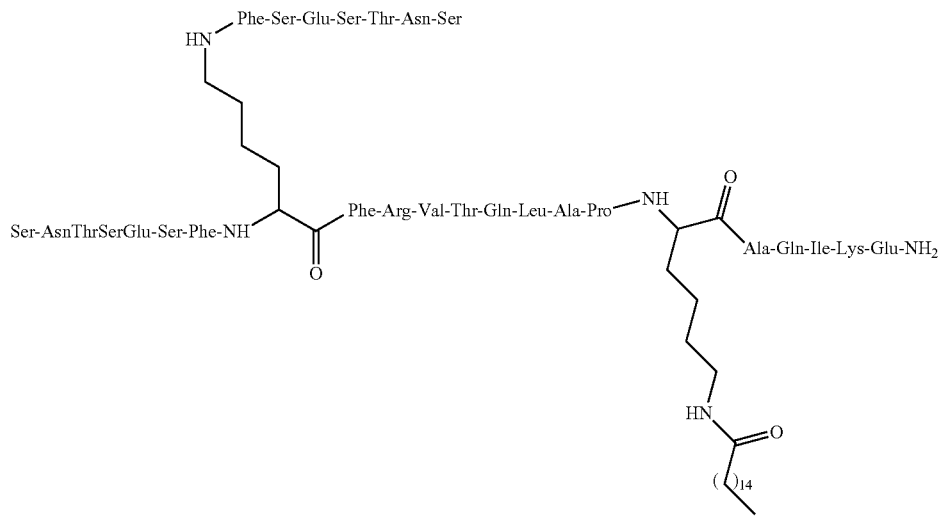

Desiccated Rink Amide MBHA-Amide resin (100-200 mesh, 0.66 mmol/g, 15 g) was distributed equally in to 5 customized solid phase peptide vessel of capacity with a sintered disc glass reactor vessel with a frit. Resin in each of the reactor was swelled in DCM (30 mL) for 1 h and DMF (30 mL) for 1 h. The Fmoc group of the Rink Amide MBHA-Amide was deprotected by treating it twice with 20% (v/v) piperidine/DMF solution for 5 and 15 min (30 mL). The resin was washed with DMF (6×30 mL), DCM (6×30 mL) and DMF (6×30 mL). Kaiser test on peptide resin aliquot upon completion of Fmoc-deprotection was positive. The C-terminal amino acid, Fmoc-Glu(OtBu)-OH (21 g; 5 mmol) dissolved in DMF distributed equally to the 5 glass reactor vessel. The concentration of each reactant in the reaction mixture was approximately 0.4 M. The mixture was rotated on a rotor at room temperature for 3 h. Resin was filtered and washed with DMF (6×30 mL), DCM (6×30 mL) and DMF (6×30 mL). Kaiser test on peptide resin aliquot upon completion of coupling was negative. The Fmoc group of the peptidyl resin was deprotected by treating it twice with 20% (v/v) piperidine/DMF solution for 5 and 15 min (30 mL). The resin was washed with DMF (6×30 mL), DCM (6×30 mL) and DMF (6×30 mL). Kaiser test on peptide resin aliquot upon completion of Fmoc-deprotection was positive.

The subsequent amino acids Fmoc-Phe-OH, Fmoc-Arg(Pbf)-OH, Fmoc-Val-OH, Fmoc-Thr(OtBu)-OH, Fmoc-Gln(Trt)-OH, Fmoc-Leu-OH, Fmoc-Ala-OH, Fmoc-Pro-OH was coupled to the peptidyl resin using 5 equivalent excess of amino acid, HOBt and DIC method. The reaction was carried out for 3 h at room temperature. The fifteenth residue from the C-terminus, Lys was coupled as Fmoc-Lys(Fmoc)-OH. Fmoc-Lys(Fmoc)-OH (17.5 g; 3 equiv. 29.7 mmol) dissolved in dry DMF was distributed in equal volume to all the five glass reactor. The coupling was initiated by addition of DIC (4.5 mL; 3 equiv, 29.7 mmol) and HOBT (4 g; 3 equiv, 29.7 mmol) dissolved DMF distributed equally to the with buffer A: 0.1% TFA/Water, buffer B: 0.1% TFA/acetonitrile. The peptide was eluted by gradient elution 0-3 min=15-25% buffer B, 3-5 min=25-38% buffer B, 5-15 min=38-50% buffer B, 15-19 min=50% buffer B with a flow rate of 15 mL/min. HPLC: (method 3): RT—17.5 min (95.4%); LCMS Calculated Mass: 3499.62, Observed Mass: 1750.3 $[M/2+H]^+$; 1167.2 $[M/3+H]^+$.

Example 13

Synthesis of Sequence Shown in SEQ ID NO: 103

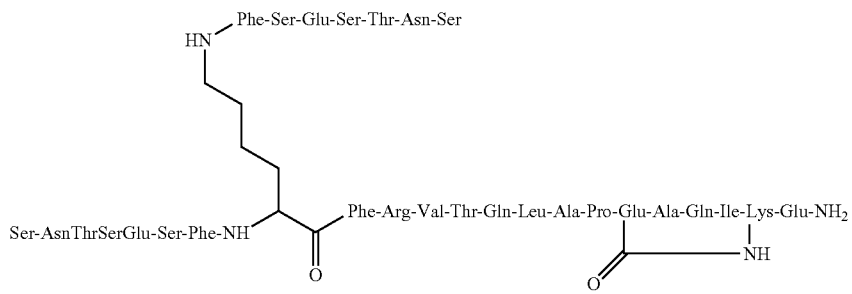

5 glass reactor vessel. The concentration of each reactant in the reaction mixture was approximately 0.4 M. The mixture was rotated on a rotor at room temperature for 3 h. Resin was filtered and washed with DMF (6×30 mL), DCM (6×30 mL) and DMF (6×30 mL). Kaiser test on peptide resin aliquot upon completion of coupling was negative.

The Fmoc group of the peptidyl resin was deprotected by treating it twice with 20% (v/v) piperidine/DMF solution for 5 and 15 min (30 mL). The resin was washed with DMF (6×30 m L), DCM (6×30 mL) and DMF (6×30 mL). After the deprotection of Fmoc-Lys(Fmoc)-attached peptidyl resin the peptide chain growth was carried out from both the free amino terminus suing 8 equivalent excess of amino acid (79 mmol), 8 equivalent excess of HOBt (79 mmol) and 10 equivalent excess of DIC (99 mmol) relative to resin loading. The reaction was carried out for 2 h at room temperature. The amino acids used in the synthesis were Fmoc-Phe-OH, Fmoc-Thr(OtBu)-OH, Fmoc-Asn (Trt)-OH, Fmoc-Ser(OtBu)-OH and Fmoc-Glu(OtBu)-OH. The N-terminal amino acid Serine was coupled as Boc-Ser(OtBu)-OH using DIC/HOBT method (8 equivalent excess relative to resin loading).

Orthogonal Deprotection of Dde Group

The ε-amino group of seventeenth residue lysine from N-terminus used as branching point was protected with Dde group. After completion of the linear peptide chain Dde protection of ε-amino group of the lysine was orthogonally deprotected by treating the resin with 2.5% (v/v) Hydrazine hydrate solution in DMF as explained in Example 1.

Coupling of Palmitic Acid

To the free ε-amino group of lysine, palmitic acid (12 g, 5 equiv, 49.5 mmol) dissolved in DMF was added in equal proportion to five reactor vessel followed by the addition of DIC (7.6 m L; 5 equiv, 49.5 mmol) and HOBT (6.7 g; 49.5 mmol) in DMF in similar manner. The peptidyl resin was cleaved as mentioned in procedure for cleavage using cleavage cocktail C to yield (22 g), 65% yield. The crude sample was preparative HPLC purified and Lyophilised. The crude material was purified by preparative HPLC on Waters X-Bridge Prep C18-OBD column (19 mm×150 mm, 5 μm)

T Desiccated Rink-Amide MBHA resin ((100-200 mesh) 0.6 mmol/g, 0.28 g) was taken in polyethylene vessels equipped with a polypropylene filter. The linear peptide synthesis on solid phase were carried out automatically, using Symphony parallel synthesizer (PTI) using the synthesis programs mentioned in the table below. Swelling, C-terminal amino acid [Fmoc-Glu(OtBu)-OH] attachment and capping of the peptidyl resin was carried out as per the protocol in Table I. Subsequent amino acid coupling was carried out as mentioned in Table II. The amino acids used in the synthesis were Fmoc Phe-OH, Fmoc-Arg(Pbf)-OH, Fmoc-Val-OH, Fmoc-Thr(OtBu)-OH, Fmoc-Gln(Trt)-OH, Fmoc-Asn(Trt)-OH, Fmoc-Lys(Boc)-OH, Fmoc-Leu-OH, Fmoc-Ala-OH, Fmoc-Pro-OH, Fmoc-Ile-OH. In the linear fragment the second amino acid from the C-terminus was coupled as Fmoc-Lys(Alloc)-OH and sixth amino acid from C-terminus was coupled as Fmoc-Glu(OAII)-OH. In the linear sequence $8^{th}$ amino acid from the N-terminus, Lys, was coupled as Fmoc-Lys(Fmoc)-OH. From the next residue onwards (Fmoc-Phe-OH) the coupling of subsequent amino acids was carried out as in Table II using 5 mL each of 0.25 M amino acid, 0.25 M HBTU in 1 M NMM/DMF as coupling reagent. The amino acids used in the synthesis were Fmoc-Thr(OtBu)-OH, Fmoc-Ser(OtBu)-OH, Fmoc-Glu(OtBu)-OH. The N-terminus amino acids at both the ends are coupled as Boc-Ser(OtBu)-OH.

Deprotection of Alloc Protecting Group

T After completion of the entire peptide sequence, the orthogonal Alloc and Allyl protecting group present in Lysine and Glutamic acid was removed from the peptidyl resin by treating with tetrakistriphenylphosphine palladium (0) (10 Equiv; 2.1 g) and Phenylsilane (20 eqv 0.32 mL) in a solution of chloroform/N-methylpyrrolidine (95/5 v/v) for 6 h under argon. The resin was washed with a solution of 10% NMP in chloroform (6×10 mL), 1% DIEPA in DMF (6×10 mL), DCM (6×10 mL), DMF (6×10 mL). The ε-free amino group of lysine and γ-free carboxyl group of Glutamic acid was kept for lactam bridging using HOBt (0.12 g; 0.92 mmol) and DIC (0.18 mL; 1.1 mmol) dissolved in NMP. After 17 h the resin was filtered and washed with DMF (6×10 mL), DCM (6×10 mL), DMF (6×10 mL). The peptidyl resin was cleaved as mentioned in procedure for cleavage using cleavage cocktail C to yield (407 mg), 68% yield. The crude material was purified by preparative HPLC on Zorbax Eclipse XDB-C18 column (9.4 mm×250 mm, 5 µm) with buffer A: 0.1% TFA/Water, buffer B: Acetonitrile. The peptide was eluted by gradient elution 0-4 min=10% buffer B, 4-21.5 min=10-30.9% buffer B, 21.5-30.9 min=30.9-35% buffer B with a flow rate of 7 mL/min. HPLC: (method 1): RT—12.5 min LCMS Calculated Mass: 3244.12, Observed Mass: 1622.9 [M/2+H]$^+$; 1082.1 [M/3+H]$^+$.

Example 14

Synthesis of Sequence Shown in SEQ ID NO: 140

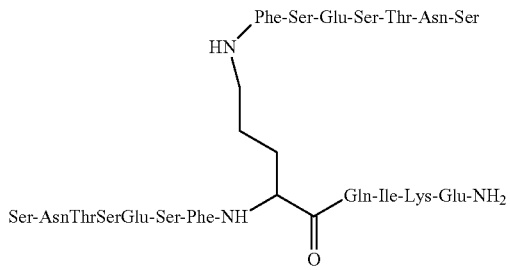

T Desiccated Rink amide MBHA (100-200 mesh) 0.66 mmol/g, 0.3 g) was taken in polyethylene vessels equipped with a polypropylene filter. The linear peptide synthesis on solid phase were carried out automatically, using Symphony parallel synthesizer (PTI) using the synthesis programs mentioned in the table below. Swelling, C-terminal amino acid [Fmoc-Glu(OtBu)-OH] attachment and capping of the peptidyl resin was carried out as per the protocol in Table I. Subsequent amino acid coupling was carried out as mentioned in Table II. In the linear sequence 8$^{th}$ amino acid from the N-terminus, Orn, was coupled as Fmoc-Orn-(Dde)-OH. The N-terminal amino acid Ser(OtBu)-OH in the linear chain of the peptide was coupled as N-Boc amino acid in the same procedure as employed for N-Fmoc amino acid.
Orthogonal Deprotection of Dde Group T The δ-amino group of eighth residue ornithine used as branching point was protected with Dde group. After completion of the linear peptide chain Dde protection of δ-amino group of the ornithine was orthogonally deprotected by treating the resin with 2.5% (v/v) Hydrazine hydrate solution in DMF (2×7.30 min) was carried out in automated synthesizer via manual addition of hydrazine hydrate solution. The resin was further washed using manual programme in synthesizer as in step 4, table II. The coupling of amino acid in the branch was carried out by the incorporation of subsequent amino acids using program for amino acid coupling as mentioned in table II. The amino acids used were Fmoc-Phe-OH, Fmoc-Thr(OtBu)-OH, Fmoc-Asn(Trt)-OH, Fmoc-Ser(OtBu)-OH, Fmoc-Glu(OtBu)-OH. OH. The N-terminal amino acid in the branch, Ser(OtBu)-OH in the linear chain of the peptide was coupled as N-Boc amino acid in the same procedure as employed for N-Fmoc amino acid.

The peptidyl resin was cleaved as mentioned in procedure for cleavage using cleavage cocktail C to yield (295 mg), 70% yield. The crude material was purified by preparative HPLC on Zorbax Eclipse XDB-C18 column 21.2 mm×150 mm, 5 µm) with buffer A: 0.1% TFA/Water, buffer B: Acetonitrile. The peptide was eluted by gradient elution 0-5 min=5-20% buffer B, 5-15 min=20-25% buffer B with a flow rate of 18 mL/min. HPLC: (method 1): RT—11.1 min LCMS Calculated Mass: 2135.77, Observed Mass: 1067.9 [M/2]$^+$; 711.9 [M/3]$^+$ Example 15

Synthesis of Sequence Shown in SEQ ID NO: 133

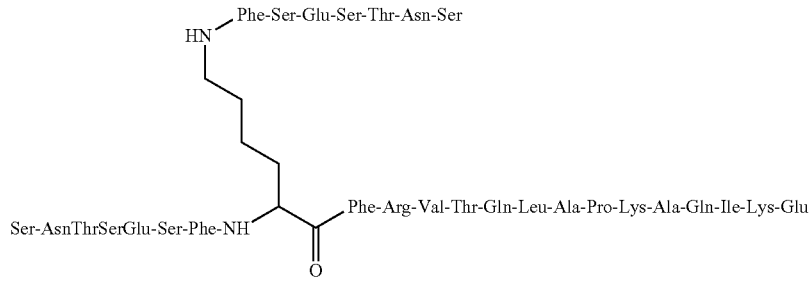

T Desiccated H-Glu (OtBu)-2-chlorotrityl chloride resin (100-200 mesh) 0.5 mmol/g, 0.35 g was taken in polyethylene vessels equipped with a polypropylene filter. The linear peptide synthesis on solid phase were carried out automatically, using Symphony parallel synthesizer (PTI) using the synthesis programs mentioned in the table below. Subsequent amino acid coupling was carried out as mentioned in Table II. The amino acids used in the synthesis were Fmoc Phe-OH, Fmoc-Arg(Pbf)-OH, Fmoc-Val-OH, Fmoc-Thr(OtBu)-OH, Fmoc-Gln(Trt)-OH, Fmoc-Asn(Trt)-OH, Fmoc-Lys(Boc)-OH, Fmoc-Leu-OH, Fmoc-Ala-OH, Fmoc-Pro-OH, Fmoc-Ile-OH. In the linear sequence 8$^{th}$ amino acid from the N-terminus, Lys, was coupled as Fmoc-Lys(Fmoc)-OH.

T From the next residue onwards (Fmoc-Phe-OH) the coupling of subsequent amino acids was carried out as in Table II using 5 mL each of 0.25 M amino acid, 0.25 M HBTU in 1 M NMM/DMF as coupling reagent. The N-terminal amino acid Ser(OtBu)-OH at the both N-terminus of the peptide was coupled as N-Boc amino acid in the same procedure as employed for N-Fmoc amino acid. The peptidyl resin was cleaved as mentioned in procedure for cleavage using cleavage cocktail C to yield (400 mg), 66% yield.

The crude material was purified by preparative HPLC on Zorbax Eclipse XDB-C18 column 21.2 mm×150 mm, 5 μm) with buffer A: 0.1% TFA/Water, buffer B: Acetonitrile. The peptide was eluted by gradient elution 0-5 min=5-20% buffer B, 5-18 min=20-27% buffer B with a flow rate of 18 mL/min. HPLC: (method 1): RT—12.1 min LCMS Calculated Mass: 3262.62, Observed Mass: 1088.6 [M/3+H]$^+$; 813.4 [M/4+H]$^+$ The other compounds of the invention were prepared by following similar procedure as described above with suitable modification known to the one ordinary skilled in the art. The identity of peptide was confirmed by LCMS (Table IV).

TABLE IV

| Comp No. | Sequence | LCMS Calc | Observed |
|---|---|---|---|
| 1 | SNTSESF-NH2 (SEQ ID NO: 42) | 769.7 | 770.0 [M]$^+$ |
| 2 | CH3—CO-SNTSESF-NH2 (SEQ ID NO: 43) | 811.81 | 812.3 [M]$^+$ |
| 3 | SNQTDKLAAFPEDSQPGQD-NH2 (SEQ ID NO: 44) | 2047.14 | 1024.3 [M/2 + H]$^+$ |
| 4 | EDRSQPGQDCR-NH2 (SEQ ID NO: 45) | 1288.35 | 1289.8 [M + H]$^+$; 645.6 [M/2 + H]$^+$ |
| 5 | CGAISLAPKAQIKES-NH2 (SEQ ID NO: 46) | 1513.81 | 1515.2 [M + H]$^+$; 758.2 [M/2 + H]$^+$ |
| 6 | FRVTQK(SNTSESF)FRVTQAhxLAPKAQIKE-NH2 (SEQ ID NO: 47) | 3237.83 | 1619.9 [M/2 + H]$^+$; 1080.2 [M/3 + H]$^+$ |
| 7 | FRVTQK(SNTSESF)FRVTQLAPKAQIKE-NH2 (SEQ ID NO: 48) | 3140.62 | 1571.2 [M/2 + H]$^+$; 1047.8 [M/3 + H]$^+$ |
| 8 | SNTSESFK(SNTSESF)FRVTQLAPKAQIKE-NH2 (SEQ ID NO: 49) | 3261.62 | 1631.6 [M/2 + H]$^+$; 1088 [M/3 + H]$^+$;); 816.2 [M/4 + H]$^+$ |
| 9 | SNQTDK (SNQTDK) FRVTQ LAPKAQIKE-NH2 (SEQ ID NO: 50) | 2975.34 | 1487.7 [M/2 + H]$^+$; 992.2 [M/3 + H]$^+$; 744.5 [M/4 + H]$^+$ |
| 10 | SNQTDK (SNQTDK) VLNWYRM LAPKAQIKE-NH2 (SEQ ID NO: 51) | 3306.78 | 1653.8 [M/2 + H]$^+$; 1102.7 [M/3 + H]$^+$; 827.4 [M/42 + H]$^+$ |
| 11 | SNTSESFK(SNQTDK)FRVTQLAPKAQIKE-NH2 (SEQ ID NO: 52) | 3182.57 | 1591.8 [M/2 + H]$^+$; 1061.7 [M/3 + H]$^+$; 796.6 [M/4 + H]$^+$ |
| 12 | SNTSESFK(SNQTDK)FRVTQK(LAP)AQIKE-NH2 (SEQ ID NO: 53) | 3182.57 | 1591.7 [M/2 + H]$^+$; 1061.2 [M/3 + H]$^+$; 796.3 [M/4 + H]$^+$ |
| 13 | sntsesfk(sntsesf)frvtqlapkaqike-NH2 (SEQ ID NO: 54) | 3261.62 | 1630.8 [M/2 + H]$^+$; 1087.5 [M/3 + H]$^+$; 815.8 [M/4 + H]$^+$ |
| 14 | EKIQAKPAYWNLVK(KDTQNS)DTQNS (SEQ ID NO: 55) | 2906 | 1454.2 [M/2 + H]$^+$; 969.5 [M/3 + H]$^+$; 727.6 [M/4 + H]$^+$ |
| 15 | Biotin-Ahx-SNTSESFK(SNTSESF)FRVTQLAPKAQIKE-NH2 (SEQ ID NO: 56) | 3601.22 | 1200.9 [M/3 + H]$^+$; 901.0 [M/4 + H]$^+$ |
| 16 | 6 lipid-SNTSESFK(SNTSESF)FRVTQLAPKAQ IKE-NH2 (SEQ ID NO: 57) | 3359.62 | 1680.4 [M/2 + H]$^+$; 1120.5 [M/3 + H]$^+$; 840.7 [M/4 + H]$^+$ |
| 17 | Ac-SNTSESFK(SNTSESF)FRVTQLAPKAQIKE-NH2 (SEQ ID NO: 58) | 3303.66 | 1653.2 [M/2 + H]$^+$; 1101.9 [M/3 + H]$^+$; 826.9 [M/4 + H]$^+$ |
| 18 | SNTSESFK(NH-(PEG)11-CO-SNTSESF)FRVTQLAPKAQIKE-NH2 (SEQ ID NO: 59) | 3861.42 | 773.6 [M/5 + H]$^+$ |
| 19 | SNTSESFK(SNTSESF)(PEG)LAPKAQIKE-NH2 (SEQ ID NO: 60) | 3229.89 | 1615.17 [M/2 + H]$^+$; 1077.1 [M/3 + H]$^+$; 808.3 [M/4 + H]$^+$ |

TABLE IV-continued

| Comp No. | Sequence | LCMS Calc | Observed |
|---|---|---|---|
| 20 | SNTSESFK(CH3(CH2)4CO-SNTSESF)FRVTQLAPKAQIKE-NH2 C6 lipid in branch (SEQ ID NO: 61) | 3359.62 | 1680.3 [M/2 + H]+; 1120.4 [M/3 + H]+; 840.5 [M/4 + H]+ |
| 21 | CH3(CH2)4CO-SNTSESFK(CH3(CH2)4CO-SNTSESF)FRVTQLAPKAQIKE-NH2 Lipidation on both Branch & N-termini (SEQ ID NO: 62) | 3457.62 | 1729.1 [M/2 + H]+; 1152 [M/3 + H]+ |
| 22 | 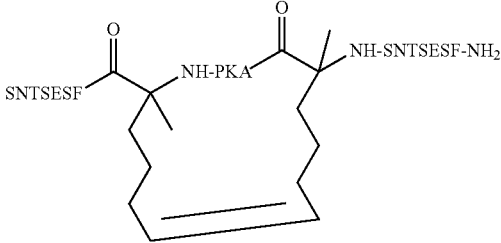 (SEQ ID NO: 63) | 2070.6 | 1035.5 [M/2 + H]+ |
| 23 | 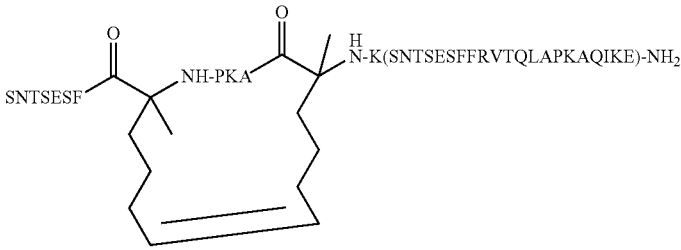 (SEQ ID NO: 64) | 3697 | 1232.5 [M/3 + H]+; 740.2 [M/5 + H]+; 924.9 [M/4 + H]+ |
| 24 | 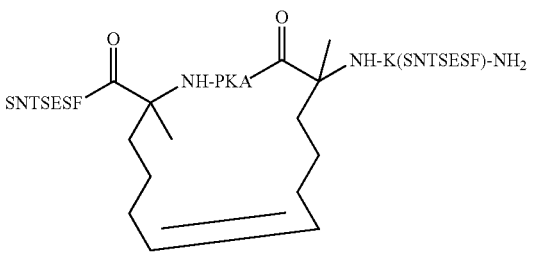 (SEQ ID NO: 65) | 2198.8 | 1099.4 [M/2 + H]+ |
| 25 | SNTSESFK(SNTSESF)FRVTQLAQIKE-NH2 (SEQ ID NO: 66) | 2965.25 | 1483 [M/2 + H]+; 988.9 [M/2 + H]+ |
| 26 | SNTSESFFRVTQLAPKAQIKE-NH2 (SEQ ID NO: 67) | 2380.71 | 1191.0 [M/2 + H]+; 794.3 [M/3 + H]+ |
| 27 | SNTSESFKFRVTQLAPKAQIKE-NH2 (SEQ ID NO: 68) | 2508.88 | 1254.9 [M/2 + H]+; 837.0 [M/3 + H]+ |
| 28 | SNTSESFKSNTSESFFRVTQLAPKAQIKE-NH2 (SEQ ID NO: 69) | 3261.8 | 1630.7 [M/2 + H]+; 1087.5 [M/3 + H]+ |
| 29 | SNTSESFK(SNTSESF)-NH2 (SEQ ID NO: 70) | 1650.69 | 1650.5 [M]+; 825.9 [M/2 + H]+ |
| 30 | SNTSESFK(SNTSESF)LAPKAQIKE-NH2 (SEQ ID NO: 71) | 2629.89 | 1315.1 [M/2 + H]+; 877.0 [M/3 + H]+ |
| 31 | SNTSESFK(SNTSESF)FRVTQKAQIKE-NH2 (SEQ ID NO: 72) | 2980.27 | 1489.9 [M/2 + H]+; 993.9 [M/3 + H]+; 745.7 [M/4 + H]+ |
| 32 | SNTSESFK(SNTSESF)KAQIKE-NH2 (SEQ ID NO: 73) | 2348.53 | 1174.5 [M/2 + H]+; 783.2 [M/3 + H]+ |

TABLE IV-continued

| Comp No. | Sequence | LCMS Calc | Observed |
|---|---|---|---|
| 33 | SNTSESFK(SNTSESF)FRVTQLAPKAQIK(CH₃(CH₂)₁₄CO)E-NH2 (SEQ ID NO: 74) | 3499.62 | 1166.8 [M/3 + H]⁺ |
| 34 | SNTSESFK(SNTSESF)FRVTQLAPK(CH₃(CH₂)₁₄CO)AQIKE-NH2 (SEQ ID NO: 75) | 3499.62 | 1750.3 [M/2 + H]⁺; 1167.2 [M/3 + H]⁺ |
| 35 | SNTSESFK(SNTSESF)FRVTQK(LAP)KAQIKE-NH2 (SEQ ID NO: 76) | 3389.8 | 1695 [M/2 + H]⁺; 1130.2 [M/3 + H]⁺; 848.3 [M/4 + H]⁺ |
| 36 | SNTSESFK(SNTSESF)FRVTQLAK(PKA)QIKE-NH2 (SEQ ID NO: 77) | 3389.8 | 1695.2 [M/2 + H]⁺; 1130.5 [M/3 + H]⁺; 848.3 [M/4 + H]⁺ |
| 37 | SNTSESFK(LAP)FRVTQLAPKAQIKE-NH2 (SEQ ID NO: 78) | 2790.24 | 1395.2 [M/2 + H]⁺; 930.6 [M/3 + H]⁺; 698.4 [M/4 + H]⁺ |
| 38 | LAPK(LAP)FRVTQLAPKAQIKE-NH2 (SEQ ID NO: 79) | 2318.86 | 1159.7 [M/2 + H]⁺; 773.6 [M/3 + H]⁺; 580.6 [M/4 + H]⁺ |
| 39 | LAPKAQIKE-NH2 (SEQ ID NO: 80) | 996.23 | 996.7 [M]⁺ |
| 40 | SNTSESFK(SNTSESF)FK(CH₃(CH₂)₁₄CO))VTQLAPKAQIKE-NH2 Arg in D strand replaced by Lys (SEQ ID NO: 81) | 3471.61 | 1736.5 [M/2 + H]⁺; 1158.2 [M/3 + H]⁺; 869.1 [M/4 + H]⁺ |
| 41 | SNTSESFK(SNTSESF)FRVTQLAP-NH2 (SEQ ID NO: 82) | 2563.78 | 1282.1 [M/2 + H]⁺; 855.1 [M/3 + H]⁺ |
| 42 | SNTSESFFRVTQK(SNTSESF)LAPKAQIKE-NH2 (SEQ ID NO: 83) | 3261.62 | 1631.6 [M/2 + H]⁺; 1088 [M/3 + H]⁺; 816.5 [M/4 + H]⁺ |
| 43 | FRVTQLAPKAQIKE-NH2 (SEQ ID NO: 84) | 1627.97 | 1627.7 [M]⁺; 814.3 [M/2 + H]⁺; 543.3 [M/3 + H]⁺ |
| 44 | SNTSESFK(SNTSESF)FK(CH₃(CH₂)₆CO)VTQLAPKAQIKE-NH2 Arg in D strand replaced by Lys (SEQ ID NO: 85) | 3359.61 | 1680.2 [M/2 + H]⁺; 1121.1 [M/3 + H]⁺ |
| 45 | SNTSESFK(SNTSESF)FRVTQLAPK(CH₃(CH₂)₆CO)AQIKE-NH2 (SEQ ID NO: 86) | 3387.62 | 1129.9 [M/3 + H]⁺; 847.3 [M/4 + H]⁺ |
| 46 | SNTSESFK(SNTSESF)FRVTQLAPKAQIK(CH₃(CH₂)₆CO)E-NH2 (SEQ ID NO: 87) | 3387.62 | 1693.8 [M/2 + H]⁺; 1129.7 [M/3 + H]⁺; 847.5 [M/4 + H]⁺ |
| 47 | SNTSESFK(sntsesf)FRVTQLAPKAQIKE-NH2 (SEQ ID NO: 88) | 3261.62 | 1631.6 [M/2 + H]⁺; 1088 [M/3 + H]⁺; 816.2 [M/4 + H]⁺ |
| 48 | EKIQAKPALQTVRFK(FSESTNS)FSESTNS-NH2 (SEQ ID NO: 89) | 3261.62 | 1631.6 [M/2 + H]⁺; 1088 [M/3 + H]⁺; 816.2 [M/4 + H]⁺ |
| 49 | ekiqakpalqtvrfk(fsestns)fsestns-NH₂ (SEQ ID NO: 90) | 3261.62 | 1630.6 [M/2 + H]⁺; 1087.5 [M/3 + H]⁺; 815.7 [M/4 + H]⁺ |
| 57 | SNTSESFK(SNTSESF)FRVTQLAPK(CH3CO)AQIKE-NH2 (SEQ ID NO: 98) | 3304.61 | 1653.3 [M/2 + H]⁺; 1102.5 [M/3 + H]⁺ |
| 59 | SNTSESFK(SNTSESF)FRVTQLAPK(CH3—(CH2)4—CO)AQIKE-NH2 (SEQ ID NO: 100) | 3359.62 | 1681.3 [M/2 + H]⁺; 1121.2 [M/3 + H]⁺ |
| 60 | Biotin-Ahx-sntsesfk(sntsesf)frvtqlapkaqike-NH2 (SEQ ID NO: 101) | 3601.22 | 1201.1 [M/3 + H]⁺; 901.3 [M/4 + H]⁺ |
| 61 | Biotin-Ahx-EKIQAKPAYWNLVK(KDTQNS)DTQNS-NH2 (SEQ ID NO: 102) | 3245.69 | 1623 [M/2 + H]⁺; 1082.3 [M/3 + H]⁺; 811.8 [M/4 + H]⁺ |

TABLE IV-continued

| Comp No. | Sequence | LCMS Calc | Observed |
|---|---|---|---|
| 62 | SNTSESFK(SNTSESF)FRVTQLAPE*AQIK*E-NH2 (SEQ ID NO: 103) | 3244.12 | 1622.9 [M/2 + H]⁺; 1082 [M/2 + H]⁺ |
| 63 | SNTSESFK(SNTSESF)FK*VTQE*APKAQIKE-NH2 (SEQ ID NO: 104) | 3232.57 | 1615.4 [M/2 + H]⁺; 1078 [M/3 + H]⁺; |
| 64 | SNTSESFK(SNTSESF)FRVTE*LAPK*AQIKE-NH2 (SEQ ID NO: 105) | 3244.12 | 1622.4 [M/2 + H]⁺; 1082.4 [M/3 + H]⁺ |
| 65 | CH3CO-SNTSESFK(CH3CO-SNTSESF)FRVTQLAPKAQIK(CH$_3$(CH$_2$)$_6$CO)E-NH2 (SEQ ID NO: 106) | 3471 | 1736 [M/2 + H]⁺; 1158 [M/3 + H]⁺ |
| 66 | CH3CO-SNTSESFK(CH3CO-SNTSESF)FRVTQLAPKAQIK(CH$_3$(CH$_2$)$_{14}$CO)E-NH2 (SEQ ID NO: 107) | 3583 | 1792.6 [M/2 + H]⁺; 1195.4 [M/3 + H]⁺ |
| 67 | CH3CO-SNTSESFK(CH3CO-SNTSESF)FRVTQLAPKAQIK(CH$_3$(CH$_2$)$_{10}$CO)E-NH2 (SEQ ID NO: 108) | 3529.2 | 1764.7 [M/2]⁺; 1176.8 [M/3]⁺ |
| 68 | CH3CO-SNTSESFK(CH3CO-SNTSESF)FRVTQLAPKAQIK(CH$_3$(CH$_2$)$_4$CO)E-NH2 (SEQ ID NO: 109) | 3442.1 | 1722.1 [M/2 + H]⁺; 1148.1 [M/3 + H]⁺ |
| 69 | SNWSEDLK(SNWSEDL)FQIIQLHPKAKIEE-NH2 (SEQ ID NO: 110) | 3484.09 | 1742.9 [M/2 + H]⁺; 1162.3 [M/3 + H]⁺ |
| 70 | EDK(ED)FRVTQLAPKAQIKE-NH2 (SEQ ID NO: 111) | 2245.54 | 1122.8 [M/2 + H]⁺; 748.9 [M/3 + H]⁺ |
| 71 | SNTSESFK(ED)FRVTQLAPKAQIKE-NH2 (SEQ ID NO: 112) | 2754.07 | 918.4 [M/3 + H]⁺; 689.3 [M/4 + H]⁺ |
| 72 | LAPKAK(ED)FRVTQLAPKAQIKE-NH2 (SEQ ID NO: 113) | 2481.0 | 828 [M/3 + H]⁺; 621.1 [M/4 + H]⁺ |
| 73 | SNQTDKK(ED)FRVTQLAPKAQIKE-NH2 (SEQ ID NO: 114) | 2674.03 | 892.0 [M/3 + H]⁺; 699.2 [M/4 + H]⁺ |
| 74 | SNQTDK(SNQTDK)GIYLCGAISLAPKAQIKE-NH2 (SEQ ID NO: 115) | 3227.66 | 1077.5 [M/3 + H]⁺ |
| 75 | SNQTDKK(VLNWYRM)GIYLCGAISLAPKAQIKE-NH2 (SEQ ID NO: 116) | 3639.22 | 1214.5 [M/3 + H]⁺; 727.8 [M/5 + H]⁺ |
| 76 | EDK(VLNWYRM)GIYLCGAISLAPKAQIKE-NH2 (SEQ ID NO: 117) | 3208.44 | 1605.8 [M/2 + H]⁺; 1070.8 [M/4 + H]⁺ |
| 77 | SNTSESFK(SNTSESF)GIYLCGAISLAPKAQIKE-NH2 (SEQ ID NO: 118) | 3506.74 | 874.0 [M/4 + H]⁺ |
| 79 | VLNWYRMK(SNQTDK)GIYLCGAISLAPKAQIKE-NH2 (SEQ ID NO: 120) | 3638.32 | 1214.1 [M/3 + H]⁺; 727.7 [M/5 + H]⁺ |
| 80 | GIYLCGAISLAPKAQIKE-NH2 (SEQ ID NO: 121) | 1873.29 | 937.6 [M/2 + H]⁺ |
| 81 | SNQTDKK(SNQTDK)FRVTQ LAPKAQIKE-NH2 (SEQ ID NO: 122) | 3103.51 | 1552.4 [M/2 + H]⁺; 1035.7 [M/3 + H]⁺; 777.0 [M/4 + H]⁺ |
| 82 | SNWSEDLK(SNWSEDL)FQIIQLHPK(CH$_3$(CH$_2$)$_{14}$CO)AKIEE-NH2 (SEQ ID NO: 123) | 3727.8 | 1241.9 [M/3]⁺ |
| 83 | SNTSESFK(SNTSESF)FRVTQLAPK(MPA—NH—CH$_2$—CH$_2$—O—CH$_2$—CH$_2$—O—CO)AQIKE-NH2 (SEQ ID NO: 124) | 3557.09 | 1779.8 [M/2 + H]⁺ 1187.1 [M/3 + H]⁺ |
| 84 | SNTSESFK(sNTSESF)FRVTQLAPKAQIKE-NH2 (D-ser in the branch) (SEQ ID NO: 125) | 3261.62 | 1631 [M/2 + H]⁺; 1088.2 [M/3 + H]⁺; 816.2 [M/4 + H]⁺ |
| 88 | SΨ[CH2NH]NTSESFK(SΨ[CH2NH]NTSESF)FRVTQLAPKAQIKE-NH2 (SEQ ID NO: 129) | 3232.8 | 1617.4 [M/2 + H]⁺; 809.6 [M/4 + H]⁺ |
| 89 | SnTSESFK(SNTSESF)FRVTQLAPKAQIKE-NH2 (SEQ ID NO: 130) D-Asn at N-terminus | 3261.62 | 1631.6 [M/2 + H]⁺; 1087.8 [M/3 + H]⁺; 816.2 [M/4 + H]⁺ |
| 90 | SNTSESFK(SnTSESF)FRVTQLAPKAQIKE-NH2 (SEQ ID NO: 131) D-Asn in the branch | 3261.62 | 1631.5 [M/2 + H]⁺; 1088.1 [M/3 + H]⁺; 816.1 [M/4 + H]⁺ |

TABLE IV-continued

| Comp No. | Sequence | Calc | LCMS Observed |
|---|---|---|---|
| 91 | SNWSEDLK(SNWSEDL)FQIIQLHPK(MPA—NH—CH$_2$—CH$_2$—O—CH$_2$—CH$_2$—O—CO)AKIEE-NH2 (SEQ ID NO: 132) | 3779.2 | 1261.1 [M/2 + H]$^+$ 946.0 [M/4 + H]$^+$ |
| 92 | SNTSESFK(SNTSESF)FRVTQLAPKAQIKE (SEQ ID NO: 133) | 3262.62 | 1088.6 [M/3 + H]$^+$; 813.4 [M/4]$^+$ |
| 98 | SNTSESFK(SNTSESF)FRVTQLAPK(CH$_3$(CH$_2$)$_{14}$CO)AQIKE (SEQ ID NO: 139) | 3500.62 | 1167.4 [M/3 + H]$^+$ |
| 99 | SNTSESF-Orn-(SNTSESF)KAQIKE-NH2 (SEQ ID NO: 140) | 2135.77 | 1067.9 [M/2]$^+$; 711.9 [M/3]$^+$ |
| 100 | SNTSESF-Dap-(SNTSESF)KAQIKE-NH2 (SEQ ID NO: 141) | 2107.8 | 1053.9 [M/2]$^+$; 703.0 [M/3]$^+$ |
| 101 | SNTSESF-Dab-(SNTSESF)KAQIKE-NH2 (SEQ ID NO: 142) | 2121.22 | 1060.5 [M/2]$^+$ |
| 106 | LAPKA-NH2 (SEQ ID NO: 147) | 497.64 | 498.3 [M + H]$^+$ |
| 107 | LAPKA(SNQTDK)FRVTQLAPKAQIKE-NH2 (SEQ ID NO: 148) | 2910.44 | 971.2 [M/3 + H]$^+$ 728.5 [M/4 + H]$^+$ |

Example 16

Binding Inhibition Analysis by Flow Cytometry
Reagents
Expression of PD1 Fusion with Murine Fc Region in Mammalian Cells Extracellular domain of human PD1 (1-167 amino acid residues) was cloned in pFUSE-Fc (Invivogen, CA). This construct was transfected into HEK293 cells (CRL 1573, ATCC) using Lipofectamine 2000 (Invitrogen) and expressed transiently. The secreted recombinant protein containing extracellular PD1 protein fused with Fc region of murine IgG was purified from the culture media in which transfected cells were grown.

Cell Lines as Source of Ligand for PD1

MDA-MB-231 cells were found to express PD-L1 by RT-PCR and therefore used as a source of PD-L1 in the assays. Recombinant PDL2 expressing HEK293 cells were used as a source of PDL2 in the cellular context.

Flow Cytometry Based Determination of Binding of PD1 with its Ligands

This assay was done to determine the effect of compounds on binding of PD1 with its ligands PD-L1 and PD-L2. Briefly, HEK 293 cells (ATCC:CRL-1573) overexpressing recombinant hPDL-2 in a stable manner and pcDNA Myc HisA transfected HEK 293 (negative control) cell lines were grown upto 60-70% confluency using complete DMEM media (Sigma D5648-1L). Cells were dissociated with cell dissociation buffer (Invitrogen—13151-014) and counted following which 2×10$^5$ cells were re-suspended in 50 µl of complete DMEM media in FACS tube.

Before dissociating cells, soluble PD1 tagged with Fc. derived from concentrated supernatant of transiently transfected cells, was incubated with test Compound #8; in a total volume of 10 µl for one hour. PD1-Neutralizing antibody (mouse monoclonal IgG2B clone 192106, Cat. No MAB1086; R&D Labs, USA) was also pre-incubated with soluble PD1 to be used as a positive control for inhibition of binding of PD1 to its ligand. The mixture of PD1/pFuse pre-incubated with Compound #8 at varying doses; Compound was added to the cells and allowed to bind.

To detect the association of PD1 to ligand expressing cells, anti-mouse secondary antibody conjugated to Alexafluor 488 (Invitrogen, Cat. No. 11001) at 1:1000 dilution was added to the cells and incubated for half hour at 4° C. Five hundred microliters of FACS sheath fluid (BD, Catalog No. 336524) was added to these tubes after half hour and analysis was done in BD FACS Calibur machine. Compound #8 was able to inhibit binding of PD1 to PD-L2 expressed in HEK 293 cells in a potent manner as shown in FIG. 1.

Example 17

Measurement of Restoration of Rat PBMC Proliferation

This assay was done to test the effect of peptides on the function of PBMC. As a consequence of the effect of peptide on the interaction between PD1 (expressed on PBMC) and its ligands (expressed on tumour cells) PBMC proliferation is affected. PBMC proliferation is expected to increase upon abrogation of binding between PD1 and its ligands in the presence of a disrupting peptide. In order to determine the effect of test compounds on this interaction, hPDL1 expressing MDA-MB231 cells (ATCC:CRL HTB-26) were seeded in a 24-well plate containing complete DMEM media (Sigma catalog no. D5648) where Geneticin at 100 µg/ml (Sigma, catalog no. G8168) was added for hPDL2 cells.

One milliliter of rat blood diluted with 5×DMEM medium along with PMA (Phorbol 12-myristate 13-acetate) at 6.25 ng/ml (Sigma, Cat. No. 8139) and lonomycin at 0.5 µg/ml (Sigma, Cat. No. 10634) was overlaid on the top of the cells. Test compounds were added at appropriate concentration in a volume not exceeding 10 µl/well along with the blood to the respective wells and the plate was incubated in CO$_2$ incubator at 37° C.

After forty eight hours, rat PBMC's were isolated using Histopaque1077 (Sigma, Cat. No. 10771) and the samples were fixed in 70% ethanol followed by treatment with RNase (Sigma, R6513) and stained with Propidium iodide (Sigma Cat. No. 81845). These samples were analyzed in BD FACS Calibur flow cytometer. As shown in FIG. 2, while minimal proliferation was observed for PMA stimulated PBMC cells in the presence of ligand expressing MDA-MB231 cells, the introduction of Compound #8 was able to restore proliferation effectively.

Example 18

Determination of Potency of Compound 8 in Rat PBMC Proliferation Rescue Assay

This study was completed using the protocol described earlier in Example 17. Various concentrations of compound 8 were tested in this assay and potency of peptide compound 8 was determined in restoration of proliferation of PMA stimulated PBMCs. This assay was done in the context of PD-L1 expressing MDA-MB231 as shown in FIG. 3.

Example 19

Measurement of Restoration of Human PBMC Proliferation

Human blood was collected with heparin and was diluted with phosphate buffered saline and peripheral blood mononuclear cells (PBMC) were isolated using Histopaque. A 24-well plate was pre-coated with anti-Cd3 and anti-Cd28 (5 ug/ml) for 3 hours. Another plate was pre-coated with Isotype control antibodies (IgG1/IgG2a) for use as negative control for proliferation induction. The PBMCs were counted and seeded at 0.6 million cells/ml per well along with recombinant hPDL1 at 1 µg/ml per well followed by test compounds at the appropriate concentrations. The plate was incubated for 48 hours and PBMCs were collected and fixed with ethanol for analysis of cell cycle profile by propidium iodide staining. Data for restoration of human PBMC proliferation for tested compounds is shown in FIG. 4.

Example 20

The Effect of Peptides on Mouse Splenocyte Proliferation Inhibited by MDMBA231 Tumour Cells Expressing PDL1
Use of MDA-MB-231 Cells as a Source of PD-L1

MDA-MB-231 cells were found to express PD-L1 by RT-PCR and therefore used as a source of PD-L1 in the assays.
Requirement Mouse splenocytes harvested from 6-8 weeks old C57 BL6 mice.; RPMI 1640 (GIBCO, Cat #11875); DMEM with high glucose (GIBCO, Cat #D6429); Fetal Bovine Serum [Hyclone, Cat #SH30071.03]; Pencilin (10000 unit/ml)-Streptomycin(10,000 µg/ml) Liquid (GIBCO, Cat #15140-122); MEM Sodium Pyruvate solution 100 mM (100×), Liquid (GIBCO, Cat #11360); Nonessential amino acid (GIBCO, Cat #11140); L-Glutamine (GIBCO, Cat #25030); Anti-CD3 antibody (eBiosciences—16-0032); Anti-CD28 antibody (eBiosciences—16-0281); ACK lysis buffer (1 mL) (GIBCO, Cat #-A10492); Histopaque (density—1.083 gm/ml) (SIGMA 10831); Trypan blue solution (SIGMA-T8154); Hemacytometer (Bright line-SIGMA Z359629); FACS Buffer (PBS/0.1% BSA): Phosphate Buffered Saline (PBS) pH 7.2 (HiMedia TS1006) with 0.1% Bovine Serum Albumin (BSA) (SIGMA A7050) and sodium azide (SIGMA 08591); 5 mM stock solution of CFSE: CFSE stock solution was prepared by diluting lyophilized CFSE with 180 µL of Di methyl Sulfoxide (DMSO $C_2H_6SO$, SIGMA-D-5879) and aliquoted in to tubes for further use. Working concentrations were titrated from 10 µM to 1 µM. (eBioscience—650850-85); 96-well format ELISA plates (Corning CLS3390); BD FACS caliber (E6016).

Protocol
Splenocyte Preparation:

Splenocytes harvested in a 50 ml falcon tube by mashing spleen in a 40 µm cell strainer were further treated with 1 ml ACK lysis buffer for 5 mins at RT. After washing with 9 ml of RPMI complete media, cells re-suspended in 3 ml of 1×PBS in a 15 ml tube. 3 ml of histopaque was added very carefully to the bottom of the tube without disturbing overlaying splenocyte suspension. Spin the tube at 800×g for 20 mins at RT. Opaque layer of lymphocytes is collected carefully without disturbing/mixing any of the layers. Cells washed twice with cold 1×PBS followed by total cell counting using trypan blue exclusion method and used further for cell based assays.
CFSE Proliferation Assay Tumour cells (MDMBA231) are cultured and maintained in high glucose complete DMEM media. $1\times10^5$ tumour cells were plated in 96 well plates along with required conc. of PD1 derived peptide and allowed to adhere at 37° C. for 4 hrs. $1\times10^6$ cells/ml of harvested splenocytes are treated with 5 µM of CFSE in pre warmed 1×PBS/0.1% BSA solution for 10 mins at 37° C. Excess CFSE was quenched using 5 volumes of ice-cold culture media to the cells and incubated on ice for 5 mins. CFSE labeled splenocytes were further given three washes with ice cold complete DMEM media. CFSE labeled $1\times10^5$ splenocytes added to above wells containing tumours cells and test compounds. Splenocytes were stimulated with anti-CD3 and anti-CD28 antibody (1 µg/ml each) and the co-culture was further incubated for 72 hrs at 37° C. with 5% $CO_2$. Cells were harvested and washed thrice with ice cold FACS buffer and % proliferation was analyzed using a FACS caliber with 488 nm excitation and 521 nm emission filters. Each experimental condition was carried out in triplicates and each experiment at least carried out three times. Splenocyte proliferation was analyzed using cell quest FACS program and fold induction was calculated by normalizing individual values to percent background proliferation.

Fold induction=Percent splenocyte proliferation/percent background proliferation Stimulated splenocytes: Splenocytes+anti-CD3/CD28 stimulation Background proliferation: Splenocytes+anti-CD3/CD28+Tumour Percent Proliferation rescue={(compound percent proliferation−Background percent proliferation)/(Stimulated percent proliferation−Background percent proliferation)}*100.

Comparison of Percentage Proliferation Rescue of Compound 8, 13 and 34 with mAb J43 Antibody mAb J43 (Int. Immunol. 1996-8(5):765-72) and test peptides were analysed for mouse splenocyte proliferation rescue studies using CFSE method as described protocol above and results are summarized in FIG. 5.
Effect of Compounds on CFSE Based Mouse Splenocyte Proliferation Rescue Studies The test compounds were analysed for mouse splenocyte proliferation rescue studies using the method as mentioned in protocol above and data is presented as percent activity in comparison with compound 8 peptide as in Table V.

TABLE V

Percent of activity for various compounds via Mouse splenocyte proliferation assay using CFSE method

| Comp No | Sequence | Percent rescue for various compounds (screened at 100 nm concentration and compared with 100 nm Comp 8) in mouse splenocyte proliferation CFSE based assay |
|---|---|---|
| 1 | SNTSESF-NH2 (SEQ ID NO: 42) | 96.5 |
| 3 | SNQTDKLAAFPEDSQPGQD-NH2 (SEQ ID NO: 44) | 37.3 |
| 4 | EDRSQPGQDCR-NH2 (SEQ ID NO: 45) | 74.7 |
| 5 | CGAISLAPKAQIKES-NH2 (SEQ ID NO: 46) | 68 |
| 7 | FRVTQK(SNTSESF)FRVTQLAPKAQIKE-NH2 (SEQ ID NO: 48) | 61.5 |
| 8 | SNTSESFK(SNTSESF)FRVTQLAPKAQIKE-NH2 (SEQ ID NO: 49) | 100 |
| 9 | SNQTDK (SNQTDK) FRVTQ LAPKAQIKE-NH2 (SEQ ID NO: 50) | 11.3 |
| 10 | SNQTDK (SNQTDK) VLNWYRM LAPKAQIKE-NH2 (SEQ ID NO: 51) | 10.6 |
| 11 | SNTSESFK(SNQTDK)FRVTQLAPKAQIKE-NH2 (SEQ ID NO: 52) | 12.4 |
| 13 | sntsesfk(sntsesf)frytqlapkaqike-NH2 (SEQ ID NO: 54) | 0-12 nM-control peptide |
| 14 | EKIQAKPAYWNLVK(KDTQNS)DTQNS-NH2 (SEQ ID NO: 55) | 18 |
| 16 | C6 lipid-SNTSESFK(SNTSESF)FRVTQLAPKAQIKE-NH2 (SEQ ID NO: 57) | 45.8 |
| 17 | Ac-SNTSESFK(SNTSESF)FRVTQLAPKAQIKE-NH2 (SEQ ID NO: 58) | 32.9 |
| 20 | SNTSESFK(CH3(CH2)4CO-SNTSESF)FRVTQLAPKAQIKE-NH2 (SEQ ID NO: 61) | 27.8 |
| 21 | CH3(CH2)4CO-SNTSESFK(CH3(CH2)4CO-SNTSESF)FRVTQLAPKAQIKE-NH2 (SEQ ID NO: 62) | 76.7 |
| 22 | SNTSESFR5PKAR5SNTSESF (SEQ ID NO: 63) | 71.4 |
| 25 | SNTSESFK(SNTSESF)FRVTQLAQIKE (SEQ ID NO: 66) | 27.6 |
| 26 | SNTSESFFRVTQLAPKAQIKE-NH2 (SEQ ID NO: 67) | 86.6 |
| 27 | SNTSESFKFRVTQLAPKAQIKE-NH2 (SEQ ID NO: 68) | 73.6 |
| 28 | SNTSESFKSNTSESFFRVTQLAPKAQIKE-NH2 (SEQ ID NO: 69) | 56.5 |
| 29 | SNTSESFK(SNTSESF)-NH2 (SEQ ID NO: 70) | 31.1 |
| 30 | SNTSESFK(SNTSESF)LAPKAQIKE-NH2 (SEQ ID NO: 71) | 58.8 |
| 31 | SNTSESFK(SNTSESF)FRVTQKAQIKE-NH2 (SEQ ID NO: 72) | 11.3 |

TABLE V-continued

Percent of activity for various compounds via Mouse splenocyte proliferation assay using CFSE method

| Comp No | Sequence | Percent rescue for various compounds (screened at 100 nm concentration and compared with 100 nm Comp 8) in mouse splenocyte proliferation CFSE based assay |
|---|---|---|
| 32 | SNTSESFK(SNTSESF)KAQIKE-NH2 (SEQ ID NO: 73) | 14.8 |
| 33 | SNTSESFK(SNTSESF)FRVTQLAPKAQIK(CH$_3$(CH$_2$)$_{14}$CO)E-NH2 (SEQ ID NO: 74) | 98 |
| 34 | SNTSESFK(SNTSESF)FRVTQLAPK(CH$_3$(CH$_2$)$_{14}$CO)AQIKE-NH2 (SEQ ID NO: 75) | 106 |
| 35 | SNTSESFK(SNTSESF)FRVTQK(LAP)KAQIKE-NH2 (SEQ ID NO: 76) | 81.2 |
| 36 | SNTSESFK(SNTSESF)FRVTQLAK(PKA)QIKE-NH2 (SEQ ID NO: 77) | 89.7 |
| 37 | SNTSESFK(LAP)FRVTQLAPKAQIKE-NH2 (SEQ ID NO: 78) | 89.60 |
| 38 | LAPK(LAP)FRVTQLAPKAQIKE-NH2 (SEQ ID NO: 79) | 51.5 |
| 40 | SNTSESFK(SNTSESF)FK(CH$_3$(CH$_2$)$_{14}$CO))VTQLAPKAQIKE-NH2 (SEQ ID NO: 81) Arg in D strand replaced by Lys | 82 |
| 41 | SNTSESFK(SNTSESF)FRVTQLAP-NH2 (SEQ ID NO: 82) | 5.1 |
| 42 | SNTSESFFRVTQK(SNTSESF)LAPKAQIKE-NH2 (SEQ ID NO: 83) | 52.9 |
| 43 | FRVTQLAPKAQIKE-NH2 (SEQ ID NO: 84) | 66 |
| 45 | SNTSESFK(SNTSESF)FRVTQLAPK(CH$_3$(CH$_2$)$_6$CO)AQIKE-NH2 (SEQ ID NO: 86) | 68 |
| 46 | SNTSESFK(SNTSESF)FRVTQLAPKAQIK(CH$_3$(CH$_2$)$_6$CO)E-NH2 (SEQ ID NO: 87) | 67 |
| 48 | EKIQAKPALQTVRFK(FSESTNS)FSESTNS NH2 (SEQ ID NO: 89) | |
| 49 | ekiqakpalqtvrfk(fsestns)fsestns-NH$_2$ (SEQ ID NO: 90) | 73 |
| 60 | Biotin-Ahx-sntsesfk(sntsesf)frvtqlapkaqike-NH2 (SEQ ID NO: 101) | 14.9 |
| 61 | Biotin-Ahx-EKIQAKPAYWNLVK(KDTQNS)DTQNS-NH2 (SEQ ID NO: 102) | 67 |
| 62 | SNTSESFK(SNTSESF)FRVTQLAPE*AQIK*E-NH2 (SEQ ID NO: 103) | 37 |
| 63 | SNTSESFK(SNTSESF)FK*VTQE*APKAQIKE (SEQ ID NO: 104) | 68 |
| 64 | SNTSESFK(SNTSESF)FRVTE*LAPK*AQIKE (SEQ ID NO: 105) | 69.1 |
| 69 | SNWSEDLK(SNWSEDL)FQIIQLHPKAKIEE-NH2 (SEQ ID NO: 110) | 48 |
| 82 | SNWSEDLK(SNWSEDL)FQIIQLHPK(CH$_3$(CH$_2$)$_{14}$CO)AKIEE-NH2 (SEQ ID NO: 123) | 58.3 |

TABLE V-continued

Percent of activity for various compounds via Mouse splenocyte proliferation assay using CFSE method

| Comp No | Sequence | Percent rescue for various compounds (screened at 100 nm concentration and compared with 100 nm Comp 8) in mouse splenocyte proliferation CFSE based assay |
|---|---|---|
| 84 | SNTSESFK(SNTSESF)FRVTQLAPK(MPA-NH-CH$_2$-CH$_2$-O-CH$_2$-CH$_2$-O-CO)AQIKE-NH2 (SEQ ID NO: 125) | 80.5 |
| 91 | SNWSEDLK(SNWSEDL)FQIIQLHPK(MPA-NH-CH$_2$-CH$_2$-O-CH$_2$-CH$_2$-O-CO)AKIEE-NH2 (SEQ ID NO: 132) | 69.4 |

Example 21

Cytotoxic T Lymphocyte IFN-γ Assay

Tumour cells are cultured and maintained in high glucose complete DMEM media. 1×10$^5$ tumour cells were plated in 96 well plates along with required concentration of test compounds and allowed to adhere at 37° C. for 4 hrs. 1×10$^5$ of harvested splenocytes was added to wells containing tumours cells and test compounds. Splenocytes were stimulated with anti-CD3 and anti-CD28 antibody (1 μg/ml each) and the co-culture was further incubated for 72 hrs at 37° C. with 5% CO$_2$. After 72 hours of incubation the cell culture supernatants were collected and processed for mouse IFN gamma measurement by ELISA following manufacturer's protocol (e Biosciences; 88-7314).

ELISA: As Per Manufacturer's Protocol

In brief, 96 well ELISA plates were coated with 100 μl/well of capture antibody in coating buffer and incubated overnight at 4° C. Plates washed five times with wash buffer and further blocked with 200 μl of 1× assay diluents for 1 hr at RT. Following wash step, 100 μl of cell culture supernatants were added to wells and further incubated for 2 hrs at RT. Appropriate standards were also included. After the wash step, plates were incubated for one hour with 100 μl/well of detection antibody. Wash steps were repeated and the plates were incubated for 30 minutes with 100 μl/well of Avidin-HRP. The plates were washed again several times with wash buffer and incubated for 15 minutes with 100 μl/well of substrate solution. 50 μl of stop solution was added to each well, and the plates were read at 450 nm. The absorbance values were then plotted against the standards and the concentration of IFN-γ was determined using Graph Pad Prism software (FIG. 6). Each experimental condition was carried out in triplicates and each experiment at least carried out three times.

Fold induction =IFN-γ released by stimulated splenocyte in absence or presence of compound/Background IFN-γ release Stimulated splenocytes: Splenocytes+anti-CD3/CD28 stimulation in absence or presence of test compound Background IFN-γ release: Splenocytes+anti-CD3/CD28+Tumour

Example 22

In Vivo Efficacy of Compound #8 on Primary Tumour Growth and Lung Metastasis in B16F10 Subcutaneous Melanoma Model Animals C57/Black6 female mice (Aurigene, Bangalore, India) aged 6 to 8 weeks were used for the experiment. Animals were acclimatized for a week in the experimental room before conducting the experiment.

On day 0, B16F10 cells grown in DMEM containing 10% FBS at 70 to 75% confluency were harvested and 1×10$^6$ cells per animal were injected to mice subcutaneously on the right flank region. On day 1, peptide (Compound #8) at 5 mg/kg dose dissolved in PBS, pH 7.4 was dosed subcutaneously at the rate of 10 ml/kg volume for fourteen days once daily. Vehicle control group of mice received only saline. Each group consisted of ten animals. Body weight and clinical signs were recorded daily. Tumour volume was measured by slide callipers. Compound #8 dosed at 5 mg/kg, inhibited the tumour growth to the extent of 44 percent (p<0.001, 2-way ANOVA). There was no body weight reduction during the period of dosing and no clinical signs observed. Mean tumour volume of vehicle treated animals was 496 mm3, whereas Compound #8 treated animals showed 276 mm$^3$ at the end of 14 days dosing period (FIG. 7). At the end of dosing period lung was harvested and analysed for metastasis by counting the black nodules. It was observed that Compound 8 showed greater than 60 percent reduction in metastasis. The picture of lung treated with vehicle and Compound 8 is shown as (FIG. 8).

Example 23

In Vivo Efficacy of Compounds #8, 34, 69, 82, 83, 91 on Inhibition of Metastasis in B16F10 Metastasis Model In the case of metastasis model, 0.1×10$^6$ B16F10 cells were injected i.v. to C57/Black6 mice. Test compounds dissolved in PBS, pH 7.4 was dosed subcutaneously at 5 mg/kg once daily. Vehicle control group of mice received only saline. Each group consisted of ten animals. Body weight and clinical signs were recorded daily. After 11 days of treatment, lung metastasis was quantitated by counting number of nodules under dissection microscope. FIG. 9 shows that at the end of 11 days of dosing.

Example 24

Effect of Compound #8 in 4T1 Orthotopic Mammary Carcinoma Model

On day 0, 4T1 cells grown in RPMI 1640 containing 10% FBS at 70 to 75% confluency were harvested and $0.1 \times 10^6$ cells per animal were injected along with matrigel orthotopically to mammary fat pad. On day 1, peptide (Compound #8) at 3 mg/kg dose dissolved in PBS, pH 7.4 was dosed subcutaneously at the rate of 10 ml/kg volume for 5.5 weeks once daily. Vehicle control group of mice received only saline. Each group consisted of ten animals. Body weight and clinical signs were recorded daily. Tumour volume was measured by slide callipers. At the end of the study, metastasis to lungs was quantitated by counting the number of tumour nodules on the lung using dissection microscope. FIG. 10 shows that at the end of 40 days of dosing, Compound #8 dosed at 3 mg/kg inhibited the primary tumour volume to the extent of 44 percent. There was no body weight reduction during dosing period. Ten percent of the animals in the Compound #8 treated group showed complete regression and another ten percent showed partial regression of tumour growth. On the $40^{th}$ day, animals were euthanized and their lungs were observed for tumour nodules under the dissection microscope. One animal though the tumour volume was similar to vehicle treated group, there was complete inhibition of metastasis (no tumour nodules were seen). The animal that showed complete regression in primary tumour volume also showed no visible tumour nodules. Compound #8 treated animals showed mean reduction in metastasis to the extent of >60 percent.

Example 25

Effect of Compound 34 & 83 in Renal Cell Carcinoma Model

Female 6- to 8-week-old BALB/c mice were kept in a temperature-controlled room on a 12/12 h light/dark schedule with food and water ad libitum. RENCA cells harvested from non confluent monolayer were injected under the renal capsule on day 1 without opening the peritoneum. The skin incision was closed with auto suture clips. Renca cells ($15 \times 10^4$) in 40 µl of medium were injected under the kidney capsule of mice on day 1. Peptides were dosed subcutaneously from day 2 at 5 mpk, qd for 21 days. At the end of dosing (21 days) animals were euthanized and tumour weight of the left and right kidney (control) were measured and plotted as percent inhibition as shown in FIG. 11.

Example 26

Procedure for Minimum Inhibitory Concentration (MIC) Determination by Broth Microdilution Method Required quantity of the compound was weighed and dissolved in water/dimethyl sulphoxide/suitable solvent to yield 1 mg/ml stock solution. The stock solution was diluted in MHB/CAMHB to yield 8 µg/ml or 64 µg/ml or 512 µg/ml solution as per requirement. Serial two fold dilutions of the compound was prepared using MHB/CAMHB in 96 well microtitre trays using a multichannel pipette. Organisms were grown in MHB/CAMHB for 4-5 hrs at $35 \pm 2°$ C., $110 \pm 10$ rpm. Optical density (OD) of the cultures is adjusted to 625 nm which corresponds to 0.5 Mc Farland standard ($1-2 \times 10^8$ cfu/ml) and further diluted to achieve a final inoculum of $(5 \pm 5) \times 10^4$ cfu/well. Broth, compound and organism controls were set up. Microdilution trays were incubated at $35 \pm 2°$ C. for 16-20 hours in an ambient air incubator. After the incubation period, growth of organism in the wells was detected by unaided eye facilitated by a viewing device. The lowest concentration of antimicrobial agent that completely inhibits growth of the organism as detected by the unaided eye was taken as MIC. MIC value indicates that test compound 8 (MIC (µg/ml)->32) do not exhibit any antibacterial activity, whereas the standards viz, levofloxacin and ciprofloxacin shows an MIC ((µg/ml) values of 0.015 and 0.007 in the same experiment.

Example 27

In Vivo Efficacy of Compound # in Mouse Model of E. coli Sepsis

Materials and Methods

Bacterial strain used was E. coli ATCC 25922 and bacterial suspension was prepared in normal saline to obtain an inoculum of $\sim 5 \times 10^8$ CFU/ml. BALB/c or Swiss albino mice weighing 18-22 gms were used for the study. Animals were quarantined for a period of 5 days in individually ventilated cages (IVCs). Food and water was provided ad libitum. Temperature was maintained at 22-26° C. with a light dark cycle of 12 hrs.

Procedure

The final inoculum containing $\sim 1-2 \times 10^8$ CFU/ml was administered to the animals by intravenous route. Treatment was initiated after 24 hrs of infection and the compound was administered thrice a day at an interval of 3 hours for 2 days. One group of animals was kept untreated to serve as infection control. After completion of treatment for two days, all the animals (treated and untreated) were sacrificed 3 hrs after the last dose and various organs (kidneys, spleen & lungs) were collected aseptically and processed for enumeration of bacterial counts. Organ samples collected were homogenized, serially diluted in normal saline and plated on TSA plates. The plates were incubated at $35 \pm 2°$ C. for 18-24 hrs and bacterial counts enumerated. Results were analyzed by comparing treated Vs control animals & suitable statistical method was applied to calculate the statistical significance as shown in FIG. 12.

Example 28

Rescue of Splenocyte Effector Function by Monitoring the Release of Interferon (IFN)-γ by ELISA Human PBMC Preparation 10 ml of peripheral blood was collected from normal healthy voluntary donor and whole blood was underlayed with equal volumes of histopaque (1077) and centrifuged at 800×g for 20 mins at room temperature, the opaque layer of peripheral blood mononuclear cells (PBMCs) was collected without disturbing the layers and washed thrice with 1×PBS. PBMCs were counted using trypan blue exclusion method and used for cell based assays.

Culture of PBMCs

Human PBMCs cells were cultured in RPMI complete media (RPMI+10% foetal bovine serum+1 mM sodium pyruvate+10,000 units/ml penicillin and 10,000 µg/ml streptomycin) and maintained in a CO2 incubator with 5% CO2 at 37° C.

Human PBMCIFN-γ Release Assay by ELISA $1 \times 10^5$ PBMCs were added to wells containing recombinant human PDL-1 (R&D systems. cat no: 156-B7-100) at 10 nM and test peptide compound 49. Human PBMCs were stimulated with anti-human CD3e ((e Bioscience—16-0039) and anti-human CD28 antibody (e Bioscience—16-0289), 1 µg/ml each and the culture was further incubated for 72 hrs at 37° C. with 5% CO2. After 72 hours of incubation the cell culture supernatants were collected after brief centrifugation of culture plates (200 g×5 mins at 4° C.) and processed for human IFN-γ measurement by ELISA following manufacturer's protocol (e Biosciences:88-7316-86). In brief, 96 well ELISA plates were coated with 100 μl/well of capture antibody in coating buffer and incubated overnight at 4° C. Plates were washed five times with wash buffer and further blocked with 200 μl of 1× assay diluents for 1 hr at RT. Following wash step, 100 μl of cell culture supernatants were added to wells and further incubated for 2 hrs at RT. Appropriate standards were also included. After wash step, plate was incubated for one hour with 100 μl/well of detection antibody. The wash step was repeated and the plate was incubated for 30 minutes with 100 μl/well of Avidin-HRP. The plate was washed 7 times with wash buffer and incubated for 15 minutes with 100 μl/well of substrate solution. 50 μl of stop solution was added to each well and the plate was read at 450 nm. The absorbance values were then plotted against the standards and the concentration of IFN-γ was determined using GraphPad Prism software. Each experimental condition was carried out in triplicates and each experiment at least carried out three times.

Data Compiling

Percent IFN-γ release for each peptide concentration was calculated by normalising individual peptide IFN-γ values to anti-CD3e+anti-CD28 stimulated IFN-γ value. The percent IFN-γ release by compound 49 was calculated using following formula:

% IFN-γ release=[(Peptide IFN-γ–PDL background control)/(anti-CD3e+anti-CD28 positive control–PDL1 background control)]*100.

Peptide IFN-γ=PBMC IFN-γ values for the well containing PBMC+anti-CD3e+anti-CD28+PDL1+Peptide.

CD3+CD28 positive control =PBMC IFN-γ values for the well containing PBMC+anti-CD3e+anti-CD28.

PDL background control =PBMC IFN-γ values for the well containing PBMC+anti-CD3e+anti-CD28+PDL1.

The effect of test peptide on IFN-γ release from human PBMCs was interpreted as % IFN-γ release with respect to above positive and negative (backgrounds) controls. EC50 was calculated by nonlinear regression curve fit using GraphPadPrism 5 software (FIG. 13)

Example 29

In Vivo Efficacy of Compound #49 on Primary Tumor Growth in CT-26 Colon Cancer Model Two million CT26 (murine colon carcinoma) cells injected to male Balb/c mice (s.c) on day 1 and dosing started on Day 5. Each group consisted of ten animals. Tumor volumes were measured 3 times a week, body weight and clinical signs monitored daily. Compound #49 dosed at 1 mg/kg, inhibited the tumor growth to the extent of 51 percent (p<0.05) (FIG. 14). There was no body weight reduction and no clinical signs during the period of dosing.

Example 30

Determination of Rat Kidney Brush Border Membrane Metabolic Stability

Preparation of KBBM

Rat kidney brush border membrane (KBBM) was prepared by following a protocol described previously by Katsila T et al. (Mass Spectrometry Reviews, 2012, 31, 110-133), and Krondahl E et al. (Peptides, 2001, 22, 613-621). Briefly, overnight fasted rats were sacrificed by cervical dislocation; kidneys were removed, washed with chilled saline and decapsulated. The renal tissue was sliced and a 5% homogenate was made in buffer containing 2 mM Tris-HCl, 50 mM mannitol pH 7.1 using 10 strokes in a Porter-Elvelhemhomogeniser. The homogenate was centrifuged at 250×g for 5 min and the pellet was re-homogenized (four strokes) in the same buffer. Both the homogenate preparations were pooled (an aliquot of sample was taken for enzyme assays), allowed to remain at 4° C. for 15 min and filtered using a nylon mesh cloth. To this, a 50% PEG solution in water was added to make a final concentration of 10% PEG, stirred for 15 min continuously at 4° C. and centrifuged at 7500×g for 10 min. The pellet was discarded and the supernatant was spun at 12,000×g for 10 min. This pellet was discarded and the supernatant was centrifuged at 27,000×g for 40 min. To the pellet, 15 ml suspension buffer containing 10 mM Tris-HCl and 300 mM mannitol, pH 7.1 was added, centrifuged at 27,000×g for 40 min. The pellet was washed twice with the same suspension buffer and finally suspended 1 ml of the same buffer using a syringe fitted with a 26-gauge needle.

For carrying out metabolic stability assay the following protocol was adapted

1. Microsomal protein working solution was prepared as mentioned above (0.55 mg/ml) in 50 mM potassium phosphate buffer (pH 7.4)

2. Test compound (compound 69) working stock solutions at concentration of 4 μM was prepared in 50 mM potassium phosphate buffer (pH 7.4)

3. 125 μL of test compound (compound 69) from step 2 diluted with 100 μL of buffer and 275 μl of microsomal protein solution from step 2 was pre-incubated separately for 10 mins at 37° C.

4. Both the test solution from step 3 was mixed together and the reaction mixture was aliquoted at various time intervals and processed by SPE method.

Kidney brush border stability of the compounds was calculated as the amount of substrate metabolized by the incubation with kidney brush border microsomes. Initial amount of substrate (concentration at T0) was measured and KBBM stability was assessed by the disappearance of compound at various time points based on the change in analyte to internal standard peak height ratio using LCMS/MS (API 4000, AB Sciex). Results are expressed as mean±SD of test compound remaining at any given time point (Table VI).

TABLE VI

Rat Kidney bursh border membrane stability

| Compound # | RKBBM % compound remaining | | | |
|---|---|---|---|---|
| | 0 min | 10 min | 30 min | 60 min |
| Compound 69 | 100 | 100 | 98 | 81 |

SEQUENCE LISTING

<160> NUMBER OF SEQ ID NOS: 219

<210> SEQ ID NO 1
<211> LENGTH: 137
<212> TYPE: PRT
<213> ORGANISM: Homo sapiens
<220> FEATURE:
<221> NAME/KEY: PEPTIDE
<222> LOCATION: 1..137
<223> OTHER INFORMATION: Human PD-1 ectodomain

<400> SEQUENCE: 1

Pro Pro Thr Phe Ser Pro Ala Leu Leu Val Val Thr Glu Gly Asp Asn
1               5                   10                  15

Ala Thr Phe Thr Cys Ser Phe Ser Asn Thr Ser Glu Ser Phe Val Leu
            20                  25                  30

Asn Trp Tyr Arg Met Ser Pro Ser Asn Gln Thr Asp Lys Leu Ala Ala
        35                  40                  45

Phe Pro Glu Asp Arg Ser Gln Pro Gly Gln Asp Cys Arg Phe Arg Val
    50                  55                  60

Thr Gln Leu Pro Asn Gly Arg Asp Phe His Met Ser Val Val Arg Ala
65                  70                  75                  80

Arg Arg Asn Asp Ser Gly Thr Tyr Leu Cys Gly Ala Ile Ser Leu Ala
                85                  90                  95

Pro Lys Ala Gln Ile Lys Glu Ser Leu Arg Ala Glu Leu Arg Val Thr
            100                 105                 110

Glu Arg Arg Ala Glu Val Pro Thr Ala His Pro Ser Pro Ser Pro Arg
        115                 120                 125

Ser Ala Gly Gln Phe Gln Thr Leu Val
    130                 135

<210> SEQ ID NO 2
<211> LENGTH: 5
<212> TYPE: PRT
<213> ORGANISM: Homo sapiens
<220> FEATURE:
<221> NAME/KEY: PEPTIDE
<222> LOCATION: 1..5
<223> OTHER INFORMATION: A strand

<400> SEQUENCE: 2

Pro Pro Thr Phe Ser
1               5

<210> SEQ ID NO 3
<211> LENGTH: 7
<212> TYPE: PRT
<213> ORGANISM: Homo sapiens
<220> FEATURE:
<221> NAME/KEY: PEPTIDE
<222> LOCATION: 17..23
<223> OTHER INFORMATION: B strand

<400> SEQUENCE: 3

Ala Thr Phe Thr Cys Ser Phe
1               5

<210> SEQ ID NO 4
<211> LENGTH: 7
<212> TYPE: PRT
<213> ORGANISM: Homo sapiens
<220> FEATURE:
<221> NAME/KEY: PEPTIDE
<222> LOCATION: 24..30

<223> OTHER INFORMATION: BC loop

<400> SEQUENCE: 4

Ser Asn Thr Ser Glu Ser Phe
1               5

<210> SEQ ID NO 5
<211> LENGTH: 7
<212> TYPE: PRT
<213> ORGANISM: Homo sapiens
<220> FEATURE:
<221> NAME/KEY: PEPTIDE
<222> LOCATION: 31..37
<223> OTHER INFORMATION: C-Strand

<400> SEQUENCE: 5

Val Leu Asn Trp Tyr Arg Met
1               5

<210> SEQ ID NO 6
<211> LENGTH: 5
<212> TYPE: PRT
<213> ORGANISM: Homo sapiens
<220> FEATURE:
<221> NAME/KEY: PEPTIDE
<222> LOCATION: 38..42
<223> OTHER INFORMATION: C-C' loop

<400> SEQUENCE: 6

Ser Pro Ser Asn Gln
1               5

<210> SEQ ID NO 7
<211> LENGTH: 8
<212> TYPE: PRT
<213> ORGANISM: Homo sapiens
<220> FEATURE:
<221> NAME/KEY: PEPTIDE
<222> LOCATION: 43..50
<223> OTHER INFORMATION: C'-strand

<400> SEQUENCE: 7

Thr Asp Lys Leu Ala Ala Phe Pro
1               5

<210> SEQ ID NO 8
<211> LENGTH: 2
<212> TYPE: PRT
<213> ORGANISM: Homo sapiens
<220> FEATURE:
<221> NAME/KEY: PEPTIDE
<222> LOCATION: 51..52
<223> OTHER INFORMATION: C'-C'' loop

<400> SEQUENCE: 8

Glu Asp
1

<210> SEQ ID NO 9
<211> LENGTH: 4
<212> TYPE: PRT
<213> ORGANISM: Homo sapiens
<220> FEATURE:
<221> NAME/KEY: PEPTIDE
<222> LOCATION: 53..56
<223> OTHER INFORMATION: C'' strand

<400> SEQUENCE: 9

Arg Ser Gln Pro
1

<210> SEQ ID NO 10
<211> LENGTH: 5
<212> TYPE: PRT
<213> ORGANISM: Homo sapiens
<220> FEATURE:
<221> NAME/KEY: PEPTIDE
<222> LOCATION: 57..61
<223> OTHER INFORMATION: C''-D-loop

<400> SEQUENCE: 10

Gly Gln Asp Cys Arg
1               5

<210> SEQ ID NO 11
<211> LENGTH: 5
<212> TYPE: PRT
<213> ORGANISM: Homo sapiens
<220> FEATURE:
<221> NAME/KEY: PEPTIDE
<222> LOCATION: 62..66
<223> OTHER INFORMATION: D-strand

<400> SEQUENCE: 11

Phe Arg Val Thr Gln
1               5

<210> SEQ ID NO 12
<211> LENGTH: 5
<212> TYPE: PRT
<213> ORGANISM: Homo sapiens
<220> FEATURE:
<221> NAME/KEY: PEPTIDE
<222> LOCATION: 67..71
<223> OTHER INFORMATION: DE loop

<400> SEQUENCE: 12

Leu Pro Asn Gly Arg
1               5

<210> SEQ ID NO 13
<211> LENGTH: 6
<212> TYPE: PRT
<213> ORGANISM: Homo sapiens
<220> FEATURE:
<221> NAME/KEY: PEPTIDE
<222> LOCATION: 72..77
<223> OTHER INFORMATION: E strand

<400> SEQUENCE: 13

Asp Phe His Met Ser Val
1               5

<210> SEQ ID NO 14
<211> LENGTH: 9
<212> TYPE: PRT
<213> ORGANISM: Homo sapiens
<220> FEATURE:
<221> NAME/KEY: PEPTIDE
<222> LOCATION: 86..94
<223> OTHER INFORMATION: F-strand

<400> SEQUENCE: 14

Gly Thr Tyr Leu Cys Gly Ala Ile Ser
1               5

```
<210> SEQ ID NO 15
<211> LENGTH: 5
<212> TYPE: PRT
<213> ORGANISM: Homo sapiens
<220> FEATURE:
<221> NAME/KEY: PEPTIDE
<222> LOCATION: 95..99
<223> OTHER INFORMATION: F-G loop

<400> SEQUENCE: 15

Leu Ala Pro Lys Ala
1               5

<210> SEQ ID NO 16
<211> LENGTH: 4
<212> TYPE: PRT
<213> ORGANISM: Homo sapiens
<220> FEATURE:
<221> NAME/KEY: PEPTIDE
<222> LOCATION: 100..103
<223> OTHER INFORMATION: G-strand

<400> SEQUENCE: 16

Gln Ile Lys Glu
1

<210> SEQ ID NO 17
<211> LENGTH: 137
<212> TYPE: PRT
<213> ORGANISM: Mus sp.
<220> FEATURE:
<221> NAME/KEY: PEPTIDE
<223> OTHER INFORMATION: Mouse-PD-1

<400> SEQUENCE: 17

Ser Leu Thr Phe Tyr Pro Ala Trp Leu Thr Val Ser Glu Gly Ala Asn
1               5                   10                  15

Ala Thr Phe Thr Cys Ser Leu Ser Asn Trp Ser Glu Asp Leu Met Leu
            20                  25                  30

Asn Trp Asn Arg Leu Ser Pro Ser Asn Gln Thr Glu Lys Gln Ala Ala
        35                  40                  45

Phe Cys Asn Gly Leu Ser Gln Pro Val Gln Asp Ala Arg Phe Gln Ile
    50                  55                  60

Ile Gln Leu Pro Asn Arg His Asp Phe His Met Asn Ile Leu Asp Thr
65                  70                  75                  80

Arg Arg Asn Asp Ser Gly Ile Tyr Leu Cys Gly Ala Ile Ser Leu His
                85                  90                  95

Pro Lys Ala Lys Ile Glu Glu Ser Pro Gly Ala Glu Leu Val Val Thr
            100                 105                 110

Glu Arg Ile Leu Glu Thr Ser Thr Arg Tyr Pro Ser Pro Ser Pro Lys
        115                 120                 125

Pro Glu Gly Arg Phe Gln Gly Met Val
    130                 135

<210> SEQ ID NO 18
<211> LENGTH: 137
<212> TYPE: PRT
<213> ORGANISM: Rattus sp.
<220> FEATURE:
<221> NAME/KEY: PEPTIDE
<223> OTHER INFORMATION: Rat-PD-1

<400> SEQUENCE: 18

Gln Leu Ser Trp Gln Ser Gly Trp Leu Leu Val Ser Glu Gly Ala Asn
```

```
                1               5                   10                  15
            Ala Thr Phe Thr Cys Ser Phe Ser Asn Trp Ser Glu Asp Leu Lys Leu
                            20                  25                  30

Asn Trp Tyr Arg Leu Ser Pro Ser Asn Gln Thr Glu Lys Gln Ala Ala
                        35                  40                  45

Phe Cys Asn Gly Tyr Ser Gln Pro Val Arg Asp Ala Arg Phe Gln Ile
                50                  55                  60

Val Gln Leu Pro Asn Gly His Asp Phe His Met Asn Ile Leu Asp Ala
            65                  70                  75                  80

Arg Arg Asn Asp Ser Gly Ile Tyr Leu Cys Gly Ala Ile Ser Leu Pro
                            85                  90                  95

Pro Lys Ala Gln Ile Lys Glu Ser Pro Gly Ala Glu Leu Val Val Thr
                        100                 105                 110

Glu Arg Ile Leu Glu Thr Pro Thr Arg Tyr Pro Arg Pro Ser Pro Lys
                        115                 120                 125

Pro Glu Gly Gln Phe Gln Gly Leu Val
                        130                 135
```

<210> SEQ ID NO 19
<211> LENGTH: 137
<212> TYPE: PRT
<213> ORGANISM: Canis sp.
<220> FEATURE:
<221> NAME/KEY: PEPTIDE
<223> OTHER INFORMATION: Dog-PD-1

<400> SEQUENCE: 19

```
            Pro Leu Thr Phe Ser Pro Ala Gln Leu Thr Val Gln Glu Gly Glu Asn
            1               5                   10                  15

Ala Thr Phe Thr Cys Ser Leu Ala Asp Ile Pro Asp Ser Phe Val Leu
                            20                  25                  30

Asn Trp Tyr Arg Leu Ser Pro Arg Asn Gln Thr Asp Lys Leu Ala Ala
                        35                  40                  45

Phe Gln Glu Asp Arg Ile Glu Pro Gly Arg Asp Arg Arg Phe Arg Val
                50                  55                  60

Met Arg Leu Pro Asn Gly Arg Asp Phe His Met Ser Ile Val Ala Ala
            65                  70                  75                  80

Arg Leu Asn Asp Ser Gly Ile Tyr Leu Cys Gly Ala Ile Tyr Leu Pro
                            85                  90                  95

Pro Asn Thr Gln Ile Asn Glu Ser Pro Arg Ala Glu Leu Ser Val Thr
                        100                 105                 110

Glu Arg Thr Leu Glu Pro Pro Thr Gln Ser Pro Ser Pro Pro Pro Arg
                        115                 120                 125

Leu Ser Gly Gln Leu Gln Gly Leu Val
                        130                 135
```

<210> SEQ ID NO 20
<211> LENGTH: 137
<212> TYPE: PRT
<213> ORGANISM: Equus sp.
<220> FEATURE:
<221> NAME/KEY: PEPTIDE
<223> OTHER INFORMATION: Horse-PD-1

<400> SEQUENCE: 20

```
            Pro Leu Thr Phe Ser Pro Ala Arg Leu Met Val Pro Glu Gly Ala Asn
            1               5                   10                  15

Ala Thr Phe Thr Cys Ser Phe Ser Asn Thr Ser Glu His Phe Val Leu
```

-continued

```
                20                  25                  30
Asn Trp Tyr Arg Met Ser Pro Ser Asn Gln Thr Asp Lys Leu Ala Ala
        35                  40                  45

Phe Pro Glu Asp Ser Ser Gln Pro Gly Arg Ser Gly Arg Phe Arg Val
    50                  55                  60

Thr Arg Leu Pro Asn Gly Arg Asp Phe His Met Ser Val Leu Ala Ala
65                  70                  75                  80

Arg Arg Asn Asp Ser Gly Ile Tyr Leu Cys Gly Ala Ile Ser Leu Pro
                85                  90                  95

Pro Lys Thr Gln Ile Asn Glu Ser Pro Arg Ala Glu Leu Thr Val Thr
            100                 105                 110

Glu Arg Ile Pro Glu Pro Thr Glu His Pro Ser Pro Pro Pro Pro Ser
        115                 120                 125

Pro Ala Gly Gln Leu Gln Gly Leu Val
        130                 135

<210> SEQ ID NO 21
<211> LENGTH: 4
<212> TYPE: PRT
<213> ORGANISM: Homo sapiens
<220> FEATURE:
<221> NAME/KEY: PEPTIDE
<222> LOCATION: 43..56
<223> OTHER INFORMATION: C' strand to C'C'' loop

<400> SEQUENCE: 21

Phe Pro Glu Asp
1

<210> SEQ ID NO 22
<211> LENGTH: 14
<212> TYPE: PRT
<213> ORGANISM: Homo sapiens
<220> FEATURE:
<221> NAME/KEY: PEPTIDE
<222> LOCATION: 43..56
<223> OTHER INFORMATION: C' strand to C'' strand

<400> SEQUENCE: 22

Thr Asp Lys Leu Ala Ala Phe Pro Glu Asp Arg Ser Gln Pro
1               5                   10

<210> SEQ ID NO 23
<211> LENGTH: 13
<212> TYPE: PRT
<213> ORGANISM: Homo sapiens
<220> FEATURE:
<221> NAME/KEY: PEPTIDE
<222> LOCATION: 38..50
<223> OTHER INFORMATION: CC' loop to C' strand

<400> SEQUENCE: 23

Ser Pro Ser Asn Gln Thr Asp Lys Leu Ala Ala Phe Pro
1               5                   10

<210> SEQ ID NO 24
<211> LENGTH: 9
<212> TYPE: PRT
<213> ORGANISM: Homo sapiens
<220> FEATURE:
<221> NAME/KEY: PEPTIDE
<222> LOCATION: 95..103
<223> OTHER INFORMATION: FG loop to G strand

<400> SEQUENCE: 24
```

```
Leu Ala Pro Lys Ala Gln Ile Lys Glu
1               5

<210> SEQ ID NO 25
<211> LENGTH: 10
<212> TYPE: PRT
<213> ORGANISM: Homo sapiens
<220> FEATURE:
<221> NAME/KEY: PEPTIDE
<222> LOCATION: 62..71
<223> OTHER INFORMATION: D strand to DE loop

<400> SEQUENCE: 25

Phe Arg Val Thr Gln Leu Pro Asn Gly Arg
1               5                   10

<210> SEQ ID NO 26
<211> LENGTH: 7
<212> TYPE: PRT
<213> ORGANISM: Mus sp
<220> FEATURE:
<221> NAME/KEY: PEPTIDE
<222> LOCATION: 17..23
<223> OTHER INFORMATION: B strand

<400> SEQUENCE: 26

Ala Thr Phe Thr Cys Ser Leu
1               5

<210> SEQ ID NO 27
<211> LENGTH: 7
<212> TYPE: PRT
<213> ORGANISM: Mus sp
<220> FEATURE:
<221> NAME/KEY: PEPTIDE
<222> LOCATION: 24..30
<223> OTHER INFORMATION: BC loop

<400> SEQUENCE: 27

Ser Asn Trp Ser Glu Asp Leu
1               5

<210> SEQ ID NO 28
<211> LENGTH: 7
<212> TYPE: PRT
<213> ORGANISM: Mus sp
<220> FEATURE:
<221> NAME/KEY: PEPTIDE
<222> LOCATION: 31..37
<223> OTHER INFORMATION: C-Strand

<400> SEQUENCE: 28

Met Leu Asn Trp Asn Arg Leu
1               5

<210> SEQ ID NO 29
<211> LENGTH: 5
<212> TYPE: PRT
<213> ORGANISM: Mus sp
<220> FEATURE:
<221> NAME/KEY: PEPTIDE
<222> LOCATION: 38..42
<223> OTHER INFORMATION: C-C' loop

<400> SEQUENCE: 29

Ser Pro Ser Asn Gln
1               5
```

<210> SEQ ID NO 30
<211> LENGTH: 8
<212> TYPE: PRT
<213> ORGANISM: Mus sp
<220> FEATURE:
<221> NAME/KEY: PEPTIDE
<222> LOCATION: 43..50
<223> OTHER INFORMATION: C'-strand

<400> SEQUENCE: 30

Thr Glu Lys Gln Ala Ala Phe Cys
1               5

<210> SEQ ID NO 31
<211> LENGTH: 4
<212> TYPE: PRT
<213> ORGANISM: Mus sp
<220> FEATURE:
<221> NAME/KEY: PEPTIDE
<222> LOCATION: 53..56
<223> OTHER INFORMATION: C'' strand

<400> SEQUENCE: 31

Leu Ser Gln Pro
1

<210> SEQ ID NO 32
<211> LENGTH: 5
<212> TYPE: PRT
<213> ORGANISM: Mus sp
<220> FEATURE:
<221> NAME/KEY: PEPTIDE
<222> LOCATION: 57..61
<223> OTHER INFORMATION: C''-D-loop

<400> SEQUENCE: 32

Val Gln Asp Ala Arg
1               5

<210> SEQ ID NO 33
<211> LENGTH: 5
<212> TYPE: PRT
<213> ORGANISM: Mus sp
<220> FEATURE:
<221> NAME/KEY: PEPTIDE
<222> LOCATION: 62..66
<223> OTHER INFORMATION: D-strand

<400> SEQUENCE: 33

Phe Gln Ile Ile Gln
1               5

<210> SEQ ID NO 34
<211> LENGTH: 9
<212> TYPE: PRT
<213> ORGANISM: Mus sp
<220> FEATURE:
<221> NAME/KEY: PEPTIDE
<222> LOCATION: 86..94
<223> OTHER INFORMATION: F-strand

<400> SEQUENCE: 34

Gly Ile Tyr Leu Cys Gly Ala Ile Ser
1               5

<210> SEQ ID NO 35
<211> LENGTH: 5
<212> TYPE: PRT

<213> ORGANISM: Mus sp
<220> FEATURE:
<221> NAME/KEY: PEPTIDE
<222> LOCATION: 95..99
<223> OTHER INFORMATION: F-G loop

<400> SEQUENCE: 35

Leu His Pro Lys Ala
1               5

<210> SEQ ID NO 36
<211> LENGTH: 4
<212> TYPE: PRT
<213> ORGANISM: Mus sp
<220> FEATURE:
<221> NAME/KEY: PEPTIDE
<222> LOCATION: 100..103
<223> OTHER INFORMATION: G-strand

<400> SEQUENCE: 36

Lys Ile Glu Glu
1

<210> SEQ ID NO 37
<211> LENGTH: 4
<212> TYPE: PRT
<213> ORGANISM: Mus sp
<220> FEATURE:
<221> NAME/KEY: PEPTIDE
<222> LOCATION: 49..52
<223> OTHER INFORMATION: C' strand to C'C'' loop

<400> SEQUENCE: 37

Phe Cys Asn Gly
1

<210> SEQ ID NO 38
<211> LENGTH: 14
<212> TYPE: PRT
<213> ORGANISM: Mus sp
<220> FEATURE:
<221> NAME/KEY: PEPTIDE
<222> LOCATION: 43..56
<223> OTHER INFORMATION: C' strand to C'' strand

<400> SEQUENCE: 38

Thr Glu Lys Gln Ala Ala Phe Cys Asn Gly Leu Ser Gln Pro
1               5                   10

<210> SEQ ID NO 39
<211> LENGTH: 13
<212> TYPE: PRT
<213> ORGANISM: Mus sp
<220> FEATURE:
<221> NAME/KEY: PEPTIDE
<222> LOCATION: 38..50
<223> OTHER INFORMATION: CC' loop to C' strand

<400> SEQUENCE: 39

Ser Pro Ser Asn Gln Thr Glu Lys Gln Ala Ala Phe Cys
1               5                   10

<210> SEQ ID NO 40
<211> LENGTH: 9
<212> TYPE: PRT
<213> ORGANISM: Mus sp
<220> FEATURE:
<221> NAME/KEY: PEPTIDE
<222> LOCATION: 95..103

```
<223> OTHER INFORMATION: FG loop to G strand

<400> SEQUENCE: 40

Leu His Pro Lys Ala Lys Ile Glu Glu
1               5

<210> SEQ ID NO 41
<211> LENGTH: 10
<212> TYPE: PRT
<213> ORGANISM: Mus sp
<220> FEATURE:
<221> NAME/KEY: PEPTIDE
<222> LOCATION: 62..71
<223> OTHER INFORMATION: D strand to DE loop

<400> SEQUENCE: 41

Phe Gln Ile Ile Gln Leu Pro Asn Arg His
1               5                   10

<210> SEQ ID NO 42
<211> LENGTH: 7
<212> TYPE: PRT
<213> ORGANISM: Artificial Sequence
<220> FEATURE:
<223> OTHER INFORMATION: C terminal modified with NH2 group
<220> FEATURE:
<221> NAME/KEY: SITE
<222> LOCATION: 7
<223> OTHER INFORMATION: BC loop having C terminal modified with NH2
      group

<400> SEQUENCE: 42

Ser Asn Thr Ser Glu Ser Phe
1               5

<210> SEQ ID NO 43
<211> LENGTH: 7
<212> TYPE: PRT
<213> ORGANISM: Artificial Sequence
<220> FEATURE:
<223> OTHER INFORMATION: Ac or CH3CO group attached at the N terminal
      and C terminal modified with NH2 group
<220> FEATURE:
<221> NAME/KEY: SITE
<222> LOCATION: 1
<223> OTHER INFORMATION: Ac group added on N terminal
<220> FEATURE:
<221> NAME/KEY: SITE
<222> LOCATION: 7
<223> OTHER INFORMATION: NH2 group added on C terminal

<400> SEQUENCE: 43

Ser Asn Thr Ser Glu Ser Phe
1               5

<210> SEQ ID NO 44
<211> LENGTH: 19
<212> TYPE: PRT
<213> ORGANISM: Artificial Sequence
<220> FEATURE:
<223> OTHER INFORMATION: C terminal modified with NH2
<220> FEATURE:
<221> NAME/KEY: SITE
<222> LOCATION: 19
<223> OTHER INFORMATION: C terminal modified with NH2

<400> SEQUENCE: 44

Ser Asn Gln Thr Asp Lys Leu Ala Ala Phe Pro Glu Asp Ser Gln Pro
1               5                   10                  15
```

Gly Gln Asp

<210> SEQ ID NO 45
<211> LENGTH: 11
<212> TYPE: PRT
<213> ORGANISM: Artificial Sequence
<220> FEATURE:
<223> OTHER INFORMATION: C terminal modified with NH2 group
<220> FEATURE:
<221> NAME/KEY: SITE
<222> LOCATION: 11
<223> OTHER INFORMATION: C terminal modified with NH2

<400> SEQUENCE: 45

Glu Asp Arg Ser Gln Pro Gly Gln Asp Cys Arg
1               5                   10

<210> SEQ ID NO 46
<211> LENGTH: 14
<212> TYPE: PRT
<213> ORGANISM: Artificial Sequence
<220> FEATURE:
<223> OTHER INFORMATION: C terminal modified with NH2 group
<220> FEATURE:
<221> NAME/KEY: SITE
<222> LOCATION: 14
<223> OTHER INFORMATION: C terminal modified with NH2 group

<400> SEQUENCE: 46

Cys Gly Ala Ile Ser Leu Ala Pro Lys Ala Gln Ile Lys Glu
1               5                   10

<210> SEQ ID NO 47
<211> LENGTH: 20
<212> TYPE: PRT
<213> ORGANISM: Artificial Sequence
<220> FEATURE:
<223> OTHER INFORMATION: Branched peptide Sequence with NH2 modified C
      terminal and branching at Lys6
<220> FEATURE:
<221> NAME/KEY: SITE
<222> LOCATION: 6
<223> OTHER INFORMATION: Branch sequence Sequence ID 4 attached to Lys6
<220> FEATURE:
<221> NAME/KEY: SITE
<222> LOCATION: 11..12
<223> OTHER INFORMATION: Amino Hexanoic acid present in between Gln 11
      and Lys12

<400> SEQUENCE: 47

Phe Arg Val Thr Gln Lys Phe Arg Val Thr Gln Leu Ala Pro Lys Ala
1               5                   10                  15

Gln Ile Lys Glu
            20

<210> SEQ ID NO 48
<211> LENGTH: 20
<212> TYPE: PRT
<213> ORGANISM: Artificial Sequence
<220> FEATURE:
<223> OTHER INFORMATION: Branched at LYS6 with Seq ID 4 and C terminal
      modified with NH2
<220> FEATURE:
<221> NAME/KEY: SITE
<222> LOCATION: 6
<223> OTHER INFORMATION: branched amino acid sequence, Seq ID 4 attached
      to the Lys6 residue
<220> FEATURE:
<221> NAME/KEY: SITE
<222> LOCATION: 20
<223> OTHER INFORMATION: C terminal modified with NH2

```
<400> SEQUENCE: 48

Phe Arg Val Thr Gln Lys Phe Arg Val Thr Gln Leu Ala Pro Lys Ala
1               5                   10                  15

Gln Ile Lys Glu
            20

<210> SEQ ID NO 49
<211> LENGTH: 22
<212> TYPE: PRT
<213> ORGANISM: Artificial Sequence
<220> FEATURE:
<223> OTHER INFORMATION: Branched peptide at LYS8 with Seq ID 4
<220> FEATURE:
<221> NAME/KEY: SITE
<222> LOCATION: 8
<223> OTHER INFORMATION: Branched amino acid sequence, Sequence ID 4
      attached to the Lys8 residue

<400> SEQUENCE: 49

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 50
<211> LENGTH: 20
<212> TYPE: PRT
<213> ORGANISM: Artificial Sequence
<220> FEATURE:
<223> OTHER INFORMATION: Branched at LYS6 with a peptide of sequence
      SNQTDK and C terminal modified with NH2
<220> FEATURE:
<221> NAME/KEY: SITE
<222> LOCATION: 6
<223> OTHER INFORMATION: Branched amino acid sequence SNQTDK attached
      to the Lys6 residue

<400> SEQUENCE: 50

Ser Asn Gln Thr Asp Lys Phe Arg Val Thr Gln Leu Ala Pro Lys Ala
1               5                   10                  15

Gln Ile Lys Glu
            20

<210> SEQ ID NO 51
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and branch amino acid sequence at Lys6 residue
<220> FEATURE:
<221> NAME/KEY: SITE
<222> LOCATION: 6
<223> OTHER INFORMATION: branched amino acid sequence SNQTDK attached
      to the Lys6 residue

<400> SEQUENCE: 51

Ser Asn Gln Thr Asp Lys Val Leu Asn Trp Tyr Arg Met Leu Ala Pro
1               5                   10                  15

Lys Ala Gln Ile Lys Glu
            20

<210> SEQ ID NO 52
<211> LENGTH: 22
<212> TYPE: PRT
<213> ORGANISM: Artificial Sequence
```

```
<220> FEATURE:
<223> OTHER INFORMATION: Branched peptide Sequence with NH2 modified C
      terminal and branch amino acid sequence at Lys8 residue
<220> FEATURE:
<221> NAME/KEY: SITE
<222> LOCATION: 8
<223> OTHER INFORMATION: Branched amino acid sequence SNQTDK attached
      to the Lys8 residue
<220> FEATURE:
<221> NAME/KEY: SITE
<222> LOCATION: 22
<223> OTHER INFORMATION: C terminal modified with NH2

<400> SEQUENCE: 52

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 53
<211> LENGTH: 19
<212> TYPE: PRT
<213> ORGANISM: Artificial Sequence
<220> FEATURE:
<223> OTHER INFORMATION: Branched peptide Sequence with NH2 modified C
      terminal and two branched amino acid sequence attached at Lys8
      residue and Lys14 residue
<220> FEATURE:
<221> NAME/KEY: SITE
<222> LOCATION: 8
<223> OTHER INFORMATION: First branch amino acid sequence SNQTDK
      attached to the Lys8 residue
<220>
<221> NAME/KEY: SITE
<222> LOCATION: 14
<223> OTHER INFORMATION: Second branch amino acid sequence LAP attached
      to the Lys14 residue
<220> FEATURE:
<221> NAME/KEY: SITE
<222> LOCATION: 19
<223> OTHER INFORMATION: C terminal modified with NH2

<400> SEQUENCE: 53

Ser Asn Thr Ser Glu Ser Phe Lys Phe Arg Val Thr Gln Lys Ala Gln
1               5                   10                  15

Ile Lys Glu

<210> SEQ ID NO 54
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branch amino acid sequence attached to the Lys8
      residue and all amino acids are D amino acids
<220> FEATURE:
<221> NAME/KEY: SITE
<222> LOCATION: 8
<223> OTHER INFORMATION: branch amino acid sequence SEQUENCE ID 4
      attached to Lys8 residue
<220> FEATURE:
<221> NAME/KEY: MISC_FEATURE
<222> LOCATION: 1-22
<223> OTHER INFORMATION: all residues are D-amino acids
<220> FEATURE:
<221> NAME/KEY: SITE
<222> LOCATION: 22
<223> OTHER INFORMATION: C terminal modified with NH2

<400> SEQUENCE: 54

Ser Asn Thr Ser Glu Ser Phe Lys Phe Arg Val Thr Gln Leu Ala Pro
1               5                   10                  15
```

```
Lys Ala Gln Ile Lys Glu
            20

<210> SEQ ID NO 55
<211> LENGTH: 19
<212> TYPE: PRT
<213> ORGANISM: Artificial Sequence
<220> FEATURE:
<223> OTHER INFORMATION: Branched peptide Sequence with NH2 modified C
      terminal and branch amino acid sequence attached to the Lys14
      residue
<220> FEATURE:
<221> NAME/KEY: SITE
<222> LOCATION: 14
<223> OTHER INFORMATION: branch amino acid sequence KDTQNS attached to
      the Lys14 residue
<220> FEATURE:
<221> NAME/KEY: SITE
<222> LOCATION: 19
<223> OTHER INFORMATION: C terminal modified with NH2

<400> SEQUENCE: 55

Glu Lys Ile Gln Ala Lys Pro Ala Tyr Trp Asn Leu Val Lys Asp Thr
1               5                   10                  15

Gln Asn Ser

<210> SEQ ID NO 56
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and Biotin-Ahx attached to the N terminal and branching
      at Lys8 residue
<220> FEATURE:
<221> NAME/KEY: SITE
<222> LOCATION: 1
<223> OTHER INFORMATION: N terminal modified with Biotin-Ahx
<220> FEATURE:
<221> NAME/KEY: SITE
<222> LOCATION: 8
<223> OTHER INFORMATION: Branch amino acid sequence Sequence ID 4
      attached to Lys8 residue
<220> FEATURE:
<221> NAME/KEY: SITE
<222> LOCATION: 22
<223> OTHER INFORMATION: C terminal modified with NH2

<400> SEQUENCE: 56

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 57
<211> LENGTH: 22
<212> TYPE: PRT
<213> ORGANISM: Artificial Sequence
<220> FEATURE:
<223> OTHER INFORMATION: Branched peptide Sequence with NH2 modified
      C terminal and C6 lipid attached to the N terminal and branching
      at Lys8
<220> FEATURE:
<221> NAME/KEY: SITE
<222> LOCATION: 1
<223> OTHER INFORMATION: N terminal modified with C6 lipid
<220> FEATURE:
<221> NAME/KEY: SITE
<222> LOCATION: 8
<223> OTHER INFORMATION: Branch amino acid Sequence ID 4 attached to
      the Lys8 residue
```

```
<220> FEATURE:
<221> NAME/KEY: SITE
<222> LOCATION: 22
<223> OTHER INFORMATION: C terminal modified with NH2

<400> SEQUENCE: 57

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 58
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and Ac (CH3CO) group attached to the N terminal and
      branching at Lys8
<220> FEATURE:
<221> NAME/KEY: SITE
<222> LOCATION: 1
<223> OTHER INFORMATION: Ac group added on N terminal
<220> FEATURE:
<221> NAME/KEY: SITE
<222> LOCATION: 8
<223> OTHER INFORMATION: Branch amino acid sequence and Sequence ID 4
      attached to the Lys8 residue
<220> FEATURE:
<221> NAME/KEY: SITE
<222> LOCATION: 22
<223> OTHER INFORMATION: C terminal modified with NH2

<400> SEQUENCE: 58

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 59
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and branch amino acid sequence at Lys8 residue
<220> FEATURE:
<221> NAME/KEY: SITE
<222> LOCATION: 8
<223> OTHER INFORMATION: Branch amino acid sequence Sequence ID 4 with
      a modified PEG molecule (NH2-(PEG)11-CO-) attached at its N
      terminal is attached to the Lys8 residue
<220> FEATURE:
<221> NAME/KEY: SITE
<222> LOCATION: 22
<223> OTHER INFORMATION: C terminal modified with NH2

<400> SEQUENCE: 59

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 60
<211> LENGTH: 17
<212> TYPE: PRT
<213> ORGANISM: Artificial Sequence
<220> FEATURE:
<223> OTHER INFORMATION: Branched peptide sequence with NH2 modified
      C terminal and branching at Lys8 and a modified PEG molecule
```

```
         NH-PEG11-CO- between Lys8 and Lue9
<220> FEATURE:
<221> NAME/KEY: SITE
<222> LOCATION: 8
<223> OTHER INFORMATION: Branched amino acid sequence Sequence ID 4
      attached to the Lys8 residue
<220> FEATURE:
<221> NAME/KEY: SITE
<222> LOCATION: 8..9
<223> OTHER INFORMATION: Modified PEG molecule NH-PEG11-CO- between Lys8
      and Lue9
<220> FEATURE:
<221> NAME/KEY: SITE
<222> LOCATION: 17
<223> OTHER INFORMATION: C terminal modified with NH2

<400> SEQUENCE: 60

Ser Asn Thr Ser Glu Ser Phe Lys Leu Ala Pro Lys Ala Gln Ile Lys
1               5                   10                  15

Glu

<210> SEQ ID NO 61
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and branching at Lys8 residue
<220> FEATURE:
<221> NAME/KEY: SITE
<222> LOCATION: 1
<223> OTHER INFORMATION: Branch amino acid sequence is Sequence ID 4
      with a C6 lipid group attached to its N terminal
<220> FEATURE:
<221> NAME/KEY: SITE
<222> LOCATION: 22
<223> OTHER INFORMATION: C terminal modified with NH2

<400> SEQUENCE: 61

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 62
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and branching at Lys8 and C6 lipid group attached to both
      branch & N-terminal
<220> FEATURE:
<221> NAME/KEY: SITE
<222> LOCATION: 1
<223> OTHER INFORMATION: N terminal modified with C6 lipid
<220> FEATURE:
<221> NAME/KEY: SITE
<222> LOCATION: 8
<223> OTHER INFORMATION: Branch amino acid sequence Sequence ID 4 with
      C6 lipid at N-terminal attached to the Lys8 residue
<220> FEATURE:
<221> NAME/KEY: SITE
<222> LOCATION: 22
<223> OTHER INFORMATION: C terminal modified with NH2

<400> SEQUENCE: 62

Ser Asn Thr Ser Glu Ser Phe Lys Phe Arg Val Thr Gln Leu Ala Pro
1               5                   10                  15

Lys Ala Gln Ile Lys Glu
            20
```

```
<210> SEQ ID NO 63
<211> LENGTH: 19
<212> TYPE: PRT
<213> ORGANISM: Artificial Sequence
<220> FEATURE:
<223> OTHER INFORMATION: Branched peptide sequence with NH2 modified C
      terminal and two olefinic amino acids joined together forming a
      loop structure
<220> FEATURE:
<221> NAME/KEY: SITE
<222> LOCATION: 8, 12
<223> OTHER INFORMATION: Xaa is any olefinic amino acid in position 8
      and 12 where the olefinic amino acids are joined forming a loop
      structure
<220> FEATURE:
<221> NAME/KEY: SITE
<222> LOCATION: 19
<223> OTHER INFORMATION: C terminal modified with NH2

<400> SEQUENCE: 63

Ser Asn Thr Ser Glu Ser Phe Xaa Pro Lys Ala Xaa Ser Asn Thr Ser
1               5                   10                  15

Glu Ser Phe

<210> SEQ ID NO 64
<211> LENGTH: 34
<212> TYPE: PRT
<213> ORGANISM: Artificial Sequence
<220> FEATURE:
<223> OTHER INFORMATION: Branched peptide sequence with NH2 modified C
      terminal and with two olefinic amino acids joined together forming
      a loop structure and a branch amino acid sequence attached to
      Lys13 residue
<220> FEATURE:
<221> NAME/KEY: SITE
<222> LOCATION: 8, 12
<223> OTHER INFORMATION: Xaa is any olefinic amino acid in position 8
      and 12 where the olefinic amino acids are joined forming a loop
      structure
<220> FEATURE:
<221> NAME/KEY: SITE
<222> LOCATION: 13
<223> OTHER INFORMATION: Branch amino acid sequence Sequence ID 4
      attached to the Lys13 residue
<220> FEATURE:
<221> NAME/KEY: SITE
<222> LOCATION: 34
<223> OTHER INFORMATION: C terminal modified with NH2

<400> SEQUENCE: 64

Ser Asn Thr Ser Glu Ser Phe Xaa Pro Lys Ala Xaa Lys Ser Asn Thr
1               5                   10                  15

Ser Glu Ser Phe Phe Arg Val Thr Gln Leu Ala Pro Lys Ala Gln Ile
            20                  25                  30

Lys Glu

<210> SEQ ID NO 65
<211> LENGTH: 13
<212> TYPE: PRT
<213> ORGANISM: Artificial Sequence
<220> FEATURE:
<223> OTHER INFORMATION: Branched peptide Sequence with NH2 modified C
      terminal and having two Xaa olefinic amino acids in position 8
      and 12 and a branching at Lys13
<220> FEATURE:
<221> NAME/KEY: SITE
<222> LOCATION: 8, 12
<223> OTHER INFORMATION: Xaa is any olefinic amino acid in position 8
      and 12 where the olefinic amino acids are joined forming a loop
      structure
```

```
<220> FEATURE:
<221> NAME/KEY: SITE
<222> LOCATION: 13
<223> OTHER INFORMATION: Branch amino acid sequence Sequence ID 4
      attached to the Lys13 residue
<220> FEATURE:
<221> NAME/KEY: SITE
<222> LOCATION: 34
<223> OTHER INFORMATION: C terminal modified with NH2

<400> SEQUENCE: 65

Ser Asn Thr Ser Glu Ser Phe Xaa Pro Lys Ala Xaa Lys
1               5                   10

<210> SEQ ID NO 66
<211> LENGTH: 19
<212> TYPE: PRT
<213> ORGANISM: Artificial Sequence
<220> FEATURE:
<223> OTHER INFORMATION: Branched peptide Sequence with NH2 modified C
      terminal and branching at Lys8
<220> FEATURE:
<221> NAME/KEY: SITE
<222> LOCATION: 8
<223> OTHER INFORMATION: Branch amino acid sequence Sequence ID 4
      attached to the Lys8 residue
<220> FEATURE:
<221> NAME/KEY: SITE
<222> LOCATION: 19
<223> OTHER INFORMATION: C terminal modified with NH2

<400> SEQUENCE: 66

Ser Asn Thr Ser Glu Ser Phe Lys Phe Arg Val Thr Gln Leu Ala Gln
1               5                   10                  15

Ile Lys Glu

<210> SEQ ID NO 67
<211> LENGTH: 21
<212> TYPE: PRT
<213> ORGANISM: Artificial Sequence
<220> FEATURE:
<223> OTHER INFORMATION: Peptide Sequence with NH2 modified C terminal
<220> FEATURE:
<221> NAME/KEY: SITE
<222> LOCATION: 21
<223> OTHER INFORMATION: C terminal modified with NH2

<400> SEQUENCE: 67

Ser Asn Thr Ser Glu Ser Phe Phe Arg Val Thr Gln Leu Ala Pro Lys
1               5                   10                  15

Ala Gln Ile Lys Glu
            20

<210> SEQ ID NO 68
<211> LENGTH: 22
<212> TYPE: PRT
<213> ORGANISM: Artificial Sequence
<220> FEATURE:
<223> OTHER INFORMATION: Peptide Sequence with NH2 modified C terminal
<220> FEATURE:
<221> NAME/KEY: SITE
<222> LOCATION: 22
<223> OTHER INFORMATION: C terminal modified with NH2

<400> SEQUENCE: 68

Ser Asn Thr Ser Glu Ser Phe Lys Phe Arg Val Thr Gln Leu Ala Pro
1               5                   10                  15

Lys Ala Gln Ile Lys Glu
            20
```

```
<210> SEQ ID NO 69
<211> LENGTH: 29
<212> TYPE: PRT
<213> ORGANISM: Artificial Sequence
<220> FEATURE:
<223> OTHER INFORMATION: Peptide Sequence with NH2 modified C terminal
<220> FEATURE:
<221> NAME/KEY: SITE
<222> LOCATION: 29
<223> OTHER INFORMATION: C terminal modified with NH2

<400> SEQUENCE: 69

Ser Asn Thr Ser Glu Ser Phe Lys Ser Asn Thr Ser Glu Ser Phe Phe
1               5                   10                  15

Arg Val Thr Gln Leu Ala Pro Lys Ala Gln Ile Lys Glu
            20                  25

<210> SEQ ID NO 70
<211> LENGTH: 8
<212> TYPE: PRT
<213> ORGANISM: Artificial Sequence
<220> FEATURE:
<223> OTHER INFORMATION: Branched peptide Sequence with NH2 modified C
      terminal and branching at Lys8
<220> FEATURE:
<221> NAME/KEY: SITE
<222> LOCATION: 8
<223> OTHER INFORMATION: Branch amino acid sequence Sequence ID 4
      attached to the Lys8 residue
<220> FEATURE:
<221> NAME/KEY: SITE
<222> LOCATION: 8
<223> OTHER INFORMATION: C terminal modified with NH2

<400> SEQUENCE: 70

Ser Asn Thr Ser Glu Ser Phe Lys
1               5

<210> SEQ ID NO 71
<211> LENGTH: 17
<212> TYPE: PRT
<213> ORGANISM: Artificial Sequence
<220> FEATURE:
<223> OTHER INFORMATION: Branched peptide Sequence with NH2 modified C
      terminal and branching at Lys8
<220> FEATURE:
<221> NAME/KEY: SITE
<222> LOCATION: 8
<223> OTHER INFORMATION: Branch amino acid Sequence ID 4 attached to
      the Lys8 residue
<220> FEATURE:
<221> NAME/KEY: SITE
<222> LOCATION: 17
<223> OTHER INFORMATION: C terminal modified with NH2

<400> SEQUENCE: 71

Ser Asn Thr Ser Glu Ser Phe Lys Leu Ala Pro Lys Ala Gln Ile Lys
1               5                   10                  15

Glu

<210> SEQ ID NO 72
<211> LENGTH: 19
<212> TYPE: PRT
<213> ORGANISM: Artificial Sequence
<220> FEATURE:
<223> OTHER INFORMATION: Branched peptide Sequence with NH2 modified C
      terminal and branching at Lys8
<220> FEATURE:
<221> NAME/KEY: SITE
```

```
<222> LOCATION: 8
<223> OTHER INFORMATION: Branch amino acid Sequence ID 4 attached to the
      Lys8 residue
<220> FEATURE:
<221> NAME/KEY: SITE
<222> LOCATION: 8
<223> OTHER INFORMATION: C terminal modified with NH2

<400> SEQUENCE: 72

Ser Asn Thr Ser Glu Ser Phe Lys Phe Arg Val Thr Gln Ala Gln
1               5                   10                  15

Ile Lys Glu

<210> SEQ ID NO 73
<211> LENGTH: 14
<212> TYPE: PRT
<213> ORGANISM: Artificial Sequence
<220> FEATURE:
<223> OTHER INFORMATION: Branched peptide Sequence with NH2 modified C
      terminal and branching at Lys8
<220> FEATURE:
<221> NAME/KEY: SITE
<222> LOCATION: 8
<223> OTHER INFORMATION: Branched amino acid sequence Sequence ID 4
      attached to the Lys8 residue
<220> FEATURE:
<221> NAME/KEY: SITE
<222> LOCATION: 14
<223> OTHER INFORMATION: C terminal modified with NH2

<400> SEQUENCE: 73

Ser Asn Thr Ser Glu Ser Phe Lys Lys Ala Gln Ile Lys Glu
1               5                   10

<210> SEQ ID NO 74
<211> LENGTH: 22
<212> TYPE: PRT
<213> ORGANISM: Artificial Sequence
<220> FEATURE:
<223> OTHER INFORMATION: Branched peptide Sequence with NH2 modified
      C terminal and branching at Lys8 residue and a lipid attached to
      Lys 21
<220> FEATURE:
<221> NAME/KEY: SITE
<222> LOCATION: 8
<223> OTHER INFORMATION: Branch amino acid sequence Sequence ID 4
      attached to the Lys8 residue
<220> FEATURE:
<221> NAME/KEY: SITE
<222> LOCATION: 21
<223> OTHER INFORMATION: C16 lipid attached to Lys 21
<220> FEATURE:
<221> NAME/KEY: SITE
<222> LOCATION: 22
<223> OTHER INFORMATION: C terminal modified with NH2

<400> SEQUENCE: 74

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 75
<211> LENGTH: 22
<212> TYPE: PRT
<213> ORGANISM: Artificial Sequence
<220> FEATURE:
<223> OTHER INFORMATION: Branched peptide Sequence with NH2 modified
      C terminal and branching at Lys8 and a lipid attached to Lys 17
<220> FEATURE:
<221> NAME/KEY: SITE
```

-continued

```
<222> LOCATION: 8
<223> OTHER INFORMATION: Branch amino acid Sequence ID 4 attached to
      the Lys8 residue
<220> FEATURE:
<221> NAME/KEY: SITE
<222> LOCATION: 17
<223> OTHER INFORMATION: C16 lipid attached to Lys 17
<220> FEATURE:
<221> NAME/KEY: SITE
<222> LOCATION: 22
<223> OTHER INFORMATION: C terminal modified with NH2

<400> SEQUENCE: 75

Ser Asn Thr Ser Glu Ser Phe Lys Phe Arg Val Thr Gln Leu Ala Pro
1               5                  10                  15

Lys Ala Gln Ile Lys Glu
            20

<210> SEQ ID NO 76
<211> LENGTH: 20
<212> TYPE: PRT
<213> ORGANISM: Artificial Sequence
<220> FEATURE:
<223> OTHER INFORMATION: Branched peptide Sequence with NH2 modified
      C terminal with two branches
<220> FEATURE:
<221> NAME/KEY: SITE
<222> LOCATION: 8
<223> OTHER INFORMATION: First branch amino acid sequence Sequence ID
      4 attached to the Lys8 residue
<220> FEATURE:
<221> NAME/KEY: SITE
<222> LOCATION: 14
<223> OTHER INFORMATION: Second branch amino acid sequence LAP attached
      to Lys 14
<220> FEATURE:
<221> NAME/KEY: SITE
<222> LOCATION: 20
<223> OTHER INFORMATION: C terminal modified with NH2

<400> SEQUENCE: 76

Ser Asn Thr Ser Glu Ser Phe Lys Phe Arg Val Thr Gln Lys Lys Ala
1               5                  10                  15

Gln Ile Lys Glu
            20

<210> SEQ ID NO 77
<211> LENGTH: 20
<212> TYPE: PRT
<213> ORGANISM: Artificial Sequence
<220> FEATURE:
<223> OTHER INFORMATION: Branched peptide sequence with NH2 modified C
      terminal and with two branches
<220> FEATURE:
<221> NAME/KEY: SITE
<222> LOCATION: 8
<223> OTHER INFORMATION: First branch amino acid sequence Sequence ID 4
      attached to the Lys8 residue
<220> FEATURE:
<221> NAME/KEY: SITE
<222> LOCATION: 16
<223> OTHER INFORMATION: Second branch PKA attached to Lys 16
<220> FEATURE:
<221> NAME/KEY: SITE
<222> LOCATION: 20
<223> OTHER INFORMATION: C terminal modified with NH2

<400> SEQUENCE: 77

Ser Asn Thr Ser Glu Ser Phe Lys Phe Arg Val Thr Gln Leu Ala Lys
1               5                  10                  15

Gln Ile Lys Glu
```

-continued

```
<210> SEQ ID NO 78
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and branching at Lys8
<220> FEATURE:
<221> NAME/KEY: SITE
<222> LOCATION: 8
<223> OTHER INFORMATION: Branch amino acid sequence LAP attached to the
      Lys8 residue
<220> FEATURE:
<221> NAME/KEY: SITE
<222> LOCATION: 22
<223> OTHER INFORMATION: C terminal modified with NH2

<400> SEQUENCE: 78

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 79
<211> LENGTH: 18
<212> TYPE: PRT
<213> ORGANISM: Artificial Sequence
<220> FEATURE:
<223> OTHER INFORMATION: Branched peptide Sequence with NH2 modified C
      terminal and branching at Lys4
<220> FEATURE:
<221> NAME/KEY: SITE
<222> LOCATION: 4
<223> OTHER INFORMATION: Branch amino acid sequence LAP attached to the
      Lys4 residue
<220> FEATURE:
<221> NAME/KEY: SITE
<222> LOCATION: 18
<223> OTHER INFORMATION: C terminal modified with NH2

<400> SEQUENCE: 79

Leu Ala Pro Lys Phe Arg Val Thr Gln Leu Ala Pro Lys Ala Gln Ile
1               5                   10                  15

Lys Glu

<210> SEQ ID NO 80
<211> LENGTH: 9
<212> TYPE: PRT
<213> ORGANISM: Artificial Sequence
<220> FEATURE:
<223> OTHER INFORMATION: Peptide sequence with NH2 modified C terminal
<220> FEATURE:
<221> NAME/KEY: SITE
<222> LOCATION: 9
<223> OTHER INFORMATION: C terminal modified with NH2

<400> SEQUENCE: 80

Leu Ala Pro Lys Ala Gln Ile Lys Glu
1               5

<210> SEQ ID NO 81
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 residue and a lipid attached to
      Lys10
```

```
<220> FEATURE:
<221> NAME/KEY: SITE
<222> LOCATION: 8
<223> OTHER INFORMATION: Branch amino acid Sequence ID 4 attached to
      the Lys8 residue
<220> FEATURE:
<221> NAME/KEY: SITE
<222> LOCATION: 10
<223> OTHER INFORMATION: C16 lipid attached to Lys 10
<220> FEATURE:
<221> NAME/KEY: SITE
<222> LOCATION: 22
<223> OTHER INFORMATION: C terminal modified with NH2

<400> SEQUENCE: 81

Ser Asn Thr Ser Glu Ser Phe Lys Phe Lys Val Thr Gln Leu Ala Pro
1               5                   10                  15

Lys Ala Gln Ile Lys Glu
            20

<210> SEQ ID NO 82
<211> LENGTH: 16
<212> TYPE: PRT
<213> ORGANISM: Artificial Sequence
<220> FEATURE:
<223> OTHER INFORMATION: Branched peptide sequence with NH2 modified C
      terminal and branching at Lys8
<220> FEATURE:
<221> NAME/KEY: SITE
<222> LOCATION: 8
<223> OTHER INFORMATION: branch amino acid Sequence ID 4 attached to
      the Lys8 residue
<220> FEATURE:
<221> NAME/KEY: SITE
<222> LOCATION: 16
<223> OTHER INFORMATION: C terminal modified with NH2

<400> SEQUENCE: 82

Ser Asn Thr Ser Glu Ser Phe Lys Phe Arg Val Thr Gln Leu Ala Pro
1               5                   10                  15

<210> SEQ ID NO 83
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys13
<220> FEATURE:
<221> NAME/KEY: SITE
<222> LOCATION: 13
<223> OTHER INFORMATION: Branch amino acid Sequence ID 4 attached to
      the Lys13 residue
<220> FEATURE:
<221> NAME/KEY: SITE
<222> LOCATION: 22
<223> OTHER INFORMATION: C terminal modified with NH2

<400> SEQUENCE: 83

Ser Asn Thr Ser Glu Ser Phe Phe Arg Val Thr Gln Lys Leu Ala Pro
1               5                   10                  15

Lys Ala Gln Ile Lys Glu
            20

<210> SEQ ID NO 84
<211> LENGTH: 14
<212> TYPE: PRT
<213> ORGANISM: Artificial Sequence
<220> FEATURE:
<223> OTHER INFORMATION: Peptide Sequence with NH2 modified C terminal
<220> FEATURE:
```

```
<221> NAME/KEY: SITE
<222> LOCATION: 14
<223> OTHER INFORMATION: C terminal modified with NH2

<400> SEQUENCE: 84

Phe Arg Val Thr Gln Leu Ala Pro Lys Ala Gln Ile Lys Glu
1               5                   10

<210> SEQ ID NO 85
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 and a lipid attached to Lys 10
<220> FEATURE:
<221> NAME/KEY: SITE
<222> LOCATION: 8
<223> OTHER INFORMATION: Branch amino acid Sequence ID 4 attached to
      the Lys8 residue
<220> FEATURE:
<221> NAME/KEY: SITE
<222> LOCATION: 10
<223> OTHER INFORMATION: C8 (CH3(CH2)6CO) lipid attached to Lys 10
<220> FEATURE:
<221> NAME/KEY: SITE
<222> LOCATION: 22
<223> OTHER INFORMATION: C terminal modified with NH2

<400> SEQUENCE: 85

Ser Asn Thr Ser Glu Ser Phe Lys Phe Lys Val Thr Gln Leu Ala Pro
1               5                   10                  15

Lys Ala Gln Ile Lys Glu
            20

<210> SEQ ID NO 86
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 and a lipid attached to Lys 17
<220> FEATURE:
<221> NAME/KEY: SITE
<222> LOCATION: 8
<223> OTHER INFORMATION: Branch amino acid Sequence ID 4 attached to
      the Lys8 residue
<220> FEATURE:
<221> NAME/KEY: SITE
<222> LOCATION: 17
<223> OTHER INFORMATION: C8 lipid attached to Lys17
<220> FEATURE:
<221> NAME/KEY: SITE
<222> LOCATION: 22
<223> OTHER INFORMATION: C terminal modified with NH2

<400> SEQUENCE: 86

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 87
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 and a lipid attached to Lys 21
<220> FEATURE:
<221> NAME/KEY: SITE
```

```
<222> LOCATION: 8
<223> OTHER INFORMATION: branch amino acid Sequence ID 4 attached to
      the Lys8 residue
<220> FEATURE:
<221> NAME/KEY: SITE
<222> LOCATION: 21
<223> OTHER INFORMATION: C8 (CH3(CH2)6CO) lipid attached to Lys21
<220> FEATURE:
<221> NAME/KEY: SITE
<222> LOCATION: 22
<223> OTHER INFORMATION: C terminal modified with NH2

<400> SEQUENCE: 87

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 88
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and branching at Lys8 and D-amino acids in the branch
<220> FEATURE:
<221> NAME/KEY: SITE
<222> LOCATION: 8
<223> OTHER INFORMATION: Branch amino acid sequence Sequence ID 4 with
      all D-amino acids attached to the Lys8 residue
<220> FEATURE:
<221> NAME/KEY: SITE
<222> LOCATION: 22
<223> OTHER INFORMATION: C terminal modified with NH2

<400> SEQUENCE: 88

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 89
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and branching at Lys15
<220> FEATURE:
<221> NAME/KEY: SITE
<222> LOCATION: 1..22
<223> OTHER INFORMATION: Branch amino acid sequence FSESTNS attached to
      Lys15 residue
<220> FEATURE:
<221> NAME/KEY: SITE
<222> LOCATION: 22
<223> OTHER INFORMATION: C terminal modified with NH2

<400> SEQUENCE: 89

Glu Lys Ile Gln Ala Lys Pro Ala Leu Gln Thr Val Arg Phe Lys Phe
1               5                   10                  15

Ser Glu Ser Thr Asn Ser
            20

<210> SEQ ID NO 90
<211> LENGTH: 22
<212> TYPE: PRT
<213> ORGANISM: Artificial Sequence
<220> FEATURE:
<223> OTHER INFORMATION: Branched peptide Sequence with NH2 modified C
``` terminal and branching at Lys15 where the peptide sequence is a
retro inverse and contains all D-amino acid
<220> FEATURE:
<221> NAME/KEY: SITE
<222> LOCATION: 15
<223> OTHER INFORMATION: Branch amino acid sequence FSESTNS attached to
      Lys15 residue
<220> FEATURE:
<221> NAME/KEY: SITE
<222> LOCATION: 22
<223> OTHER INFORMATION: C terminal modified with NH2
<220> FEATURE:
<221> NAME/KEY: MISC_FEATURE
<222> LOCATION: 1..22
<223> OTHER INFORMATION: All amino acids are D-amino acids

<400> SEQUENCE: 90

Glu Lys Ile Gln Ala Lys Pro Ala Leu Gln Thr Val Arg Phe Lys Phe
1               5                   10                  15

Ser Glu Ser Thr Asn Ser
            20

<210> SEQ ID NO 91
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 residue and PEG-20 attached to
      Lys21
<220> FEATURE:
<221> NAME/KEY: SITE
<222> LOCATION: 8
<223> OTHER INFORMATION: Branch amino acid SEQUENCE ID 4 attached to the
      Lys8 residue
<220> FEATURE:
<221> NAME/KEY: SITE
<222> LOCATION: 21
<223> OTHER INFORMATION: PEG-20 attached to the Lys21
<220> FEATURE:
<221> NAME/KEY: SITE
<222> LOCATION: 22
<223> OTHER INFORMATION: C terminal modified with NH2

<400> SEQUENCE: 91

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 92
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 and PEG-20 attached to Lys21
<220> FEATURE:
<221> NAME/KEY: SITE
<222> LOCATION: 8
<223> OTHER INFORMATION: Branch amino acid SEQUENCE ID 4 attached to
      the Lys8 residue
<220> FEATURE:
<221> NAME/KEY: SITE
<222> LOCATION: 21
<223> OTHER INFORMATION: PEG-20 attached to the Lys21
<220> FEATURE:
<221> NAME/KEY: SITE
<222> LOCATION: 22
<223> OTHER INFORMATION: C terminal modified with NH2

<400> SEQUENCE: 92

```
Ser Asn Thr Ser Glu Ser Phe Lys Phe Arg Val Thr Gln Leu Ala Pro
1               5                   10                  15

Lys Ala Gln Ile Lys Glu
            20
```

<210> SEQ ID NO 93
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and branching at Lys8 and PEG-20 attached to Lys17
<220> FEATURE:
<221> NAME/KEY: SITE
<222> LOCATION: 8
<223> OTHER INFORMATION: Branch amino acid SEQUENCE ID 4 attached to
      the Lys8 residue
<220> FEATURE:
<221> NAME/KEY: SITE
<222> LOCATION: 17
<223> OTHER INFORMATION: PEG-20 attached to the Lys17
<220> FEATURE:
<221> NAME/KEY: SITE
<222> LOCATION: 22
<223> OTHER INFORMATION: C terminal modified with NH2

<400> SEQUENCE: 93

```
Ser Asn Thr Ser Glu Ser Phe Lys Phe Arg Val Thr Gln Leu Ala Pro
1               5                   10                  15

Lys Ala Gln Ile Lys Glu
            20
```

<210> SEQ ID NO 94
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and branching at Lys8 residue and a mini PEG molecule
      attached to Lys10
<220> FEATURE:
<221> NAME/KEY: SITE
<222> LOCATION: 8
<223> OTHER INFORMATION: Branch amino acid SEQUENCE ID 4 attached to
      the Lys8 residue
<220> FEATURE:
<221> NAME/KEY: SITE
<222> LOCATION: 10
<223> OTHER INFORMATION: mini PEG molecule attached to the Lys10
<220> FEATURE:
<221> NAME/KEY: SITE
<222> LOCATION: 22
<223> OTHER INFORMATION: C terminal modified with NH2

<400> SEQUENCE: 94

```
Ser Asn Thr Ser Glu Ser Phe Lys Phe Lys Val Thr Gln Leu Ala Pro
1               5                   10                  15

Lys Ala Gln Ile Lys Glu
            20
```

<210> SEQ ID NO 95
<211> LENGTH: 22
<212> TYPE: PRT
<213> ORGANISM: Artificial Sequence
<220> FEATURE:
<223> OTHER INFORMATION: Branched peptide Sequence with NH2 modified
      C terminal and branching at Lys8 residue and PEG-10 attached to
      Lys17
<220> FEATURE:
<221> NAME/KEY: SITE
<222> LOCATION: 8

```
<223> OTHER INFORMATION: Branch amino acid SEQUENCE ID 4 attached to
      the Lys8 residue
<220> FEATURE:
<221> NAME/KEY: SITE
<222> LOCATION: 17
<223> OTHER INFORMATION: PEG-10 attached to the Lys17
<220> FEATURE:
<221> NAME/KEY: SITE
<222> LOCATION: 22
<223> OTHER INFORMATION: C terminal modified with NH2

<400> SEQUENCE: 95

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 96
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and branching at Lys8 residue and PEG-20 attached to
      Lys21
<220> FEATURE:
<221> NAME/KEY: SITE
<222> LOCATION: 8
<223> OTHER INFORMATION: Branch amino acid SEQUENCE ID 4 attached to
      the Lys8 residue
<220> FEATURE:
<221> NAME/KEY: SITE
<222> LOCATION: 21
<223> OTHER INFORMATION: PEG-20 attached to the Lys21
<220> FEATURE:
<221> NAME/KEY: SITE
<222> LOCATION: 22
<223> OTHER INFORMATION: C terminal modified with NH2

<400> SEQUENCE: 96

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 97
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and
      branching at Lys8 residue and CH3CO group attached to the Lys10
<220> FEATURE:
<221> NAME/KEY: SITE
<222> LOCATION: 8
<223> OTHER INFORMATION: Branch amino acid SEQUENCE ID 4 attached to
      the Lys8 residue
<220> FEATURE:
<221> NAME/KEY: SITE
<222> LOCATION: 10
<223> OTHER INFORMATION: CH3CO group attached to the Lys17
<220> FEATURE:
<221> NAME/KEY: SITE
<222> LOCATION: 22
<223> OTHER INFORMATION: C terminal modified with NH2

<400> SEQUENCE: 97

Ser Asn Thr Ser Glu Ser Phe Lys Phe Lys Val Thr Gln Leu Ala Pro
1               5                   10                  15

Lys Ala Gln Ile Lys Glu
```

<210> SEQ ID NO 98
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and branching at Lys8 and CH3CO group attached to Lys17
<220> FEATURE:
<221> NAME/KEY: SITE
<222> LOCATION: 8
<223> OTHER INFORMATION: Branch amino acid SEQUENCE ID 4 attached to
      the Lys8 residue
<220> FEATURE:
<221> NAME/KEY: SITE
<222> LOCATION: 17
<223> OTHER INFORMATION: CH3CO group attached to the Lys17
<220> FEATURE:
<221> NAME/KEY: SITE
<222> LOCATION: 22
<223> OTHER INFORMATION: C terminal modified with NH2

<400> SEQUENCE: 98

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 99
<211> LENGTH: 22
<212> TYPE: PRT
<213> ORGANISM: Artificial Sequence
<220> FEATURE:
<223> OTHER INFORMATION: Branched peptide sequence with NH2 modified
      C terminal
<220> FEATURE:
<221> NAME/KEY: SITE
<222> LOCATION: 8
<223> OTHER INFORMATION: Branch amino acid SEQUENCE ID 4 attached to
      the Lys8 residue
<220> FEATURE:
<221> NAME/KEY: SITE
<222> LOCATION: 21
<223> OTHER INFORMATION: CH3CO group attached to the Lys21
<220> FEATURE:
<221> NAME/KEY: SITE
<222> LOCATION: 22
<223> OTHER INFORMATION: C terminal modified with NH2

<400> SEQUENCE: 99

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 100
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 and lipid group attached
<220> FEATURE:
<221> NAME/KEY: SITE
<222> LOCATION: 8
<223> OTHER INFORMATION: Branch amino acid SEQUENCE ID 4 attached to the
      Lys8 residue
<220> FEATURE:
<221> NAME/KEY: SITE
<222> LOCATION: 17
<223> OTHER INFORMATION: C6 lipid group attached to the Lys17

```
<220> FEATURE:
<221> NAME/KEY: SITE
<222> LOCATION: 22
<223> OTHER INFORMATION: C terminal modified with NH2

<400> SEQUENCE: 100

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 101
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and Biotin-Ahx attached at the N terminal and branching
      at Lys8 residue where all are D Amino acids
<220> FEATURE:
<221> NAME/KEY: SITE
<222> LOCATION: 1
<223> OTHER INFORMATION: N terminal modified with Biotin-Ahx
<220> FEATURE:
<221> NAME/KEY: SITE
<222> LOCATION: 8
<223> OTHER INFORMATION: Branch amino acid sequence KDTQNS attached to
      the Lys8 residue
<220> FEATURE:
<221> NAME/KEY: SITE
<222> LOCATION: 22
<223> OTHER INFORMATION: C terminal modified with NH2
<220> FEATURE:
<221> NAME/KEY: MISC_FEATURE
<222> LOCATION: 1..22
<223> OTHER INFORMATION: All amino acids are D-amino acids

<400> SEQUENCE: 101

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 102
<211> LENGTH: 19
<212> TYPE: PRT
<213> ORGANISM: Artificial Sequence
<220> FEATURE:
<223> OTHER INFORMATION: Branched peptide Sequence with NH2 modified C
      terminal and Biotin-Ahx attached at the N terminal and branching
      at Lys14
<220> FEATURE:
<221> NAME/KEY: SITE
<222> LOCATION: 1
<223> OTHER INFORMATION: N terminal modified with Biotin-Ahx
<220> FEATURE:
<221> NAME/KEY: SITE
<222> LOCATION: 14
<223> OTHER INFORMATION: Branch amino acid sequence KDTQNS attached to
      the Lys14 residue
<220> FEATURE:
<221> NAME/KEY: SITE
<222> LOCATION: 19
<223> OTHER INFORMATION: C terminal modified with NH2

<400> SEQUENCE: 102

Glu Lys Ile Gln Ala Lys Pro Ala Tyr Trp Asn Leu Val Lys Asp Thr
1               5                   10                  15

Gln Asn Ser
```

```
<210> SEQ ID NO 103
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and branching at Lys8 and lactum bond present between
      Glu17 and Lys21
<220> FEATURE:
<221> NAME/KEY: SITE
<222> LOCATION: 8
<223> OTHER INFORMATION: Branch amino acid SEQUENCE ID 4 attached to the
      Lys8 residue
<220> FEATURE:
<221> NAME/KEY: SITE
<222> LOCATION: 17..21
<223> OTHER INFORMATION: Lactam bond between Glu17 and Lys21
<220> FEATURE:
<221> NAME/KEY: SITE
<222> LOCATION: 22
<223> OTHER INFORMATION: C terminal modified with NH2

<400> SEQUENCE: 103

Ser Asn Thr Ser Glu Ser Phe Lys Phe Arg Val Thr Gln Leu Ala Pro
1               5                   10                  15

Glu Ala Gln Ile Lys Glu
            20

<210> SEQ ID NO 104
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and branching at Lys8 with lactam bond present between
      Lys10 and Glu14
<220> FEATURE:
<221> NAME/KEY: SITE
<222> LOCATION: 8
<223> OTHER INFORMATION: Branch amino acid SEQUENCE ID 4 attached to
      the Lys8 residue
<220> FEATURE:
<221> NAME/KEY: SITE
<222> LOCATION: 10..14
<223> OTHER INFORMATION: Lactam bond between Lys10 and Glu14
<220> FEATURE:
<221> NAME/KEY: SITE
<222> LOCATION: 22
<223> OTHER INFORMATION: C terminal modified with NH2

<400> SEQUENCE: 104

Ser Asn Thr Ser Glu Ser Phe Lys Phe Lys Val Thr Gln Glu Ala Pro
1               5                   10                  15

Lys Ala Gln Ile Lys Glu
            20

<210> SEQ ID NO 105
<211> LENGTH: 22
<212> TYPE: PRT
<213> ORGANISM: Artificial Sequence
<220> FEATURE:
<223> OTHER INFORMATION: Branched peptide Sequence with NH2 modified C
      terminal and branching at Lys8 residue and lactum bond present
      between Glu13 and Lys17
<220> FEATURE:
<221> NAME/KEY: SITE
<222> LOCATION: 8
<223> OTHER INFORMATION: Branch amino acid SEQUENCE ID 4 attached to
      the Lys8 residue
<220> FEATURE:
<221> NAME/KEY: SITE
<222> LOCATION: 13..17
<223> OTHER INFORMATION: Lactam bond between Glu13 and Lys17
```

```
<220> FEATURE:
<221> NAME/KEY: SITE
<222> LOCATION: 22
<223> OTHER INFORMATION: C terminal modified with NH2

<400> SEQUENCE: 105

Ser Asn Thr Ser Glu Ser Phe Lys Phe Arg Val Thr Glu Leu Ala Pro
1               5                   10                  15

Lys Ala Gln Ile Lys Glu
            20

<210> SEQ ID NO 106
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 residue and a lipid attached to
      Lys21 and Ac (CH3CO) group attached to both N terminal and branch
<220> FEATURE:
<221> NAME/KEY: SITE
<222> LOCATION: 1
<223> OTHER INFORMATION: N terminal modified with Ac (CH3CO)
<220> FEATURE:
<221> NAME/KEY: SITE
<222> LOCATION: 8
<223> OTHER INFORMATION: Branch amino acid SEQUENCE ID 4 with Ac (CH3CO)
      group at N-terminal is attached to the Lys8 residue
<220> FEATURE:
<221> NAME/KEY: SITE
<222> LOCATION: 21
<223> OTHER INFORMATION: Lys21 modified with a C8 lipid
<220> FEATURE:
<221> NAME/KEY: SITE
<222> LOCATION: 22
<223> OTHER INFORMATION: C terminal modified with NH2

<400> SEQUENCE: 106

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 107
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 residue and lipid attached to Lys21
      and Ac (CH3CO) group attached to both N terminal and branch
<220> FEATURE:
<221> NAME/KEY: SITE
<222> LOCATION: 1
<223> OTHER INFORMATION: N terminal modified with Ac (CH3CO)
<220> FEATURE:
<221> NAME/KEY: SITE
<222> LOCATION: 8
<223> OTHER INFORMATION: Branch amino acid SEQUENCE ID 4 with Ac (CH3CO)
      group at N-terminal is attached to the Lys8 residue
<220> FEATURE:
<221> NAME/KEY: SITE
<222> LOCATION: 21
<223> OTHER INFORMATION: Lys21 modified with a lipid
<220> FEATURE:
<221> NAME/KEY: SITE
<222> LOCATION: 22
<223> OTHER INFORMATION: C terminal modified with NH2

<400> SEQUENCE: 107

Ser Asn Thr Ser Glu Ser Phe Lys Phe Arg Val Thr Gln Leu Ala Pro
1               5                   10                  15
```

```
Lys Ala Gln Ile Lys Glu
            20

<210> SEQ ID NO 108
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and a branching at Lys8  and a lipid attached to Lys21
      and Ac (CH3CO) group attached to both N terminal of straight chain
      and branch
<220> FEATURE:
<221> NAME/KEY: SITE
<222> LOCATION: 1
<223> OTHER INFORMATION: N terminal modified with Ac (CH3CO)
<220> FEATURE:
<221> NAME/KEY: SITE
<222> LOCATION: 8
<223> OTHER INFORMATION: Branch amino acid SEQUENCE ID 4 with Ac (CH3CO)
      group at N-terminal is attached to the Lys8 residue
<220> FEATURE:
<221> NAME/KEY: SITE
<222> LOCATION: 21
<223> OTHER INFORMATION: Lys21 modified with a lipid
<220> FEATURE:
<221> NAME/KEY: SITE
<222> LOCATION: 22
<223> OTHER INFORMATION: C terminal modified with NH2

<400> SEQUENCE: 108

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 109
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 and a lipid attached to Lys21 and
      Ac (CH3CO) group attached to both N terminal and branch
<220> FEATURE:
<221> NAME/KEY: SITE
<222> LOCATION: 1
<223> OTHER INFORMATION: N terminal modified with Ac (CH3CO)
<220> FEATURE:
<221> NAME/KEY: SITE
<222> LOCATION: 8
<223> OTHER INFORMATION: Branch amino acid SEQUENCE ID 4 with Ac (CH3CO)
      group at N-terminal is attached to the Lys8 residue
<220> FEATURE:
<221> NAME/KEY: SITE
<222> LOCATION: 21
<223> OTHER INFORMATION: Lys21 modified with a lipid
<220> FEATURE:
<221> NAME/KEY: SITE
<222> LOCATION: 22
<223> OTHER INFORMATION: C terminal modified with NH2

<400> SEQUENCE: 109

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 110
<211> LENGTH: 22
<212> TYPE: PRT
```

```
<213> ORGANISM: Artificial Sequence
<220> FEATURE:
<223> OTHER INFORMATION: Branched peptide sequence with NH2 modified C
      terminal and branching at Lys8
<220> FEATURE:
<221> NAME/KEY: SITE
<222> LOCATION: 8
<223> OTHER INFORMATION: Branch amino acid sequence SNWSEDL attached to
      the Lys8 residue
<220> FEATURE:
<221> NAME/KEY: SITE
<222> LOCATION: 22
<223> OTHER INFORMATION: C terminal modified with NH2

<400> SEQUENCE: 110

Ser Asn Trp Ser Glu Asp Leu Lys Phe Gln Ile Ile Gln Leu His Pro
1               5                   10                  15

Lys Ala Lys Ile Glu Glu
            20

<210> SEQ ID NO 111
<211> LENGTH: 17
<212> TYPE: PRT
<213> ORGANISM: Artificial Sequence
<220> FEATURE:
<223> OTHER INFORMATION: Branched peptide sequence with NH2 modified C
      terminal and branching at Lys3
<220> FEATURE:
<221> NAME/KEY: SITE
<222> LOCATION: 3
<223> OTHER INFORMATION: Branch amino acid SEQUENCE ID 8 attached to the
      Lys3 residue
<220> FEATURE:
<221> NAME/KEY: SITE
<222> LOCATION: 17
<223> OTHER INFORMATION: C terminal modified with NH2

<400> SEQUENCE: 111

Glu Asp Lys Phe Arg Val Thr Gln Leu Ala Pro Lys Ala Gln Ile Lys
1               5                   10                  15

Glu

<210> SEQ ID NO 112
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8
<220> FEATURE:
<221> NAME/KEY: SITE
<222> LOCATION: 3
<223> OTHER INFORMATION: Branch amino acid SEQUENCE ID 8 attached to the
      Lys3 residue
<220> FEATURE:
<221> NAME/KEY: SITE
<222> LOCATION: 22
<223> OTHER INFORMATION: C terminal modified with NH2

<400> SEQUENCE: 112

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 113
<211> LENGTH: 20
<212> TYPE: PRT
<213> ORGANISM: Artificial Sequence
<220> FEATURE:
```

```
<223> OTHER INFORMATION: Branched peptide sequence with NH2 modified C
      terminal and branching at Lys6
<220> FEATURE:
<221> NAME/KEY: SITE
<222> LOCATION: 6
<223> OTHER INFORMATION: Branch amino acid SEQUENCE ID 8 attached to the
      Lys6 residue
<220> FEATURE:
<221> NAME/KEY: SITE
<222> LOCATION: 20
<223> OTHER INFORMATION: C terminal modified with NH2

<400> SEQUENCE: 113

Leu Ala Pro Lys Ala Lys Phe Arg Val Thr Gln Leu Ala Pro Lys Ala
1               5                   10                  15

Gln Ile Lys Glu
            20

<210> SEQ ID NO 114
<211> LENGTH: 21
<212> TYPE: PRT
<213> ORGANISM: Artificial Sequence
<220> FEATURE:
<223> OTHER INFORMATION: Branched peptide sequence with NH2 modified C
      terminal and branching at Lys7
<220> FEATURE:
<221> NAME/KEY: SITE
<222> LOCATION: 7
<223> OTHER INFORMATION: Branch amino acid SEQUENCE ID 8 attached to the
      Lys7 residue
<220> FEATURE:
<221> NAME/KEY: SITE
<222> LOCATION: 21
<223> OTHER INFORMATION: C terminal modified with NH2

<400> SEQUENCE: 114

Ser Asn Gln Thr Asp Lys Lys Phe Arg Val Thr Gln Leu Ala Pro Lys
1               5                   10                  15

Ala Gln Ile Lys Glu
            20

<210> SEQ ID NO 115
<211> LENGTH: 24
<212> TYPE: PRT
<213> ORGANISM: Artificial Sequence
<220> FEATURE:
<223> OTHER INFORMATION: Branched peptide sequence with NH2 modified C
      terminal and branching at Lys6
<220> FEATURE:
<221> NAME/KEY: SITE
<222> LOCATION: 1..24
<223> OTHER INFORMATION: Branch amino acid sequence SNQTDK attached to
      the Lys6 residue

<400> SEQUENCE: 115

Ser Asn Gln Thr Asp Lys Gly Ile Tyr Leu Cys Gly Ala Ile Ser Leu
1               5                   10                  15

Ala Pro Lys Ala Gln Ile Lys Glu
            20

<210> SEQ ID NO 116
<211> LENGTH: 25
<212> TYPE: PRT
<213> ORGANISM: Artificial Sequence
<220> FEATURE:
<223> OTHER INFORMATION: Branched peptide sequence with NH2 modified C
      terminal and branching at Lys7
<220> FEATURE:
<221> NAME/KEY: SITE
<222> LOCATION: 7
```

```
<223> OTHER INFORMATION: Branch amino acid sequence VLNWYRM attached to
      the Lys7 residue
<220> FEATURE:
<221> NAME/KEY: SITE
<222> LOCATION: 25
<223> OTHER INFORMATION: C terminal modified with NH2

<400> SEQUENCE: 116

Ser Asn Gln Thr Asp Lys Lys Gly Ile Tyr Leu Cys Gly Ala Ile Ser
1               5                   10                  15

Leu Ala Pro Lys Ala Gln Ile Lys Glu
            20                  25

<210> SEQ ID NO 117
<211> LENGTH: 21
<212> TYPE: PRT
<213> ORGANISM: Artificial Sequence
<220> FEATURE:
<223> OTHER INFORMATION: Branched peptide sequence with NH2 modified C
      terminal and branching at Lys3
<220> FEATURE:
<221> NAME/KEY: SITE
<222> LOCATION: 3
<223> OTHER INFORMATION: Branch amino acid sequence VLNWYRM attached to
      the Lys3 residue
<220> FEATURE:
<221> NAME/KEY: SITE
<222> LOCATION: 21
<223> OTHER INFORMATION: C terminal modified with NH2

<400> SEQUENCE: 117

Glu Asp Lys Gly Ile Tyr Leu Cys Gly Ala Ile Ser Leu Ala Pro Lys
1               5                   10                  15

Ala Gln Ile Lys Glu
            20

<210> SEQ ID NO 118
<211> LENGTH: 26
<212> TYPE: PRT
<213> ORGANISM: Artificial Sequence
<220> FEATURE:
<223> OTHER INFORMATION: Branched peptide sequence with NH2 modified C
      terminal and branching at Lys8
<220> FEATURE:
<221> NAME/KEY: SITE
<222> LOCATION: 8
<223> OTHER INFORMATION: Branch amino acid SEQUENCE ID 4 attached to
      the Lys8 residue
<220> FEATURE:
<221> NAME/KEY: SITE
<222> LOCATION: 26
<223> OTHER INFORMATION: C terminal modified with NH2

<400> SEQUENCE: 118

Ser Asn Thr Ser Glu Ser Phe Lys Gly Ile Tyr Leu Cys Gly Ala Ile
1               5                   10                  15

Ser Leu Ala Pro Lys Ala Gln Ile Lys Glu
            20                  25

<210> SEQ ID NO 119
<211> LENGTH: 24
<212> TYPE: PRT
<213> ORGANISM: Artificial Sequence
<220> FEATURE:
<223> OTHER INFORMATION: Branched peptide sequence with NH2 modified C
      terminal and branching at Lys8
<220> FEATURE:
<221> NAME/KEY: SITE
<222> LOCATION: 8
<223> OTHER INFORMATION: Branch amino acid SEQUENCE ID 4 attached to
```

```
        the Lys8 residue
<220> FEATURE:
<221> NAME/KEY: SITE
<222> LOCATION: 24
<223> OTHER INFORMATION: C terminal modified with NH2

<400> SEQUENCE: 119

Ser Asn Thr Ser Glu Ser Phe Lys Val Leu Asn Trp Tyr Arg Met Leu
1               5                   10                  15

Ala Pro Lys Ala Gln Ile Lys Glu
            20

<210> SEQ ID NO 120
<211> LENGTH: 26
<212> TYPE: PRT
<213> ORGANISM: Artificial Sequence
<220> FEATURE:
<223> OTHER INFORMATION: Branched peptide sequence with NH2 modified C
      terminal and branching at Lys8
<220> FEATURE:
<221> NAME/KEY: SITE
<222> LOCATION: 8
<223> OTHER INFORMATION: Branch amino acid sequence SNQTDK attached to
      the Lys8 residue
<220> FEATURE:
<221> NAME/KEY: SITE
<222> LOCATION: 26
<223> OTHER INFORMATION: C terminal modified with NH2

<400> SEQUENCE: 120

Val Leu Asn Trp Tyr Arg Met Lys Gly Ile Tyr Leu Cys Gly Ala Ile
1               5                   10                  15

Ser Leu Ala Pro Lys Ala Gln Ile Lys Glu
            20                  25

<210> SEQ ID NO 121
<211> LENGTH: 18
<212> TYPE: PRT
<213> ORGANISM: Artificial Sequence
<220> FEATURE:
<223> OTHER INFORMATION: Peptide sequence with NH2 modified C terminal
<220> FEATURE:
<221> NAME/KEY: SITE
<222> LOCATION: 18
<223> OTHER INFORMATION: C terminal modified with NH2

<400> SEQUENCE: 121

Gly Ile Tyr Leu Cys Gly Ala Ile Ser Leu Ala Pro Lys Ala Gln Ile
1               5                   10                  15

Lys Glu

<210> SEQ ID NO 122
<211> LENGTH: 21
<212> TYPE: PRT
<213> ORGANISM: Artificial Sequence
<220> FEATURE:
<223> OTHER INFORMATION: Branched peptide sequence with NH2 modified C
      terminal and branching at Lys7
<220> FEATURE:
<221> NAME/KEY: SITE
<222> LOCATION: 1..21
<223> OTHER INFORMATION: Branch amino acid sequence SNQTDK attached to
      the Lys7 residue

<400> SEQUENCE: 122

Ser Asn Gln Thr Asp Lys Lys Phe Arg Val Thr Gln Leu Ala Pro Lys
1               5                   10                  15

Ala Gln Ile Lys Glu
            20
```

```
<210> SEQ ID NO 123
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 and lipid attached to Lys19
<220> FEATURE:
<221> NAME/KEY: SITE
<222> LOCATION: 8
<223> OTHER INFORMATION: Branch amino acid sequence SNWSEDL attached to
      the Lys8 residue
<220> FEATURE:
<221> NAME/KEY: SITE
<222> LOCATION: 19
<223> OTHER INFORMATION: C16 lipid branch attached to the Lys19 residue
<220> FEATURE:
<221> NAME/KEY: SITE
<222> LOCATION: 22
<223> OTHER INFORMATION: C terminal modified with NH2

<400> SEQUENCE: 123

Ser Asn Trp Ser Glu Asp Leu Lys Phe Gln Ile Ile Gln Leu His Pro
1               5                   10                  15

Lys Ala Lys Ile Glu Glu
            20

<210> SEQ ID NO 124
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and with two branches
<220> FEATURE:
<221> NAME/KEY: SITE
<222> LOCATION: 14
<223> OTHER INFORMATION: First branch amino acid SEQUENCE ID 4 attached
      to the Lys8 residue
<220> FEATURE:
<221> NAME/KEY: SITE
<222> LOCATION: 17
<223> OTHER INFORMATION: Second branch MPA-NH-CH2-CH2-O-CH2-CH2-O-CO
      attached to the Lys17 residue
<220> FEATURE:
<221> NAME/KEY: SITE
<222> LOCATION: 22
<223> OTHER INFORMATION: C terminal modified with NH2

<400> SEQUENCE: 124

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 125
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8
<220> FEATURE:
<221> NAME/KEY: MISC_FEATURE
<222> LOCATION: 1
<223> OTHER INFORMATION: Ser is D amino acid
<220> FEATURE:
<221> NAME/KEY: SITE
<222> LOCATION: 8
<223> OTHER INFORMATION: Branch amino acid sequence sNTSESF attached to
```

```
            the Lys8 residue
<220> FEATURE:
<221> NAME/KEY: SITE
<222> LOCATION: 22
<223> OTHER INFORMATION: C terminal modified with NH2

<400> SEQUENCE: 125

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 126
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 and Ser1 is D amino acid
<220> FEATURE:
<221> NAME/KEY: MISC_FEATURE
<222> LOCATION: 1
<223> OTHER INFORMATION: Ser is D amino acid
<220> FEATURE:
<221> NAME/KEY: SITE
<222> LOCATION: 8
<223> OTHER INFORMATION: Branch amino acid SEQUENCE ID 4 attached to the
      Lys8 residue
<220> FEATURE:
<221> NAME/KEY: SITE
<222> LOCATION: 22
<223> OTHER INFORMATION: C terminal modified with NH2

<400> SEQUENCE: 126

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 127
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 and Ser in N terminal and branch
      are D amino acid
<220> FEATURE:
<221> NAME/KEY: MISC_FEATURE
<222> LOCATION: 1
<223> OTHER INFORMATION: Ser is D amino acid
<220> FEATURE:
<221> NAME/KEY: SITE
<222> LOCATION: 8
<223> OTHER INFORMATION: Branch amino acid SEQUENCE ID 4 with D-Ser at
      N terminal is attached to the Lys8 residue
<220> FEATURE:
<221> NAME/KEY: SITE
<222> LOCATION: 22
<223> OTHER INFORMATION: C terminal modified with NH2

<400> SEQUENCE: 127

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 128
<211> LENGTH: 22
<212> TYPE: PRT
```

<213> ORGANISM: Artificial Sequence
<220> FEATURE:
<223> OTHER INFORMATION: Branched peptide sequence with NH2 modified C
      terminal and with two branches
<220> FEATURE:
<221> NAME/KEY: SITE
<222> LOCATION: 8
<223> OTHER INFORMATION: First branch amino acid SEQUENCE ID 4 attached
      to Lys8 residue
<220> FEATURE:
<221> NAME/KEY: SITE
<222> LOCATION: 21
<223> OTHER INFORMATION: Second branch MPA-NH-CH2-CH2-O-CH2-CH2-O-CO
      attached to the Lys21 residue
<220> FEATURE:
<221> NAME/KEY: SITE
<222> LOCATION: 22
<223> OTHER INFORMATION: C terminal modified with NH2

<400> SEQUENCE: 128

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 129
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 residue and with amide bond between
      Ser1 and Asn2 reduced at both the N terminal and branch
<220> FEATURE:
<221> NAME/KEY: SITE
<222> LOCATION: 8
<223> OTHER INFORMATION: Branch amino acid SEQUENCE ID 4 attached to the
      Lys8 residue
<220> FEATURE:
<221> NAME/KEY: SITE
<222> LOCATION: 1..2
<223> OTHER INFORMATION: amide bond reduced between Ser1 and Asn2 reduced
      at the N terminal and branch
<220> FEATURE:
<221> NAME/KEY: SITE
<222> LOCATION: 22
<223> OTHER INFORMATION: C terminal modified with NH2

<400> SEQUENCE: 129

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 130
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 residue and D-Asn at N-terminus
<220> FEATURE:
<221> NAME/KEY: SITE
<222> LOCATION: 8
<223> OTHER INFORMATION: Branch amino acid SEQUENCE ID 4 with D-Asn at
      the N-terminus is attached to the Lys8 residue
<220> FEATURE:
<221> NAME/KEY: SITE
<222> LOCATION: 22
<223> OTHER INFORMATION: C terminal modified with NH2

<400> SEQUENCE: 130

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 131
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 residue and D-Asn in the branch
<220> FEATURE:
<221> NAME/KEY: SITE
<222> LOCATION: 8
<223> OTHER INFORMATION: Branch amino acid SEQUENCE ID 4 attached to the
      Lys8 residue
<220> FEATURE:
<221> NAME/KEY: MISC_FEATURE
<222> LOCATION: 8
<223> OTHER INFORMATION: Asn in the SEQUENCE ID 4 branch is a D-amino
      acid
<220> FEATURE:
<221> NAME/KEY: SITE
<222> LOCATION: 22
<223> OTHER INFORMATION: C terminal modified with NH2

<400> SEQUENCE: 131

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 132
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and two branches
<220> FEATURE:
<221> NAME/KEY: SITE
<222> LOCATION: 8
<223> OTHER INFORMATION: First branch amino acid sequence SNWSEDL
      attached to the Lys8 residue
<220> FEATURE:
<221> NAME/KEY: SITE
<222> LOCATION: 17
<223> OTHER INFORMATION: Second branch MPA-NH-CH2-CH2-O-CH2-CH2-O-CO
      attached to the Lys17 residue
<220> FEATURE:
<221> NAME/KEY: SITE
<222> LOCATION: 22
<223> OTHER INFORMATION: C terminal modified with NH2

<400> SEQUENCE: 132

Ser Asn Trp Ser Glu Asp Leu Lys Phe Gln Ile Ile Gln Leu His Pro
1               5                   10                  15

Lys Ala Lys Ile Glu Glu
            20

<210> SEQ ID NO 133
<211> LENGTH: 22
<212> TYPE: PRT
<213> ORGANISM: Artificial Sequence
<220> FEATURE:
<223> OTHER INFORMATION: Branched peptide sequence with branching at
      Lys8
<220> FEATURE:
<221> NAME/KEY: SITE
<222> LOCATION: 8

<223> OTHER INFORMATION: Branch amino acid SEQUENCE ID 4 attached to
      the Lys8 residue

<400> SEQUENCE: 133

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 134
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 the amide bond between Ser1 and
      Asn2 at the N terminal is reduced
<220> FEATURE:
<221> NAME/KEY: SITE
<222> LOCATION: 8
<223> OTHER INFORMATION: Branch amino acid SEQUENCE ID 4 attached to
      the Lys8 residue
<220> FEATURE:
<221> NAME/KEY: SITE
<222> LOCATION: 1..2
<223> OTHER INFORMATION: Amide bond reduced between Ser1 and Asn2 at the
      N terminal of the branch
<220> FEATURE:
<221> NAME/KEY: SITE
<222> LOCATION: 22
<223> OTHER INFORMATION: C terminal modified with NH2

<400> SEQUENCE: 134

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 135
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal with branching at Lys8
<220> FEATURE:
<221> NAME/KEY: SITE
<222> LOCATION: 8
<223> OTHER INFORMATION: Branch amino acid SEQUENCE ID 4 attached to the
      Lys8 residue
<220> FEATURE:
<221> NAME/KEY: SITE
<222> LOCATION: 22
<223> OTHER INFORMATION: C terminal modified with NH2

<400> SEQUENCE: 135

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 136
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 residue and the amide bond between
      Asn2 and Thr3 at the N terminal is reduced
<220> FEATURE:

-continued

```
<221> NAME/KEY: SITE
<222> LOCATION: 8
<223> OTHER INFORMATION: Branch amino acid SEQUENCE ID 4 attached to the
      Lys8 residue
<220> FEATURE:
<221> NAME/KEY: SITE
<222> LOCATION: 2..3
<223> OTHER INFORMATION: Amide bond reduced between Asn2 and Thr3 at N
      terminal of the branch
<220> FEATURE:
<221> NAME/KEY: SITE
<222> LOCATION: 22
<223> OTHER INFORMATION: C terminal modified with NH2

<400> SEQUENCE: 136

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 137
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8
<220> FEATURE:
<221> NAME/KEY: SITE
<222> LOCATION: 8
<223> OTHER INFORMATION: Branch amino acid SEQUENCE ID 4 attached to the
      Lys8 residue
<220> FEATURE:
<221> NAME/KEY: SITE
<222> LOCATION: 2..3
<223> OTHER INFORMATION: Amide bonds reduced between Asn2 and Thr3 at N
      terminal of the branch
<220> FEATURE:
<221> NAME/KEY: SITE
<222> LOCATION: 22
<223> OTHER INFORMATION: C terminal modified with NH2

<400> SEQUENCE: 137

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 138
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 residue and the amide bonds between
      Asn2 and Thr3 at the N terminal and the branch are reduced
<220> FEATURE:
<221> NAME/KEY: SITE
<222> LOCATION: 8
<223> OTHER INFORMATION: Branch amino acid SEQUENCE ID 4 attached to the
      Lys8 residue
<220> FEATURE:
<221> NAME/KEY: SITE
<222> LOCATION: 2..3
<223> OTHER INFORMATION: Amide bonds reduced between Asn2 and Thr3 at N
      terminal of the branch
<220> FEATURE:
<221> NAME/KEY: SITE
<222> LOCATION: 22
<223> OTHER INFORMATION: C terminal modified with NH2

<400> SEQUENCE: 138
```

```
Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 139
<211> LENGTH: 22
<212> TYPE: PRT
<213> ORGANISM: Artificial Sequence
<220> FEATURE:
<223> OTHER INFORMATION: Branched peptide sequence with two branches
<220> FEATURE:
<221> NAME/KEY: SITE
<222> LOCATION: 8
<223> OTHER INFORMATION: First branch amino acid SEQUENCE ID 4 attached
      to the Lys8 residue
<220> FEATURE:
<221> NAME/KEY: SITE
<222> LOCATION: 17
<223> OTHER INFORMATION: Second branch C16 lipid attached to the Lys 17
      residue

<400> SEQUENCE: 139

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 140
<211> LENGTH: 14
<212> TYPE: PRT
<213> ORGANISM: Artificial Sequence
<220> FEATURE:
<223> OTHER INFORMATION: Branched peptide sequence with NH2 modified C
      terminal and Xaa is Orn residue present at the 8th position and
      branch amino acid sequence attached to the Orn8 residue
<220> FEATURE:
<221> NAME/KEY: SITE
<222> LOCATION: 8
<223> OTHER INFORMATION: Xaa is ornithine at position 8
<220> FEATURE:
<221> NAME/KEY: SITE
<222> LOCATION: 8
<223> OTHER INFORMATION: Branch amino acid SEQUENCE ID 4 attached to the
      Orn8 residue
<220> FEATURE:
<221> NAME/KEY: SITE
<222> LOCATION: 14
<223> OTHER INFORMATION: C terminal modified with NH2

<400> SEQUENCE: 140

Ser Asn Thr Ser Glu Ser Phe Xaa Lys Ala Gln Ile Lys Glu
1               5                   10

<210> SEQ ID NO 141
<211> LENGTH: 14
<212> TYPE: PRT
<213> ORGANISM: Artificial Sequence
<220> FEATURE:
<223> OTHER INFORMATION: Branched peptide sequence with NH2 modified C
      terminal and Xaa is 2,3-diaminopropionic acid residue present at
      the 8th position and a branch amino acid sequence attached to the
      Xaa residue
<220> FEATURE:
<221> NAME/KEY: SITE
<222> LOCATION: 8
<223> OTHER INFORMATION: Xaa is 2,3-diaminopropionic acid at position 8
<220> FEATURE:
<221> NAME/KEY: SITE
<222> LOCATION: 8
<223> OTHER INFORMATION: Branch amino acid SEQUENCE ID 4 attached to the
      Dpr8 residue
```

```
<220> FEATURE:
<221> NAME/KEY: SITE
<222> LOCATION: 14
<223> OTHER INFORMATION: C terminal modified with NH2

<400> SEQUENCE: 141

Ser Asn Thr Ser Glu Ser Phe Xaa Lys Ala Gln Ile Lys Glu
1               5                   10

<210> SEQ ID NO 142
<211> LENGTH: 14
<212> TYPE: PRT
<213> ORGANISM: Artificial Sequence
<220> FEATURE:
<223> OTHER INFORMATION: Branched peptide sequence with NH2 modified C
      terminal and Xaa is 2,4-diaminobutric acid residue present at the
      8th position and a branch amino acid sequence, attached to the Xaa
      residue
<220> FEATURE:
<221> NAME/KEY: SITE
<222> LOCATION: 8
<223> OTHER INFORMATION: Xaa is 2,3-diaminobutric acid at position 8
<220> FEATURE:
<221> NAME/KEY: SITE
<222> LOCATION: 8
<223> OTHER INFORMATION: Branch amino acid SEQUENCE ID 4 attached to the
      Dbu8 residue
<220> FEATURE:
<221> NAME/KEY: SITE
<222> LOCATION: 14
<223> OTHER INFORMATION: C terminal modified with NH2

<400> SEQUENCE: 142

Ser Asn Thr Ser Glu Ser Phe Xaa Lys Ala Gln Ile Lys Glu
1               5                   10

<210> SEQ ID NO 143
<211> LENGTH: 23
<212> TYPE: PRT
<213> ORGANISM: Artificial Sequence
<220> FEATURE:
<223> OTHER INFORMATION: Branched peptide sequence with NH2 modified C
      terminal and branching at Lys8 residue; lactam bond present
      between Lys17 and Glu21
<220> FEATURE:
<221> NAME/KEY: SITE
<222> LOCATION: 8
<223> OTHER INFORMATION: Branch amino acid SEQUENCE ID 4 attached to the
      Lys8 residue
<220> FEATURE:
<221> NAME/KEY: SITE
<222> LOCATION: 17..21
<223> OTHER INFORMATION: lactam bond between Lys17 and Glu21
<220> FEATURE:
<221> NAME/KEY: SITE
<222> LOCATION: 23
<223> OTHER INFORMATION: C terminal modified with NH2

<400> SEQUENCE: 143

Ser Asn Thr Ser Glu Ser Phe Lys Phe Arg Val Thr Gln Leu Ala Pro
1               5                   10                  15

Lys Ile Ala Gln Glu Lys Glu
            20

<210> SEQ ID NO 144
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 residue and lactam bond present
      between Lys9 and Glu13
```

```
<220> FEATURE:
<221> NAME/KEY: SITE
<222> LOCATION: 8
<223> OTHER INFORMATION: Branch amino acid SEQUENCE ID 4 attached to
      the Lys8 residue
<220> FEATURE:
<221> NAME/KEY: SITE
<222> LOCATION: 9..13
<223> OTHER INFORMATION: lactam bond between Lys9 and Glu 13
<220> FEATURE:
<221> NAME/KEY: SITE
<222> LOCATION: 22
<223> OTHER INFORMATION: C terminal modified with NH2

<400> SEQUENCE: 144

Ser Asn Thr Ser Glu Ser Phe Lys Lys Arg Val Thr Glu Leu Ala Pro
1               5                   10                  15

Lys Ala Gln Ile Lys Glu
            20

<210> SEQ ID NO 145
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 residue and lactum bond present
      between Lys11 and Glu15
<220> FEATURE:
<221> NAME/KEY: SITE
<222> LOCATION: 8
<223> OTHER INFORMATION: Branch amino acid SEQUENCE ID 4 attached to
      the Lys8 residue
<220> FEATURE:
<221> NAME/KEY: SITE
<222> LOCATION: 11..15
<223> OTHER INFORMATION: Lactam bond between Lys11 and Glu15
<220> FEATURE:
<221> NAME/KEY: SITE
<222> LOCATION: 22
<223> OTHER INFORMATION: C terminal modified with NH2

<400> SEQUENCE: 145

Ser Asn Thr Ser Glu Ser Phe Lys Phe Arg Lys Thr Gln Leu Glu Pro
1               5                   10                  15

Lys Ala Gln Ile Lys Glu
            20

<210> SEQ ID NO 146
<211> LENGTH: 22
<212> TYPE: PRT
<213> ORGANISM: Artificial Sequence
<220> FEATURE:
<223> OTHER INFORMATION: Branched peptide sequence with NH2 modified C
      terminal and branching at Lys8 residue and lactam bond present
      between Glu12 and Lys16
<220> FEATURE:
<221> NAME/KEY: SITE
<222> LOCATION: 8
<223> OTHER INFORMATION: Branch amino acid SEQUENCE ID 4 attached to the
      Lys8 residue
<220> FEATURE:
<221> NAME/KEY: SITE
<222> LOCATION: 12..16
<223> OTHER INFORMATION: Lactam bond between Glu12 and Lys 16
<220> FEATURE:
<221> NAME/KEY: SITE
<222> LOCATION: 22
<223> OTHER INFORMATION: C terminal modified with NH2

<400> SEQUENCE: 146

Ser Asn Thr Ser Glu Ser Phe Lys Phe Arg Val Glu Gln Leu Ala Lys
```

```
                 1               5                  10                  15

Pro Ala Gln Ile Lys Glu
             20

<210> SEQ ID NO 147
<211> LENGTH: 5
<212> TYPE: PRT
<213> ORGANISM: Artificial Sequence
<220> FEATURE:
<223> OTHER INFORMATION: Peptide sequence with NH2 modified C terminal
<220> FEATURE:
<221> NAME/KEY: SITE
<222> LOCATION: 5
<223> OTHER INFORMATION: C terminal modified with NH2

<400> SEQUENCE: 147

Leu Ala Pro Lys Ala
1               5

<210> SEQ ID NO 148
<211> LENGTH: 19
<212> TYPE: PRT
<213> ORGANISM: Artificial Sequence
<220> FEATURE:
<223> OTHER INFORMATION: Branched peptide sequence with NH2 modified C
      terminal and branching at Ala5
<220> FEATURE:
<221> NAME/KEY: SITE
<222> LOCATION: 5
<223> OTHER INFORMATION: Branch amino acid sequence SNQTDK attached to
      the Ala5 residue
<220> FEATURE:
<221> NAME/KEY: SITE
<222> LOCATION: 19
<223> OTHER INFORMATION: C terminal modified with NH2

<400> SEQUENCE: 148

Leu Ala Pro Lys Ala Phe Arg Val Thr Gln Leu Ala Pro Lys Ala Gln
1               5                  10                  15

Ile Lys Glu

<210> SEQ ID NO 149
<211> LENGTH: 5
<212> TYPE: PRT
<213> ORGANISM: Homo sapiens
<220> FEATURE:
<223> OTHER INFORMATION: PD-1 Fragment

<400> SEQUENCE: 149

Asn Ala Thr Phe Thr
1               5

<210> SEQ ID NO 150
<211> LENGTH: 5
<212> TYPE: PRT
<213> ORGANISM: Artificial Sequence
<220> FEATURE:
<223> OTHER INFORMATION: Fragment

<400> SEQUENCE: 150

Phe Thr Cys Ser Pro
1               5

<210> SEQ ID NO 151
<211> LENGTH: 5
<212> TYPE: PRT
<213> ORGANISM: Homo sapiens
<220> FEATURE:
```

```
<223> OTHER INFORMATION: C-strand fragment

<400> SEQUENCE: 151

Val Leu Asn Trp Tyr
1               5

<210> SEQ ID NO 152
<211> LENGTH: 5
<212> TYPE: PRT
<213> ORGANISM: Homo Sapiens
<220> FEATURE:
<223> OTHER INFORMATION: C-strand fragment

<400> SEQUENCE: 152

Asn Trp Tyr Arg Met
1               5

<210> SEQ ID NO 153
<211> LENGTH: 6
<212> TYPE: PRT
<213> ORGANISM: Homo Sapiens
<220> FEATURE:
<223> OTHER INFORMATION: C C' loop to C' Strand fragment

<400> SEQUENCE: 153

Ser Asn Gln Thr Asp Lys
1               5

<210> SEQ ID NO 154
<211> LENGTH: 6
<212> TYPE: PRT
<213> ORGANISM: Homo sapiens
<220> FEATURE:
<223> OTHER INFORMATION: C' Strand fragment

<400> SEQUENCE: 154

Thr Asp Lys Leu Ala Ala
1               5

<210> SEQ ID NO 155
<211> LENGTH: 6
<212> TYPE: PRT
<213> ORGANISM: Homo sapiens
<220> FEATURE:
<223> OTHER INFORMATION: C' Strand fragment

<400> SEQUENCE: 155

Lys Leu Ala Ala Phe Pro
1               5

<210> SEQ ID NO 156
<211> LENGTH: 6
<212> TYPE: PRT
<213> ORGANISM: Artificial Sequence
<220> FEATURE:
<223> OTHER INFORMATION: Fragment

<400> SEQUENCE: 156

Pro Glu Asp Ser Gln Pro
1               5

<210> SEQ ID NO 157
<211> LENGTH: 5
<212> TYPE: PRT
<213> ORGANISM: Homo sapiens
<220> FEATURE:
<223> OTHER INFORMATION: C' strand to C'' strand fragment
```

<400> SEQUENCE: 157

Glu Asp Arg Ser Gln
1               5

<210> SEQ ID NO 158
<211> LENGTH: 5
<212> TYPE: PRT
<213> ORGANISM: Homo sapiens
<220> FEATURE:
<223> OTHER INFORMATION: F-strand fragment

<400> SEQUENCE: 158

Gly Thr Tyr Leu Cys
1               5

<210> SEQ ID NO 159
<211> LENGTH: 5
<212> TYPE: PRT
<213> ORGANISM: Homo sapiens
<220> FEATURE:
<223> OTHER INFORMATION: F-strand fragment

<400> SEQUENCE: 159

Cys Gly Ala Ile Ser
1               5

<210> SEQ ID NO 160
<211> LENGTH: 5
<212> TYPE: PRT
<213> ORGANISM: Mus sp.
<220> FEATURE:
<223> OTHER INFORMATION: A-Strand

<400> SEQUENCE: 160

Ser Leu Thr Phe Tyr
1               5

<210> SEQ ID NO 161
<211> LENGTH: 5
<212> TYPE: PRT
<213> ORGANISM: Mus sp.
<220> FEATURE:
<223> OTHER INFORMATION: Mouse D-E loop

<400> SEQUENCE: 161

Leu Pro Asn Arg His
1               5

<210> SEQ ID NO 162
<211> LENGTH: 6
<212> TYPE: PRT
<213> ORGANISM: Mus sp.
<220> FEATURE:
<223> OTHER INFORMATION: Mouse E Strand

<400> SEQUENCE: 162

Asp Phe His Met Asn Ile
1               5

<210> SEQ ID NO 163
<211> LENGTH: 5
<212> TYPE: PRT
<213> ORGANISM: Rattus sp.
<220> FEATURE:
<223> OTHER INFORMATION: Rat A-strand

<400> SEQUENCE: 163

Gln Leu Ser Trp Gln
1               5

<210> SEQ ID NO 164
<211> LENGTH: 7
<212> TYPE: PRT
<213> ORGANISM: Rattus sp.
<220> FEATURE:
<223> OTHER INFORMATION: Rat B-strand

<400> SEQUENCE: 164

Ala Thr Phe Thr Cys Ser Phe
1               5

<210> SEQ ID NO 165
<211> LENGTH: 7
<212> TYPE: PRT
<213> ORGANISM: Rattus sp.
<220> FEATURE:
<223> OTHER INFORMATION: Rat BC Loop

<400> SEQUENCE: 165

Ser Asn Trp Ser Glu Asp Leu
1               5

<210> SEQ ID NO 166
<211> LENGTH: 7
<212> TYPE: PRT
<213> ORGANISM: Rattus sp.
<220> FEATURE:
<223> OTHER INFORMATION: Rat C Strand

<400> SEQUENCE: 166

Lys Leu Asn Trp Tyr Arg Leu
1               5

<210> SEQ ID NO 167
<211> LENGTH: 5
<212> TYPE: PRT
<213> ORGANISM: Rattus sp.
<220> FEATURE:
<223> OTHER INFORMATION: Rat C - C' loop

<400> SEQUENCE: 167

Ser Pro Ser Asn Gln
1               5

<210> SEQ ID NO 168
<211> LENGTH: 8
<212> TYPE: PRT
<213> ORGANISM: Rattus sp.
<220> FEATURE:
<223> OTHER INFORMATION: Rat C' strand

<400> SEQUENCE: 168

Thr Glu Lys Gln Ala Ala Phe Cys
1               5

<210> SEQ ID NO 169
<211> LENGTH: 4
<212> TYPE: PRT
<213> ORGANISM: Rattus sp.
<220> FEATURE:
<223> OTHER INFORMATION: Rat C'' Strand

<400> SEQUENCE: 169

Tyr Ser Gln Pro
1

<210> SEQ ID NO 170
<211> LENGTH: 5
<212> TYPE: PRT
<213> ORGANISM: Rattus sp.
<220> FEATURE:
<223> OTHER INFORMATION: Rat C''-D loop

<400> SEQUENCE: 170

Val Arg Asp Ala Arg
1               5

<210> SEQ ID NO 171
<211> LENGTH: 5
<212> TYPE: PRT
<213> ORGANISM: Rattus sp.
<220> FEATURE:
<223> OTHER INFORMATION: Rat D strand

<400> SEQUENCE: 171

Phe Gln Ile Val Gln
1               5

<210> SEQ ID NO 172
<211> LENGTH: 5
<212> TYPE: PRT
<213> ORGANISM: Rattus sp.
<220> FEATURE:
<223> OTHER INFORMATION: Rat D-E loop

<400> SEQUENCE: 172

Leu Pro Asn Gly His
1               5

<210> SEQ ID NO 173
<211> LENGTH: 6
<212> TYPE: PRT
<213> ORGANISM: Rattus sp.
<220> FEATURE:
<223> OTHER INFORMATION: Rat E-Strand

<400> SEQUENCE: 173

Asp Phe His Met Asn Ile
1               5

<210> SEQ ID NO 174
<211> LENGTH: 9
<212> TYPE: PRT
<213> ORGANISM: Rattus sp.
<220> FEATURE:
<223> OTHER INFORMATION: Rat F Strand

<400> SEQUENCE: 174

Gly Ile Tyr Leu Cys Gly Ala Ile Ser
1               5

<210> SEQ ID NO 175
<211> LENGTH: 5
<212> TYPE: PRT
<213> ORGANISM: Rattus sp.
<220> FEATURE:
<223> OTHER INFORMATION: Rat FG Loop

<400> SEQUENCE: 175

```
Leu Pro Pro Lys Ala
1               5

<210> SEQ ID NO 176
<211> LENGTH: 4
<212> TYPE: PRT
<213> ORGANISM: Rattus sp.
<220> FEATURE:
<223> OTHER INFORMATION: Rat G Strand

<400> SEQUENCE: 176

Gln Ile Lys Glu
1

<210> SEQ ID NO 177
<211> LENGTH: 4
<212> TYPE: PRT
<213> ORGANISM: Rattus sp.
<220> FEATURE:
<223> OTHER INFORMATION: Rat C' Strand to C'- C'' loop

<400> SEQUENCE: 177

Phe Cys Asn Gly
1

<210> SEQ ID NO 178
<211> LENGTH: 13
<212> TYPE: PRT
<213> ORGANISM: Rattus sp.
<220> FEATURE:
<223> OTHER INFORMATION: Rat C C' loop to C' Strand

<400> SEQUENCE: 178

Ser Pro Ser Asn Gln Thr Glu Lys Gln Ala Ala Phe Cys
1               5                   10

<210> SEQ ID NO 179
<211> LENGTH: 14
<212> TYPE: PRT
<213> ORGANISM: Rattus sp.
<220> FEATURE:
<223> OTHER INFORMATION: Rat C' strand to C'' strand

<400> SEQUENCE: 179

Thr Glu Lys Gln Ala Ala Phe Cys Asn Gly Tyr Ser Gln Pro
1               5                   10

<210> SEQ ID NO 180
<211> LENGTH: 10
<212> TYPE: PRT
<213> ORGANISM: Rattus sp.
<220> FEATURE:
<223> OTHER INFORMATION: Rat D strand to DE loop

<400> SEQUENCE: 180

Phe Gln Ile Val Gln Leu Pro Asn Gly His
1               5                   10

<210> SEQ ID NO 181
<211> LENGTH: 9
<212> TYPE: PRT
<213> ORGANISM: Rattus sp.
<220> FEATURE:
<223> OTHER INFORMATION: Rat FG Loop to G Strand

<400> SEQUENCE: 181

Leu Pro Pro Lys Ala Gln Ile Lys Glu
```

```
1               5

<210> SEQ ID NO 182
<211> LENGTH: 5
<212> TYPE: PRT
<213> ORGANISM: Canis sp.
<220> FEATURE:
<223> OTHER INFORMATION: Dog A-strand

<400> SEQUENCE: 182

Pro Leu Thr Phe Ser
1               5

<210> SEQ ID NO 183
<211> LENGTH: 7
<212> TYPE: PRT
<213> ORGANISM: Canis sp.
<220> FEATURE:
<223> OTHER INFORMATION: Dog B Strand

<400> SEQUENCE: 183

Ala Thr Phe Thr Cys Ser Leu
1               5

<210> SEQ ID NO 184
<211> LENGTH: 7
<212> TYPE: PRT
<213> ORGANISM: Canis sp.
<220> FEATURE:
<223> OTHER INFORMATION: Dog BC Loop

<400> SEQUENCE: 184

Ala Asp Ile Pro Asp Ser Phe
1               5

<210> SEQ ID NO 185
<211> LENGTH: 7
<212> TYPE: PRT
<213> ORGANISM: Canis sp.
<220> FEATURE:
<223> OTHER INFORMATION: Dog C Strand

<400> SEQUENCE: 185

Val Leu Asn Trp Tyr Arg Leu
1               5

<210> SEQ ID NO 186
<211> LENGTH: 5
<212> TYPE: PRT
<213> ORGANISM: Canis sp.
<220> FEATURE:
<223> OTHER INFORMATION: Dog C-C' loop

<400> SEQUENCE: 186

Ser Pro Arg Asn Gln
1               5

<210> SEQ ID NO 187
<211> LENGTH: 8
<212> TYPE: PRT
<213> ORGANISM: Canis sp.
<220> FEATURE:
<223> OTHER INFORMATION: Dog C' strand

<400> SEQUENCE: 187

Thr Asp Lys Leu Ala Ala Phe Gln
1               5
```

<210> SEQ ID NO 188
<211> LENGTH: 4
<212> TYPE: PRT
<213> ORGANISM: Canis sp.
<220> FEATURE:
<223> OTHER INFORMATION: Dog C'' Strand

<400> SEQUENCE: 188

Arg Ile Glu Pro
1

<210> SEQ ID NO 189
<211> LENGTH: 5
<212> TYPE: PRT
<213> ORGANISM: Canis sp.
<220> FEATURE:
<223> OTHER INFORMATION: Dog C''-D loop

<400> SEQUENCE: 189

Gly Arg Asp Arg Arg
1               5

<210> SEQ ID NO 190
<211> LENGTH: 5
<212> TYPE: PRT
<213> ORGANISM: Canis sp.
<220> FEATURE:
<223> OTHER INFORMATION: Dog D Strand

<400> SEQUENCE: 190

Phe Arg Val Met Arg
1               5

<210> SEQ ID NO 191
<211> LENGTH: 5
<212> TYPE: PRT
<213> ORGANISM: Canis sp.
<220> FEATURE:
<223> OTHER INFORMATION: Dog D-E loop

<400> SEQUENCE: 191

Leu Pro Asn Gly Arg
1               5

<210> SEQ ID NO 192
<211> LENGTH: 6
<212> TYPE: PRT
<213> ORGANISM: Canis sp.
<220> FEATURE:
<223> OTHER INFORMATION: Dog E Strand

<400> SEQUENCE: 192

Asp Phe His Met Ser Ile
1               5

<210> SEQ ID NO 193
<211> LENGTH: 9
<212> TYPE: PRT
<213> ORGANISM: Canis sp.
<220> FEATURE:
<223> OTHER INFORMATION: Dog F Strand

<400> SEQUENCE: 193

Gly Ile Tyr Leu Cys Gly Ala Ile Tyr
1               5

<210> SEQ ID NO 194
<211> LENGTH: 5
<212> TYPE: PRT
<213> ORGANISM: Canis sp.
<220> FEATURE:
<223> OTHER INFORMATION: Dog FG Loop

<400> SEQUENCE: 194

Leu Pro Pro Asn Thr
1               5

<210> SEQ ID NO 195
<211> LENGTH: 4
<212> TYPE: PRT
<213> ORGANISM: Canis sp.
<220> FEATURE:
<223> OTHER INFORMATION: Dog G Strand

<400> SEQUENCE: 195

Gln Ile Asn Glu
1

<210> SEQ ID NO 196
<211> LENGTH: 4
<212> TYPE: PRT
<213> ORGANISM: Canis sp.
<220> FEATURE:
<223> OTHER INFORMATION: Dog C' Strand to C'-C'' loop

<400> SEQUENCE: 196

Phe Gln Glu Asp
1

<210> SEQ ID NO 197
<211> LENGTH: 13
<212> TYPE: PRT
<213> ORGANISM: Canis sp.
<220> FEATURE:
<223> OTHER INFORMATION: Dog C C' loop to C' Strand

<400> SEQUENCE: 197

Ser Pro Arg Asn Gln Thr Asp Lys Leu Ala Ala Phe Gln
1               5                   10

<210> SEQ ID NO 198
<211> LENGTH: 14
<212> TYPE: PRT
<213> ORGANISM: Canis sp.
<220> FEATURE:
<223> OTHER INFORMATION: Dog C' strand to C'' strand

<400> SEQUENCE: 198

Thr Asp Lys Leu Ala Ala Phe Gln Glu Asp Arg Ile Glu Pro
1               5                   10

<210> SEQ ID NO 199
<211> LENGTH: 10
<212> TYPE: PRT
<213> ORGANISM: Canis sp.
<220> FEATURE:
<223> OTHER INFORMATION: Dog D strand to DE loop

<400> SEQUENCE: 199

Phe Arg Val Met Arg Leu Pro Asn Gly Arg
1               5                   10

```
<210> SEQ ID NO 200
<211> LENGTH: 9
<212> TYPE: PRT
<213> ORGANISM: Canis sp.
<220> FEATURE:
<223> OTHER INFORMATION: Dog FG loop to G strand

<400> SEQUENCE: 200

Leu Pro Pro Asn Thr Gln Ile Asn Glu
1               5

<210> SEQ ID NO 201
<211> LENGTH: 5
<212> TYPE: PRT
<213> ORGANISM: Equus sp.
<220> FEATURE:
<223> OTHER INFORMATION: Horse A strand

<400> SEQUENCE: 201

Pro Leu Thr Phe Ser
1               5

<210> SEQ ID NO 202
<211> LENGTH: 7
<212> TYPE: PRT
<213> ORGANISM: Equus sp.
<220> FEATURE:
<223> OTHER INFORMATION: Horse B Strand

<400> SEQUENCE: 202

Ala Thr Phe Thr Cys Ser Phe
1               5

<210> SEQ ID NO 203
<211> LENGTH: 7
<212> TYPE: PRT
<213> ORGANISM: Equus sp.
<220> FEATURE:
<223> OTHER INFORMATION: Horse BC Loop

<400> SEQUENCE: 203

Ser Asn Thr Ser Glu His Phe
1               5

<210> SEQ ID NO 204
<211> LENGTH: 7
<212> TYPE: PRT
<213> ORGANISM: Equus sp.
<220> FEATURE:
<223> OTHER INFORMATION: Horse C Strand

<400> SEQUENCE: 204

Val Leu Asn Trp Tyr Arg Met
1               5

<210> SEQ ID NO 205
<211> LENGTH: 5
<212> TYPE: PRT
<213> ORGANISM: Equus sp.
<220> FEATURE:
<223> OTHER INFORMATION: Horse C-C' loop

<400> SEQUENCE: 205

Ser Pro Ser Asn Gln
1               5

<210> SEQ ID NO 206
```

```
<211> LENGTH: 8
<212> TYPE: PRT
<213> ORGANISM: Equus sp.
<220> FEATURE:
<223> OTHER INFORMATION: Horse C' Strand

<400> SEQUENCE: 206

Thr Asp Lys Leu Ala Ala Phe Pro
1               5

<210> SEQ ID NO 207
<211> LENGTH: 4
<212> TYPE: PRT
<213> ORGANISM: Equus sp.
<220> FEATURE:
<223> OTHER INFORMATION: Horse C'' Strand

<400> SEQUENCE: 207

Ser Ser Gln Pro
1

<210> SEQ ID NO 208
<211> LENGTH: 5
<212> TYPE: PRT
<213> ORGANISM: Equus sp.
<220> FEATURE:
<223> OTHER INFORMATION: Horse C'' -D loop

<400> SEQUENCE: 208

Gly Arg Ser Gly Arg
1               5

<210> SEQ ID NO 209
<211> LENGTH: 5
<212> TYPE: PRT
<213> ORGANISM: Equus sp.
<220> FEATURE:
<223> OTHER INFORMATION: Horse D Strand

<400> SEQUENCE: 209

Phe Arg Val Thr Arg
1               5

<210> SEQ ID NO 210
<211> LENGTH: 5
<212> TYPE: PRT
<213> ORGANISM: Equus sp.
<220> FEATURE:
<223> OTHER INFORMATION: Horse D-E loop

<400> SEQUENCE: 210

Leu Pro Asn Gly Arg
1               5

<210> SEQ ID NO 211
<211> LENGTH: 6
<212> TYPE: PRT
<213> ORGANISM: Equus sp.
<220> FEATURE:
<223> OTHER INFORMATION: Horse E Strand

<400> SEQUENCE: 211

Asp Phe His Met Ser Val
1               5

<210> SEQ ID NO 212
<211> LENGTH: 9
```

```
<212> TYPE: PRT
<213> ORGANISM: Equus sp.
<220> FEATURE:
<223> OTHER INFORMATION: Horse F Strand

<400> SEQUENCE: 212

Gly Ile Tyr Leu Cys Gly Ala Ile Ser
1               5

<210> SEQ ID NO 213
<211> LENGTH: 5
<212> TYPE: PRT
<213> ORGANISM: Equus sp.
<220> FEATURE:
<223> OTHER INFORMATION: Horse FG Loope

<400> SEQUENCE: 213

Leu Pro Pro Lys Thr
1               5

<210> SEQ ID NO 214
<211> LENGTH: 4
<212> TYPE: PRT
<213> ORGANISM: Equus sp.
<220> FEATURE:
<223> OTHER INFORMATION: Horse G Strand

<400> SEQUENCE: 214

Gln Ile Asn Glu
1

<210> SEQ ID NO 215
<211> LENGTH: 4
<212> TYPE: PRT
<213> ORGANISM: Equus sp.
<220> FEATURE:
<223> OTHER INFORMATION: Horse C' strand to C'-C'' loop

<400> SEQUENCE: 215

Phe Pro Glu Asp
1

<210> SEQ ID NO 216
<211> LENGTH: 11
<212> TYPE: PRT
<213> ORGANISM: Equus sp.
<220> FEATURE:
<223> OTHER INFORMATION: Horse C C' loop to C' strand

<400> SEQUENCE: 216

Ser Asn Gln Thr Asp Lys Leu Ala Ala Phe Pro
1               5                   10

<210> SEQ ID NO 217
<211> LENGTH: 14
<212> TYPE: PRT
<213> ORGANISM: Equus sp.
<220> FEATURE:
<223> OTHER INFORMATION: Horse C' strand to C'' strand

<400> SEQUENCE: 217

Thr Asp Lys Leu Ala Ala Phe Pro Glu Asp Ser Ser Gln Pro
1               5                   10

<210> SEQ ID NO 218
<211> LENGTH: 10
<212> TYPE: PRT
```

```
<213> ORGANISM: Equus sp.
<220> FEATURE:
<223> OTHER INFORMATION: Horse D strand to DE loop

<400> SEQUENCE: 218

Phe Arg Val Thr Arg Leu Pro Asn Gly Arg
1               5                   10

<210> SEQ ID NO 219
<211> LENGTH: 9
<212> TYPE: PRT
<213> ORGANISM: Equus sp.
<220> FEATURE:
<223> OTHER INFORMATION: Horse FG Loop to G strand

<400> SEQUENCE: 219

Leu Pro Pro Lys Thr Gln Ile Asn Glu
1               5
```

What is claimed is:

1. A compound of formula (I)

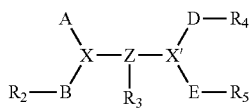

(I)

or pharmaceutically acceptable salt thereof; wherein;

A is an amino acid sequence of from three amino acids to the full length of a peptide sequence of mammalian PD1 ectodomain fragments selected from FG loop, BC loop, C strand, or C' strand to C'-C" loop;

B is an amino acid sequence of from three amino acids to the full length of a peptide sequence of mammalian PD1 ectodomain fragments selected from BC loop, FG loop, C C' loop to C' strand, D strand, C' strand to C'-C" loop, or is absent;

with the proviso that if A is the amino acid sequence SNTSESF (SEQ ID NO: 4) and X is lysine then B cannot be the amino acid sequence SNTSESF SEQ ID NO: 4);

Z is the amino acid sequence FRVTQLAPKAQIKE (SEQ ID NO: 84);

D is up to two peptide sequences arranged in any order each being of from three amino acids up to the full length of a mammalian PD1 ectodomain fragment selected from BC loop, FG loop, or is absent;

E is up to four peptide sequences arranged in any order each being of from three amino acids up to the full length of a mammalian PD1 ectodomain fragment selected from D strand, FG loop, G strand, or is absent;

X and X' are independently selected from lysine, ornithine, diaminopropionic acid, diaminobutyric acid or olefinic amino acid of formula

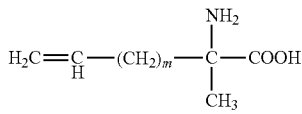

which is optionally linked with an additional lysine; or

X and X' combine together forming a ring with olefinic amino acid which is optionally linked with an additional lysine; or X' is absent;

'm' is an integer selected from 1 to 6, both inclusive;

$R_2$ and $R_3$ are independently selected from group consisting of $C_2$-$C_{20}$ acyl, absent or $R_a$-L';

$R_a$ is maleimido propionic acid;

L' is —CO(CH$_2$—CH$_2$—O—)$_n$ NH; and

'n' is an integer selected from 2 to 10, both inclusive;

$R_4$ and $R_5$ are independently NH$_2$, or one or both of $R_4$ or $R_5$ are absent, with the proviso to the compound of Formula (I), that in a compound of Formula (I) as above defined:

a) up to 5 but not more than 25% of the amino acids may be substituted with other natural or unnatural amino acids;

b) not more than 30% of the amino acids may be omitted;

c) in each said peptide sequence up to 2 amino acids may be added individually at any position;

d) up to 5 but not more than 25% of the peptide bonds may instead be replaced by reduced amide bond (—CH$_2$NH—);

e) up to 100% of the amino acids may be D-amino acids;

f) up to 100% of the amino acids may be in reverse order.

2. The compound according to claim 1, wherein said mammalian PD1 ectodomain fragments are from human, murine, dog, horse or rat PD1.

3. The compound according to claim 1, wherein;

A is an amino acid sequence of from three amino acids to the full length of a peptide sequence of human or murine PD1 ectodomain fragments selected from FG loop, BC loop, C strand, or C' strand to C'-C" loop as in table below;

| | hPD-1 | mPD-1 |
|---|---|---|
| BC Loop | SNTSESF (SEQ ID NO: 4) | SNWSEDL (SEQ ID NO: 27) |
| C Strand | VLNWYRM (SEQ ID NO: 5) | MLNWNRL (SEQ ID NO: 28) |

-continued

|  | hPD-1 | mPD-1 |
|---|---|---|
| C' strand to C'-C" loop | FPED (SEQ ID NO: 21) | FCNG (SEQ ID NO: 37) |
| FG loop | LAPKA (SEQ ID NO: 15) | LHPKA (SEQ ID NO: 35) |

B is an amino acid sequence of from three amino acids to the full length of a peptide sequence of human or murine PD1 ectodomain fragments selected from BC loop, FG loop, C C' loop to C' strand, D strand, C' strand to C'-C" loop as -continued

| Comp. No. | Compound | Sequence ID |
|---|---|---|
| 11 | SNTSESFK(SNQTDK)FRVTQLAPKAQIKE-NH2 | 52 |
| 12 | SNTSESFK(SNQTDK)FRVTQK(LAP)AQIKE-NH2 | 53 |
| 22 | 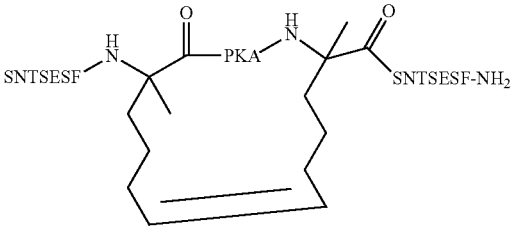 | 63 |
| 23 | 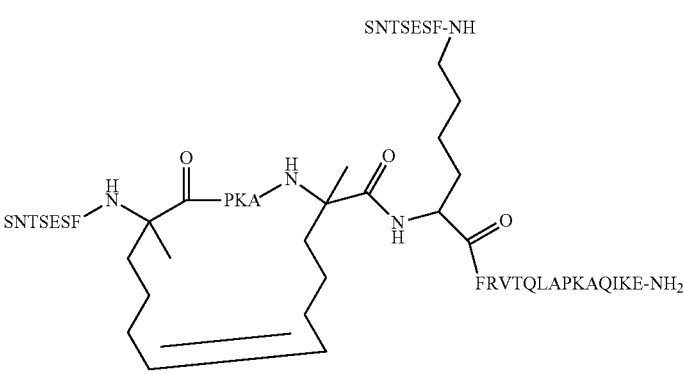 | 64 |
| 24 | 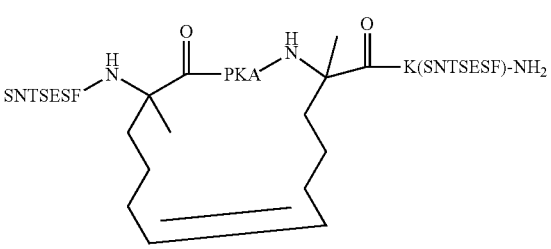 | 65 |
| 27 | SNTSESFKFRVTQLAPKAQIKE-NH2 | 68 |
| 28 | SNTSESFKSNTSESFFRVTQLAPKAQIKE-NH2 | 69 |
| 37 | SNTSESFK(LAP)FRVTQLAPKAQIKE-NH2 | 78 |
| 38 | LAPK(LAP)FRVTQLAPKAQIKE-NH2 | 79 |
| 39 | LAPKAQIKE-NH2 | 80 |
| 48 | EKIQAKPALQTVRFK(FSESTNS)FSESTNS-NH2 | 89 |
| 49 | ekiqakpalqtvrfk(fsestns)fsestns-NH2 Retro inverso (All D-amino acid) | 90 |
| 69 | SNWSEDLK(SNWSEDL)FQIIQLHPKAKIEE-NH2 | 110 |
| 70 | EDK(ED)FRVTQLAPKAQIKE-NH2 | 111 |
| 71 | SNTSESFK(ED)FRVTQLAPKAQIKE-NH2 | 112 |
| 72 | LAPKAK(ED)FRVTQLAPKAQIKE-NH2 | 113 |
| 73 | SNQTDKK(ED)FRVTQLAPKAQIKE-NH2 | 114 |
| 75 | SNQTDKK(VLNWYRM)GIYLCGAISLAPKAQIKE-NH2 | 116 |
| 76 | EDK(VLNWYRM)GIYLCGAISLAPKAQIKE-NH2 | 117 |
| 79 | VLNWYRM(SNQTDK)GIYLCGAISLAPKAQIKE-NH2 | 120 |

-continued

| Comp. No. | Compound | Sequence ID |
|---|---|---|
| 82 | SNWSEDLK(SNWSEDL)FQIIQLHPK(CH$_3$(CH$_2$)$_{14}$CO)AKIEE-NH2 | 123 |
| 91 | SNWSEDLK(SNWSEDL)FQIIQLHPK(MPA—NH—CH$_2$—CH$_2$—O—CH$_2$—CH$_2$—O—CO)AKIEE-NH2 | 132 |
| 99 | SNTSESF-Orn-(SNTSESF)KAQIKE-NH2 | 140 |
| 100 | SNTSESF-Dap-(SNTSESF)KAQIKE-NH2 | 141 |
| 101 | SNTSESF-Dab-(SNTSESF)KAQIKE-NH2 | 142 |
| 107 | LAPKA(SNQTDK)FRVTQLAPKAQIKE-NH2 | 148. |

9. A compound according to claim 3 having formula (Ia)

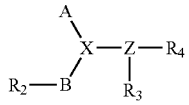

(Ia)

or pharmaceutically acceptable salt thereof;
wherein;
A is an amino acid sequence of from three amino acids to the full length of a peptide sequence of human or murine PD1 ectodomain fragments selected from FG loop, BC loop, C strand, or C' strand to C'-C" loop;
B is an amino acid sequence of from three amino acids to the full length of a peptide sequence of human or murine PD1 ectodomain fragments selected from BC loop, FG loop, C-C' loop to C' strand, D strand, C' strand to C'-C" loop or is absent;
with the proviso that if A is the amino acid sequence SNTSESF (SEQ ID NO: 4) and X is lysine then B cannot be the amino acid sequence SNTSESF SEQ ID NO: 4);
Z is the amino acid sequence FRVTQLAPKAQIKE (SEQ ID NO: 84); and
X is lysine.

10. The compound according to claim 9, wherein A and B are independently an amino acid sequence of from three amino acids to the full length of said BC loop, with the proviso that if A is the amino acid sequence SNTSESF (SEQ ID NO: 4) and X is lysine then B cannot be the amino acid sequence SNTSESF (SEQ ID NO: 4).

11. The compound according to claim 9, wherein R$_2$ and R$_3$ are absent.

12. The compound according to claim 9, wherein R$_3$ is C16-acyl.

13. The compound according to claim 9, wherein up to three amino acids are D-amino acids.

14. The compound according to claim 9, wherein all amino acids are D-amino acids.

15. The compound according to claim 9, comprising up to three reduced amide bonds (—CH$_2$NH—).

16. A pharmaceutical composition comprising a compound of formula (I) or a pharmaceutically acceptable salt thereof as claimed in claim 1, and a pharmaceutically acceptable diluent or carrier.

17. A method of modulating an immune response mediated by PD-1 signaling pathway in a subject, comprising administering to the subject a therapeutically effective amount of the compound according to claim 1, such that the immune response in the subject is modulated.

18. A method of inhibiting growth of tumor cells and/or metastasis in a subject, comprising administering to the subject a therapeutically effective amount of the compound according to claim 1 capable of inhibiting the programmed cell death 1 (PD1) signaling pathway.

19. The method of claim 18, wherein the tumor cells are of a cancer selected from the group consisting of melanoma, renal cancer, prostate cancer, breast cancer, colon cancer, and lung cancer.

20. The method of claim 19, wherein the tumor cells are of a cancer selected from bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

21. A method of treating an infectious disease in a subject, comprising administering to the subject a therapeutically effective amount of the compound according to claim 1 to inhibit the programmed cell death 1 (PD1) signaling pathway such that the subject is treated for the infectious disease.

22. A method of treating bacterial and viral infections in a subject, comprising administering to the subject a therapeutically effective amount of the compound according to claim 1 to inhibit the programmed cell death 1 (PD1) signaling pathway such that the subject is treated for the bacterial and viral infections.

* * * * *